US006416975B1

(12) United States Patent
Gallagher et al.

(10) Patent No.: US 6,416,975 B1
(45) Date of Patent: Jul. 9, 2002

(54) HUMAN GLYCINE TRANSPORTER TYPE 2

(75) Inventors: Michael J. Gallagher, Shaker Heights; Loyd H. Burgess, Solon; Kurt R. Brunden, Aurora, all of OH (US)

(73) Assignee: Gliatech, Inc., Cleveland, OH (US)

( * ) Notice: Subject to any disclaimer, the term of this patent is extended or adjusted under 35 U.S.C. 154(b) by 0 days.

(21) Appl. No.: 09/191,468

(22) Filed: Nov. 12, 1998

(51) Int. Cl.[7] .............................................. C12D 21/06
(52) U.S. Cl. .................. 435/69.1; 435/252.3; 435/320; 435/325; 536/23.5
(58) Field of Search ............................. 435/69.1, 320.1, 435/252.3, 325; 536/23.5

(56) References Cited

U.S. PATENT DOCUMENTS

| | | | |
|---|---|---|---|
| 3,376,110 A | 4/1968 | Shiraeff | 423/272 |
| 4,016,043 A | 4/1977 | Schuurs et al. | 435/5 |
| 4,391,904 A | 7/1983 | Litman et al. | 435/7.91 |
| 5,641,670 A | 6/1997 | Treco et al. | 435/325 |
| 5,733,761 A | 3/1998 | Treco et al. | 435/463 |
| 5,919,653 A | * 7/1999 | Albert et al. | 435/69.1 |

FOREIGN PATENT DOCUMENTS

| | | | |
|---|---|---|---|
| WO | WO 98/07854 | 2/1998 | |
| WO | 98/07854 | * 2/1998 | 435/69.1 |

OTHER PUBLICATIONS

Morrow et al (FEBS Lett 439(3): 334–40, see abstract, Nov. 1998.*
Rudinger (In Peptide Hormones, J.A. Parsons Ed. University Park press, Baltimore, See p. 6, last paragraph, Jun. 1996.*
Ngo (In The Protein Folding Problem and Tertiary Structure Prediction, Merz and Le Grand Eds. Birkhauser, Boston. See p. 492, second full paragraph, Jun. 1994.*
Crook (In Basic Principles of Antisense Therapeutics, Springer–Verlag, Eds, New York, pp. 1 and 4, Jul. 1998.*
Branch. Trends in Biochemical Sciences 23: 45–50, especially p. 45, col. 3. first para., p. 48, last para. through p. 49, Feb. 1998.*
Orkin (Report and Recommendations of the Panel to Assess the NIH Investment in Research on Gene Therapy, see p. 1, item 3, and p. 9, Dec. 1995.*
Verma et al. Nature 389: 239–242, especially p. 239, Sep. 1997.*
Anderson et al. Nature 392: 25–30, especially pp. 25 and 30, Apr. 1998.*
Kim et al (Mol. Pharm. 45(4): 608–617, See Fig.1, especially nucleotides 898–926, and p. 609 col. 2, last paragraph, 1994.*
Gallagher, et al. ,Society for Neuroscience Abstracts, vol. 24, p. 2073, 28th annual meeting of the Society for Neuroscience, Nov. 7–12, 1998 (Abstract).
Agris, et al., Bichemistry 25:6268 (1986).
Alki, et al., Nature Genetics 3:224 (1993).

Altschul, et al., J. Mol. Biol., 215:403–410 (1990).
Bannon, et al. J. Neurochem. 54:706–708 (1990).
Becker, FASEB J. 4:2767–2775 (1990).
Behr, et al., Pro. Natl. Acad. Sci. U.S.A. 86:6982–6986 (1989).
Betz, et al., Q. Rev. Biophys. 25:381–394 (1992).
Borden, et al., J. Biol. Chem. 267:21096–21104 (1992).
Boris–Lawrie, et al., Ann. N.Y. Acad. Sci. 716:59 (1994).
Borowsky et al., Neuron 10:851–863 (1993).
Chou, et al., Biochemistry 13:211 (1974).
Devereux, J., et al., Nucleic Acids Research 12(1):387–(1984).
Eisenberg, et al., Proc. Natl. Acad. Sci. USA 81:140–144 (1984).
Engelman, et al., Ann. Rev. Biophys. Chem. 15:321–353.
Fedele, et al., Brain Res. 572:154–163 (1992).
Fremeau, et al., Neuron 8:915–926 (1992).
Froman, et al., Proc. Natl. Acad. Sci. USA 85:8998 (1998).
Gallagher, et al., Brain Res.: Molecular Brain Res. 70:101–115 (1999).
Gillan, et al., Gene 8:81–97 (1979).
Gittman, et al., Proc. Natl. Acad. Sci. U.S.A. 82:7309–7313 (1985).
Goeddel, et al., Proc. Natl. Acad. Sci, USA 76:106–110 (1979).
Graham, et al., Virology 52:456 (1983).
Grimwood, et al., Molec. Pharmacol. 41:923–930 (1992) or 49.
Guastella, et al., Proc. Natl. Acad. Sci.(USA) 89:7189–7193 (1992).
Guastella, et al., Science 249:1303–1306 (1990).
Hoffman, et al., Science 254:579–580 (1991).
Huse, et al., Science 246:1275–1281 (1989).
Jursky, et al., J. Neurochem. 67:336–344 (1996).
Kanner, Biochemistry 17:1207–1211, (1978).
Karlsson, S Blood 78:2481 (1991).
Kemp, et al., Trends. Pharmacol Sci. 14:20–25 (1993).
Kim, et al., Mol. Pharmacol. 45:608–617 (1994).
Kohler et al., Nature 256:495 (1975).
Litzinger, et al., Biochem. Biophys. Acta 1113:201 (1992).
Liu, et al., FEBS Letters 305:110–114 (1992a).
Liu, et al., J. Biol. Chem. 268:22802–22808 (1993).
Liu, et al., Proc. Natl. Acad. Sci. USA) 89:12145–12149 (1992b).
Loh, et al., Science 243:217 (1989).
Lopez–Corcuera, et al., J. Biol. Chem. 266:24809–24814 (1991).
Marks, et al., J. Biol. Chem., 267:16007–16010 (1992).
Marks, et al., J. Biol. 222:581–597 (1991).
McLachlin, et al., Progr. Nucle. Acids, Res. Mol. Biol. 38:91 (1990).

(List continued on next page.)

Primary Examiner—James Ketter
Assistant Examiner—Richard Schnizer
(74) Attorney, Agent, or Firm—McAndrews, Held & Malloy

(57) ABSTRACT

Nucleic acids and proteins derived from sequences of the human glycine transporter type 2 are described.

82 Claims, 6 Drawing Sheets

OTHER PUBLICATIONS

Morrow et al., *FEBS Lett.* 439:334–340 (1998).
Morsy, et al., *J.A.M.A. 270*:2338 (1993).
Needleman and Wunsch, *J. Mol. Biol., 48*:443–455 (1970).
Nishimura, et al., *Eur. J. Immunol., 18*:747–753 (1988).
Pacholczyk, et al., *Nature 350*:350–354 (1991).
Pines, et al., *Nature 360*:464–466 (1993).
Ponce, et al. *Neurosci. Lett. 242*:25–28 (1998).
Potter, et al., *Proc. Natl. Acad. Sci. 81*:7161–7165 (1984).
Roberts, et al., *Nature 328*:731–734 (1987).
Shea, et al., *Nucleic Acids Res. 18*:3777–3783 (1990).
Smith, et al., *Neuron 8*:927–935 (1992).
Spiess, et al., *Cell 44*:177 (1986).
Walter, et al., *Meth. Enzymol. 96*:84 (1983).
Wang, et al., *Proc. Natl. Acad. Sci. 84*:7851–7855 (1987).
Wu, et al., *Biochemistry 27*:887–892 (1988).
Zafra, et al., *J. Neurosci. 15*:3952–3969 (1995).

* cited by examiner

Fig. 2A

```
AGAAGATGGG TAATCCAGCC CACAGAACAC CGGTCCCTGG CTGGCTTCCT   50
CTTCCATGTT CTGGTCTTGG CACACACTCT AAAGGAAGAA ACGGCTGAGG  100
GAGGGGGTGT GGTGAAGGTT TTTTTTTGTG GGGAGGGGTT AATTAGGAAC  150
CTGCTTGCTG GGAACTCCAG GCATGATGTT GGGGGAGCCT GCTTGCCAAA  200
TAAATTCTTG GAGGACGAGC AAGGGGATGA GGATAAGGCC CGAGGGAACT  250
GGTCCAGCAA ACTGGACTTC ATCCTGTCCA TGGTGGGGTA CGCAGTGGGG  300
CTGGGCAATG TCTGGAGGTT TCCCTACCTG GCCTTCCAGA ACGGGAGGC   350
GGAATTTGTT GCAGCAGAAC GGACAGGTGC TGCACCACCG GACGGGTTAA  400
AGCGCAAAAC ATAGGCCACT ACTCCCGTCC TCTCCAGTTC CAAATTAGGG  450
ACACTTTGAC AAGTACTTAT GAGGACCTCA GAGCATTTGC CATCGGGGGT  500
                                          M   M   L
GCCCTGAAAA CAGACCAGGT GCTTTCCTCA TCCCTTACCT GATGATGCTG  550
  A   L   A   G   L   P
GCTCTGGCTG GATTACCC
```

Fig. 2B

```
                          490                  500
                   T  L  S  S  Y  S  K  F  H  N  N  C  Y  R  D  T  L
hGlyT2 (wild-type)  ACTCTCTCTTCTTACAGCAAATTCCACAACAACTGCTACAGGGACACTCT 1508
hGlyT2 (3'-Deletion) ACTCTCTCTTCTTACAACAAATTCCAC- - - - - - - - - - - -
                   T  L  S  S  Y  N  K  F  H I  V  T  C  T  N  510 S  A  T  S  I  F  A  G  F  V
hGlyT2 (wild-type)  AATTGTCACCTGCACCAACAGTGCCACAAGCATCTTTGCCGGCTTCGTC  1557
hGlyT2 (3'-Deletion) - - - - - - - - - GTGCCAACAAGCATCTTTGCCGGCTTCGTC  1515
                                        V  P  T  S  I  F  A  G  F  V
```

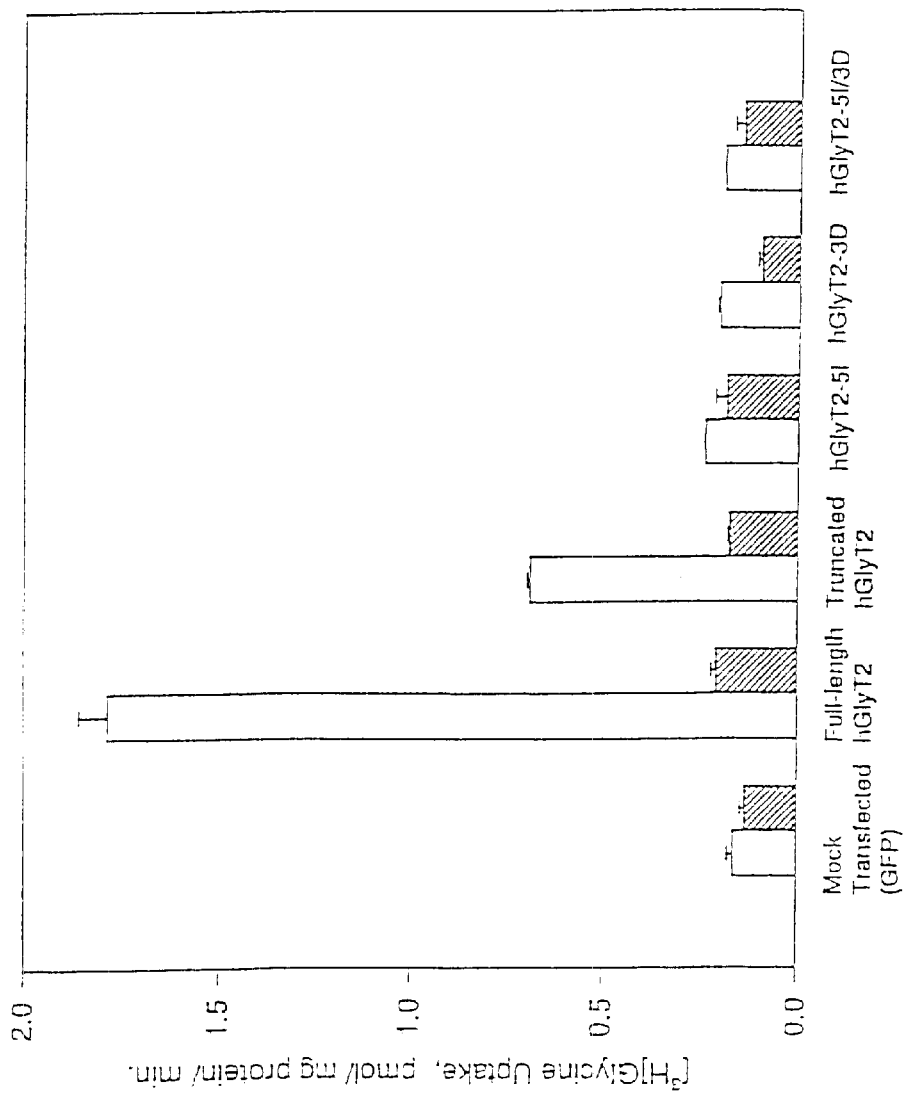

Glycine Uptake Mediated by hGlyT2 (Full Length)

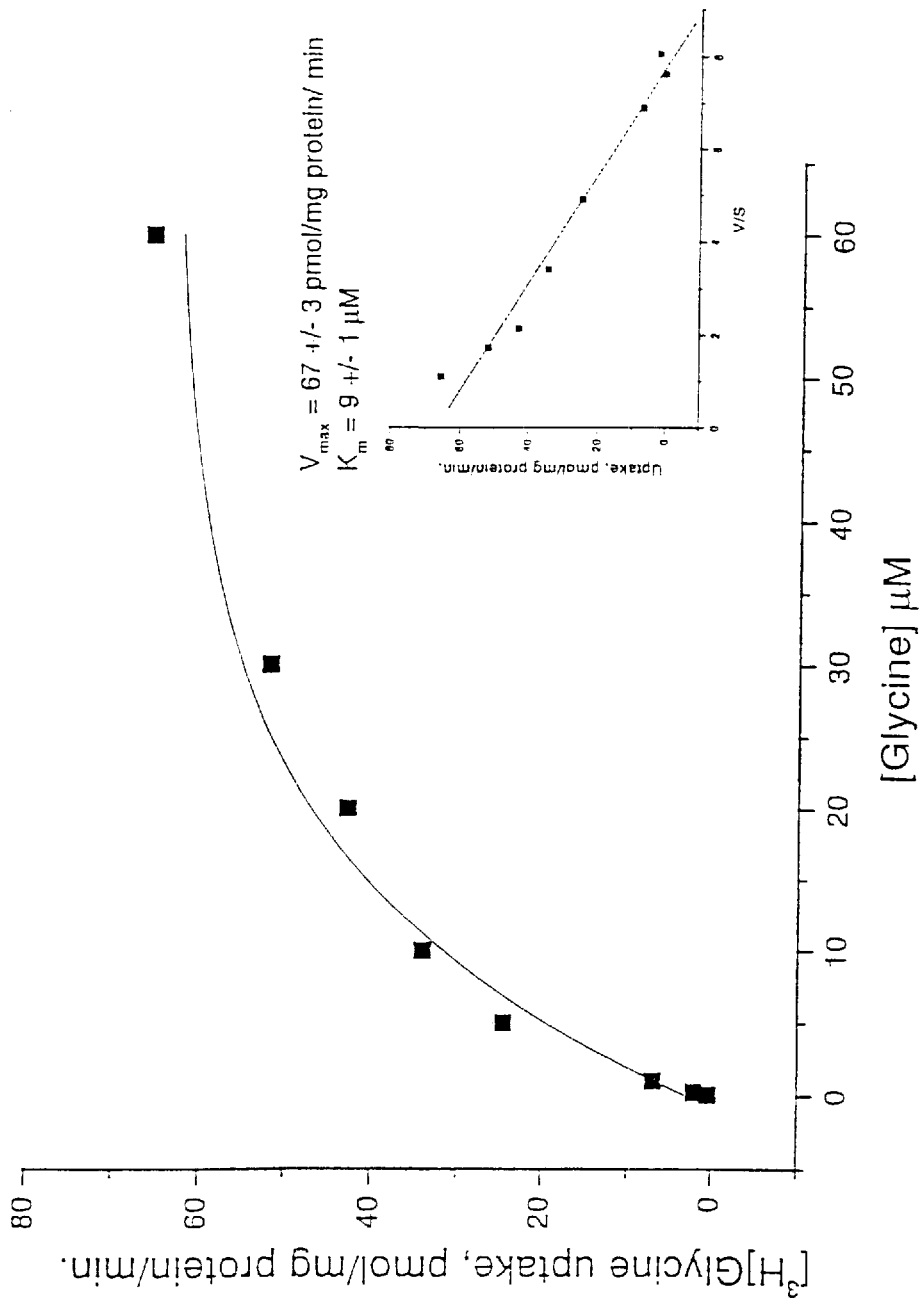

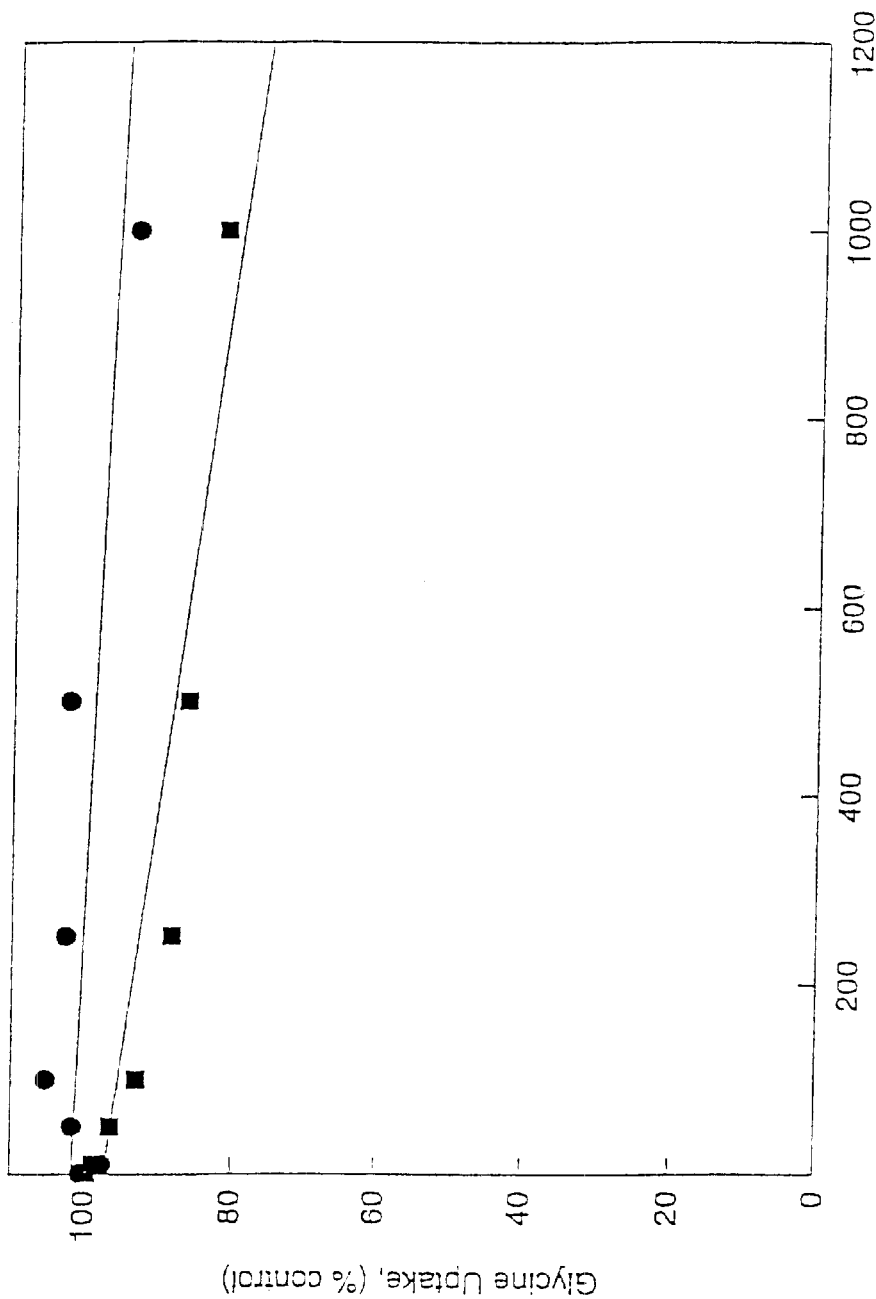

SEQUENCE LISTING

<160> NUMBER OF SEQ ID NOS: 124

<210> SEQ ID NO 1
<211> LENGTH: 42
<212> TYPE: DNA
<213> ORGANISM: Human

```
<220> FEATURE:
<223> OTHER INFORMATION: Primer A (Sense) corresponding to 892-921; nt
      1-42
<220> FEATURE:
<221> NAME/KEY: misc_feature
<222> LOCATION: (30)
<223> OTHER INFORMATION: n at position 30 = any nucleotide(s) from the
      group g, a, c or t(u)

<400> SEQUENCE: 1
cuacuacuac uaggcgccuu ccusaucccn uayyusauga ug                    42

<210> SEQ ID NO 2
<211> LENGTH: 42
<212> TYPE: DNA
<213> ORGANISM: Human
<220> FEATURE:
<223> OTHER INFORMATION: Primer B (Anti-sense) corresponding to
      1506-1477; nt 1-42

<400> SEQUENCE: 2
caucaucauc aucacguagg ggaasguggc sguraaruas ac                    42

<210> SEQ ID NO 3
<211> LENGTH: 40
<212> TYPE: DNA
<213> ORGANISM: human
<220> FEATURE:
<223> OTHER INFORMATION: Primer C (Sense) corresponding to 1477-1504; nt
      1-40
<220> FEATURE:
<221> NAME/KEY: misc_feature
<222> LOCATION: (36)
<223> OTHER INFORMATION: n at position 36 = any nucleotide(s) from the
      group g, a, c or t(u)

<400> SEQUENCE: 3
cuacuacuac uagugacuu cacggccacs uuyccnuayg                        40

<210> SEQ ID NO 4
<211> LENGTH: 41
<212> TYPE: DNA
<213> ORGANISM: Human
<220> FEATURE:
<223> OTHER INFORMATION: Primer D (Anti-sense) corresponding to
      2231-2203; nt 1-41

<400> SEQUENCE: 4
caucaucauc auggcuggaa bccraucauc auyucdauru c                     41

<210> SEQ ID NO 5
<211> LENGTH: 39
<212> TYPE: DNA
<213> ORGANISM: Human
<220> FEATURE:
<223> OTHER INFORMATION: Primer E (Sense) corresponding to 2158-2184; nt
      1-39

<400> SEQUENCE: 5
cuacuacuac uacucgaggg gaucuccuau gugauauggc                       39

<210> SEQ ID NO 6
<211> LENGTH: 52
<212> TYPE: DNA
<213> ORGANISM: Human
<220> FEATURE:
<223> OTHER INFORMATION: Primer F (Anti-sense) corresponding to
      2609-2571; nt 1-52
<220> FEATURE:
```

```
<221> NAME/KEY: misc_feature
<222> LOCATION: (50)
<223> OTHER INFORMATION: n at position 50 = any nucleotide(s) from the
      group g, a, c or t(u)

<400> SEQUENCE: 6
caucaucauc auagaucuag cacugggugc ccaguucsar rucyuusacn gg                52

<210> SEQ ID NO 7
<211> LENGTH: 37
<212> TYPE: DNA
<213> ORGANISM: Human
<220> FEATURE:
<223> OTHER INFORMATION: Primer G (Anti-sense) corresponding to 999-976;
      nt 1-37

<400> SEQUENCE: 7
caucaucauc aucacagaac accggucccu ggcuggc                                 37

<210> SEQ ID NO 8
<211> LENGTH: 42
<212> TYPE: DNA
<213> ORGANISM: Human
<220> FEATURE:
<223> OTHER INFORMATION: Primer H (Sense) corresponding to 791-820; nt
      1-42

<400> SEQUENCE: 8
cuacuacuac uaacuggucc agcaaacugg acuucauccu gu                           42

<210> SEQ ID NO 9
<211> LENGTH: 33
<212> TYPE: DNA
<213> ORGANISM: Human
<220> FEATURE:
<223> OTHER INFORMATION: Primer I (Anti-sense) corresponding to
      1054-1030; nt 1-33

<400> SEQUENCE: 9
caucaucauc augaugauca gcaucgcgau gcc                                     33

<210> SEQ ID NO 10
<211> LENGTH: 20
<212> TYPE: DNA
<213> ORGANISM: Human
<220> FEATURE:
<223> OTHER INFORMATION: Primer J (Anti-sense) corresponding to
      1054-1030; nt 1-20

<400> SEQUENCE: 10
cagagaugau cagcaucgcg                                                    20

<210> SEQ ID NO 11
<211> LENGTH: 20
<212> TYPE: DNA
<213> ORGANISM: Human
<220> FEATURE:
<223> OTHER INFORMATION: Primer K (Anti-sense) corresponding to 941-922;
      nt 1-20

<400> SEQUENCE: 11
gguaauccag ccagagccag                                                    20

<210> SEQ ID NO 12
<211> LENGTH: 41
<212> TYPE: DNA
<213> ORGANISM: Human
```

```
<220> FEATURE:
<223> OTHER INFORMATION: Primer L (Anti-sense) corresponding to 782-754;
      nt 1-41

<400> SEQUENCE: 12
caucaucauc augccttatc ctcatcccct tgctcgtcct c                    41

<210> SEQ ID NO 13
<211> LENGTH: 33
<212> TYPE: DNA
<213> ORGANISM: Human
<220> FEATURE:
<223> OTHER INFORMATION: Primer M (Sense) corresponding to 189-210; nt
      1-33

<400> SEQUENCE: 13
cuacuacuac uactgttgtc cgcatcagac atg                             33

<210> SEQ ID NO 14
<211> LENGTH: 37
<212> TYPE: DNA
<213> ORGANISM: Human
<220> FEATURE:
<223> OTHER INFORMATION: Primer N (Anti-sense) corresponding to 529-505;
      nt 1- 37

<400> SEQUENCE: 14
caucaucauc auaggcctgc gcgctttgcg cctctct                         37

<210> SEQ ID NO 15
<211> LENGTH: 30
<212> TYPE: DNA
<213> ORGANISM: Human
<220> FEATURE:
<223> OTHER INFORMATION: Primer O (Sense); nt 1-30

<400> SEQUENCE: 15
cuacuacuac uaatttaggt gacactatag                                 30

<210> SEQ ID NO 16
<211> LENGTH: 42
<212> TYPE: DNA
<213> ORGANISM: Human
<220> FEATURE:
<223> OTHER INFORMATION: Primer P (Anti-sense) corresponding to 804-763;
      nt 1-42

<400> SEQUENCE: 16
tttgctggac cagttccctc gggccttatc ctcatcccct tg                   42

<210> SEQ ID NO 17
<211> LENGTH: 54
<212> TYPE: DNA
<213> ORGANISM: Human
<220> FEATURE:
<223> OTHER INFORMATION: Primer Q (Anti-sense) corresponding to 785-726;
      nt 1-54

<400> SEQUENCE: 17
caucaucauc auccatggac aggatgaagt ccagtttgct ggaccagttc cctc      54

<210> SEQ ID NO 18
<211> LENGTH: 42
<212> TYPE: DNA
<213> ORGANISM: Human
<220> FEATURE:
<223> OTHER INFORMATION: Primer R (Anti-sense) corresponding to
```

-continued 1007-965; nt 1-42

<400> SEQUENCE: 18
gccttccaca cagacaccgg tccctggctg gcaaactggc cc         42

<210> SEQ ID NO 19
<211> LENGTH: 42
<212> TYPE: DNA
<213> ORGANISM: Human
<220> FEATURE:
<223> OTHER INFORMATION: Primer S (Sense) corresponding to 2155-2184;
      nt 1-42

<400> SEQUENCE: 19
cuacuacuac uagagctcgt ggggatctcc tatgtgtatg gc         42

<210> SEQ ID NO 20
<211> LENGTH: 32
<212> TYPE: DNA
<213> ORGANISM: Human
<220> FEATURE:
<223> OTHER INFORMATION: Primer T (Anti-sense); nt 1-32

<400> SEQUENCE: 20
caucaucauc autaatacga ctcactatag gg         32

<210> SEQ ID NO 21
<211> LENGTH: 38
<212> TYPE: DNA
<213> ORGANISM: Human
<220> FEATURE:
<223> OTHER INFORMATION: Primer U (Sense) corresponding to 1532-1504; nt
      1-38

<400> SEQUENCE: 21
cuacuacuac uagtactagt gatcctcctc atccgagg         38

<210> SEQ ID NO 22
<211> LENGTH: 313
<212> TYPE: DNA
<213> ORGANISM: Human
<220> FEATURE:
<221> NAME/KEY: CDS
<222> LOCATION: (3)..(311)
<223> OTHER INFORMATION: Seq 2(A)S1 - HSpC-1; nt 257-569; nt 266 is T
      not C (consensus); nt 304 is G not A (consensus)

<400> SEQUENCE: 22

```
gg gcg cag gtg gcc tct gca gct ctg cgg gac ttg aga gag gcg caa      47
   Ala Gln Val Ala Ser Ala Ala Leu Arg Asp Leu Arg Glu Ala Gln
   1               5                  10                  15 ggc gcg cag gcc tcg ccc cct ccc ggg agc tct ggg ccc ggc aac gcg      95
Gly Ala Gln Ala Ser Pro Pro Pro Gly Ser Ser Gly Pro Gly Asn Ala
              20                  25                  30 ttg cac tgt aag atc cct tct ctg cga ggc ccg gag ggg gat gcg aac     143
Leu His Cys Lys Ile Pro Ser Leu Arg Gly Pro Glu Gly Asp Ala Asn
          35                  40                  45 gtg agt gtg ggc aag ggc acc ctg gag cgg aac aat acc cct gtt gtg     191
Val Ser Val Gly Lys Gly Thr Leu Glu Arg Asn Asn Thr Pro Val Val
      50                  55                  60 ggc tgg gtg aac atg ggc cag agc acc gtg gtg ctg ggc acg gat gga     239
Gly Trp Val Asn Met Gly Gln Ser Thr Val Val Leu Gly Thr Asp Gly
 65                  70                  75 atc acg tcc gtg ctc ccg ggc agc gtg gcc acc gtt gcc acc cag gag     287
Ile Thr Ser Val Leu Pro Gly Ser Val Ala Thr Val Ala Thr Gln Glu
```

```
                80              85              90              95
gac gag caa ggg gat gag gat aag gc                                    313
Asp Glu Gln Gly Asp Glu Asp Lys
                100

<210> SEQ ID NO 23
<211> LENGTH: 103
<212> TYPE: PRT
<213> ORGANISM: Human

<400> SEQUENCE: 23

Ala Gln Val Ala Ser Ala Ala Leu Arg Asp Leu Arg Glu Ala Gln Gly
 1               5                  10                  15

Ala Gln Ala Ser Pro Pro Gly Ser Ser Gly Pro Gly Asn Ala Leu
            20                  25                  30

His Cys Lys Ile Pro Ser Leu Arg Gly Pro Glu Gly Asp Ala Asn Val
        35                  40                  45

Ser Val Gly Lys Gly Thr Leu Glu Arg Asn Asn Thr Pro Val Val Gly
    50                  55                  60

Trp Val Asn Met Gly Gln Ser Thr Val Val Leu Gly Thr Asp Gly Ile
65                  70                  75                  80

Thr Ser Val Leu Pro Gly Ser Val Ala Thr Val Ala Thr Gln Glu Asp
                85                  90                  95

Glu Gln Gly Asp Glu Asp Lys
            100

<210> SEQ ID NO 24
<211> LENGTH: 312
<212> TYPE: DNA
<213> ORGANISM: Human
<220> FEATURE:
<221> NAME/KEY: CDS
<222> LOCATION: (2)..(310)
<223> OTHER INFORMATION: Seq 14(A)S2 - HSpC-2; nt 258-569; nt 521 is A
      not T (consensus)

<400> SEQUENCE: 24 g gcg cag gcg gcc tct gca gct ctg cgg gac ttg aga gag gca caa agc      49
  Ala Gln Ala Ala Ser Ala Ala Leu Arg Asp Leu Arg Glu Ala Gln Ser
   1               5                  10                  15 gcg cag gcc tcg ccc cct ccc ggg agc tct ggg ccc ggc aac gcg ttg        97
Ala Gln Ala Ser Pro Pro Pro Gly Ser Ser Gly Pro Gly Asn Ala Leu
            20                  25                  30 cac tgt aag atc cct tct ctg cga ggc ccg gag ggg gat gcg aac gtg       145
His Cys Lys Ile Pro Ser Leu Arg Gly Pro Glu Gly Asp Ala Asn Val
        35                  40                  45 agt gtg ggc aag ggc acc ctg gag cgg aac aat acc cct gtt gtg ggc       193
Ser Val Gly Lys Gly Thr Leu Glu Arg Asn Asn Thr Pro Val Val Gly
    50                  55                  60 tgg gtg aac atg ggc cag agc acc gtg gtg ctg ggc acg gat gga atc       241
Trp Val Asn Met Gly Gln Ser Thr Val Val Leu Gly Thr Asp Gly Ile
65                  70                  75                  80 acg tcc gtg ctc ccg ggc agc gag gcc acc gtt gcc acc cag gag gac       289
Thr Ser Val Leu Pro Gly Ser Glu Ala Thr Val Ala Thr Gln Glu Asp
                85                  90                  95 gag caa ggg gat gag gat aag gc                                         312
Glu Gln Gly Asp Glu Asp Lys
            100

<210> SEQ ID NO 25
<211> LENGTH: 103
```

<212> TYPE: PRT
<213> ORGANISM: Human

<400> SEQUENCE: 25

Ala Gln Ala Ala Ser Ala Ala Leu Arg Asp Leu Arg Glu Ala Gln Ser
1               5                   10                  15

Ala Gln Ala Ser Pro Pro Pro Gly Ser Ser Gly Pro Gly Asn Ala Leu
            20                  25                  30

His Cys Lys Ile Pro Ser Leu Arg Gly Pro Glu Gly Asp Ala Asn Val
        35                  40                  45

Ser Val Gly Lys Gly Thr Leu Glu Arg Asn Asn Thr Pro Val Val Gly
    50                  55                  60

Trp Val Asn Met Gly Gln Ser Thr Val Val Leu Gly Thr Asp Gly Ile
65                  70                  75                  80

Thr Ser Val Leu Pro Gly Ser Glu Ala Thr Val Ala Thr Gln Glu Asp
                85                  90                  95

Glu Gln Gly Asp Glu Asp Lys
            100

<210> SEQ ID NO 26
<211> LENGTH: 312
<212> TYPE: DNA
<213> ORGANISM: Human
<220> FEATURE:
<221> NAME/KEY: CDS
<222> LOCATION: (2)..(310)
<223> OTHER INFORMATION: Seq 15(A)S3 - HSpC3; nt 258-569

<400> SEQUENCE: 26 g gcg cag gcg gcc tct gca gct ctg cgg gac ttg aga gag gcg caa agc      49
  Ala Gln Ala Ala Ser Ala Ala Leu Arg Asp Leu Arg Glu Ala Gln Ser
  1               5                   10                  15 gcg cag gcc tcg ccc cct ccc ggg agc tct ggg ccc ggc aac gcg ttg        97
Ala Gln Ala Ser Pro Pro Pro Gly Ser Ser Gly Pro Gly Asn Ala Leu
            20                  25                  30 cac tgt aag atc cct tct ctg cga ggc ccg gag ggg gat gcg aac gtg       145
His Cys Lys Ile Pro Ser Leu Arg Gly Pro Glu Gly Asp Ala Asn Val
        35                  40                  45 agt gtg ggc aag ggc acc ctg gag cgg aac aat acc cct gtt gtg ggc       193
Ser Val Gly Lys Gly Thr Leu Glu Arg Asn Asn Thr Pro Val Val Gly
    50                  55                  60 tgg gtg aac atg ggc cag agc acc gtg gtg ctg ggc acg gat gga atc       241
Trp Val Asn Met Gly Gln Ser Thr Val Val Leu Gly Thr Asp Gly Ile
65                  70                  75                  80 acg tcc gtg ctc ccg ggc agc gtg gcc acc gtt gcc acc cag gag gac       289
Thr Ser Val Leu Pro Gly Ser Val Ala Thr Val Ala Thr Gln Glu Asp
                85                  90                  95 gag caa ggg gat gag gat aag gc                                        312
Glu Gln Gly Asp Glu Asp Lys
            100

<210> SEQ ID NO 27
<211> LENGTH: 103
<212> TYPE: PRT
<213> ORGANISM: Human

<400> SEQUENCE: 27

Ala Gln Ala Ala Ser Ala Ala Leu Arg Asp Leu Arg Glu Ala Gln Ser
1               5                   10                  15

Ala Gln Ala Ser Pro Pro Pro Gly Ser Ser Gly Pro Gly Asn Ala Leu
            20                  25                  30

```
His Cys Lys Ile Pro Ser Leu Arg Gly Pro Glu Gly Asp Ala Asn Val
         35                  40                  45

Ser Val Gly Lys Gly Thr Leu Glu Arg Asn Asn Thr Pro Val Val Gly
 50                  55                  60

Trp Val Asn Met Gly Gln Ser Thr Val Val Leu Gly Thr Asp Gly Ile
 65                  70                  75                  80

Thr Ser Val Leu Pro Gly Ser Val Ala Thr Val Ala Thr Gln Glu Asp
                 85                  90                  95

Glu Gln Gly Asp Glu Asp Lys
            100

<210> SEQ ID NO 28
<211> LENGTH: 312
<212> TYPE: DNA
<213> ORGANISM: Human
<220> FEATURE:
<221> NAME/KEY: CDS
<222> LOCATION: (2)..(310)
<223> OTHER INFORMATION: Seq 16(A)S3 - HSpC-3; nt 258-569

<400> SEQUENCE: 28 g gcg cag gcg gcc tct gca gct ctg cgg gac ttg aga gag gcg caa agc      49
  Ala Gln Ala Ala Ser Ala Ala Leu Arg Asp Leu Arg Glu Ala Gln Ser
   1               5                  10                  15 gcg cag gcc tcg ccc cct ccc ggg agc tct ggg ccc ggc aac gcg ttg        97
Ala Gln Ala Ser Pro Pro Pro Gly Ser Ser Gly Pro Gly Asn Ala Leu
             20                  25                  30 cac tgt aag atc cct tct ctg cga ggc ccg gag ggg gat gcg aac gtg       145
His Cys Lys Ile Pro Ser Leu Arg Gly Pro Glu Gly Asp Ala Asn Val
         35                  40                  45 agt gtg ggc aag ggc acc ctg gag cgg aac aat acc cct gtt gtg ggc       193
Ser Val Gly Lys Gly Thr Leu Glu Arg Asn Asn Thr Pro Val Val Gly
 50                  55                  60 tgg gtg aac atg ggc cag agc acc gtg gtg ctg ggc acg gat gga atc       241
Trp Val Asn Met Gly Gln Ser Thr Val Val Leu Gly Thr Asp Gly Ile
 65                  70                  75                  80 acg tcc gtg ctc ccg ggc agc gtg gcc acc gtt gcc acc cag gag gac       289
Thr Ser Val Leu Pro Gly Ser Val Ala Thr Val Ala Thr Gln Glu Asp
                 85                  90                  95 gag caa ggg gat gag gat aag gc                                         312
Glu Gln Gly Asp Glu Asp Lys
            100

<210> SEQ ID NO 29
<211> LENGTH: 103
<212> TYPE: PRT
<213> ORGANISM: Human

<400> SEQUENCE: 29

Ala Gln Ala Ala Ser Ala Ala Leu Arg Asp Leu Arg Glu Ala Gln Ser
 1               5                  10                  15

Ala Gln Ala Ser Pro Pro Pro Gly Ser Ser Gly Pro Gly Asn Ala Leu
             20                  25                  30

His Cys Lys Ile Pro Ser Leu Arg Gly Pro Glu Gly Asp Ala Asn Val
         35                  40                  45

Ser Val Gly Lys Gly Thr Leu Glu Arg Asn Asn Thr Pro Val Val Gly
 50                  55                  60

Trp Val Asn Met Gly Gln Ser Thr Val Val Leu Gly Thr Asp Gly Ile
 65                  70                  75                  80
```

```
Thr Ser Val Leu Pro Gly Ser Val Ala Thr Val Ala Thr Gln Glu Asp
            85                  90                  95

Glu Gln Gly Asp Glu Asp Lys
            100
```

<210> SEQ ID NO 30
<211> LENGTH: 312
<212> TYPE: DNA
<213> ORGANISM: Human
<220> FEATURE:
<221> NAME/KEY: CDS
<222> LOCATION: (2)..(310)
<223> OTHER INFORMATION: Seq 17(A)S3 - HSpC-3; nt 258-569

<400> SEQUENCE: 30

```
g gcg cag gcg gcc tct gca gct ctg cgg gac ttg aga gag gcg caa agc      49
  Ala Gln Ala Ala Ser Ala Ala Leu Arg Asp Leu Arg Glu Ala Gln Ser
   1               5                  10                  15 gcg cag gcc tcg ccc cct ccc ggg agc tct ggg ccc ggc aac gcg ttg        97
Ala Gln Ala Ser Pro Pro Pro Gly Ser Ser Gly Pro Gly Asn Ala Leu
             20                  25                  30 cac tgt aag atc cct tct ctg cga ggc ccg gag ggg gat gcg aac gtg       145
His Cys Lys Ile Pro Ser Leu Arg Gly Pro Glu Gly Asp Ala Asn Val
         35                  40                  45 agt gtg ggc aag ggc acc ctg gag cgg aac aat acc cct gtt gtg ggc       193
Ser Val Gly Lys Gly Thr Leu Glu Arg Asn Asn Thr Pro Val Val Gly
     50                  55                  60 tgg gtg aac atg ggc cag agc acc gtg gtg ctg ggc acg gat gga atc       241
Trp Val Asn Met Gly Gln Ser Thr Val Val Leu Gly Thr Asp Gly Ile
 65                  70                  75                  80 acg tcc gtg ctc ccg ggc agc gtg gcc acc gtt gcc acc cag gag gac       289
Thr Ser Val Leu Pro Gly Ser Val Ala Thr Val Ala Thr Gln Glu Asp
                 85                  90                  95 gag caa ggg gat gag gat aag gc                                        312
Glu Gln Gly Asp Glu Asp Lys
            100
```

<210> SEQ ID NO 31
<211> LENGTH: 103
<212> TYPE: PRT
<213> ORGANISM: Human

<400> SEQUENCE: 31

```
Ala Gln Ala Ala Ser Ala Ala Leu Arg Asp Leu Arg Glu Ala Gln Ser
 1               5                  10                  15

Ala Gln Ala Ser Pro Pro Pro Gly Ser Ser Gly Pro Gly Asn Ala Leu
             20                  25                  30

His Cys Lys Ile Pro Ser Leu Arg Gly Pro Glu Gly Asp Ala Asn Val
         35                  40                  45

Ser Val Gly Lys Gly Thr Leu Glu Arg Asn Asn Thr Pro Val Val Gly
     50                  55                  60

Trp Val Asn Met Gly Gln Ser Thr Val Val Leu Gly Thr Asp Gly Ile
 65                  70                  75                  80

Thr Ser Val Leu Pro Gly Ser Val Ala Thr Val Ala Thr Gln Glu Asp
                 85                  90                  95

Glu Gln Gly Asp Glu Asp Lys
            100
```

<210> SEQ ID NO 32
<211> LENGTH: 312
<212> TYPE: DNA

```
<213> ORGANISM: Human
<220> FEATURE:
<221> NAME/KEY: CDS
<222> LOCATION: (2)..(310)
<223> OTHER INFORMATION: Seq 18(A)U - U373MG; nt 258-569

<400> SEQUENCE: 32 g gcg cag gcg gcc tct gca gct ctg cgg gac ttg aga gag gcg caa agc    49
  Ala Gln Ala Ala Ser Ala Ala Leu Arg Asp Leu Arg Glu Ala Gln Ser
   1               5                  10                  15 gcg cag gcc tcg ccc cct ccc ggg agc tct ggg ccc ggc aac gcg ttg       97
Ala Gln Ala Ser Pro Pro Pro Gly Ser Ser Gly Pro Gly Asn Ala Leu
             20                  25                  30 cac tgt aag atc cct tct ctg cga ggc ccg gag ggg gat gcg aac gtg      145
His Cys Lys Ile Pro Ser Leu Arg Gly Pro Glu Gly Asp Ala Asn Val
         35                  40                  45 agt gtg ggc aag ggc acc ctg gag cgg aac aat acc cct gtt gtg ggc      193
Ser Val Gly Lys Gly Thr Leu Glu Arg Asn Asn Thr Pro Val Val Gly
     50                  55                  60 tgg gtg aac atg ggc cag agc acc gtg gtg ctg ggc acg gat gga atc      241
Trp Val Asn Met Gly Gln Ser Thr Val Val Leu Gly Thr Asp Gly Ile
 65                  70                  75                  80 acg tcc gtg ctc ccg ggc agc gtg gcc acc gtt gcc acc cag gag gac      289
Thr Ser Val Leu Pro Gly Ser Val Ala Thr Val Ala Thr Gln Glu Asp
                 85                  90                  95 gag caa ggg gat gag gat aag gc                                        312
Glu Gln Gly Asp Glu Asp Lys
            100

<210> SEQ ID NO 33
<211> LENGTH: 103
<212> TYPE: PRT
<213> ORGANISM: Human

<400> SEQUENCE: 33

Ala Gln Ala Ala Ser Ala Ala Leu Arg Asp Leu Arg Glu Ala Gln Ser
 1               5                  10                  15

Ala Gln Ala Ser Pro Pro Pro Gly Ser Ser Gly Pro Gly Asn Ala Leu
             20                  25                  30

His Cys Lys Ile Pro Ser Leu Arg Gly Pro Glu Gly Asp Ala Asn Val
         35                  40                  45

Ser Val Gly Lys Gly Thr Leu Glu Arg Asn Asn Thr Pro Val Val Gly
     50                  55                  60

Trp Val Asn Met Gly Gln Ser Thr Val Val Leu Gly Thr Asp Gly Ile
 65                  70                  75                  80

Thr Ser Val Leu Pro Gly Ser Val Ala Thr Val Ala Thr Gln Glu Asp
                 85                  90                  95

Glu Gln Gly Asp Glu Asp Lys
            100

<210> SEQ ID NO 34
<211> LENGTH: 312
<212> TYPE: DNA
<213> ORGANISM: human
<220> FEATURE:
<221> NAME/KEY: CDS
<222> LOCATION: (2)..(310)
<223> OTHER INFORMATION: Seq 19(A)U - U373MG; nt 258-569

<400> SEQUENCE: 34 g gcg cag gcg gcc tct gca gct ctg cgg gac ttg aga gag gcg caa agc    49
  Ala Gln Ala Ala Ser Ala Ala Leu Arg Asp Leu Arg Glu Ala Gln Ser
   1               5                  10                  15
```

```
                1               5              10              15
gcg cag gcc tcg ccc cct ccc ggg agc tct ggg ccc ggc aac gcg ttg      97
Ala Gln Ala Ser Pro Pro Pro Gly Ser Ser Gly Pro Gly Asn Ala Leu
                            20              25              30 cac tgt aag atc cct tct ctg cga ggc ccg gag ggg gat gcg aac gtg     145
His Cys Lys Ile Pro Ser Leu Arg Gly Pro Glu Gly Asp Ala Asn Val
            35              40              45 agt gtg ggc aag ggc acc ctg gag cgg aac aat acc cct gtt gtg ggc     193
Ser Val Gly Lys Gly Thr Leu Glu Arg Asn Asn Thr Pro Val Val Gly
    50              55              60 tgg gtg aac atg ggc cag agc acc gtg gtg ctg ggc acg gat gga atc     241
Trp Val Asn Met Gly Gln Ser Thr Val Val Leu Gly Thr Asp Gly Ile
65              70              75              80 acg tcc gtg ctc ccg ggc agc gtg gcc acc gtt gcc acc cag gag gac     289
Thr Ser Val Leu Pro Gly Ser Val Ala Thr Val Ala Thr Gln Glu Asp
                85              90              95 gag caa ggg gat gag gat aag gc                                       312
Glu Gln Gly Asp Glu Asp Lys
                100
```

<210> SEQ ID NO 35
<211> LENGTH: 103
<212> TYPE: PRT
<213> ORGANISM: human

<400> SEQUENCE: 35

```
Ala Gln Ala Ala Ser Ala Ala Leu Arg Asp Leu Arg Glu Ala Gln Ser
  1               5                  10                  15

Ala Gln Ala Ser Pro Pro Pro Gly Ser Ser Gly Pro Gly Asn Ala Leu
                 20                  25                  30

His Cys Lys Ile Pro Ser Leu Arg Gly Pro Glu Gly Asp Ala Asn Val
             35                  40                  45

Ser Val Gly Lys Gly Thr Leu Glu Arg Asn Asn Thr Pro Val Val Gly
         50                  55                  60

Trp Val Asn Met Gly Gln Ser Thr Val Val Leu Gly Thr Asp Gly Ile
 65                  70                  75                  80

Thr Ser Val Leu Pro Gly Ser Val Ala Thr Val Ala Thr Gln Glu Asp
                 85                  90                  95

Glu Gln Gly Asp Glu Asp Lys
                100
```

<210> SEQ ID NO 36
<211> LENGTH: 312
<212> TYPE: DNA
<213> ORGANISM: Human
<220> FEATURE:
<221> NAME/KEY: CDS
<222> LOCATION: (2)..(310)
<223> OTHER INFORMATION: Seq 20(A)U - U373MG; nt 258-569

<400> SEQUENCE: 36

```
g gcg cag gcg gcc tct gca gct ctg cgg gac ttg aga gag gcg caa agc    49
  Ala Gln Ala Ala Ser Ala Ala Leu Arg Asp Leu Arg Glu Ala Gln Ser
   1               5                  10                  15 gcg cag gcc tcg ccc cct ccc ggg agc tct ggg ccc ggc aac gcg ttg      97
Ala Gln Ala Ser Pro Pro Pro Gly Ser Ser Gly Pro Gly Asn Ala Leu
                 20                  25                  30 cac tgt aag atc cct tct ctg cga ggc ccg gag ggg gat gcg aac gtg     145
His Cys Lys Ile Pro Ser Leu Arg Gly Pro Glu Gly Asp Ala Asn Val
             35                  40                  45
```

```
agt gtg ggc aag ggc acc ctg gag cgg aac aat acc cct gtt gtg ggc      193
Ser Val Gly Lys Gly Thr Leu Glu Arg Asn Asn Thr Pro Val Val Gly
 50                  55                  60 tgg gtg aac atg ggc cag agc acc gtg gtg ctg ggc acg gat gga atc      241
Trp Val Asn Met Gly Gln Ser Thr Val Val Leu Gly Thr Asp Gly Ile
 65                  70                  75                  80 acg tcc gtg ctc ccg ggc agc gtg gcc acc gtt gcc acc cag gag gac      289
Thr Ser Val Leu Pro Gly Ser Val Ala Thr Val Ala Thr Gln Glu Asp
                 85                  90                  95 gag caa ggg gat gag gat aag gc                                       312
Glu Gln Gly Asp Glu Asp Lys
            100

<210> SEQ ID NO 37
<211> LENGTH: 103
<212> TYPE: PRT
<213> ORGANISM: Human

<400> SEQUENCE: 37

Ala Gln Ala Ala Ser Ala Ala Leu Arg Asp Leu Arg Glu Ala Gln Ser
 1               5                  10                  15

Ala Gln Ala Ser Pro Pro Gly Ser Ser Gly Pro Gly Asn Ala Leu
                 20                  25                  30

His Cys Lys Ile Pro Ser Leu Arg Gly Pro Gly Gly Asp Ala Asn Val
             35                  40                  45

Ser Val Gly Lys Gly Thr Leu Glu Arg Asn Asn Thr Pro Val Val Gly
 50                  55                  60

Trp Val Asn Met Gly Gln Ser Thr Val Val Leu Gly Thr Asp Gly Ile
 65                  70                  75                  80

Thr Ser Val Leu Pro Gly Ser Val Ala Thr Val Ala Thr Gln Glu Asp
                 85                  90                  95

Glu Gln Gly Asp Glu Asp Lys
            100

<210> SEQ ID NO 38
<211> LENGTH: 264
<212> TYPE: DNA
<213> ORGANISM: Human
<220> FEATURE:
<221> NAME/KEY: CDS
<222> LOCATION: (2)..(262)
<223> OTHER INFORMATION: Seq 3(B)S1 - HSpC-1; nt 578-841; nt 678 is G
      not A (consensus)

<400> SEQUENCE: 38 a ctg gtc cag caa act gga ctt cat cct gtc cat ggt ggg gta cgc agt    49
  Leu Val Gln Gln Thr Gly Leu His Pro Val His Gly Gly Val Arg Ser
   1               5                  10                  15 ggg gct ggg caa tgt ctg gag gtt tcc cta cct ggc ctt cca gaa cgg      97
Gly Ala Gly Gln Cys Leu Glu Val Ser Leu Pro Gly Leu Pro Glu Arg
             20                  25                  30 ggg ggt tgc ttt cct cat ccc tta cct gat gat gct ggc tct ggc tgg     145
Gly Gly Cys Phe Pro His Pro Leu Pro Asp Asp Ala Gly Ser Gly Trp
         35                      40                  45 att acc cat ctt ctt ctt gga ggt gtc gct ggg cca gtt tgc cag cca     193
Ile Thr His Leu Leu Leu Gly Gly Val Ala Gly Pro Val Cys Gln Pro
 50                  55                  60 ggg acc ggt gtc tgt gtg gaa ggc cat ccc agc tct aca agg ctg tgg     241
Gly Thr Gly Val Cys Val Glu Gly His Pro Ser Ser Thr Arg Leu Trp
 65                  70                  75                  80 cat cgc gat gct gat cat ctc tg                                      264
```

His Arg Asp Ala Asp His Leu
            85

<210> SEQ ID NO 39
<211> LENGTH: 87
<212> TYPE: PRT
<213> ORGANISM: Human

<400> SEQUENCE: 39

Leu Val Gln Gln Thr Gly Leu His Pro Val His Gly Gly Val Arg Ser
 1               5                  10                  15

Gly Ala Gly Gln Cys Leu Glu Val Ser Leu Pro Gly Leu Pro Glu Arg
            20                  25                  30

Gly Gly Cys Phe Pro His Pro Leu Pro Asp Asp Ala Gly Ser Gly Trp
        35                  40                  45

Ile Thr His Leu Leu Gly Gly Val Ala Gly Pro Val Cys Gln Pro
    50                  55                  60

Gly Thr Gly Val Cys Val Glu Gly His Pro Ser Ser Thr Arg Leu Trp
65                  70                  75                  80

His Arg Asp Ala Asp His Leu
            85

<210> SEQ ID NO 40
<211> LENGTH: 264
<212> TYPE: DNA
<213> ORGANISM: Human
<220> FEATURE:
<221> NAME/KEY: CDS
<222> LOCATION: (3)..(263)
<223> OTHER INFORMATION: Seq 21(B)S2 - HSpC-2; nt 578-841; nt 583 is C
      not T (consensus); nt 765 is T not C (consensus)

<400> SEQUENCE: 40 ac tgg ccc agc aaa ctg gac ttc atc ctg tcc atg gtg ggg tac gca        47
   Trp Pro Ser Lys Leu Asp Phe Ile Leu Ser Met Val Gly Tyr Ala
    1               5                  10                  15 gtg ggg ctg ggc aat gtc tgg agg ttt ccc tac ctg gcc ttc cag aac       95
Val Gly Leu Gly Asn Val Trp Arg Phe Pro Tyr Leu Ala Phe Gln Asn
            20                  25                  30 ggg gga ggt gct ttc ctc atc cct tac ctg atg atg ctg gct ctg gct      143
Gly Gly Gly Ala Phe Leu Ile Pro Tyr Leu Met Met Leu Ala Leu Ala
        35                  40                  45 gga tta ccc atc ttc ttc ttg gag gtg tcg ctg ggc cag ttt gct agc      191
Gly Leu Pro Ile Phe Phe Leu Glu Val Ser Leu Gly Gln Phe Ala Ser
    50                  55                  60 cag gga ccg gtg tct gtg tgg aag gcc atc cca gct cta caa ggc tgt      239
Gln Gly Pro Val Ser Val Trp Lys Ala Ile Pro Ala Leu Gln Gly Cys
65                  70                  75 ggc atc gcg atg ctg atc atc tct g                                    264
Gly Ile Ala Met Leu Ile Ile Ser
80                  85

<210> SEQ ID NO 41
<211> LENGTH: 87
<212> TYPE: PRT
<213> ORGANISM: Human

<400> SEQUENCE: 41

Trp Pro Ser Lys Leu Asp Phe Ile Leu Ser Met Val Gly Tyr Ala Val
 1               5                  10                  15

Gly Leu Gly Asn Val Trp Arg Phe Pro Tyr Leu Ala Phe Gln Asn Gly

```
                         20                  25                  30

Gly Gly Ala Phe Leu Ile Pro Tyr Leu Met Met Leu Ala Leu Ala Gly
            35                  40                  45

Leu Pro Ile Phe Phe Leu Glu Val Ser Leu Gly Gln Phe Ala Ser Gln
        50                  55                  60

Gly Pro Val Ser Val Trp Lys Ala Ile Pro Ala Leu Gln Gly Cys Gly
65                  70                  75                  80

Ile Ala Met Leu Ile Ile Ser
                85

<210> SEQ ID NO 42
<211> LENGTH: 264
<212> TYPE: DNA
<213> ORGANISM: Human
<220> FEATURE:
<221> NAME/KEY: CDS
<222> LOCATION: (3)..(263)
<223> OTHER INFORMATION: Seq 22(B)S3 - HSpC-3; nt 578-841; nt 596 is G
      not A (consensus)

<400> SEQUENCE: 42 ac tgg tcc agc aaa ctg ggc ttc atc ctg tcc atg gtg ggg tac gca         47
   Trp Ser Ser Lys Leu Gly Phe Ile Leu Ser Met Val Gly Tyr Ala
    1               5                   10                  15 gtg ggg ctg ggc aat gtc tgg agg ttt ccc tac ctg gcc ttc cag aac        95
Val Gly Leu Gly Asn Val Trp Arg Phe Pro Tyr Leu Ala Phe Gln Asn
             20                  25                  30 ggg gga ggt gct ttc ctc atc cct tac ctg atg atg ctg gct ctg gct       143
Gly Gly Gly Ala Phe Leu Ile Pro Tyr Leu Met Met Leu Ala Leu Ala
         35                  40                  45 gga tta ccc atc ttc ttc ttg gag gtg tcg ctg ggc cag ttt gcc agc       191
Gly Leu Pro Ile Phe Phe Leu Glu Val Ser Leu Gly Gln Phe Ala Ser
     50                  55                  60 cag gga ccg gtg tct gtg tgg aag gcc atc cca gct cta caa ggc tgt       239
Gln Gly Pro Val Ser Val Trp Lys Ala Ile Pro Ala Leu Gln Gly Cys
 65                  70                  75 ggc atc gcg atg ctg atc atc tct g                                     264
Gly Ile Ala Met Leu Ile Ile Ser
 80                  85

<210> SEQ ID NO 43
<211> LENGTH: 87
<212> TYPE: PRT
<213> ORGANISM: Human

<400> SEQUENCE: 43

Trp Ser Ser Lys Leu Gly Phe Ile Leu Ser Met Val Gly Tyr Ala Val
  1               5                  10                  15

Gly Leu Gly Asn Val Trp Arg Phe Pro Tyr Leu Ala Phe Gln Asn Gly
             20                  25                  30

Gly Gly Ala Phe Leu Ile Pro Tyr Leu Met Met Leu Ala Leu Ala Gly
         35                  40                  45

Leu Pro Ile Phe Phe Leu Glu Val Ser Leu Gly Gln Phe Ala Ser Gln
     50                  55                  60

Gly Pro Val Ser Val Trp Lys Ala Ile Pro Ala Leu Gln Gly Cys Gly
 65                  70                  75                  80

Ile Ala Met Leu Ile Ile Ser
                85

<210> SEQ ID NO 44
```

```
<211> LENGTH: 264
<212> TYPE: DNA
<213> ORGANISM: Human
<220> FEATURE:
<221> NAME/KEY: CDS
<222> LOCATION: (3)..(263)
<223> OTHER INFORMATION: Seq 23(B)S3 - HSpC-3; nt 578-841

<400> SEQUENCE: 44 ac tgg tcc agc aaa ctg gac ttc atc ctg tcc atg gtg ggg tac gca      47
   Trp Ser Ser Lys Leu Asp Phe Ile Leu Ser Met Val Gly Tyr Ala
   1               5                  10                  15 gtg ggg ctg ggc aat gtc tgg agg ttt ccc tac ctg gcc ttc cag aac     95
Val Gly Leu Gly Asn Val Trp Arg Phe Pro Tyr Leu Ala Phe Gln Asn
             20                  25                  30 ggg gga ggt gct ttc ctc atc cct tac ctg atg atg ctg gct ctg gct    143
Gly Gly Gly Ala Phe Leu Ile Pro Tyr Leu Met Met Leu Ala Leu Ala
         35                  40                  45 gga tta ccc atc ttc ttc ttg gag gtg tcg ctg ggc cag ttt gcc agc    191
Gly Leu Pro Ile Phe Phe Leu Glu Val Ser Leu Gly Gln Phe Ala Ser
     50                  55                  60 cag gga ccg gtg tct gtg tgg aag gcc atc cca gct cta caa ggc tgt    239
Gln Gly Pro Val Ser Val Trp Lys Ala Ile Pro Ala Leu Gln Gly Cys
 65                  70                  75 ggc atc gcg atg ctg atc atc tct g                                  264
Gly Ile Ala Met Leu Ile Ile Ser
 80                  85

<210> SEQ ID NO 45
<211> LENGTH: 87
<212> TYPE: PRT
<213> ORGANISM: Human

<400> SEQUENCE: 45

Trp Ser Ser Lys Leu Asp Phe Ile Leu Ser Met Val Gly Tyr Ala Val
1               5                  10                  15

Gly Leu Gly Asn Val Trp Arg Phe Pro Tyr Leu Ala Phe Gln Asn Gly
            20                  25                  30

Gly Gly Ala Phe Leu Ile Pro Tyr Leu Met Met Leu Ala Leu Ala Gly
        35                  40                  45

Leu Pro Ile Phe Phe Leu Glu Val Ser Leu Gly Gln Phe Ala Ser Gln
    50                  55                  60

Gly Pro Val Ser Val Trp Lys Ala Ile Pro Ala Leu Gln Gly Cys Gly
65                  70                  75                  80

Ile Ala Met Leu Ile Ile Ser
                85

<210> SEQ ID NO 46
<211> LENGTH: 264
<212> TYPE: DNA
<213> ORGANISM: Human
<220> FEATURE:
<221> NAME/KEY: CDS
<222> LOCATION: (3)..(263)
<223> OTHER INFORMATION: Seq 24(B)S3 - HSpC-3; nt 578-841

<400> SEQUENCE: 46 ac tgg tcc agc aaa ctg gac ttc atc ctg tcc atg gtg ggg tac gca      47
   Trp Ser Ser Lys Leu Asp Phe Ile Leu Ser Met Val Gly Tyr Ala
   1               5                  10                  15 gtg ggg ctg ggc aat gtc tgg agg ttt ccc tac ctg gcc ttc cag aac     95
Val Gly Leu Gly Asn Val Trp Arg Phe Pro Tyr Leu Ala Phe Gln Asn
             20                  25                  30
```

```
ggg gga ggt gct ttc ctc atc cct tac ctg atg atg ctg gct ctg gct         143
Gly Gly Gly Ala Phe Leu Ile Pro Tyr Leu Met Met Leu Ala Leu Ala
             35                  40                  45 gga tta ccc atc ttc ttc ttg gag gtg tcg ctg ggc cag ttt gcc agc         191
Gly Leu Pro Ile Phe Phe Leu Glu Val Ser Leu Gly Gln Phe Ala Ser
     50                  55                  60 cag gga ccg gtg tct gtg tgg aag gcc atc cca gct cta caa ggc tgt         239
Gln Gly Pro Val Ser Val Trp Lys Ala Ile Pro Ala Leu Gln Gly Cys
 65                  70                  75 ggc atc gcg atg ctg atc atc tct g                                       264
Gly Ile Ala Met Leu Ile Ile Ser
 80                  85
```

<210> SEQ ID NO 47
<211> LENGTH: 87
<212> TYPE: PRT
<213> ORGANISM: Human

<400> SEQUENCE: 47

```
Trp Ser Ser Lys Leu Asp Phe Ile Leu Ser Met Val Gly Tyr Ala Val
 1               5                  10                  15

Gly Leu Gly Asn Val Trp Arg Phe Pro Tyr Leu Ala Phe Gln Asn Gly
             20                  25                  30

Gly Gly Ala Phe Leu Ile Pro Tyr Leu Met Met Leu Ala Leu Ala Gly
         35                  40                  45

Leu Pro Ile Phe Phe Leu Glu Val Ser Leu Gly Gln Phe Ala Ser Gln
     50                  55                  60

Gly Pro Val Ser Val Trp Lys Ala Ile Pro Ala Leu Gln Gly Cys Gly
 65                  70                  75                  80

Ile Ala Met Leu Ile Ile Ser
             85
```

<210> SEQ ID NO 48
<211> LENGTH: 264
<212> TYPE: DNA
<213> ORGANISM: Human
<220> FEATURE:
<221> NAME/KEY: CDS
<222> LOCATION: (3)..(263)
<223> OTHER INFORMATION: Seq 25(B)U - U373MG; nt 578-841

<400> SEQUENCE: 48

```
ac tgg tcc agc aaa ctg gac ttc atc ctg tcc atg gtg ggg tac gca           47
   Trp Ser Ser Lys Leu Asp Phe Ile Leu Ser Met Val Gly Tyr Ala
    1               5                  10                  15 gtg ggg ctg ggc aat gtc tgg agg ttt ccc tac ctg gcc ttc cag aac          95
Val Gly Leu Gly Asn Val Trp Arg Phe Pro Tyr Leu Ala Phe Gln Asn
             20                  25                  30 ggg gga ggt gct ttc ctc atc cct tac ctg atg atg ctg gct ctg gct         143
Gly Gly Gly Ala Phe Leu Ile Pro Tyr Leu Met Met Leu Ala Leu Ala
             35                  40                  45 gga tta ccc atc ttc ttc ttg gag gtg tcg ctg ggc cag ttt gcc agc         191
Gly Leu Pro Ile Phe Phe Leu Glu Val Ser Leu Gly Gln Phe Ala Ser
     50                  55                  60 cag gga ccg gtg tct gtg tgg aag gcc atc cca gct cta caa ggc tgt         239
Gln Gly Pro Val Ser Val Trp Lys Ala Ile Pro Ala Leu Gln Gly Cys
 65                  70                  75 ggc atc gcg atg ctg atc atc tct g                                       264
Gly Ile Ala Met Leu Ile Ile Ser
 80                  85
```

-continued

<210> SEQ ID NO 49
<211> LENGTH: 87
<212> TYPE: PRT
<213> ORGANISM: Human

<400> SEQUENCE: 49

```
Trp Ser Ser Lys Leu Asp Phe Ile Leu Ser Met Val Gly Tyr Ala Val
  1               5                  10                  15

Gly Leu Gly Asn Val Trp Arg Phe Pro Tyr Leu Ala Phe Gln Asn Gly
             20                  25                  30

Gly Gly Ala Phe Leu Ile Pro Tyr Leu Met Met Leu Ala Leu Ala Gly
         35                  40                  45

Leu Pro Ile Phe Phe Leu Glu Val Ser Leu Gly Gln Phe Ala Ser Gln
     50                  55                  60

Gly Pro Val Ser Val Trp Lys Ala Ile Pro Ala Leu Gln Gly Cys Gly
 65                  70                  75                  80

Ile Ala Met Leu Ile Ile Ser
                 85
```

<210> SEQ ID NO 50
<211> LENGTH: 264
<212> TYPE: DNA
<213> ORGANISM: Human
<220> FEATURE:
<221> NAME/KEY: CDS
<222> LOCATION: (3)..(263)
<223> OTHER INFORMATION: Seq 26(B)U - U373MG; nt 578-841

<400> SEQUENCE: 50

```
ac tgg tcc agc aaa ctg gac ttc atc ctg tcc atg gtg ggg tac gca         47
   Trp Ser Ser Lys Leu Asp Phe Ile Leu Ser Met Val Gly Tyr Ala
     1               5                  10                  15 gtg ggg ctg ggc aat gtc tgg agg ttt ccc tac ctg gcc ttc cag aac        95
Val Gly Leu Gly Asn Val Trp Arg Phe Pro Tyr Leu Ala Phe Gln Asn
                 20                  25                  30 ggg gga ggt gct ttc ctc atc cct tac ctg atg atg ctg gct ctg gct       143
Gly Gly Gly Ala Phe Leu Ile Pro Tyr Leu Met Met Leu Ala Leu Ala
             35                  40                  45 gga tta ccc atc ttc ttc ttg gag gtg tcg ctg ggc cag ttt gcc agc       191
Gly Leu Pro Ile Phe Phe Leu Glu Val Ser Leu Gly Gln Phe Ala Ser
         50                  55                  60 cag gga ccg gtg tct gtg tgg aag gcc atc cca gct cta caa ggc tgt       239
Gln Gly Pro Val Ser Val Trp Lys Ala Ile Pro Ala Leu Gln Gly Cys
     65                  70                  75 ggc atc gcg atg ctg atc atc tct g                                     264
Gly Ile Ala Met Leu Ile Ile Ser
 80                  85
```

<210> SEQ ID NO 51
<211> LENGTH: 87
<212> TYPE: PRT
<213> ORGANISM: Human

<400> SEQUENCE: 51

```
Trp Ser Ser Lys Leu Asp Phe Ile Leu Ser Met Val Gly Tyr Ala Val
  1               5                  10                  15

Gly Leu Gly Asn Val Trp Arg Phe Pro Tyr Leu Ala Phe Gln Asn Gly
             20                  25                  30

Gly Gly Ala Phe Leu Ile Pro Tyr Leu Met Met Leu Ala Leu Ala Gly
         35                  40                  45
```

```
Leu Pro Ile Phe Phe Leu Glu Val Ser Leu Gly Gln Phe Ala Ser Gln
         50                  55                  60

Gly Pro Val Ser Val Trp Lys Ala Ile Pro Ala Leu Gln Gly Cys Gly
 65                  70                  75                  80

Ile Ala Met Leu Ile Ile Ser
                 85

<210> SEQ ID NO 52
<211> LENGTH: 264
<212> TYPE: DNA
<213> ORGANISM: Human
<220> FEATURE:
<221> NAME/KEY: CDS
<222> LOCATION: (3)..(263)
<223> OTHER INFORMATION: Seq 27(B)U - U373MG; nt 578-841

<400> SEQUENCE: 52 ac tgg tcc agc aaa ctg gac ttc atc ctg tcc atg gtg ggg tac gca       47
   Trp Ser Ser Lys Leu Asp Phe Ile Leu Ser Met Val Gly Tyr Ala
    1               5                  10                  15 gtg ggg ctg ggc aat gtc tgg agg ttt ccc tac ctg gcc ttc cag aac      95
Val Gly Leu Gly Asn Val Trp Arg Phe Pro Tyr Leu Ala Phe Gln Asn
             20                  25                  30 ggg gga ggt gct ttc ctc atc cct tac ctg atg atg ctg gct ctg gct     143
Gly Gly Gly Ala Phe Leu Ile Pro Tyr Leu Met Met Leu Ala Leu Ala
         35                  40                  45 gga tta ccc atc ttc ttc ttg gag gtg tcg ctg ggc cag ttt gcc agc     191
Gly Leu Pro Ile Phe Phe Leu Glu Val Ser Leu Gly Gln Phe Ala Ser
     50                  55                  60 cag gga ccg gtg tct gtg tgg aag gcc atc cca gct cta caa ggc tgt     239
Gln Gly Pro Val Ser Val Trp Lys Ala Ile Pro Ala Leu Gln Gly Cys
 65                  70                  75 ggc atc gcg atg ctg atc atc tct g                                   264
Gly Ile Ala Met Leu Ile Ile Ser
 80                  85

<210> SEQ ID NO 53
<211> LENGTH: 87
<212> TYPE: PRT
<213> ORGANISM: Human

<400> SEQUENCE: 53

Trp Ser Ser Lys Leu Asp Phe Ile Leu Ser Met Val Gly Tyr Ala Val
 1               5                  10                  15

Gly Leu Gly Asn Val Trp Arg Phe Pro Tyr Leu Ala Phe Gln Asn Gly
             20                  25                  30

Gly Gly Ala Phe Leu Ile Pro Tyr Leu Met Met Leu Ala Leu Ala Gly
         35                  40                  45

Leu Pro Ile Phe Phe Leu Glu Val Ser Leu Gly Gln Phe Ala Ser Gln
     50                  55                  60

Gly Pro Val Ser Val Trp Lys Ala Ile Pro Ala Leu Gln Gly Cys Gly
 65                  70                  75                  80

Ile Ala Met Leu Ile Ile Ser
                 85

<210> SEQ ID NO 54
<211> LENGTH: 615
<212> TYPE: DNA
<213> ORGANISM: Human
<220> FEATURE:
<221> NAME/KEY: CDS
<222> LOCATION: (1)..(615)
```

<223> OTHER INFORMATION: Seq 4(C)S1 - HSpC-1; nt 679-1293

<400> SEQUENCE: 54

| | | | | | | | | | | | | | | | | |
|---|---|---|---|---|---|---|---|---|---|---|---|---|---|---|---|---|
| ggt | gct | ttc | ctc | atc | cct | tac | ctg | atg | atg | ctg | gct | ctg | gct | gga | tta | 48 |
| Gly | Ala | Phe | Leu | Ile | Pro | Tyr | Leu | Met | Met | Leu | Ala | Leu | Ala | Gly | Leu | |
| 1 | | | | 5 | | | | | 10 | | | | | 15 | | |
| ccc | atc | ttc | ttc | ttg | gag | gtg | tcg | ctg | ggc | cag | ttt | gcc | agc | cag | gga | 96 |
| Pro | Ile | Phe | Phe | Leu | Glu | Val | Ser | Leu | Gly | Gln | Phe | Ala | Ser | Gln | Gly | |
| | | | 20 | | | | | 25 | | | | | 30 | | | |
| ccg | gtg | tct | gtg | tgg | aag | gcc | atc | cca | gct | cta | caa | ggc | tgt | ggc | atc | 144 |
| Pro | Val | Ser | Val | Trp | Lys | Ala | Ile | Pro | Ala | Leu | Gln | Gly | Cys | Gly | Ile | |
| | | 35 | | | | | 40 | | | | | 45 | | | | |
| gcg | atg | ctg | atc | atc | tct | gtc | cta | ata | gcc | ata | tac | tac | aat | gta | att | 192 |
| Ala | Met | Leu | Ile | Ile | Ser | Val | Leu | Ile | Ala | Ile | Tyr | Tyr | Asn | Val | Ile | |
| 50 | | | | | 55 | | | | | 60 | | | | | | |
| att | tgc | tat | aca | ctt | ttc | tac | ctg | ttt | gcc | tct | tgt | gtg | tct | gta | cta | 240 |
| Ile | Cys | Tyr | Thr | Leu | Phe | Tyr | Leu | Phe | Ala | Ser | Cys | Val | Ser | Val | Leu | |
| 65 | | | | 70 | | | | | 75 | | | | | 80 | | |
| ccc | tgg | ggc | tcc | tgc | aac | aac | cct | tgg | aat | acg | cca | gaa | tgc | aaa | gat | 288 |
| Pro | Trp | Gly | Ser | Cys | Asn | Asn | Pro | Trp | Asn | Thr | Pro | Glu | Cys | Lys | Asp | |
| | | | 85 | | | | | 90 | | | | | 95 | | | |
| aaa | acc | aaa | ctt | tta | tta | gat | tcc | tgt | gtt | atc | agt | gac | cat | ccc | aaa | 336 |
| Lys | Thr | Lys | Leu | Leu | Leu | Asp | Ser | Cys | Val | Ile | Ser | Asp | His | Pro | Lys | |
| | | 100 | | | | | 105 | | | | | 110 | | | | |
| ata | cag | atc | aag | aac | tcg | act | ttc | tgc | atg | acc | gct | tat | ccc | aac | gtg | 384 |
| Ile | Gln | Ile | Lys | Asn | Ser | Thr | Phe | Cys | Met | Thr | Ala | Tyr | Pro | Asn | Val | |
| | 115 | | | | | 120 | | | | | 125 | | | | | |
| aca | atg | gtt | aat | ttc | acc | agc | ctg | gcc | aat | aag | aca | ttt | gtc | agt | gga | 432 |
| Thr | Met | Val | Asn | Phe | Thr | Ser | Leu | Ala | Asn | Lys | Thr | Phe | Val | Ser | Gly | |
| 130 | | | | | 135 | | | | | 140 | | | | | | |
| agt | gaa | gag | tac | ttc | aag | tac | ttt | gtg | ctg | aag | att | tct | gca | ggg | att | 480 |
| Ser | Glu | Glu | Tyr | Phe | Lys | Tyr | Phe | Val | Leu | Lys | Ile | Ser | Ala | Gly | Ile | |
| 145 | | | | | 150 | | | | | 155 | | | | | 160 | |
| gaa | tat | cct | ggc | gag | atc | agg | tgg | cca | cta | gct | ctc | tgc | ctc | ttc | ctg | 528 |
| Glu | Tyr | Pro | Gly | Glu | Ile | Arg | Trp | Pro | Leu | Ala | Leu | Cys | Leu | Phe | Leu | |
| | | | 165 | | | | | 170 | | | | | 175 | | | |
| gct | tgg | gtc | att | gtg | tat | gca | tcg | ttg | gct | aaa | gga | atc | aag | act | tca | 576 |
| Ala | Trp | Val | Ile | Val | Tyr | Ala | Ser | Leu | Ala | Lys | Gly | Ile | Lys | Thr | Ser | |
| | | | 180 | | | | | 185 | | | | | 190 | | | |
| gga | aaa | gtg | gtg | tat | ttt | acc | gcc | acg | ttc | ccc | tac | gtg | | | | 615 |
| Gly | Lys | Val | Val | Tyr | Phe | Thr | Ala | Thr | Phe | Pro | Tyr | Val | | | | |
| | | 195 | | | | | 200 | | | | | 205 | | | | |

<210> SEQ ID NO 55
<211> LENGTH: 205
<212> TYPE: PRT
<213> ORGANISM: Human

<400> SEQUENCE: 55

| | | | | | | | | | | | | | | | |
|---|---|---|---|---|---|---|---|---|---|---|---|---|---|---|---|
| Gly | Ala | Phe | Leu | Ile | Pro | Tyr | Leu | Met | Met | Leu | Ala | Leu | Ala | Gly | Leu |
| 1 | | | | 5 | | | | | 10 | | | | | 15 | |

| | | | | | | | | | | | | | | | |
|---|---|---|---|---|---|---|---|---|---|---|---|---|---|---|---|
| Pro | Ile | Phe | Phe | Leu | Glu | Val | Ser | Leu | Gly | Gln | Phe | Ala | Ser | Gln | Gly |
| | | | 20 | | | | | 25 | | | | | 30 | | |

| | | | | | | | | | | | | | | | |
|---|---|---|---|---|---|---|---|---|---|---|---|---|---|---|---|
| Pro | Val | Ser | Val | Trp | Lys | Ala | Ile | Pro | Ala | Leu | Gln | Gly | Cys | Gly | Ile |
| | | 35 | | | | | 40 | | | | | 45 | | | |

| | | | | | | | | | | | | | | | |
|---|---|---|---|---|---|---|---|---|---|---|---|---|---|---|---|
| Ala | Met | Leu | Ile | Ile | Ser | Val | Leu | Ile | Ala | Ile | Tyr | Tyr | Asn | Val | Ile |
| 50 | | | | | 55 | | | | | 60 | | | | | |

| | | | | | | | | | | | | | | | |
|---|---|---|---|---|---|---|---|---|---|---|---|---|---|---|---|
| Ile | Cys | Tyr | Thr | Leu | Phe | Tyr | Leu | Phe | Ala | Ser | Cys | Val | Ser | Val | Leu |
| 65 | | | | 70 | | | | | 75 | | | | | 80 | |

```
Pro Trp Gly Ser Cys Asn Asn Pro Trp Asn Thr Pro Glu Cys Lys Asp
            85                  90                  95

Lys Thr Lys Leu Leu Leu Asp Ser Cys Val Ile Ser Asp His Pro Lys
            100                 105                 110

Ile Gln Ile Lys Asn Ser Thr Phe Cys Met Thr Ala Tyr Pro Asn Val
            115                 120                 125

Thr Met Val Asn Phe Thr Ser Leu Ala Asn Lys Thr Phe Val Ser Gly
            130                 135                 140

Ser Glu Glu Tyr Phe Lys Tyr Phe Val Leu Lys Ile Ser Ala Gly Ile
145                 150                 155                 160

Glu Tyr Pro Gly Glu Ile Arg Trp Pro Leu Ala Leu Cys Leu Phe Leu
            165                 170                 175

Ala Trp Val Ile Val Tyr Ala Ser Leu Ala Lys Gly Ile Lys Thr Ser
            180                 185                 190

Gly Lys Val Val Tyr Phe Thr Ala Thr Phe Pro Tyr Val
            195                 200                 205
```

<210> SEQ ID NO 56
<211> LENGTH: 615
<212> TYPE: DNA
<213> ORGANISM: Human
<220> FEATURE:
<221> NAME/KEY: CDS
<222> LOCATION: (1)..(615)
<223> OTHER INFORMATION: Seq 28(C)S2 - HSpC-2; nt 679-1293; nt 681 is C not T (consensus); nt 750 is C not G (consensus); nt 777 is C not G (consensus); nt 867 is G not A (consensus); nt 1085 is A not T (consensus);
<220> FEATURE:
<223> OTHER INFORMATION: nt 1292 is C not T (consensus)

<400> SEQUENCE: 56

```
ggc gct ttc ctc atc cct tac ctg atg atg ctg gct ctg gct gga tta        48
Gly Ala Phe Leu Ile Pro Tyr Leu Met Met Leu Ala Leu Ala Gly Leu
 1               5                  10                  15 ccc atc ttc ttc ttg gag gtg tcc ctg ggc cag ttt gcc agc cag gga        96
Pro Ile Phe Phe Leu Glu Val Ser Leu Gly Gln Phe Ala Ser Gln Gly
             20                  25                  30 ccc gtg tct gtg tgg aag gcc atc cca gct cta caa ggc tgt ggc atc       144
Pro Val Ser Val Trp Lys Ala Ile Pro Ala Leu Gln Gly Cys Gly Ile
         35                  40                  45 gcg atg ctg atc atc tct gtc cta ata gcc ata tac aat gtg att          192
Ala Met Leu Ile Ile Ser Val Leu Ile Ala Ile Tyr Tyr Asn Val Ile
     50                  55                  60 att tgc tat aca ctt ttc tac ctg ttt gcc tcc ttt gtg tct gta cta       240
Ile Cys Tyr Thr Leu Phe Tyr Leu Phe Ala Ser Phe Val Ser Val Leu
 65                  70                  75                  80 ccc tgg ggc tcc tgc aac aac cct tgg aat acg cca gaa tgc aaa gat       288
Pro Trp Gly Ser Cys Asn Asn Pro Trp Asn Thr Pro Glu Cys Lys Asp
             85                  90                  95 aaa acc aaa ctt tta tta gat tcc tgt gtt atc agt gac cat ccc aaa       336
Lys Thr Lys Leu Leu Leu Asp Ser Cys Val Ile Ser Asp His Pro Lys
            100                 105                 110 ata cag atc aag aac tcg act ttc tgc atg acc gct tat ccc aac gtg       384
Ile Gln Ile Lys Asn Ser Thr Phe Cys Met Thr Ala Tyr Pro Asn Val
            115                 120                 125 aca atg gtt aat ttc acc agc cag gcc aat aag aca ttt gtc agt gga       432
Thr Met Val Asn Phe Thr Ser Gln Ala Asn Lys Thr Phe Val Ser Gly
            130                 135                 140 agt gaa gag tac ttc aag tac ttt gtg ctg aag att tct gca ggg att       480
Ser Glu Glu Tyr Phe Lys Tyr Phe Val Leu Lys Ile Ser Ala Gly Ile
```

```
                                                                           -continued
145                  150                   155                   160
gaa tat cct ggc gag atc agg tgg cca cta gct ctc tgc ctc ttc ctg            528
Glu Tyr Pro Gly Glu Ile Arg Trp Pro Leu Ala Leu Cys Leu Phe Leu
                165                   170                   175 gct tgg gtc att gtg tat gca tcg ttg gct aaa gga atc aag act tca            576
Ala Trp Val Ile Val Tyr Ala Ser Leu Ala Lys Gly Ile Lys Thr Ser
            180                   185                   190 gga aaa gtg gtg tac ttc acg gcc acg ttc ccg tat gcc                        615
Gly Lys Val Val Tyr Phe Thr Ala Thr Phe Pro Tyr Ala
        195                   200                   205

<210> SEQ ID NO 57
<211> LENGTH: 205
<212> TYPE: PRT
<213> ORGANISM: Human

<400> SEQUENCE: 57

Gly Ala Phe Leu Ile Pro Tyr Leu Met Met Leu Ala Leu Ala Gly Leu
 1               5                  10                  15

Pro Ile Phe Phe Leu Glu Val Ser Leu Gly Gln Phe Ala Ser Gln Gly
            20                  25                  30

Pro Val Ser Val Trp Lys Ala Ile Pro Ala Leu Gln Gly Cys Gly Ile
        35                  40                  45

Ala Met Leu Ile Ile Ser Val Leu Ile Ala Ile Tyr Tyr Asn Val Ile
    50                  55                  60

Ile Cys Tyr Thr Leu Phe Tyr Leu Phe Ala Ser Phe Val Ser Val Leu
65                  70                  75                  80

Pro Trp Gly Ser Cys Asn Asn Pro Trp Asn Thr Pro Glu Cys Lys Asp
                85                  90                  95

Lys Thr Lys Leu Leu Leu Asp Ser Cys Val Ile Ser Asp His Pro Lys
           100                 105                 110

Ile Gln Ile Lys Asn Ser Thr Phe Cys Met Thr Ala Tyr Pro Asn Val
       115                 120                 125

Thr Met Val Asn Phe Thr Ser Gln Ala Asn Lys Thr Phe Val Ser Gly
   130                 135                 140

Ser Glu Glu Tyr Phe Lys Tyr Phe Val Leu Lys Ile Ser Ala Gly Ile
145                 150                 155                 160

Glu Tyr Pro Gly Glu Ile Arg Trp Pro Leu Ala Leu Cys Leu Phe Leu
                165                 170                 175

Ala Trp Val Ile Val Tyr Ala Ser Leu Ala Lys Gly Ile Lys Thr Ser
            180                 185                 190

Gly Lys Val Val Tyr Phe Thr Ala Thr Phe Pro Tyr Ala
        195                 200                 205

<210> SEQ ID NO 58
<211> LENGTH: 615
<212> TYPE: DNA
<213> ORGANISM: Human
<220> FEATURE:
<221> NAME/KEY: CDS
<222> LOCATION: (1)..(615)
<223> OTHER INFORMATION: Seq 29(C)S3 - HSpC-3; nt 679-1293; nt 777 is A
      not G (consensus); nt 917 is C not T (consensus)

<400> SEQUENCE: 58 ggt gct ttc ctc atc cct tac ctg atg atg ctg gct ctg gct gga tta            48
Gly Ala Phe Leu Ile Pro Tyr Leu Met Met Leu Ala Leu Ala Gly Leu
 1               5                  10                  15 ccc atc ttc ttc ttg gag gtg tcg ctg ggc cag ttt gcc agc cag gga            96
```

```
Pro Ile Phe Phe Leu Glu Val Ser Leu Gly Gln Phe Ala Ser Gln Gly
            20                  25                  30 cca gtg tct gtg tgg aag gcc atc cca gct cta caa ggc tgt ggc atc     144
Pro Val Ser Val Trp Lys Ala Ile Pro Ala Leu Gln Gly Cys Gly Ile
        35                  40                  45 gcg atg ctg atc atc tct gtc cta ata gcc ata tac tac aat gta att     192
Ala Met Leu Ile Ile Ser Val Leu Ile Ala Ile Tyr Tyr Asn Val Ile
    50                  55                  60 att tgc tat aca ctt ttc tac ctg ttt gcc tcc ttt gtg tct gta cca     240
Ile Cys Tyr Thr Leu Phe Tyr Leu Phe Ala Ser Phe Val Ser Val Pro
65                  70                  75                  80 ccc tgg ggc tcc tgc aac aac cct tgg aat acg cca gaa tgc aaa gat     288
Pro Trp Gly Ser Cys Asn Asn Pro Trp Asn Thr Pro Glu Cys Lys Asp
                85                  90                  95 aaa acc aaa ctt tta tta gat tcc tgt gtt atc agt gac cat ccc aaa     336
Lys Thr Lys Leu Leu Leu Asp Ser Cys Val Ile Ser Asp His Pro Lys
            100                 105                 110 ata cag atc aag aac tcg act ttc tgc atg acc gct tat ccc aac gtg     384
Ile Gln Ile Lys Asn Ser Thr Phe Cys Met Thr Ala Tyr Pro Asn Val
        115                 120                 125 aca atg gtt aat ttc acc agc ctg gcc aat aag aca ttt gtc agt gga     432
Thr Met Val Asn Phe Thr Ser Leu Ala Asn Lys Thr Phe Val Ser Gly
    130                 135                 140 agt gaa gag tac ttc aag tac ttt gtg ctg aag att tct gca ggg att     480
Ser Glu Glu Tyr Phe Lys Tyr Phe Val Leu Lys Ile Ser Ala Gly Ile
145                 150                 155                 160 gaa tat cct ggc gag atc agg tgg cca cta gct ctc tgc ctc ttc ctg     528
Glu Tyr Pro Gly Glu Ile Arg Trp Pro Leu Ala Leu Cys Leu Phe Leu
                165                 170                 175 gct tgg gtc att gtg tat gca tcg ttg gct aaa gga atc aag act tca     576
Ala Trp Val Ile Val Tyr Ala Ser Leu Ala Lys Gly Ile Lys Thr Ser
            180                 185                 190 gga aaa gtg gtg tac ttc acg gcc acg ttc ccg tat gtc                 615
Gly Lys Val Val Tyr Phe Thr Ala Thr Phe Pro Tyr Val
        195                 200                 205

<210> SEQ ID NO 59
<211> LENGTH: 205
<212> TYPE: PRT
<213> ORGANISM: Human

<400> SEQUENCE: 59

Gly Ala Phe Leu Ile Pro Tyr Leu Met Met Leu Ala Leu Ala Gly Leu
1               5                   10                  15

Pro Ile Phe Phe Leu Glu Val Ser Leu Gly Gln Phe Ala Ser Gln Gly
            20                  25                  30

Pro Val Ser Val Trp Lys Ala Ile Pro Ala Leu Gln Gly Cys Gly Ile
        35                  40                  45

Ala Met Leu Ile Ile Ser Val Leu Ile Ala Ile Tyr Tyr Asn Val Ile
    50                  55                  60

Ile Cys Tyr Thr Leu Phe Tyr Leu Phe Ala Ser Phe Val Ser Val Pro
65                  70                  75                  80

Pro Trp Gly Ser Cys Asn Asn Pro Trp Asn Thr Pro Glu Cys Lys Asp
                85                  90                  95

Lys Thr Lys Leu Leu Leu Asp Ser Cys Val Ile Ser Asp His Pro Lys
            100                 105                 110

Ile Gln Ile Lys Asn Ser Thr Phe Cys Met Thr Ala Tyr Pro Asn Val
        115                 120                 125
```

```
Thr Met Val Asn Phe Thr Ser Leu Ala Asn Lys Thr Phe Val Ser Gly
    130                 135                 140

Ser Glu Glu Tyr Phe Lys Tyr Phe Val Leu Lys Ile Ser Ala Gly Ile
145                 150                 155                 160

Glu Tyr Pro Gly Glu Ile Arg Trp Pro Leu Ala Leu Cys Leu Phe Leu
                165                 170                 175

Ala Trp Val Ile Val Tyr Ala Ser Leu Ala Lys Gly Ile Lys Thr Ser
                180                 185                 190

Gly Lys Val Val Tyr Phe Thr Ala Thr Phe Pro Tyr Val
        195                 200                 205

<210> SEQ ID NO 60
<211> LENGTH: 615
<212> TYPE: DNA
<213> ORGANISM: Human
<220> FEATURE:
<221> NAME/KEY: CDS
<222> LOCATION: (1)..(615)
<223> OTHER INFORMATION: Seq 30(C)S3 - HSpC-3; nt 679-1293; nt 745 is T
      not G (consensus)

<400> SEQUENCE: 60 ggt gct ttc ctc atc cct tac ctg atg atg ctg gct ctg gct gga tta      48
Gly Ala Phe Leu Ile Pro Tyr Leu Met Met Leu Ala Leu Ala Gly Leu
  1               5                  10                  15 ccc atc ttc ttc ttg gag ttg tcg ctg ggc cag ttt gcc agc cag gga      96
Pro Ile Phe Phe Leu Glu Leu Ser Leu Gly Gln Phe Ala Ser Gln Gly
                 20                  25                  30 ccg gtg tct gtg tgg aag gcc atc cca gct cta caa ggc tgt ggc atc     144
Pro Val Ser Val Trp Lys Ala Ile Pro Ala Leu Gln Gly Cys Gly Ile
             35                  40                  45 gcg atg ctg atc atc tct gtc cta ata gcc ata tac aat gta att         192
Ala Met Leu Ile Ile Ser Val Leu Ile Ala Ile Tyr Tyr Asn Val Ile
         50                  55                  60 att tgc tat aca ctt ttc tac ctg ttt gcc tcc ttt gtg tct gta cta     240
Ile Cys Tyr Thr Leu Phe Tyr Leu Phe Ala Ser Phe Val Ser Val Leu
 65                  70                  75                  80 ccc tgg ggc tcc tgc aac aac cct tgg aat acg cca gaa tgc aaa gat     288
Pro Trp Gly Ser Cys Asn Asn Pro Trp Asn Thr Pro Glu Cys Lys Asp
                 85                  90                  95 aaa acc aaa ctt tta tta gat tcc tgt gtt atc agt gac cat ccc aaa     336
Lys Thr Lys Leu Leu Leu Asp Ser Cys Val Ile Ser Asp His Pro Lys
             100                 105                 110 ata cag atc aag aac tcg act ttc tgc atg acc gct tat ccc aac gtg     384
Ile Gln Ile Lys Asn Ser Thr Phe Cys Met Thr Ala Tyr Pro Asn Val
         115                 120                 125 aca atg gtt aat ttc acc agc ctg gcc aat aag aca ttt gtc agt gga     432
Thr Met Val Asn Phe Thr Ser Leu Ala Asn Lys Thr Phe Val Ser Gly
130                 135                 140 agt gaa gag tac ttc aag tac ttt gtg ctg aag att tct gca ggg att     480
Ser Glu Glu Tyr Phe Lys Tyr Phe Val Leu Lys Ile Ser Ala Gly Ile
145                 150                 155                 160 gaa tat cct ggc gag atc agg tgg cca cta gct ctc tgc ctc ttc ctg     528
Glu Tyr Pro Gly Glu Ile Arg Trp Pro Leu Ala Leu Cys Leu Phe Leu
                165                 170                 175 gct tgg gtc att gtg tat gca tcg ttg gct aaa gga atc aag act tca     576
Ala Trp Val Ile Val Tyr Ala Ser Leu Ala Lys Gly Ile Lys Thr Ser
                180                 185                 190 gga aaa gtg gtg tac ttc acg gcc acg ttc ccg tat gtc                 615
Gly Lys Val Val Tyr Phe Thr Ala Thr Phe Pro Tyr Val
                195                 200                 205
```

<210> SEQ ID NO 61
<211> LENGTH: 205
<212> TYPE: PRT
<213> ORGANISM: Human

<400> SEQUENCE: 61

```
Gly Ala Phe Leu Ile Pro Tyr Leu Met Met Leu Ala Leu Ala Gly Leu
 1               5                  10                  15

Pro Ile Phe Phe Leu Glu Leu Ser Leu Gly Gln Phe Ala Ser Gln Gly
             20                  25                  30

Pro Val Ser Val Trp Lys Ala Ile Pro Ala Leu Gln Gly Cys Gly Ile
         35                  40                  45

Ala Met Leu Ile Ile Ser Val Leu Ile Ala Ile Tyr Tyr Asn Val Ile
     50                  55                  60

Ile Cys Tyr Thr Leu Phe Tyr Leu Phe Ala Ser Phe Val Ser Val Leu
 65                  70                  75                  80

Pro Trp Gly Ser Cys Asn Asn Pro Trp Asn Thr Pro Glu Cys Lys Asp
                 85                  90                  95

Lys Thr Lys Leu Leu Leu Asp Ser Cys Val Ile Ser Asp His Pro Lys
            100                 105                 110

Ile Gln Ile Lys Asn Ser Thr Phe Cys Met Thr Ala Tyr Pro Asn Val
        115                 120                 125

Thr Met Val Asn Phe Thr Ser Leu Ala Asn Lys Thr Phe Val Ser Gly
    130                 135                 140

Ser Glu Glu Tyr Phe Lys Tyr Phe Val Leu Lys Ile Ser Ala Gly Ile
145                 150                 155                 160

Glu Tyr Pro Gly Glu Ile Arg Trp Pro Leu Ala Leu Cys Leu Phe Leu
                165                 170                 175

Ala Trp Val Ile Val Tyr Ala Ser Leu Ala Lys Gly Ile Lys Thr Ser
            180                 185                 190

Gly Lys Val Val Tyr Phe Thr Ala Thr Phe Pro Tyr Val
        195                 200                 205
```

<210> SEQ ID NO 62
<211> LENGTH: 615
<212> TYPE: DNA
<213> ORGANISM: Human
<220> FEATURE:
<221> NAME/KEY: CDS
<222> LOCATION: (1)..(615)
<223> OTHER INFORMATION: Seq 31(C)S3 - HSpC-3; nt 679-1293

<400> SEQUENCE: 62

```
ggt gct ttc ctc atc cct tac ctg atg atg ctg gct ctg gct gga tta       48
Gly Ala Phe Leu Ile Pro Tyr Leu Met Met Leu Ala Leu Ala Gly Leu
 1               5                  10                  15 ccc atc ttc ttc ttg gag gtg tcg ctg ggc cag ttt gcc agc cag gga       96
Pro Ile Phe Phe Leu Glu Val Ser Leu Gly Gln Phe Ala Ser Gln Gly
             20                  25                  30 ccg gtg tct gtg tgg aag gcc atc cca gct cta caa ggc tgt ggc atc      144
Pro Val Ser Val Trp Lys Ala Ile Pro Ala Leu Gln Gly Cys Gly Ile
         35                  40                  45 gcg atg ctg atc atc tct gtc cta ata gcc ata tac aat gta att          192
Ala Met Leu Ile Ile Ser Val Leu Ile Ala Ile Tyr Tyr Asn Val Ile
     50                  55                  60 att tgc tat aca ctt ttc tac ctg ttt gcc tcc ttt gtg tct gta cta      240
Ile Cys Tyr Thr Leu Phe Tyr Leu Phe Ala Ser Phe Val Ser Val Leu
 65                  70                  75                  80
```

```
ccc tgg ggc tcc tgc aac aac cct tgg aat acg cca gaa tgc aaa gat       288
Pro Trp Gly Ser Cys Asn Asn Pro Trp Asn Thr Pro Glu Cys Lys Asp
                85                  90                  95 aaa acc aaa ctt tta tta gat tcc tgt gtt atc agt gac cat ccc aaa       336
Lys Thr Lys Leu Leu Leu Asp Ser Cys Val Ile Ser Asp His Pro Lys
            100                 105                 110 ata cag atc aag aac tcg act ttc tgc atg acc gct tat ccc aac gtg       384
Ile Gln Ile Lys Asn Ser Thr Phe Cys Met Thr Ala Tyr Pro Asn Val
        115                 120                 125 aca atg gtt aat ttc acc agc ctg gcc aat aag aca ttt gtc agt gga       432
Thr Met Val Asn Phe Thr Ser Leu Ala Asn Lys Thr Phe Val Ser Gly
    130                 135                 140 agt gaa gag tac ttc aag tac ttt gtg ctg aag att tct gca ggg att       480
Ser Glu Glu Tyr Phe Lys Tyr Phe Val Leu Lys Ile Ser Ala Gly Ile
145                 150                 155                 160 gaa tat cct ggc gag atc agg tgg cca cta gct ctc tgc ctc ttc ctg       528
Glu Tyr Pro Gly Glu Ile Arg Trp Pro Leu Ala Leu Cys Leu Phe Leu
                165                 170                 175 gct tgg gtc att gtg tat gca tcg ttg gct aaa gga atc aag act tca       576
Ala Trp Val Ile Val Tyr Ala Ser Leu Ala Lys Gly Ile Lys Thr Ser
            180                 185                 190 gga aaa gtg gtg tac ttc acg gcc acg ttc ccg tat gtc                   615
Gly Lys Val Val Tyr Phe Thr Ala Thr Phe Pro Tyr Val
        195                 200                 205

<210> SEQ ID NO 63
<211> LENGTH: 205
<212> TYPE: PRT
<213> ORGANISM: Human

<400> SEQUENCE: 63

Gly Ala Phe Leu Ile Pro Tyr Leu Met Met Leu Ala Leu Ala Gly Leu
  1               5                  10                  15

Pro Ile Phe Phe Leu Glu Val Ser Leu Gly Gln Phe Ala Ser Gln Gly
                 20                  25                  30

Pro Val Ser Val Trp Lys Ala Ile Pro Ala Leu Gln Gly Cys Gly Ile
             35                  40                  45

Ala Met Leu Ile Ile Ser Val Leu Ile Ala Ile Tyr Tyr Asn Val Ile
         50                  55                  60

Ile Cys Tyr Thr Leu Phe Tyr Leu Phe Ala Ser Phe Val Ser Val Leu
 65                  70                  75                  80

Pro Trp Gly Ser Cys Asn Asn Pro Trp Asn Thr Pro Glu Cys Lys Asp
                 85                  90                  95

Lys Thr Lys Leu Leu Leu Asp Ser Cys Val Ile Ser Asp His Pro Lys
            100                 105                 110

Ile Gln Ile Lys Asn Ser Thr Phe Cys Met Thr Ala Tyr Pro Asn Val
        115                 120                 125

Thr Met Val Asn Phe Thr Ser Leu Ala Asn Lys Thr Phe Val Ser Gly
    130                 135                 140

Ser Glu Glu Tyr Phe Lys Tyr Phe Val Leu Lys Ile Ser Ala Gly Ile
145                 150                 155                 160

Glu Tyr Pro Gly Glu Ile Arg Trp Pro Leu Ala Leu Cys Leu Phe Leu
                165                 170                 175

Ala Trp Val Ile Val Tyr Ala Ser Leu Ala Lys Gly Ile Lys Thr Ser
            180                 185                 190

Gly Lys Val Val Tyr Phe Thr Ala Thr Phe Pro Tyr Val
        195                 200                 205
```

<210> SEQ ID NO 64
<211> LENGTH: 615
<212> TYPE: DNA
<213> ORGANISM: Human
<220> FEATURE:
<221> NAME/KEY: CDS
<222> LOCATION: (1)..(615)
<223> OTHER INFORMATION: Seq 32(C)U - U373MG; nt 679-1293; nt 1182 is A
      not G (consensus)

<400> SEQUENCE: 64

```
ggt gct ttc ctc atc cct tac ctg atg atg ctg gct ctg gct gga tta      48
Gly Ala Phe Leu Ile Pro Tyr Leu Met Met Leu Ala Leu Ala Gly Leu
 1               5                  10                  15 ccc atc ttc ttc ttg gag gtg tcg ctg ggc cag ttt gcc agc cag gga      96
Pro Ile Phe Phe Leu Glu Val Ser Leu Gly Gln Phe Ala Ser Gln Gly
                20                  25                  30 ccg gtg tct gtg tgg aag gcc atc cca gct cta caa ggc tgt ggc atc     144
Pro Val Ser Val Trp Lys Ala Ile Pro Ala Leu Gln Gly Cys Gly Ile
            35                  40                  45 gcg atg ctg atc atc tct gtc cta ata gcc ata tac tac aat gta att     192
Ala Met Leu Ile Ile Ser Val Leu Ile Ala Ile Tyr Tyr Asn Val Ile
        50                  55                  60 att tgc tat aca ctt ttc tac ctg ttt gcc tcc ttt gtg tct gta cta     240
Ile Cys Tyr Thr Leu Phe Tyr Leu Phe Ala Ser Phe Val Ser Val Leu
 65                  70                  75                  80 ccc tgg ggc tcc tgc aac aac cct tgg aat acg cca gaa tgc aaa gat     288
Pro Trp Gly Ser Cys Asn Asn Pro Trp Asn Thr Pro Glu Cys Lys Asp
                85                  90                  95 aaa acc aaa ctt tta tta gat tcc tgt gtt atc agt gac cat ccc aaa     336
Lys Thr Lys Leu Leu Leu Asp Ser Cys Val Ile Ser Asp His Pro Lys
               100                 105                 110 ata cag atc aag aac tcg act ttc tgc atg acc gct tat ccc aac gtg     384
Ile Gln Ile Lys Asn Ser Thr Phe Cys Met Thr Ala Tyr Pro Asn Val
           115                 120                 125 aca atg gtt aat ttc acc agc ctg gcc aat aag aca ttt gtc agt gga     432
Thr Met Val Asn Phe Thr Ser Leu Ala Asn Lys Thr Phe Val Ser Gly
       130                 135                 140 agt gaa gag tac ttc aag tac ttt gtg ctg aag att tct gca ggg att     480
Ser Glu Glu Tyr Phe Lys Tyr Phe Val Leu Lys Ile Ser Ala Gly Ile
145                 150                 155                 160 gaa tat cct ggc gag atc agg tga cca cta gct ctc tgc ctc ttc ctg     528
Glu Tyr Pro Gly Glu Ile Arg     Pro Leu Ala Leu Cys Leu Phe Leu
                165                 170                 175 gct tgg gtc att gtg tat gca tcg ttg gct aaa gga atc aag act tca     576
Ala Trp Val Ile Val Tyr Ala Ser Leu Ala Lys Gly Ile Lys Thr Ser
            180                 185                 190 gga aaa gtg gtg tac ttc acg gcc acg ttc ccg tat gtc                 615
Gly Lys Val Val Tyr Phe Thr Ala Thr Phe Pro Tyr Val
        195                 200                 205
```

<210> SEQ ID NO 65
<211> LENGTH: 167
<212> TYPE: PRT
<213> ORGANISM: Human

<400> SEQUENCE: 65

```
Gly Ala Phe Leu Ile Pro Tyr Leu Met Met Leu Ala Leu Ala Gly Leu
 1               5                  10                  15

Pro Ile Phe Phe Leu Glu Val Ser Leu Gly Gln Phe Ala Ser Gln Gly
                20                  25                  30
```

```
Pro Val Ser Val Trp Lys Ala Ile Pro Ala Leu Gln Gly Cys Gly Ile
        35                  40                  45

Ala Met Leu Ile Ile Ser Val Leu Ile Ala Ile Tyr Tyr Asn Val Ile
    50                  55                  60

Ile Cys Tyr Thr Leu Phe Tyr Leu Phe Ala Ser Phe Val Ser Val Leu
 65                  70                  75                  80

Pro Trp Gly Ser Cys Asn Asn Pro Trp Asn Thr Pro Glu Cys Lys Asp
                85                  90                  95

Lys Thr Lys Leu Leu Leu Asp Ser Cys Val Ile Ser Asp His Pro Lys
            100                 105                 110

Ile Gln Ile Lys Asn Ser Thr Phe Cys Met Thr Ala Tyr Pro Asn Val
        115                 120                 125

Thr Met Val Asn Phe Thr Ser Leu Ala Asn Lys Thr Phe Val Ser Gly
    130                 135                 140

Ser Glu Glu Tyr Phe Lys Tyr Phe Val Leu Lys Ile Ser Ala Gly Ile
145                 150                 155                 160

Glu Tyr Pro Gly Glu Ile Arg
                165
```

<210> SEQ ID NO 66
<211> LENGTH: 37
<212> TYPE: PRT
<213> ORGANISM: Human

<400> SEQUENCE: 66

```
Pro Leu Ala Leu Cys Leu Phe Leu Ala Trp Val Ile Val Tyr Ala Ser
 1               5                  10                  15

Leu Ala Lys Gly Ile Lys Thr Ser Gly Lys Val Val Tyr Phe Thr Ala
            20                  25                  30

Thr Phe Pro Tyr Val
        35
```

<210> SEQ ID NO 67
<211> LENGTH: 615
<212> TYPE: DNA
<213> ORGANISM: Human
<220> FEATURE:
<221> NAME/KEY: CDS
<222> LOCATION: (1)..(615)
<223> OTHER INFORMATION: Seq 33(C)U - U373MG; nt 679-1293

<400> SEQUENCE: 67

```
ggt gct ttc ctc atc cct tac ctg atg atg ctg gct ctg gct gga tta      48
Gly Ala Phe Leu Ile Pro Tyr Leu Met Met Leu Ala Leu Ala Gly Leu
 1               5                  10                  15 ccc atc ttc ttc ttg gag gtg tcg ctg ggc cag ttt gcc agc cag gga      96
Pro Ile Phe Phe Leu Glu Val Ser Leu Gly Gln Phe Ala Ser Gln Gly
            20                  25                  30 ccg gtg tct gtg tgg aag gcc atc cca gct cta caa ggc tgt ggc atc     144
Pro Val Ser Val Trp Lys Ala Ile Pro Ala Leu Gln Gly Cys Gly Ile
        35                  40                  45 gcg atg ctg atc atc tct gtc cta ata gcc ata tac tac aat gta att     192
Ala Met Leu Ile Ile Ser Val Leu Ile Ala Ile Tyr Tyr Asn Val Ile
    50                  55                  60 att tgc tat aca ctt ttc tac ctg ttt gcc tcc ttt gtg tct gta cta     240
Ile Cys Tyr Thr Leu Phe Tyr Leu Phe Ala Ser Phe Val Ser Val Leu
 65                  70                  75                  80 ccc tgg ggc tcc tgc aac aac cct tgg aat acg cca gaa tgc aaa gat     288
Pro Trp Gly Ser Cys Asn Asn Pro Trp Asn Thr Pro Glu Cys Lys Asp
```

```
                    85                   90                   95
aaa acc aaa ctt tta tta gat tcc tgt gtt atc agt gac cat ccc aaa    336
Lys Thr Lys Leu Leu Leu Asp Ser Cys Val Ile Ser Asp His Pro Lys
            100                 105                 110 ata cag atc aag aac tcg act ttc tgc atg acc gct tat ccc aac gtg    384
Ile Gln Ile Lys Asn Ser Thr Phe Cys Met Thr Ala Tyr Pro Asn Val
            115                 120                 125 aca atg gtt aat ttc acc agc ctg gcc aat aag aca ttt gtc agt gga    432
Thr Met Val Asn Phe Thr Ser Leu Ala Asn Lys Thr Phe Val Ser Gly
        130                 135                 140 agt gaa gag tac ttc aag tac ttt gtg ctg aag att tct gca ggg att    480
Ser Glu Glu Tyr Phe Lys Tyr Phe Val Leu Lys Ile Ser Ala Gly Ile
145                 150                 155                 160 gaa tat cct ggc gag atc agg tgg cca cta gct ctc tgc ctc ttc ctg    528
Glu Tyr Pro Gly Glu Ile Arg Trp Pro Leu Ala Leu Cys Leu Phe Leu
                165                 170                 175 gct tgg gtc att gtg tat gca tcg ttg gct aaa gga atc aag act tca    576
Ala Trp Val Ile Val Tyr Ala Ser Leu Ala Lys Gly Ile Lys Thr Ser
                180                 185                 190 gga aaa gtg gtg tac ttc acg gcc acg ttc ccg tat gtc                615
Gly Lys Val Val Tyr Phe Thr Ala Thr Phe Pro Tyr Val
                195                 200                 205

<210> SEQ ID NO 68
<211> LENGTH: 205
<212> TYPE: PRT
<213> ORGANISM: Human

<400> SEQUENCE: 68

Gly Ala Phe Leu Ile Pro Tyr Leu Met Met Leu Ala Leu Ala Gly Leu
 1               5                  10                  15

Pro Ile Phe Phe Leu Glu Val Ser Leu Gly Gln Phe Ala Ser Gln Gly
            20                  25                  30

Pro Val Ser Val Trp Lys Ala Ile Pro Ala Leu Gln Gly Cys Gly Ile
        35                  40                  45

Ala Met Leu Ile Ile Ser Val Leu Ile Ala Ile Tyr Tyr Asn Val Ile
    50                  55                  60

Ile Cys Tyr Thr Leu Phe Tyr Leu Phe Ala Ser Phe Val Ser Val Leu
65                  70                  75                  80

Pro Trp Gly Ser Cys Asn Asn Pro Trp Asn Thr Pro Glu Cys Lys Asp
                85                  90                  95

Lys Thr Lys Leu Leu Leu Asp Ser Cys Val Ile Ser Asp His Pro Lys
            100                 105                 110

Ile Gln Ile Lys Asn Ser Thr Phe Cys Met Thr Ala Tyr Pro Asn Val
        115                 120                 125

Thr Met Val Asn Phe Thr Ser Leu Ala Asn Lys Thr Phe Val Ser Gly
    130                 135                 140

Ser Glu Glu Tyr Phe Lys Tyr Phe Val Leu Lys Ile Ser Ala Gly Ile
145                 150                 155                 160

Glu Tyr Pro Gly Glu Ile Arg Trp Pro Leu Ala Leu Cys Leu Phe Leu
                165                 170                 175

Ala Trp Val Ile Val Tyr Ala Ser Leu Ala Lys Gly Ile Lys Thr Ser
                180                 185                 190

Gly Lys Val Val Tyr Phe Thr Ala Thr Phe Pro Tyr Val
                195                 200                 205

<210> SEQ ID NO 69
```

```
<211> LENGTH: 615
<212> TYPE: DNA
<213> ORGANISM: Human
<220> FEATURE:
<221> NAME/KEY: CDS
<222> LOCATION: (1)..(615)
<223> OTHER INFORMATION: Seq 34 (C)U - U373MG; nt 679-1293; nt 1256 is A
      not G (consensus)

<400> SEQUENCE: 69 ggt gct ttc ctc atc cct tac ctg atg atg ctg gct ctg gct gga tta         48
Gly Ala Phe Leu Ile Pro Tyr Leu Met Met Leu Ala Leu Ala Gly Leu
  1               5                  10                  15 ccc atc ttc ttc ttg gag gtg tcg ctg ggc cag ttt gcc agc cag gga         96
Pro Ile Phe Phe Leu Glu Val Ser Leu Gly Gln Phe Ala Ser Gln Gly
             20                  25                  30 ccg gtg tct gtg tgg aag gcc atc cca gct cta caa ggc tgt ggc atc        144
Pro Val Ser Val Trp Lys Ala Ile Pro Ala Leu Gln Gly Cys Gly Ile
         35                  40                  45 gcg atg ctg atc atc tct gtc cta ata gcc ata tac tac aat gta att        192
Ala Met Leu Ile Ile Ser Val Leu Ile Ala Ile Tyr Tyr Asn Val Ile
     50                  55                  60 att tgc tat aca ctt ttc tac ctg ttt gcc tcc ttt gtg tct gta cta        240
Ile Cys Tyr Thr Leu Phe Tyr Leu Phe Ala Ser Phe Val Ser Val Leu
 65                  70                  75                  80 ccc tgg ggc tcc tgc aac aac cct tgg aat acg cca gaa tgc aaa gat        288
Pro Trp Gly Ser Cys Asn Asn Pro Trp Asn Thr Pro Glu Cys Lys Asp
                 85                  90                  95 aaa acc aaa ctt tta tta gat tcc tgt gtt atc agt gac cat ccc aaa        336
Lys Thr Lys Leu Leu Leu Asp Ser Cys Val Ile Ser Asp His Pro Lys
            100                 105                 110 ata cag atc aag aac tcg act ttc tgc atg acc gct tat ccc aac gtg        384
Ile Gln Ile Lys Asn Ser Thr Phe Cys Met Thr Ala Tyr Pro Asn Val
        115                 120                 125 aca atg gtt aat ttc acc agc ctg gcc aat aag aca ttt gtc agt gga        432
Thr Met Val Asn Phe Thr Ser Leu Ala Asn Lys Thr Phe Val Ser Gly
    130                 135                 140 agt gaa gag tac ttc aag tac ttt gtg ctg aag att tct gca ggg att        480
Ser Glu Glu Tyr Phe Lys Tyr Phe Val Leu Lys Ile Ser Ala Gly Ile
145                 150                 155                 160 gaa tat cct ggc gag atc agg tgg cca cta gct ctc tgc ctc ttc ctg        528
Glu Tyr Pro Gly Glu Ile Arg Trp Pro Leu Ala Leu Cys Leu Phe Leu
                165                 170                 175 gct tgg gtc att gtg tat gca tcg ttg gct aaa gga atc aag act tca        576
Ala Trp Val Ile Val Tyr Ala Ser Leu Ala Lys Gly Ile Lys Thr Ser
            180                 185                 190 gaa aaa gtg gtg tac ttc acg gcc acg ttc ccg tat gtc                    615
Glu Lys Val Val Tyr Phe Thr Ala Thr Phe Pro Tyr Val
        195                 200                 205

<210> SEQ ID NO 70
<211> LENGTH: 205
<212> TYPE: PRT
<213> ORGANISM: Human

<400> SEQUENCE: 70

Gly Ala Phe Leu Ile Pro Tyr Leu Met Met Leu Ala Leu Ala Gly Leu
  1               5                  10                  15

Pro Ile Phe Phe Leu Glu Val Ser Leu Gly Gln Phe Ala Ser Gln Gly
             20                  25                  30

Pro Val Ser Val Trp Lys Ala Ile Pro Ala Leu Gln Gly Cys Gly Ile
         35                  40                  45
```

-continued

```
Ala Met Leu Ile Ile Ser Val Leu Ile Ala Ile Tyr Tyr Asn Val Ile
        50                  55                  60

Ile Cys Tyr Thr Leu Phe Tyr Leu Phe Ala Ser Phe Val Ser Val Leu
 65                  70                  75                  80

Pro Trp Gly Ser Cys Asn Asn Pro Trp Asn Thr Pro Glu Cys Lys Asp
                 85                  90                  95

Lys Thr Lys Leu Leu Leu Asp Ser Cys Val Ile Ser Asp His Pro Lys
            100                 105                 110

Ile Gln Ile Lys Asn Ser Thr Phe Cys Met Thr Ala Tyr Pro Asn Val
        115                 120                 125

Thr Met Val Asn Phe Thr Ser Leu Ala Asn Lys Thr Phe Val Ser Gly
    130                 135                 140

Ser Glu Glu Tyr Phe Lys Tyr Phe Val Leu Lys Ile Ser Ala Gly Ile
145                 150                 155                 160

Glu Tyr Pro Gly Glu Ile Arg Trp Pro Leu Ala Leu Cys Leu Phe Leu
                165                 170                 175

Ala Trp Val Ile Val Tyr Ala Ser Leu Ala Lys Gly Ile Lys Thr Ser
            180                 185                 190

Glu Lys Val Val Tyr Phe Thr Ala Thr Phe Pro Tyr Val
        195                 200                 205

<210> SEQ ID NO 71
<211> LENGTH: 755
<212> TYPE: DNA
<213> ORGANISM: Human
<220> FEATURE:
<221> NAME/KEY: CDS
<222> LOCATION: (1)..(753)
<223> OTHER INFORMATION: Seq 5(D)S1 - HSpC1; nt 1264-2018

<400> SEQUENCE: 71 gtg tat ttt acc gcc acg ttc ccc tac gtg gta cta gtg atc ctc ctc     48
Val Tyr Phe Thr Ala Thr Phe Pro Tyr Val Val Leu Val Ile Leu Leu
 1               5                  10                  15 atc cga gga gtc acc ctg cct gga gct gga gct ggg atc tgg tac ttc     96
Ile Arg Gly Val Thr Leu Pro Gly Ala Gly Ala Gly Ile Trp Tyr Phe
             20                  25                  30 atc aca ccc aag tgg gag aaa ctc acg gat gcc acg gtg tgg aaa gat    144
Ile Thr Pro Lys Trp Glu Lys Leu Thr Asp Ala Thr Val Trp Lys Asp
         35                  40                  45 gct gcc act cag att ttc ttc tct tta tct gct gca tgg gga ggc ctg    192
Ala Ala Thr Gln Ile Phe Phe Ser Leu Ser Ala Ala Trp Gly Gly Leu
     50                  55                  60 atc act ctc tct tct tac aac aaa ttc cac aac aac tgc tac agg gac    240
Ile Thr Leu Ser Ser Tyr Asn Lys Phe His Asn Asn Cys Tyr Arg Asp
 65                  70                  75                  80 act cta att gtc acc tgc acc aac agt gcc aca agc atc ttt gcc ggc    288
Thr Leu Ile Val Thr Cys Thr Asn Ser Ala Thr Ser Ile Phe Ala Gly
             85                  90                  95 ttc gtc atc ttc tcc gtt atc ggc ttc atg gcc aat gaa cgc aaa gtc    336
Phe Val Ile Phe Ser Val Ile Gly Phe Met Ala Asn Glu Arg Lys Val
            100                 105                 110 aac att gag aat gtg gct gac caa ggg cca ggc att gca ttt gtg gtt    384
Asn Ile Glu Asn Val Ala Asp Gln Gly Pro Gly Ile Ala Phe Val Val
        115                 120                 125 tac ccg gaa gcc tta acc agg ctg cct ctc tct ccg ttc tgg gcc atc    432
Tyr Pro Glu Ala Leu Thr Arg Leu Pro Leu Ser Pro Phe Trp Ala Ile
    130                 135                 140
```

```
atc ttt ttc ctg atg ctc ctc act ctt gga ctt gac act atg ttt gcc    480
Ile Phe Phe Leu Met Leu Leu Thr Leu Gly Leu Asp Thr Met Phe Ala
145                 150                 155                 160 tcc atc gag acc ata gtg acc tcc atc tca gac gag ttt ccc aag tac    528
Ser Ile Glu Thr Ile Val Thr Ser Ile Ser Asp Glu Phe Pro Lys Tyr
                165                 170                 175 cta cgc aca cac aag cca gtg ttt act ctg ggc tgc tgc att tgt ttc    576
Leu Arg Thr His Lys Pro Val Phe Thr Leu Gly Cys Cys Ile Cys Phe
            180                 185                 190 ttc atc atg ggt ttt cca atg atc act cag ggt gga att tac atg ttt    624
Phe Ile Met Gly Phe Pro Met Ile Thr Gln Gly Gly Ile Tyr Met Phe
        195                 200                 205 cag ctt gtg gac acc tat gct gcc tcc tat gcc ctt gtc atc att gcc    672
Gln Leu Val Asp Thr Tyr Ala Ala Ser Tyr Ala Leu Val Ile Ile Ala
    210                 215                 220 att ttt gag ctc gtg ggg atc tct tat gtg tat ggc ttg caa aga ttc    720
Ile Phe Glu Leu Val Gly Ile Ser Tyr Val Tyr Gly Leu Gln Arg Phe
225                 230                 235                 240 tgt gaa gat ata gag atg atg att gga ttc cag cc                     755
Cys Glu Asp Ile Glu Met Met Ile Gly Phe Gln
                245                 250
```

<210> SEQ ID NO 72
<211> LENGTH: 251
<212> TYPE: PRT
<213> ORGANISM: Human

<400> SEQUENCE: 72

```
Val Tyr Phe Thr Ala Thr Phe Pro Tyr Val Val Leu Val Ile Leu Leu
 1               5                  10                  15

Ile Arg Gly Val Thr Leu Pro Gly Ala Gly Ala Gly Ile Trp Tyr Phe
                20                  25                  30

Ile Thr Pro Lys Trp Glu Lys Leu Thr Asp Ala Thr Val Trp Lys Asp
            35                  40                  45

Ala Ala Thr Gln Ile Phe Phe Ser Leu Ser Ala Ala Trp Gly Gly Leu
        50                  55                  60

Ile Thr Leu Ser Ser Tyr Asn Lys Phe His Asn Asn Cys Tyr Arg Asp
 65                  70                  75                  80

Thr Leu Ile Val Thr Cys Thr Asn Ser Ala Thr Ser Ile Phe Ala Gly
                85                  90                  95

Phe Val Ile Phe Ser Val Ile Gly Phe Met Ala Asn Glu Arg Lys Val
                100                 105                 110

Asn Ile Glu Asn Val Ala Asp Gln Gly Pro Gly Ile Ala Phe Val Val
            115                 120                 125

Tyr Pro Glu Ala Leu Thr Arg Leu Pro Leu Ser Pro Phe Trp Ala Ile
        130                 135                 140

Ile Phe Phe Leu Met Leu Leu Thr Leu Gly Leu Asp Thr Met Phe Ala
145                 150                 155                 160

Ser Ile Glu Thr Ile Val Thr Ser Ile Ser Asp Glu Phe Pro Lys Tyr
                165                 170                 175

Leu Arg Thr His Lys Pro Val Phe Thr Leu Gly Cys Cys Ile Cys Phe
            180                 185                 190

Phe Ile Met Gly Phe Pro Met Ile Thr Gln Gly Gly Ile Tyr Met Phe
        195                 200                 205

Gln Leu Val Asp Thr Tyr Ala Ala Ser Tyr Ala Leu Val Ile Ile Ala
    210                 215                 220

Ile Phe Glu Leu Val Gly Ile Ser Tyr Val Tyr Gly Leu Gln Arg Phe
```

-continued

```
225                 230                 235                 240
Cys Glu Asp Ile Glu Met Met Ile Gly Phe Gln
                245                 250

<210> SEQ ID NO 73
<211> LENGTH: 755
<212> TYPE: DNA
<213> ORGANISM: Human
<220> FEATURE:
<221> NAME/KEY: CDS
<222> LOCATION: (1)..(753)
<223> OTHER INFORMATION: Seq 35 (D)S2 - HSpC-2; nt 1264-2018; nt 1299
      is C not A (consensus); nt 1325 is A not C (consensus); nt 1364 is
      A not C (consensus); nt 1374 is C not G (consensus); nt 1392 is A
      not C (consensus);
<220> FEATURE:
<223> OTHER INFORMATION: nt 1454 is C not T (consensus); nt 1478 is G
      not A (consensus); nt 1617 is A not T (consensus); nt 1744 is A
      not T (consensus); nt 1854 is C not T (consensus)

<400> SEQUENCE: 73 gtg tac ttc acg gcc acg ttc ccg tat gtc gta ctc gtg atc ctc ctc        48
Val Tyr Phe Thr Ala Thr Phe Pro Tyr Val Val Leu Val Ile Leu Leu
  1               5                  10                  15 atc cga gga gtc aac ctg cct gga gct gga gct ggg atc tgg tac ttc        96
Ile Arg Gly Val Asn Leu Pro Gly Ala Gly Ala Gly Ile Trp Tyr Phe
             20                  25                  30 atc aaa ccc aag tgc gag aaa ctc acg gat gca acg gtg tgg aaa gat       144
Ile Lys Pro Lys Cys Glu Lys Leu Thr Asp Ala Thr Val Trp Lys Asp
         35                  40                  45 gct gcc act cag att ttc ttc tct tta tct gct gca tgg gga ggc ccg       192
Ala Ala Thr Gln Ile Phe Phe Ser Leu Ser Ala Ala Trp Gly Gly Pro
     50                  55                  60 atc act ctc tct tct tac aac aga ttc cac aac aac tgc tac agg gac       240
Ile Thr Leu Ser Ser Tyr Asn Arg Phe His Asn Asn Cys Tyr Arg Asp
 65                  70                  75                  80 act cta att gtc acc tgc acc aac agt gcc aca agc atc ttt gcc ggc       288
Thr Leu Ile Val Thr Cys Thr Asn Ser Ala Thr Ser Ile Phe Ala Gly
                 85                  90                  95 ttc gtc atc ttc tcc gtt atc ggc ttc atg gcc aat gaa cgc aaa gtc       336
Phe Val Ile Phe Ser Val Ile Gly Phe Met Ala Asn Glu Arg Lys Val
            100                 105                 110 aac att gag aat gtg gca gac caa ggg cca ggc att gca ttt gtg gtt       384
Asn Ile Glu Asn Val Ala Asp Gln Gly Pro Gly Ile Ala Phe Val Val
        115                 120                 125 tac ccg gaa gcc tta acc agg ctg cct ctc tct ccg ttc tgg gcc atc       432
Tyr Pro Glu Ala Leu Thr Arg Leu Pro Leu Ser Pro Phe Trp Ala Ile
    130                 135                 140 atc ttt ttc ctg atg ctc ctc act ctt gga ctt gac act atg ttt gcc       480
Ile Phe Phe Leu Met Leu Leu Thr Leu Gly Leu Asp Thr Met Phe Ala
145                 150                 155                 160 acc atc gag acc ata gtg acc tcc atc tca gac gag ttt ccc aag tac       528
Thr Ile Glu Thr Ile Val Thr Ser Ile Ser Asp Glu Phe Pro Lys Tyr
                165                 170                 175 cta cgc aca cac aag cca gtg ttt act ctg ggc tgc tgc att tgt ttc       576
Leu Arg Thr His Lys Pro Val Phe Thr Leu Gly Cys Cys Ile Cys Phe
            180                 185                 190 ttc atc atg ggt ttc cca atg atc act cag ggt gga att tac atg ttt       624
Phe Ile Met Gly Phe Pro Met Ile Thr Gln Gly Gly Ile Tyr Met Phe
        195                 200                 205 cag ctt gtg gac acc tat gct gcc tcc tat gcc ctt gtc atc att gcc       672
Gln Leu Val Asp Thr Tyr Ala Ala Ser Tyr Ala Leu Val Ile Ile Ala
    210                 215                 220
```

```
att ttt gag ctc gtg ggg atc tct tat gtg tat ggc ttg caa aga ttc         720
Ile Phe Glu Leu Val Gly Ile Ser Tyr Val Tyr Gly Leu Gln Arg Phe
225             230                 235                 240 tgt gaa gat ata gag atg atg att gga ttc cag cc                          755
Cys Glu Asp Ile Glu Met Met Ile Gly Phe Gln
                245                 250
```

<210> SEQ ID NO 74
<211> LENGTH: 251
<212> TYPE: PRT
<213> ORGANISM: Human

<400> SEQUENCE: 74

```
Val Tyr Phe Thr Ala Thr Phe Pro Tyr Val Val Leu Val Ile Leu Leu
 1               5                  10                  15

Ile Arg Gly Val Asn Leu Pro Gly Ala Gly Ala Gly Ile Trp Tyr Phe
                20                  25                  30

Ile Lys Pro Lys Cys Glu Lys Leu Thr Asp Ala Thr Val Trp Lys Asp
            35                  40                  45

Ala Ala Thr Gln Ile Phe Phe Ser Leu Ser Ala Ala Trp Gly Gly Pro
        50                  55                  60

Ile Thr Leu Ser Ser Tyr Asn Arg Phe His Asn Asn Cys Tyr Arg Asp
 65                 70                  75                  80

Thr Leu Ile Val Thr Cys Thr Asn Ser Ala Thr Ser Ile Phe Ala Gly
                85                  90                  95

Phe Val Ile Phe Ser Val Ile Gly Phe Met Ala Asn Glu Arg Lys Val
            100                 105                 110

Asn Ile Glu Asn Val Ala Asp Gln Gly Pro Gly Ile Ala Phe Val Val
        115                 120                 125

Tyr Pro Glu Ala Leu Thr Arg Leu Pro Leu Ser Pro Phe Trp Ala Ile
    130                 135                 140

Ile Phe Phe Leu Met Leu Leu Thr Leu Gly Leu Asp Thr Met Phe Ala
145                 150                 155                 160

Thr Ile Glu Thr Ile Val Thr Ser Ile Ser Asp Glu Phe Pro Lys Tyr
                165                 170                 175

Leu Arg Thr His Lys Pro Val Phe Thr Leu Gly Cys Cys Ile Cys Phe
            180                 185                 190

Phe Ile Met Gly Phe Pro Met Ile Thr Gln Gly Gly Ile Tyr Met Phe
        195                 200                 205

Gln Leu Val Asp Thr Tyr Ala Ala Ser Tyr Ala Leu Val Ile Ile Ala
    210                 215                 220

Ile Phe Glu Leu Val Gly Ile Ser Tyr Val Tyr Gly Leu Gln Arg Phe
225                 230                 235                 240

Cys Glu Asp Ile Glu Met Met Ile Gly Phe Gln
                245                 250
```

<210> SEQ ID NO 75
<211> LENGTH: 755
<212> TYPE: DNA
<213> ORGANISM: Human
<220> FEATURE:
<221> NAME/KEY: CDS
<222> LOCATION: (1)..(753)
<223> OTHER INFORMATION: Seq 36(D)S3 - HSpC-3; nt 1264-2018; nt 1292 is
      C not T (consensus)

<400> SEQUENCE: 75

```
gtg tac ttc acg gcc acg ttc ccg tat gcc gta cta gtg atc ctc ctc         48
```

```
                                                               -continued

Val Tyr Phe Thr Ala Thr Phe Pro Tyr Ala Val Leu Val Ile Leu Leu
 1               5                  10                  15 atc cga gga gtc acc ctg cct gga gct gga gct ggg atc tgg tac ttc      96
Ile Arg Gly Val Thr Leu Pro Gly Ala Gly Ala Gly Ile Trp Tyr Phe
                 20                  25                  30 atc aca ccc aag tgg gag aaa ctc acg gat gcc acg gtg tgg aaa gat     144
Ile Thr Pro Lys Trp Glu Lys Leu Thr Asp Ala Thr Val Trp Lys Asp
             35                  40                  45 gct gcc act cag att ttc ttc tct tta tct gct gca tgg gga ggc ctg     192
Ala Ala Thr Gln Ile Phe Phe Ser Leu Ser Ala Ala Trp Gly Gly Leu
         50                  55                  60 atc act ctc tct tct tac aac aaa ttc cac aac aac tgc tac agg gac     240
Ile Thr Leu Ser Ser Tyr Asn Lys Phe His Asn Asn Cys Tyr Arg Asp
 65                  70                  75                  80 act cta att gtc acc tgc acc aac agt gcc aca agc atc ttt gcc ggc     288
Thr Leu Ile Val Thr Cys Thr Asn Ser Ala Thr Ser Ile Phe Ala Gly
                 85                  90                  95 ttc gtc atc ttc tcc gtt atc ggc ttc atg gcc aat gaa cgc aaa gtc     336
Phe Val Ile Phe Ser Val Ile Gly Phe Met Ala Asn Glu Arg Lys Val
            100                 105                 110 aac att gag aat gtg gct gac caa ggg cca ggc att gca ttt gtg gtt     384
Asn Ile Glu Asn Val Ala Asp Gln Gly Pro Gly Ile Ala Phe Val Val
        115                 120                 125 tac ccg gaa gcc tta acc agg ctg cct ctc tct ccg ttc tgg gcc atc     432
Tyr Pro Glu Ala Leu Thr Arg Leu Pro Leu Ser Pro Phe Trp Ala Ile
    130                 135                 140 atc ttt ttc ctg atg ctc ctc act ctt gga ctt gac act atg ttt gcc     480
Ile Phe Phe Leu Met Leu Leu Thr Leu Gly Leu Asp Thr Met Phe Ala
145                 150                 155                 160 tcc atc gag acc ata gtg acc tcc atc tca gac gag ttt ccc aag tac     528
Ser Ile Glu Thr Ile Val Thr Ser Ile Ser Asp Glu Phe Pro Lys Tyr
                165                 170                 175 cta cgc aca cac aag cca gtg ttt act ctg ggc tgc tgc att tgt ttc     576
Leu Arg Thr His Lys Pro Val Phe Thr Leu Gly Cys Cys Ile Cys Phe
            180                 185                 190 ttc atc atg ggt ttt cca atg atc act cag ggt gga att tac atg ttt     624
Phe Ile Met Gly Phe Pro Met Ile Thr Gln Gly Gly Ile Tyr Met Phe
        195                 200                 205 cag ctt gtg gac acc tat gct gcc tcc tat gcc ctt gtc atc att gcc     672
Gln Leu Val Asp Thr Tyr Ala Ala Ser Tyr Ala Leu Val Ile Ile Ala
    210                 215                 220 att ttt gag ctc gtg ggg atc tct tat gtg tat ggc ttg caa aga ttc     720
Ile Phe Glu Leu Val Gly Ile Ser Tyr Val Tyr Gly Leu Gln Arg Phe
225                 230                 235                 240 tgt gaa gat ata gag atg atg att gga ttc cag cc                      755
Cys Glu Asp Ile Glu Met Met Ile Gly Phe Gln
                245                 250

<210> SEQ ID NO 76
<211> LENGTH: 251
<212> TYPE: PRT
<213> ORGANISM: Human

<400> SEQUENCE: 76

Val Tyr Phe Thr Ala Thr Phe Pro Tyr Ala Val Leu Val Ile Leu Leu
 1               5                  10                  15

Ile Arg Gly Val Thr Leu Pro Gly Ala Gly Ala Gly Ile Trp Tyr Phe
                 20                  25                  30

Ile Thr Pro Lys Trp Glu Lys Leu Thr Asp Ala Thr Val Trp Lys Asp
             35                  40                  45
```

```
Ala Ala Thr Gln Ile Phe Phe Ser Leu Ser Ala Ala Trp Gly Gly Leu
         50                  55                  60

Ile Thr Leu Ser Ser Tyr Asn Lys Phe His Asn Asn Cys Tyr Arg Asp
 65                  70                  75                  80

Thr Leu Ile Val Thr Cys Thr Asn Ser Ala Thr Ser Ile Phe Ala Gly
                 85                  90                  95

Phe Val Ile Phe Ser Val Ile Gly Phe Met Ala Asn Glu Arg Lys Val
             100                 105                 110

Asn Ile Glu Asn Val Ala Asp Gln Gly Pro Gly Ile Ala Phe Val Val
         115                 120                 125

Tyr Pro Glu Ala Leu Thr Arg Leu Pro Leu Ser Pro Phe Trp Ala Ile
     130                 135                 140

Ile Phe Phe Leu Met Leu Leu Thr Leu Gly Leu Asp Thr Met Phe Ala
145                 150                 155                 160

Ser Ile Glu Thr Ile Val Thr Ser Ile Ser Asp Glu Phe Pro Lys Tyr
                 165                 170                 175

Leu Arg Thr His Lys Pro Val Phe Thr Leu Gly Cys Cys Ile Cys Phe
             180                 185                 190

Phe Ile Met Gly Phe Pro Met Ile Thr Gln Gly Gly Ile Tyr Met Phe
         195                 200                 205

Gln Leu Val Asp Thr Tyr Ala Ala Ser Tyr Ala Leu Val Ile Ile Ala
     210                 215                 220

Ile Phe Glu Leu Val Gly Ile Ser Tyr Val Tyr Gly Leu Gln Arg Phe
225                 230                 235                 240

Cys Glu Asp Ile Glu Met Met Ile Gly Phe Gln
                 245                 250

<210> SEQ ID NO 77
<211> LENGTH: 755
<212> TYPE: DNA
<213> ORGANISM: Human
<220> FEATURE:
<221> NAME/KEY: CDS
<222> LOCATION: (1)..(753)
<223> OTHER INFORMATION: Seq 37(D)S3 - HSpC-3; nt 1264-2018; nt 1292 is
      C not T (consensus); nt 1454 is C not T (consensus)

<400> SEQUENCE: 77 gtg tac ttc acg gcc acg ttc ccg tat gcc gta cta gtg atc ctc ctc      48
Val Tyr Phe Thr Ala Thr Phe Pro Tyr Ala Val Leu Val Ile Leu Leu
 1               5                  10                  15 atc cga gga gtc acc ctg cct gga gct gga gct ggg atc tgg tac ttc      96
Ile Arg Gly Val Thr Leu Pro Gly Ala Gly Ala Gly Ile Trp Tyr Phe
             20                  25                  30 atc aca ccc aag tgg gag aaa ctc acg gat gcc acg gtg tgg aaa gat     144
Ile Thr Pro Lys Trp Glu Lys Leu Thr Asp Ala Thr Val Trp Lys Asp
         35                  40                  45 gct gcc act cag att ttc ttc tct tta tct gct gca tgg gga ggc ccg     192
Ala Ala Thr Gln Ile Phe Phe Ser Leu Ser Ala Ala Trp Gly Gly Pro
     50                  55                  60 atc act ctc tct tct tac aac aaa ttc cac aac aac tgc tac agg gac     240
Ile Thr Leu Ser Ser Tyr Asn Lys Phe His Asn Asn Cys Tyr Arg Asp
 65                  70                  75                  80 act cta att gtc acc tgc acc aac agt gcc aca agc atc ttt gcc ggc     288
Thr Leu Ile Val Thr Cys Thr Asn Ser Ala Thr Ser Ile Phe Ala Gly
                 85                  90                  95 ttc gtc atc ttc tcc gtt atc ggc ttc atg gcc aat gaa cgc aaa gtc     336
Phe Val Ile Phe Ser Val Ile Gly Phe Met Ala Asn Glu Arg Lys Val
             100                 105                 110
```

```
aac att gag aat gtg gct gac caa ggg cca ggc att gca ttt gtg gtt        384
Asn Ile Glu Asn Val Ala Asp Gln Gly Pro Gly Ile Ala Phe Val Val
            115                 120                 125 tac ccg gaa gcc tta acc agg ctg cct ctc tct ccg ttc tgg gcc atc        432
Tyr Pro Glu Ala Leu Thr Arg Leu Pro Leu Ser Pro Phe Trp Ala Ile
130                 135                 140 atc ttt ttc ctg atg ctc ctc act ctt gga ctt gac act atg ttt gcc        480
Ile Phe Phe Leu Met Leu Leu Thr Leu Gly Leu Asp Thr Met Phe Ala
145                 150                 155                 160 tcc atc gag acc ata gtg acc tcc atc tca gac gag ttt ccc aag tac        528
Ser Ile Glu Thr Ile Val Thr Ser Ile Ser Asp Glu Phe Pro Lys Tyr
            165                 170                 175 cta cgc aca cac aag cca gtg ttt act ctg ggc tgc tgc att tgt ttc        576
Leu Arg Thr His Lys Pro Val Phe Thr Leu Gly Cys Cys Ile Cys Phe
            180                 185                 190 ttc atc atg ggt ttt cca atc act cag ggt gga att tac atg ttt            624
Phe Ile Met Gly Phe Pro Met Ile Thr Gln Gly Gly Ile Tyr Met Phe
            195                 200                 205 cag ctt gtg gac acc tat gct gcc tcc tat gcc ctt gtc atc att gcc        672
Gln Leu Val Asp Thr Tyr Ala Ala Ser Tyr Ala Leu Val Ile Ile Ala
            210                 215                 220 att ttt gag ctc gtg ggg atc tct tat gtg tat ggc ttg caa aga ttc        720
Ile Phe Glu Leu Val Gly Ile Ser Tyr Val Tyr Gly Leu Gln Arg Phe
225                 230                 235                 240 tgt gaa gat ata gag atg atg att gga ttc cag cc                         755
Cys Glu Asp Ile Glu Met Met Ile Gly Phe Gln
                    245                 250

<210> SEQ ID NO 78
<211> LENGTH: 251
<212> TYPE: PRT
<213> ORGANISM: Human

<400> SEQUENCE: 78

Val Tyr Phe Thr Ala Thr Phe Pro Tyr Ala Val Leu Val Ile Leu Leu
 1               5                  10                  15

Ile Arg Gly Val Thr Leu Pro Gly Ala Gly Ala Gly Ile Trp Tyr Phe
                20                  25                  30

Ile Thr Pro Lys Trp Glu Lys Leu Thr Asp Ala Thr Val Trp Lys Asp
            35                  40                  45

Ala Ala Thr Gln Ile Phe Phe Ser Leu Ser Ala Ala Trp Gly Gly Pro
        50                  55                  60

Ile Thr Leu Ser Ser Tyr Asn Lys Phe His Asn Asn Cys Tyr Arg Asp
 65                 70                  75                  80

Thr Leu Ile Val Thr Cys Thr Asn Ser Ala Thr Ser Ile Phe Ala Gly
                85                  90                  95

Phe Val Ile Phe Ser Val Ile Gly Phe Met Ala Asn Glu Arg Lys Val
                100                 105                 110

Asn Ile Glu Asn Val Ala Asp Gln Gly Pro Gly Ile Ala Phe Val Val
            115                 120                 125

Tyr Pro Glu Ala Leu Thr Arg Leu Pro Leu Ser Pro Phe Trp Ala Ile
        130                 135                 140

Ile Phe Phe Leu Met Leu Leu Thr Leu Gly Leu Asp Thr Met Phe Ala
145                 150                 155                 160

Ser Ile Glu Thr Ile Val Thr Ser Ile Ser Asp Glu Phe Pro Lys Tyr
                165                 170                 175
```

```
Leu Arg Thr His Lys Pro Val Phe Thr Leu Gly Cys Cys Ile Cys Phe
        180                 185                 190

Phe Ile Met Gly Phe Pro Met Ile Thr Gln Gly Gly Ile Tyr Met Phe
            195                 200                 205

Gln Leu Val Asp Thr Tyr Ala Ala Ser Tyr Ala Leu Val Ile Ile Ala
        210                 215                 220

Ile Phe Glu Leu Val Gly Ile Ser Tyr Val Tyr Gly Leu Gln Arg Phe
225                 230                 235                 240

Cys Glu Asp Ile Glu Met Met Ile Gly Phe Gln
            245                 250

<210> SEQ ID NO 79
<211> LENGTH: 755
<212> TYPE: DNA
<213> ORGANISM: Human
<220> FEATURE:
<221> NAME/KEY: CDS
<222> LOCATION: (1)..(753)
<223> OTHER INFORMATION: Seq 38(D)S3 - HSpC-3; nt 1264-2018; nt 1292 is
      C not T (consensus)

<400> SEQUENCE: 79 gtg tac ttc acg gcc acg ttc ccg tat gcc gta cta gtg atc ctc ctc      48
Val Tyr Phe Thr Ala Thr Phe Pro Tyr Ala Val Leu Val Ile Leu Leu
 1               5                  10                  15 atc cga gga gtc acc ctg cct gga gct gga gct ggg atc tgg tac ttc      96
Ile Arg Gly Val Thr Leu Pro Gly Ala Gly Ala Gly Ile Trp Tyr Phe
            20                  25                  30 atc aca ccc aag tgc gag aaa ctc acg gat gcc acg gtg tgg aaa gat     144
Ile Thr Pro Lys Cys Glu Lys Leu Thr Asp Ala Thr Val Trp Lys Asp
        35                  40                  45 gct gcc act cag att ttc ttc tct tta tct gct gca tgg gga ggc ctg     192
Ala Ala Thr Gln Ile Phe Phe Ser Leu Ser Ala Ala Trp Gly Gly Leu
    50                  55                  60 atc act ctc tct tct tac aac aaa ttc cac aac aac tgc tac agg gac     240
Ile Thr Leu Ser Ser Tyr Asn Lys Phe His Asn Asn Cys Tyr Arg Asp
65                  70                  75                  80 act cta att gtc acc tgc acc aac agt gcc aca agc atc ttt gcc ggc     288
Thr Leu Ile Val Thr Cys Thr Asn Ser Ala Thr Ser Ile Phe Ala Gly
                85                  90                  95 ttc gtc atc ttc tcc gtt atc ggc ttc atg gcc aat gaa cgc aaa gtc     336
Phe Val Ile Phe Ser Val Ile Gly Phe Met Ala Asn Glu Arg Lys Val
            100                 105                 110 aac att gag aat gtg gct gac caa ggg cca ggc att gca ttt gtg gtt     384
Asn Ile Glu Asn Val Ala Asp Gln Gly Pro Gly Ile Ala Phe Val Val
        115                 120                 125 tac ccg gaa gcc tta acc agg ctg cct ctc tct ccg ttc tgg gcc atc     432
Tyr Pro Glu Ala Leu Thr Arg Leu Pro Leu Ser Pro Phe Trp Ala Ile
    130                 135                 140 atc ttt ttc ctg atg ctc ctc act ctt gga ctt gac act atg ttt gcc     480
Ile Phe Phe Leu Met Leu Leu Thr Leu Gly Leu Asp Thr Met Phe Ala
145                 150                 155                 160 tcc atc gag acc ata gtg acc tcc atc tca gac gag ttt ccc aag tac     528
Ser Ile Glu Thr Ile Val Thr Ser Ile Ser Asp Glu Phe Pro Lys Tyr
                165                 170                 175 cta cgc aca cac aag cca gtg ttt act ctg ggc tgc tgc att tgt ttc     576
Leu Arg Thr His Lys Pro Val Phe Thr Leu Gly Cys Cys Ile Cys Phe
            180                 185                 190 ttc atc atg ggt ttt cca atg atc act cag ggt gga att tac atg ttt     624
Phe Ile Met Gly Phe Pro Met Ile Thr Gln Gly Gly Ile Tyr Met Phe
        195                 200                 205
```

```
cag ctt gtg gac acc tat gct gcc tcc tat gcc ctt gtc atc att gcc      672
Gln Leu Val Asp Thr Tyr Ala Ala Ser Tyr Ala Leu Val Ile Ile Ala
    210                 215                 220 att ttt gag ctc gtg ggg atc tct tat gtg tat ggc ttg caa aga ttc      720
Ile Phe Glu Leu Val Gly Ile Ser Tyr Val Tyr Gly Leu Gln Arg Phe
225                 230                 235                 240 tgt gaa gat ata gag atg atg att gga ttc cag cc                       755
Cys Glu Asp Ile Glu Met Met Ile Gly Phe Gln
                245                 250
```

<210> SEQ ID NO 80
<211> LENGTH: 251
<212> TYPE: PRT
<213> ORGANISM: Human

<400> SEQUENCE: 80

```
Val Tyr Phe Thr Ala Thr Phe Pro Tyr Ala Val Leu Val Ile Leu Leu
  1               5                  10                  15

Ile Arg Gly Val Thr Leu Pro Gly Ala Gly Ala Gly Ile Trp Tyr Phe
                 20                  25                  30

Ile Thr Pro Lys Cys Glu Lys Leu Thr Asp Ala Thr Val Trp Lys Asp
             35                  40                  45

Ala Ala Thr Gln Ile Phe Phe Ser Leu Ser Ala Ala Trp Gly Gly Leu
         50                  55                  60

Ile Thr Leu Ser Ser Tyr Asn Lys Phe His Asn Asn Cys Tyr Arg Asp
 65                  70                  75                  80

Thr Leu Ile Val Thr Cys Thr Asn Ser Ala Thr Ser Ile Phe Ala Gly
                 85                  90                  95

Phe Val Ile Phe Ser Val Ile Gly Phe Met Ala Asn Glu Arg Lys Val
                100                 105                 110

Asn Ile Glu Asn Val Ala Asp Gln Gly Pro Gly Ile Ala Phe Val Val
            115                 120                 125

Tyr Pro Glu Ala Leu Thr Arg Leu Pro Leu Ser Pro Phe Trp Ala Ile
        130                 135                 140

Ile Phe Phe Leu Met Leu Leu Thr Leu Gly Leu Asp Thr Met Phe Ala
145                 150                 155                 160

Ser Ile Glu Thr Ile Val Thr Ser Ile Ser Asp Glu Phe Pro Lys Tyr
                165                 170                 175

Leu Arg Thr His Lys Pro Val Phe Thr Leu Gly Cys Cys Ile Cys Phe
                180                 185                 190

Phe Ile Met Gly Phe Pro Met Ile Thr Gln Gly Gly Ile Tyr Met Phe
            195                 200                 205

Gln Leu Val Asp Thr Tyr Ala Ala Ser Tyr Ala Leu Val Ile Ile Ala
    210                 215                 220

Ile Phe Glu Leu Val Gly Ile Ser Tyr Val Tyr Gly Leu Gln Arg Phe
225                 230                 235                 240

Cys Glu Asp Ile Glu Met Met Ile Gly Phe Gln
                245                 250
```

<210> SEQ ID NO 81
<211> LENGTH: 755
<212> TYPE: DNA
<213> ORGANISM: Human
<220> FEATURE:
<221> NAME/KEY: CDS
<222> LOCATION: (1)..(753)
<223> OTHER INFORMATION: Seq 39(D)U - U373MG; nt 1264-2018; nt 1292 is
      C not T (consensus); nt 1392 is A not C (consensus)

<400> SEQUENCE: 81

```
gtg tac ttc acg gcc acg ttc ccg tat gcc gta cta gtg atc ctc ctc        48
Val Tyr Phe Thr Ala Thr Phe Pro Tyr Ala Val Leu Val Ile Leu Leu
 1               5                  10                  15 atc cga gga gtc acc ctg cct gga gct gga gct ggg atc tgg tac ttc        96
Ile Arg Gly Val Thr Leu Pro Gly Ala Gly Ala Gly Ile Trp Tyr Phe
             20                  25                  30 atc aca ccc aag tgg gag aaa ctc acg gat gca acg gtg tgg aaa gat       144
Ile Thr Pro Lys Trp Glu Lys Leu Thr Asp Ala Thr Val Trp Lys Asp
         35                  40                  45 gct gcc act cag att ttc ttc tct tta tct gct gca tgg gga ggc ctg       192
Ala Ala Thr Gln Ile Phe Phe Ser Leu Ser Ala Ala Trp Gly Gly Leu
     50                  55                  60 atc act ctc tct tct tac aac aaa ttc cac aac aac tgc tac agg gac       240
Ile Thr Leu Ser Ser Tyr Asn Lys Phe His Asn Asn Cys Tyr Arg Asp
 65                  70                  75                  80 act cta att gtc acc tgc acc aac agt gcc aca agc atc ttt gcc ggc       288
Thr Leu Ile Val Thr Cys Thr Asn Ser Ala Thr Ser Ile Phe Ala Gly
                 85                  90                  95 ttc gtc atc ttc tcc gtt atc ggc ttc atg gcc aat gaa cgc aaa gtc       336
Phe Val Ile Phe Ser Val Ile Gly Phe Met Ala Asn Glu Arg Lys Val
            100                 105                 110 aac att gag aat gtg gct gac caa ggg cca ggc att gca ttt gtg gtt       384
Asn Ile Glu Asn Val Ala Asp Gln Gly Pro Gly Ile Ala Phe Val Val
        115                 120                 125 tac ccg gaa gcc tta acc agg ctg cct ctc tct ccg ttc tgg gcc atc       432
Tyr Pro Glu Ala Leu Thr Arg Leu Pro Leu Ser Pro Phe Trp Ala Ile
    130                 135                 140 atc ttt ttc ctg atg ctc ctc act ctt gga ctt gac act atg ttt gcc       480
Ile Phe Phe Leu Met Leu Leu Thr Leu Gly Leu Asp Thr Met Phe Ala
145                 150                 155                 160 tcc atc gag acc ata gtg acc tcc atc tca gac gag ttt ccc aag tac       528
Ser Ile Glu Thr Ile Val Thr Ser Ile Ser Asp Glu Phe Pro Lys Tyr
                165                 170                 175 cta cgc aca cac aag cca gtg ttt act ctg ggc tgc tgc att tgt ttc       576
Leu Arg Thr His Lys Pro Val Phe Thr Leu Gly Cys Cys Ile Cys Phe
            180                 185                 190 ttc atc atg ggt ttt cca atg atc act cag ggt gga att tac atg ttt       624
Phe Ile Met Gly Phe Pro Met Ile Thr Gln Gly Gly Ile Tyr Met Phe
        195                 200                 205 cag ctt gtg gac acc tat gct gcc tcc tat gcc ctt gtc atc att gcc       672
Gln Leu Val Asp Thr Tyr Ala Ala Ser Tyr Ala Leu Val Ile Ile Ala
    210                 215                 220 att ttt gag ctc gtg ggg atc tct tat gtg tat ggc ttg caa aga ttc       720
Ile Phe Glu Leu Val Gly Ile Ser Tyr Val Tyr Gly Leu Gln Arg Phe
225                 230                 235                 240 tgt gaa gat ata gag atg atg att gga ttc cag cc                        755
Cys Glu Asp Ile Glu Met Met Ile Gly Phe Gln
                245                 250
```

<210> SEQ ID NO 82
<211> LENGTH: 251
<212> TYPE: PRT
<213> ORGANISM: Human

<400> SEQUENCE: 82

```
Val Tyr Phe Thr Ala Thr Phe Pro Tyr Ala Val Leu Val Ile Leu Leu
 1               5                  10                  15

Ile Arg Gly Val Thr Leu Pro Gly Ala Gly Ala Gly Ile Trp Tyr Phe
```

```
                    20                  25                  30
Ile Thr Pro Lys Trp Glu Lys Leu Thr Asp Ala Thr Val Trp Lys Asp
             35                  40                  45

Ala Ala Thr Gln Ile Phe Phe Ser Leu Ser Ala Ala Trp Gly Gly Leu
         50                  55                  60

Ile Thr Leu Ser Ser Tyr Asn Lys Phe His Asn Asn Cys Tyr Arg Asp
 65                  70                  75                  80

Thr Leu Ile Val Thr Cys Thr Asn Ser Ala Thr Ser Ile Phe Ala Gly
                 85                  90                  95

Phe Val Ile Phe Ser Val Ile Gly Phe Met Ala Asn Glu Arg Lys Val
            100                 105                 110

Asn Ile Glu Asn Val Ala Asp Gln Gly Pro Gly Ile Ala Phe Val Val
        115                 120                 125

Tyr Pro Glu Ala Leu Thr Arg Leu Pro Leu Ser Pro Phe Trp Ala Ile
    130                 135                 140

Ile Phe Phe Leu Met Leu Leu Thr Leu Gly Leu Asp Thr Met Phe Ala
145                 150                 155                 160

Ser Ile Glu Thr Ile Val Thr Ser Ile Ser Asp Glu Phe Pro Lys Tyr
                165                 170                 175

Leu Arg Thr His Lys Pro Val Phe Thr Leu Gly Cys Cys Ile Cys Phe
            180                 185                 190

Phe Ile Met Gly Phe Pro Met Ile Thr Gln Gly Gly Ile Tyr Met Phe
        195                 200                 205

Gln Leu Val Asp Thr Tyr Ala Ala Ser Tyr Ala Leu Val Ile Ile Ala
    210                 215                 220

Ile Phe Glu Leu Val Gly Ile Ser Tyr Val Tyr Gly Leu Gln Arg Phe
225                 230                 235                 240

Cys Glu Asp Ile Glu Met Met Ile Gly Phe Gln
                245                 250
```

<210> SEQ ID NO 83
<211> LENGTH: 755
<212> TYPE: DNA
<213> ORGANISM: Human
<220> FEATURE:
<221> NAME/KEY: CDS
<222> LOCATION: (1)..(753)
<223> OTHER INFORMATION: Seq 40(D)U - U373MG; nt 1264-2018; nt 1292 is
      C not T (consensus)

<400> SEQUENCE: 83

```
gtg tac ttc acg gcc acg ttc ccg tat gcc gta cta gtg atc ctc ctc      48
Val Tyr Phe Thr Ala Thr Phe Pro Tyr Ala Val Leu Val Ile Leu Leu
 1               5                  10                  15 atc cga gga gtc acc ctg cct gga gct gga gct ggg atc tgg tac ttc      96
Ile Arg Gly Val Thr Leu Pro Gly Ala Gly Ala Gly Ile Trp Tyr Phe
             20                  25                  30 atc aca ccc aag tgg gag aaa ctc acg gat gcc acg gtg tgg aaa gat     144
Ile Thr Pro Lys Trp Glu Lys Leu Thr Asp Ala Thr Val Trp Lys Asp
         35                  40                  45 gct gcc act cag att ttc ttc tct tta tct gct gca tgg gga ggc ctg     192
Ala Ala Thr Gln Ile Phe Phe Ser Leu Ser Ala Ala Trp Gly Gly Leu
     50                  55                  60 atc act ctc tct tct tac aac aaa ttc cac aac aac tgc tac agg gac     240
Ile Thr Leu Ser Ser Tyr Asn Lys Phe His Asn Asn Cys Tyr Arg Asp
 65                  70                  75                  80 act cta att gtc acc tgc acc aac agt gcc aca agc atc ttt gcc ggc     288
Thr Leu Ile Val Thr Cys Thr Asn Ser Ala Thr Ser Ile Phe Ala Gly
```

```
ttc gtc atc ttc tcc gtt atc ggc ttc atg gcc aat gaa cgc aaa gtc      336
Phe Val Ile Phe Ser Val Ile Gly Phe Met Ala Asn Glu Arg Lys Val
            100                 105                 110 aac att gag aat gtg gct gac caa ggg cca ggc att gca ttt gtg gtt      384
Asn Ile Glu Asn Val Ala Asp Gln Gly Pro Gly Ile Ala Phe Val Val
            115                 120                 125 tac ccg gaa gcc tta acc agg ctg cct ctc tct ccg ttc tgg gcc atc      432
Tyr Pro Glu Ala Leu Thr Arg Leu Pro Leu Ser Pro Phe Trp Ala Ile
    130                 135                 140 atc ttt ttc ctg atg ctc ctc act ctt gga ctt gac act atg ttt gcc      480
Ile Phe Phe Leu Met Leu Leu Thr Leu Gly Leu Asp Thr Met Phe Ala
145                 150                 155                 160 tcc atc gag acc ata gtg acc tcc atc tca gac gag ttt ccc aag tac      528
Ser Ile Glu Thr Ile Val Thr Ser Ile Ser Asp Glu Phe Pro Lys Tyr
            165                 170                 175 cta cgc aca cac aag cca gtg ttt act ctg ggc tgc tgc att tgt ttc      576
Leu Arg Thr His Lys Pro Val Phe Thr Leu Gly Cys Cys Ile Cys Phe
            180                 185                 190 ttc atc atg ggt ttt cca atg atc act cag ggt gga att tac atg ttt      624
Phe Ile Met Gly Phe Pro Met Ile Thr Gln Gly Gly Ile Tyr Met Phe
            195                 200                 205 cag ctt gtg gac acc tat gct gcc tcc tat gcc ctt gtc atc att gcc      672
Gln Leu Val Asp Thr Tyr Ala Ala Ser Tyr Ala Leu Val Ile Ile Ala
    210                 215                 220 att ttt gag ctc gtg ggg atc tct tat gtg tat ggc ttg caa aga ttc      720
Ile Phe Glu Leu Val Gly Ile Ser Tyr Val Tyr Gly Leu Gln Arg Phe
225                 230                 235                 240 tgt gaa gat ata gag atg atg att gga ttc cag cc                       755
Cys Glu Asp Ile Glu Met Met Ile Gly Phe Gln
                245                 250

<210> SEQ ID NO 84
<211> LENGTH: 251
<212> TYPE: PRT
<213> ORGANISM: Human

<400> SEQUENCE: 84

Val Tyr Phe Thr Ala Thr Phe Pro Tyr Ala Val Leu Val Ile Leu Leu
  1               5                  10                  15

Ile Arg Gly Val Thr Leu Pro Gly Ala Gly Ala Gly Ile Trp Tyr Phe
                 20                  25                  30

Ile Thr Pro Lys Trp Glu Lys Leu Thr Asp Ala Thr Val Trp Lys Asp
             35                  40                  45

Ala Ala Thr Gln Ile Phe Ser Leu Ser Ala Ala Trp Gly Gly Leu
      50                  55                  60

Ile Thr Leu Ser Ser Tyr Asn Lys Phe His Asn Asn Cys Tyr Arg Asp
 65                  70                  75                  80

Thr Leu Ile Val Thr Cys Thr Asn Ser Ala Thr Ser Ile Phe Ala Gly
                 85                  90                  95

Phe Val Ile Phe Ser Val Ile Gly Phe Met Ala Asn Glu Arg Lys Val
            100                 105                 110

Asn Ile Glu Asn Val Ala Asp Gln Gly Pro Gly Ile Ala Phe Val Val
            115                 120                 125

Tyr Pro Glu Ala Leu Thr Arg Leu Pro Leu Ser Pro Phe Trp Ala Ile
    130                 135                 140

Ile Phe Phe Leu Met Leu Leu Thr Leu Gly Leu Asp Thr Met Phe Ala
145                 150                 155                 160
```

```
Ser Ile Glu Thr Ile Val Thr Ser Ile Ser Asp Glu Phe Pro Lys Tyr
            165                 170                 175

Leu Arg Thr His Lys Pro Val Phe Thr Leu Gly Cys Cys Ile Cys Phe
        180                 185                 190

Phe Ile Met Gly Phe Pro Met Ile Thr Gln Gly Gly Ile Tyr Met Phe
            195                 200                 205

Gln Leu Val Asp Thr Tyr Ala Ala Ser Tyr Ala Leu Val Ile Ile Ala
        210                 215                 220

Ile Phe Glu Leu Val Gly Ile Ser Tyr Val Tyr Gly Leu Gln Arg Phe
225                 230                 235                 240

Cys Glu Asp Ile Glu Met Met Ile Gly Phe Gln
            245                 250
```

<210> SEQ ID NO 85
<211> LENGTH: 755
<212> TYPE: DNA
<213> ORGANISM: Human
<220> FEATURE:
<221> NAME/KEY: CDS
<222> LOCATION: (1)..(753)
<223> OTHER INFORMATION: Seq 41(D)U - U373MG; nt 1264-2018; nt 1292 is
      C not T (consensus)

<400> SEQUENCE: 85

```
gtg tac ttc acg gcc acg ttc ccg tat gcc gta cta gtg atc ctc ctc      48
Val Tyr Phe Thr Ala Thr Phe Pro Tyr Ala Val Leu Val Ile Leu Leu
 1               5                   10                  15 atc cga gga gtc acc ctg cct gga gct gga gct ggg atc tgg tac ttc      96
Ile Arg Gly Val Thr Leu Pro Gly Ala Gly Ala Gly Ile Trp Tyr Phe
             20                  25                  30 atc aca ccc aag tgg gag aaa ctc acg gat gcc acg gtg tgg aaa gat     144
Ile Thr Pro Lys Trp Glu Lys Leu Thr Asp Ala Thr Val Trp Lys Asp
         35                  40                  45 gct gcc act cag att ttc ttc tct tta tct gct gca tgg gga ggc ctg     192
Ala Ala Thr Gln Ile Phe Phe Ser Leu Ser Ala Ala Trp Gly Gly Leu
     50                  55                  60 atc act ctc tct tct tac aac aaa ttc cac aac aac tgc tac agg gac     240
Ile Thr Leu Ser Ser Tyr Asn Lys Phe His Asn Asn Cys Tyr Arg Asp
 65                  70                  75                  80 act cta att gtc acc tgc acc aac agt gcc aca agc atc ttt gcc ggc     288
Thr Leu Ile Val Thr Cys Thr Asn Ser Ala Thr Ser Ile Phe Ala Gly
                 85                  90                  95 ttc gtc atc ttc tcc gtt atc ggc ttc atg gcc aat gaa cgc aaa gtc     336
Phe Val Ile Phe Ser Val Ile Gly Phe Met Ala Asn Glu Arg Lys Val
            100                 105                 110 aac att gag aat gtg gct gac caa ggg cca ggc att gca ttt gtg gtt     384
Asn Ile Glu Asn Val Ala Asp Gln Gly Pro Gly Ile Ala Phe Val Val
        115                 120                 125 tac ccg gaa gcc tta acc agg ctg cct ctc tct ccg ttc tgg gcc atc     432
Tyr Pro Glu Ala Leu Thr Arg Leu Pro Leu Ser Pro Phe Trp Ala Ile
    130                 135                 140 atc ttt ttc ctg atg ctc ctc act ctt gga ctt gac act atg ttt gcc     480
Ile Phe Phe Leu Met Leu Leu Thr Leu Gly Leu Asp Thr Met Phe Ala
145                 150                 155                 160 tcc atc gag acc ata gtg acc tcc atc tca gac gag ttt ccc aag tac     528
Ser Ile Glu Thr Ile Val Thr Ser Ile Ser Asp Glu Phe Pro Lys Tyr
                165                 170                 175 cta cgc aca cac aag cca gtg ttt act ctg ggc tgc tgc att tgt ttc     576
Leu Arg Thr His Lys Pro Val Phe Thr Leu Gly Cys Cys Ile Cys Phe
            180                 185                 190
```

```
ttc atc atg ggt ttt cca atg atc act cag ggt gga att tac atg ttt    624
Phe Ile Met Gly Phe Pro Met Ile Thr Gln Gly Gly Ile Tyr Met Phe
        195                 200                 205 cag ctt gtg gac acc tat gct gcc tcc tat gcc ctt gtc atc att gcc    672
Gln Leu Val Asp Thr Tyr Ala Ala Ser Tyr Ala Leu Val Ile Ile Ala
    210                 215                 220 att ttt gag ctc gtg ggg atc tct tat gtg tat ggc ttg caa aga ttc    720
Ile Phe Glu Leu Val Gly Ile Ser Tyr Val Tyr Gly Leu Gln Arg Phe
225                 230                 235                 240 tgt gaa gat ata gag atg atg att gga ttc cag cc                     755
Cys Glu Asp Ile Glu Met Met Ile Gly Phe Gln
                245                 250
```

<210> SEQ ID NO 86
<211> LENGTH: 251
<212> TYPE: PRT
<213> ORGANISM: Human

<400> SEQUENCE: 86

```
Val Tyr Phe Thr Ala Thr Phe Pro Tyr Ala Val Leu Val Ile Leu Leu
  1               5                  10                  15

Ile Arg Gly Val Thr Leu Pro Gly Ala Gly Ala Gly Ile Trp Tyr Phe
             20                  25                  30

Ile Thr Pro Lys Trp Glu Lys Leu Thr Asp Ala Thr Val Trp Lys Asp
         35                  40                  45

Ala Ala Thr Gln Ile Phe Phe Ser Leu Ser Ala Ala Trp Gly Gly Leu
     50                  55                  60

Ile Thr Leu Ser Ser Tyr Asn Lys Phe His Asn Asn Cys Tyr Arg Asp
 65                  70                  75                  80

Thr Leu Ile Val Thr Cys Thr Asn Ser Ala Thr Ser Ile Phe Ala Gly
                 85                  90                  95

Phe Val Ile Phe Ser Val Ile Gly Phe Met Ala Asn Glu Arg Lys Val
            100                 105                 110

Asn Ile Glu Asn Val Ala Asp Gln Gly Pro Gly Ile Ala Phe Val Val
        115                 120                 125

Tyr Pro Glu Ala Leu Thr Arg Leu Pro Leu Ser Pro Phe Trp Ala Ile
    130                 135                 140

Ile Phe Phe Leu Met Leu Leu Thr Leu Gly Leu Asp Thr Met Phe Ala
145                 150                 155                 160

Ser Ile Glu Thr Ile Val Thr Ser Ile Ser Asp Glu Phe Pro Lys Tyr
                165                 170                 175

Leu Arg Thr His Lys Pro Val Phe Thr Leu Gly Cys Cys Ile Cys Phe
            180                 185                 190

Phe Ile Met Gly Phe Pro Met Ile Thr Gln Gly Gly Ile Tyr Met Phe
        195                 200                 205

Gln Leu Val Asp Thr Tyr Ala Ala Ser Tyr Ala Leu Val Ile Ile Ala
    210                 215                 220

Ile Phe Glu Leu Val Gly Ile Ser Tyr Val Tyr Gly Leu Gln Arg Phe
225                 230                 235                 240

Cys Glu Asp Ile Glu Met Met Ile Gly Phe Gln
                245                 250
```

<210> SEQ ID NO 87
<211> LENGTH: 453
<212> TYPE: DNA
<213> ORGANISM: Human
<220> FEATURE:

```
<221> NAME/KEY: CDS
<222> LOCATION: (1)..(450)
<223> OTHER INFORMATION: Seq 6(E)S1 - HSpC-1; nt 1942-2394

<400> SEQUENCE: 87 gag ctc gtg ggg atc tct tat gtg tat ggc ttg caa aga ttc tgt gaa         48
Glu Leu Val Gly Ile Ser Tyr Val Tyr Gly Leu Gln Arg Phe Cys Glu
 1               5                  10                  15 gat ata gag atg atg att gga ttc cag cct aac atc ttc tgg aaa gtc         96
Asp Ile Glu Met Met Ile Gly Phe Gln Pro Asn Ile Phe Trp Lys Val
                20                  25                  30 tgc tgg gca ttt gta acc cca acc att tta acc ttt atc ctt tgc ttc        144
Cys Trp Ala Phe Val Thr Pro Thr Ile Leu Thr Phe Ile Leu Cys Phe
            35                  40                  45 agc ttt tac cag tgg gaa ccc atg acc tat ggc tct tac cgc tat cct        192
Ser Phe Tyr Gln Trp Glu Pro Met Thr Tyr Gly Ser Tyr Arg Tyr Pro
        50                  55                  60 aac tgg tcc atg gtg ctc gga tgg cta atg ctc gcc tgt tcc gtc atc        240
Asn Trp Ser Met Val Leu Gly Trp Leu Met Leu Ala Cys Ser Val Ile
65                  70                  75                  80 tgg atc cca att atg ttt gtg ata aaa atg cat ctg gcc cct gga aga        288
Trp Ile Pro Ile Met Phe Val Ile Lys Met His Leu Ala Pro Gly Arg
                85                  90                  95 ttt att gag agg ctg aag ttg gtg tgc tcg cca cag ccg gac tgg ggc        336
Phe Ile Glu Arg Leu Lys Leu Val Cys Ser Pro Gln Pro Asp Trp Gly
            100                 105                 110 cca ttc tta gct caa cac cgc ggg gag cgt tac aag aac atg atc gac        384
Pro Phe Leu Ala Gln His Arg Gly Glu Arg Tyr Lys Asn Met Ile Asp
        115                 120                 125 ccc ttg gga acc tct tcc ttg gga ctc aaa ctg cct gtg aag gac ttc        432
Pro Leu Gly Thr Ser Ser Leu Gly Leu Lys Leu Pro Val Lys Asp Phe
    130                 135                 140 gaa ctg ggc acc cag tgc tag                                             453
Glu Leu Gly Thr Gln Cys
145                 150

<210> SEQ ID NO 88

<211> LENGTH:    150
<212> TYPE: PRT
<213> ORGANISM: Human

<400> SEQUENCE: 88

Glu Leu Val Gly Ile Ser Tyr Val Tyr Gly Leu Gln Arg Phe Cys     Glu
 1               5                  10                  15

Asp Ile Glu Met Met Ile Gly Phe Gln Pro Asn Ile Phe Trp Lys     Val
                20                  25                  30

Cys Trp Ala Phe Val Thr Pro Thr Ile Leu Thr Phe Ile Leu Cys     Phe
            35                  40                  45

Ser Phe Tyr Gln Trp Glu Pro Met Thr Tyr Gly Ser Tyr Arg Tyr Pro
        50                  55                  60

Asn Trp Ser Met Val Leu Gly Trp Leu Met Leu Ala Cys Ser Val Ile
65                  70                  75                  80

Trp Ile Pro Ile Met Phe Val Ile Lys Met His Leu Ala Pro Gly Arg
                85                  90                  95

Phe Ile Glu Arg Leu Lys Leu Val Cys Ser Pro Gln Pro Asp Trp Gly
```

|   |   |   | 100 |   |   |   | 105 |   |   |   | 110 |   |
|---|---|---|---|---|---|---|---|---|---|---|---|---|

Pro Phe Leu Ala Gln His Arg Gly Glu Arg Tyr Lys Asn Met Ile Asp
    115                  120                125

Pro Leu Gly Thr Ser Ser Leu Gly Leu Lys Leu Pro Val Lys Asp Phe
   130                  135                140

Glu Leu Gly Thr Gln Cys
145              150

<210> SEQ ID NO 89
<211> LENGTH: 453
<212> TYPE: DNA
<213> ORGANISM: Human
<220> FEATURE:
<221> NAME/KEY: CDS
<222> LOCATION: (1)..(450)
<223> OTHER INFORMATION: Seq 42(E)S2 - HSpC-2; nt 1942-2394; nt 1949 is
     A not T (consensus); nt 1959 is C not T (consensus); nt 2130 is C
     not T (consensus)

<400> SEQUENCE: 89

```
gag ctc gag ggg atc tcc tat gtg tat ggc ttg caa aga ttc tgt gaa      48
Glu Leu Glu Gly Ile Ser Tyr Val Tyr Gly Leu Gln Arg Phe Cys Glu
 1               5                  10                  15 gat ata gag atg atg att gga ttc cag cct aac atc ttc tgg aaa gtc      96
Asp Ile Glu Met Met Ile Gly Phe Gln Pro Asn Ile Phe Trp Lys Val
             20                  25                  30 tgc tgg gca ttt gta acc cca acc att tta acc ttt atc ctt tgc ttc     144
Cys Trp Ala Phe Val Thr Pro Thr Ile Leu Thr Phe Ile Leu Cys Phe
         35                  40                  45 agc ttt tac cag tgg gaa ccc atg acc tat ggc tct tac cgc tac cct     192
Ser Phe Tyr Gln Trp Glu Pro Met Thr Tyr Gly Ser Tyr Arg Tyr Pro
     50                  55                  60 aac tgg tcc atg gtg ctc gga tgg cta atg ctc gcc tgt tcc gtc atc     240
Asn Trp Ser Met Val Leu Gly Trp Leu Met Leu Ala Cys Ser Val Ile
 65                  70                  75                  80 tgg atc cca att atg ttt gtg ata aaa atg cat ctg gcc cct gga aga     288
Trp Ile Pro Ile Met Phe Val Ile Lys Met His Leu Ala Pro Gly Arg
                 85                  90                  95 ttt att gag agg ctg aag ttg gtg tgc tcg cca cag ccg gac tgg ggc     336
Phe Ile Glu Arg Leu Lys Leu Val Cys Ser Pro Gln Pro Asp Trp Gly
            100                 105                 110 cca ttc tta gct caa cac cgc ggg gag cgt tac aag aac atg atc gac     384
Pro Phe Leu Ala Gln His Arg Gly Glu Arg Tyr Lys Asn Met Ile Asp
        115                 120                 125 ccc ttg gga acc tct tcc ttg gga ctc aaa ctg cca gtg aag gat ttg     432
Pro Leu Gly Thr Ser Ser Leu Gly Leu Lys Leu Pro Val Lys Asp Leu
    130                 135                 140 gaa ctg ggc act cag tgc tag                                          453
Glu Leu Gly Thr Gln Cys
145                 150
```

<210> SEQ ID NO 90
<211> LENGTH: 150
<212> TYPE: PRT
<213> ORGANISM: Human

<400> SEQUENCE: 90

Glu Leu Glu Gly Ile Ser Tyr Val Tyr Gly Leu Gln Arg Phe Cys Glu
 1               5                  10                  15

```
Asp Ile Glu Met Met Ile Gly Phe Gln Pro Asn Ile Phe Trp Lys Val
            20                  25                  30

Cys Trp Ala Phe Val Thr Pro Thr Ile Leu Thr Phe Ile Leu Cys Phe
        35                  40                  45

Ser Phe Tyr Gln Trp Glu Pro Met Thr Tyr Gly Ser Tyr Arg Tyr Pro
    50                  55                  60

Asn Trp Ser Met Val Leu Gly Trp Leu Met Leu Ala Cys Ser Val Ile
 65                 70                  75                  80

Trp Ile Pro Ile Met Phe Val Ile Lys Met His Leu Ala Pro Gly Arg
                85                  90                  95

Phe Ile Glu Arg Leu Lys Leu Val Cys Ser Pro Gln Pro Asp Trp Gly
            100                 105                 110

Pro Phe Leu Ala Gln His Arg Gly Glu Arg Tyr Lys Asn Met Ile Asp
        115                 120                 125

Pro Leu Gly Thr Ser Ser Leu Gly Leu Lys Leu Pro Val Lys Asp Leu
    130                 135                 140

Glu Leu Gly Thr Gln Cys
145                 150

<210> SEQ ID NO 91
<211> LENGTH: 453
<212> TYPE: DNA
<213> ORGANISM: Human
<220> FEATURE:
<221> NAME/KEY: CDS
<222> LOCATION: (1)..(450)
<223> OTHER INFORMATION: Seq 43(E)S3 - HSpC-3; nt 1942-2394; nt 1959 is
      C not T (consensus)

<400> SEQUENCE: 91 gag ctc gtg ggg atc tcc tat gtg tat ggc ttg caa aga ttc tgt gaa      48
Glu Leu Val Gly Ile Ser Tyr Val Tyr Gly Leu Gln Arg Phe Cys Glu
  1               5                  10                  15 gat ata gag atg atg att gga ttc cag cct aac atc ttc tgg aaa gtc      96
Asp Ile Glu Met Met Ile Gly Phe Gln Pro Asn Ile Phe Trp Lys Val
             20                  25                  30 tgc tgg gca ttt gta acc cca acc att tta acc ttt atc ctt tgc ttc     144
Cys Trp Ala Phe Val Thr Pro Thr Ile Leu Thr Phe Ile Leu Cys Phe
         35                  40                  45 agc ttt tac cag tgg gaa ccc atg acc tat ggc tct tac cgc tat cct     192
Ser Phe Tyr Gln Trp Glu Pro Met Thr Tyr Gly Ser Tyr Arg Tyr Pro
     50                  55                  60 aac tgg tcc atg gtg ctc gga tgg cta atg ctc gcc tgt tcc gtc atc     240
Asn Trp Ser Met Val Leu Gly Trp Leu Met Leu Ala Cys Ser Val Ile
 65                  70                  75                  80 tgg atc cca att atg ttt gtg ata aaa atg cat ctg gcc cct gga aga     288
Trp Ile Pro Ile Met Phe Val Ile Lys Met His Leu Ala Pro Gly Arg
                 85                  90                  95 ttt att gag agg ctg aag ttg gtg tgc tcg cca cag ccg gac tgg ggc     336
Phe Ile Glu Arg Leu Lys Leu Val Cys Ser Pro Gln Pro Asp Trp Gly
            100                 105                 110 cca ttc tta gct caa cac cgc ggg gag cgt tac aag aac atg atc gac     384
Pro Phe Leu Ala Gln His Arg Gly Glu Arg Tyr Lys Asn Met Ile Asp
        115                 120                 125 ccc ttg gga acc tct tcc ttg gga ctc aaa ctg cca gtg aag gat ttg     432
Pro Leu Gly Thr Ser Ser Leu Gly Leu Lys Leu Pro Val Lys Asp Leu
    130                 135                 140 gaa ctg ggc act cag tgc tag                                         453
Glu Leu Gly Thr Gln Cys
145
```

```
<210> SEQ ID NO 92
<211> LENGTH: 150
<212> TYPE: PRT
<213> ORGANISM: Human

<400> SEQUENCE: 92

Glu Leu Val Gly Ile Ser Tyr Val Tyr Gly Leu Gln Arg Phe Cys Glu
  1               5                  10                  15

Asp Ile Glu Met Met Ile Gly Phe Gln Pro Asn Ile Phe Trp Lys Val
             20                  25                  30

Cys Trp Ala Phe Val Thr Pro Thr Ile Leu Thr Phe Ile Leu Cys Phe
         35                  40                  45

Ser Phe Tyr Gln Trp Glu Pro Met Thr Tyr Gly Ser Tyr Arg Tyr Pro
     50                  55                  60

Asn Trp Ser Met Val Leu Gly Trp Leu Met Leu Ala Cys Ser Val Ile
 65                  70                  75                  80

Trp Ile Pro Ile Met Phe Val Ile Lys Met His Leu Ala Pro Gly Arg
                 85                  90                  95

Phe Ile Glu Arg Leu Lys Leu Val Cys Ser Pro Gln Pro Asp Trp Gly
            100                 105                 110

Pro Phe Leu Ala Gln His Arg Gly Glu Arg Tyr Lys Asn Met Ile Asp
        115                 120                 125

Pro Leu Gly Thr Ser Ser Leu Gly Leu Lys Leu Pro Val Lys Asp Leu
    130                 135                 140

Glu Leu Gly Thr Gln Cys
145                 150

<210> SEQ ID NO 93
<211> LENGTH: 453
<212> TYPE: DNA
<213> ORGANISM: Human
<220> FEATURE:
<221> NAME/KEY: CDS
<222> LOCATION: (1)..(450)
<223> OTHER INFORMATION: Seq 44(E)S3 - HSpC-3; nt 1942-2394

<400> SEQUENCE: 93 gag ctc gtg ggg atc tct tat gtg tat ggc ttg caa aga ttc tgt gaa     48
Glu Leu Val Gly Ile Ser Tyr Val Tyr Gly Leu Gln Arg Phe Cys Glu
  1               5                  10                  15 gat ata gag atg atg att gga ttc cag cct aac atc ttc tgg aaa gtc     96
Asp Ile Glu Met Met Ile Gly Phe Gln Pro Asn Ile Phe Trp Lys Val
             20                  25                  30 tgc tgg gca ttt gta acc cca acc att tta acc ttt atc ctt tgc ttc    144
Cys Trp Ala Phe Val Thr Pro Thr Ile Leu Thr Phe Ile Leu Cys Phe
         35                  40                  45 agc ttt tac cag tgg gaa ccc atg acc tat ggc tct tac cgc tat cct    192
Ser Phe Tyr Gln Trp Glu Pro Met Thr Tyr Gly Ser Tyr Arg Tyr Pro
     50                  55                  60 aac tgg tcc atg gtg ctc gga tgg cta atg ctc gcc tgt tcc gtc atc    240
Asn Trp Ser Met Val Leu Gly Trp Leu Met Leu Ala Cys Ser Val Ile
 65                  70                  75                  80 tgg atc cca att atg ttt gtg ata aaa atg cat ctg gcc cct gga aga    288
Trp Ile Pro Ile Met Phe Val Ile Lys Met His Leu Ala Pro Gly Arg
                 85                  90                  95 ttt att gag agg ctg aag ttg gtg tgc tcg cca cag ccg gac tgg ggc    336
Phe Ile Glu Arg Leu Lys Leu Val Cys Ser Pro Gln Pro Asp Trp Gly
            100                 105                 110
```

```
cca ttc tta gct caa cac cgc ggg gag cgt tac aag aac atg atc gac     384
Pro Phe Leu Ala Gln His Arg Gly Glu Arg Tyr Lys Asn Met Ile Asp
        115                 120                 125 ccc ttg gga acc tct tcc ttg gga ctc aaa ctg cca gtg aag gat ttg     432
Pro Leu Gly Thr Ser Ser Leu Gly Leu Lys Leu Pro Val Lys Asp Leu
130                 135                 140 gaa ctg ggc act cag tgc tag                                         453
Glu Leu Gly Thr Gln Cys
145                 150
```

<210> SEQ ID NO 94
<211> LENGTH: 150
<212> TYPE: PRT
<213> ORGANISM: Human

<400> SEQUENCE: 94

```
Glu Leu Val Gly Ile Ser Tyr Val Tyr Gly Leu Gln Arg Phe Cys Glu
 1               5                  10                  15

Asp Ile Glu Met Met Ile Gly Phe Gln Pro Asn Ile Phe Trp Lys Val
            20                  25                  30

Cys Trp Ala Phe Val Thr Pro Thr Ile Leu Thr Phe Ile Leu Cys Phe
        35                  40                  45

Ser Phe Tyr Gln Trp Glu Pro Met Thr Tyr Gly Ser Tyr Arg Tyr Pro
    50                  55                  60

Asn Trp Ser Met Val Leu Gly Trp Leu Met Leu Ala Cys Ser Val Ile
65                  70                  75                  80

Trp Ile Pro Ile Met Phe Val Ile Lys Met His Leu Ala Pro Gly Arg
                85                  90                  95

Phe Ile Glu Arg Leu Lys Leu Val Cys Ser Pro Gln Pro Asp Trp Gly
            100                 105                 110

Pro Phe Leu Ala Gln His Arg Gly Glu Arg Tyr Lys Asn Met Ile Asp
        115                 120                 125

Pro Leu Gly Thr Ser Ser Leu Gly Leu Lys Leu Pro Val Lys Asp Leu
    130                 135                 140

Glu Leu Gly Thr Gln Cys
145                 150
```

<210> SEQ ID NO 95
<211> LENGTH: 453
<212> TYPE: DNA
<213> ORGANISM: Human
<220> FEATURE:
<221> NAME/KEY: CDS
<222> LOCATION: (1)..(450)
<223> OTHER INFORMATION: Seq 45(E)S3 - HSpC-3; nt 1942-2394

<400> SEQUENCE: 95

```
gag ctc gtg ggg atc tct tat gtg tat ggc ttg caa aga ttc tgt gaa     48
Glu Leu Val Gly Ile Ser Tyr Val Tyr Gly Leu Gln Arg Phe Cys Glu
 1               5                  10                  15 gat ata gag atg atg att gga ttc cag cct aac atc ttc tgg aaa gtc     96
Asp Ile Glu Met Met Ile Gly Phe Gln Pro Asn Ile Phe Trp Lys Val
            20                  25                  30 tgc tgg gca ttt gta acc cca acc att tta acc ttt atc ctt tgc ttc    144
Cys Trp Ala Phe Val Thr Pro Thr Ile Leu Thr Phe Ile Leu Cys Phe
        35                  40                  45 agc ttt tac cag tgg gaa ccc atg acc tat ggc tct tac cgc tat cct    192
Ser Phe Tyr Gln Trp Glu Pro Met Thr Tyr Gly Ser Tyr Arg Tyr Pro
    50                  55                  60
```

-continued

```
aac tgg tcc atg gtg ctc gga tgg cta atg ctc gcc tgt tcc gtc atc        240
Asn Trp Ser Met Val Leu Gly Trp Leu Met Leu Ala Cys Ser Val Ile
 65                  70                  75                  80 tgg atc cca att atg ttt gtg ata aaa atg cat ctg gcc cct gga aga        288
Trp Ile Pro Ile Met Phe Val Ile Lys Met His Leu Ala Pro Gly Arg
                 85                  90                  95 ttt att gag agg ctg aag ttg gtg tgc tcg cca cag ccg gac tgg ggc        336
Phe Ile Glu Arg Leu Lys Leu Val Cys Ser Pro Gln Pro Asp Trp Gly
            100                 105                 110 cca ttc tta gct caa cac cgc ggg gag cgt tac aag aac atg atc gac        384
Pro Phe Leu Ala Gln His Arg Gly Glu Arg Tyr Lys Asn Met Ile Asp
        115                 120                 125 ccc ttg gga acc tct tcc ttg gga ctc aaa ctg cca gtg aag gat ttg        432
Pro Leu Gly Thr Ser Ser Leu Gly Leu Lys Leu Pro Val Lys Asp Leu
    130                 135                 140 gaa ctg ggc act cag tgc tag                                            453
Glu Leu Gly Thr Gln Cys
145                 150
```

<210> SEQ ID NO 96
<211> LENGTH: 150
<212> TYPE: PRT
<213> ORGANISM: Human

<400> SEQUENCE: 96

```
Glu Leu Val Gly Ile Ser Tyr Val Tyr Gly Leu Gln Arg Phe Cys Glu
  1               5                  10                  15

Asp Ile Glu Met Met Ile Gly Phe Gln Pro Asn Ile Phe Trp Lys Val
                 20                  25                  30

Cys Trp Ala Phe Val Thr Pro Thr Ile Leu Thr Phe Ile Leu Cys Phe
             35                  40                  45

Ser Phe Tyr Gln Trp Glu Pro Met Thr Tyr Gly Ser Tyr Arg Tyr Pro
         50                  55                  60

Asn Trp Ser Met Val Leu Gly Trp Leu Met Leu Ala Cys Ser Val Ile
 65                  70                  75                  80

Trp Ile Pro Ile Met Phe Val Ile Lys Met His Leu Ala Pro Gly Arg
                 85                  90                  95

Phe Ile Glu Arg Leu Lys Leu Val Cys Ser Pro Gln Pro Asp Trp Gly
            100                 105                 110

Pro Phe Leu Ala Gln His Arg Gly Glu Arg Tyr Lys Asn Met Ile Asp
        115                 120                 125

Pro Leu Gly Thr Ser Ser Leu Gly Leu Lys Leu Pro Val Lys Asp Leu
    130                 135                 140

Glu Leu Gly Thr Gln Cys
145                 150
```

<210> SEQ ID NO 97
<211> LENGTH: 453
<212> TYPE: DNA
<213> ORGANISM: Human
<220> FEATURE:
<221> NAME/KEY: CDS
<222> LOCATION: (1)..(450)
<223> OTHER INFORMATION: Seq 46(E)U - U373MG; nt 1942-2394

<400> SEQUENCE: 97

```
gag ctc gtg ggg atc tct tat gtg tat ggc ttg caa aga ttc tgt gaa         48
Glu Leu Val Gly Ile Ser Tyr Val Tyr Gly Leu Gln Arg Phe Cys Glu
  1               5                  10                  15 gat ata gag atg atg att gga ttc cag cct aac atc ttc tgg aaa gtc         96
```

```
Asp Ile Glu Met Met Ile Gly Phe Gln Pro Asn Ile Phe Trp Lys Val
             20                  25                  30 tgc tgg gca ttt gta acc cca acc att tta acc ttt atc ctt tgc ttc     144
Cys Trp Ala Phe Val Thr Pro Thr Ile Leu Thr Phe Ile Leu Cys Phe
         35                  40                  45 agc ttt tac cag tgg gaa ccc atg acc tat ggc tct tac cgc tat cct     192
Ser Phe Tyr Gln Trp Glu Pro Met Thr Tyr Gly Ser Tyr Arg Tyr Pro
     50                  55                  60 aac tgg tcc atg gtg ctc gga tgg cta atg ctc gcc tgt tcc gtc atc     240
Asn Trp Ser Met Val Leu Gly Trp Leu Met Leu Ala Cys Ser Val Ile
 65                  70                  75                  80 tgg atc cca att atg ttt gtg ata aaa atg cat ctg gcc cct gga aga     288
Trp Ile Pro Ile Met Phe Val Ile Lys Met His Leu Ala Pro Gly Arg
                 85                  90                  95 ttt att gag agg ctg aag ttg gtg tgc tcg cca cag ccg gac tgg ggc     336
Phe Ile Glu Arg Leu Lys Leu Val Cys Ser Pro Gln Pro Asp Trp Gly
            100                 105                 110 cca ttc tta gct caa cac cgc ggg gag cgt tac aag aac atg atc gac     384
Pro Phe Leu Ala Gln His Arg Gly Glu Arg Tyr Lys Asn Met Ile Asp
        115                 120                 125 ccc ttg gga acc tct tcc ttg gga ctc aaa ctg cca gtg aag gat ttg     432
Pro Leu Gly Thr Ser Ser Leu Gly Leu Lys Leu Pro Val Lys Asp Leu
    130                 135                 140 gaa ctg ggc act cag tgc tag                                         453
Glu Leu Gly Thr Gln Cys
145                 150

<210> SEQ ID NO 98
<211> LENGTH: 150
<212> TYPE: PRT
<213> ORGANISM: Human

<400> SEQUENCE: 98

Glu Leu Val Gly Ile Ser Tyr Val Tyr Gly Leu Gln Arg Phe Cys Glu
 1               5                  10                  15

Asp Ile Glu Met Met Ile Gly Phe Gln Pro Asn Ile Phe Trp Lys Val
             20                  25                  30

Cys Trp Ala Phe Val Thr Pro Thr Ile Leu Thr Phe Ile Leu Cys Phe
         35                  40                  45

Ser Phe Tyr Gln Trp Glu Pro Met Thr Tyr Gly Ser Tyr Arg Tyr Pro
     50                  55                  60

Asn Trp Ser Met Val Leu Gly Trp Leu Met Leu Ala Cys Ser Val Ile
 65                  70                  75                  80

Trp Ile Pro Ile Met Phe Val Ile Lys Met His Leu Ala Pro Gly Arg
                 85                  90                  95

Phe Ile Glu Arg Leu Lys Leu Val Cys Ser Pro Gln Pro Asp Trp Gly
            100                 105                 110

Pro Phe Leu Ala Gln His Arg Gly Glu Arg Tyr Lys Asn Met Ile Asp
        115                 120                 125

Pro Leu Gly Thr Ser Ser Leu Gly Leu Lys Leu Pro Val Lys Asp Leu
    130                 135                 140

Glu Leu Gly Thr Gln Cys
145                 150

<210> SEQ ID NO 99
<211> LENGTH: 453
<212> TYPE: DNA
<213> ORGANISM: Human
<220> FEATURE:
```

```
<221> NAME/KEY: CDS
<222> LOCATION: (1)..(450)
<223> OTHER INFORMATION: Seq 47(E)U - U373MG; nt 1942-2394

<400> SEQUENCE: 99 gag ctc gtg ggg atc tct tat gtg tat ggc ttg caa aga ttc tgt gaa      48
Glu Leu Val Gly Ile Ser Tyr Val Tyr Gly Leu Gln Arg Phe Cys Glu
  1               5                  10                  15 gat ata gag atg atg att gga ttc cag cct aac atc ttc tgg aaa gtc      96
Asp Ile Glu Met Met Ile Gly Phe Gln Pro Asn Ile Phe Trp Lys Val
                 20                  25                  30 tgc tgg gca ttt gta acc cca acc att tta acc ttt atc ctt tgc ttc     144
Cys Trp Ala Phe Val Thr Pro Thr Ile Leu Thr Phe Ile Leu Cys Phe
             35                  40                  45 agc ttt tac cag tgg gaa ccc atg acc tat ggc tct tac cgc tat cct     192
Ser Phe Tyr Gln Trp Glu Pro Met Thr Tyr Gly Ser Tyr Arg Tyr Pro
         50                  55                  60 aac tgg tcc atg gtg ctc gga tgg cta atg ctc gcc tgt tcc gtc atc     240
Asn Trp Ser Met Val Leu Gly Trp Leu Met Leu Ala Cys Ser Val Ile
 65                  70                  75                  80 tgg atc cca att atg ttt gtg ata aaa atg cat ctg gcc cct gga aga     288
Trp Ile Pro Ile Met Phe Val Ile Lys Met His Leu Ala Pro Gly Arg
                 85                  90                  95 ttt att gag agg ctg aag ttg gtg tgc tcg cca cag ccg gac tgg ggc     336
Phe Ile Glu Arg Leu Lys Leu Val Cys Ser Pro Gln Pro Asp Trp Gly
            100                 105                 110 cca ttc tta gct caa cac cgc ggg gag cgt tac aag aac atg atc gac     384
Pro Phe Leu Ala Gln His Arg Gly Glu Arg Tyr Lys Asn Met Ile Asp
        115                 120                 125 ccc ttg gga acc tct tcc ttg gga ctc aaa ctg cca gtg aag gat ttg     432
Pro Leu Gly Thr Ser Ser Leu Gly Leu Lys Leu Pro Val Lys Asp Leu
    130                 135                 140 gaa ctg ggc act cag tgc tag                                         453
Glu Leu Gly Thr Gln Cys
145                 150

<210> SEQ ID NO 100
<211> LENGTH: 150
<212> TYPE: PRT
<213> ORGANISM: Human

<400> SEQUENCE: 100

Glu Leu Val Gly Ile Ser Tyr Val Tyr Gly Leu Gln Arg Phe Cys Glu
  1               5                  10                  15

Asp Ile Glu Met Met Ile Gly Phe Gln Pro Asn Ile Phe Trp Lys Val
                 20                  25                  30

Cys Trp Ala Phe Val Thr Pro Thr Ile Leu Thr Phe Ile Leu Cys Phe
             35                  40                  45

Ser Phe Tyr Gln Trp Glu Pro Met Thr Tyr Gly Ser Tyr Arg Tyr Pro
         50                  55                  60

Asn Trp Ser Met Val Leu Gly Trp Leu Met Leu Ala Cys Ser Val Ile
 65                  70                  75                  80

Trp Ile Pro Ile Met Phe Val Ile Lys Met His Leu Ala Pro Gly Arg
                 85                  90                  95

Phe Ile Glu Arg Leu Lys Leu Val Cys Ser Pro Gln Pro Asp Trp Gly
            100                 105                 110

Pro Phe Leu Ala Gln His Arg Gly Glu Arg Tyr Lys Asn Met Ile Asp
        115                 120                 125

Pro Leu Gly Thr Ser Ser Leu Gly Leu Lys Leu Pro Val Lys Asp Leu
```

```
                130             135             140
Glu Leu Gly Thr Gln Cys
145                 150

<210> SEQ ID NO 101
<211> LENGTH: 453
<212> TYPE: DNA
<213> ORGANISM: Human
<220> FEATURE:
<221> NAME/KEY: CDS
<222> LOCATION: (1)..(450)
<223> OTHER INFORMATION: Seq 48(E)U - U373MG; nt 1942-2394

<400> SEQUENCE: 101 gag ctc gtg ggg atc tct tat gtg tat ggc ttg caa aga ttc tgt gaa        48
Glu Leu Val Gly Ile Ser Tyr Val Tyr Gly Leu Gln Arg Phe Cys Glu
 1               5                  10                  15 gat ata gag atg atg att gga ttc cag cct aac atc ttc tgg aaa gtc        96
Asp Ile Glu Met Met Ile Gly Phe Gln Pro Asn Ile Phe Trp Lys Val
             20                  25                  30 tgc tgg gca ttt gta acc cca acc att tta acc ttt atc ctt tgc ttc       144
Cys Trp Ala Phe Val Thr Pro Thr Ile Leu Thr Phe Ile Leu Cys Phe
         35                  40                  45 agc ttt tac cag tgg gaa ccc atg acc tat ggc tct tac cgc tat cct       192
Ser Phe Tyr Gln Trp Glu Pro Met Thr Tyr Gly Ser Tyr Arg Tyr Pro
     50                  55                  60 aac tgg tcc atg gtg ctc gga tgg cta atg ctc gcc tgt tcc gtc atc       240
Asn Trp Ser Met Val Leu Gly Trp Leu Met Leu Ala Cys Ser Val Ile
 65                  70                  75                  80 tgg atc cca att atg ttt gtg ata aaa atg cat ctg gcc cct gga aga       288
Trp Ile Pro Ile Met Phe Val Ile Lys Met His Leu Ala Pro Gly Arg
                 85                  90                  95 ttt att gag agg ctg aag ttg gtg tgc tcg cca cag ccg gac tgg ggc       336
Phe Ile Glu Arg Leu Lys Leu Val Cys Ser Pro Gln Pro Asp Trp Gly
            100                 105                 110 cca ttc tta gct caa cac cgc ggg gag cgt tac aag aac atg atc gac       384
Pro Phe Leu Ala Gln His Arg Gly Glu Arg Tyr Lys Asn Met Ile Asp
        115                 120                 125 ccc ttg gga acc tct tcc ttg gga ctc aaa ctg cca gtg aag gat ttg       432
Pro Leu Gly Thr Ser Ser Leu Gly Leu Lys Leu Pro Val Lys Asp Leu
    130                 135                 140 gaa ctg ggc act cag tgc tag                                            453
Glu Leu Gly Thr Gln Cys
145                 150

<210> SEQ ID NO 102
<211> LENGTH: 150
<212> TYPE: PRT
<213> ORGANISM: Human

<400> SEQUENCE: 102

Glu Leu Val Gly Ile Ser Tyr Val Tyr Gly Leu Gln Arg Phe Cys Glu
 1               5                  10                  15

Asp Ile Glu Met Met Ile Gly Phe Gln Pro Asn Ile Phe Trp Lys Val
             20                  25                  30

Cys Trp Ala Phe Val Thr Pro Thr Ile Leu Thr Phe Ile Leu Cys Phe
         35                  40                  45

Ser Phe Tyr Gln Trp Glu Pro Met Thr Tyr Gly Ser Tyr Arg Tyr Pro
     50                  55                  60

Asn Trp Ser Met Val Leu Gly Trp Leu Met Leu Ala Cys Ser Val Ile
 65                  70                  75                  80
```

```
Trp Ile Pro Ile Met Phe Val Ile Lys Met His Leu Ala Pro Gly Arg
                85                  90                  95

Phe Ile Glu Arg Leu Lys Leu Val Cys Ser Pro Gln Pro Asp Trp Gly
            100                 105                 110

Pro Phe Leu Ala Gln His Arg Gly Glu Arg Tyr Lys Asn Met Ile Asp
        115                 120                 125

Pro Leu Gly Thr Ser Ser Leu Gly Leu Lys Leu Pro Val Lys Asp Leu
    130                 135                 140

Glu Leu Gly Thr Gln Cys
145                 150

<210> SEQ ID NO 103
<211> LENGTH: 316
<212> TYPE: DNA
<213> ORGANISM: Human
<220> FEATURE:
<221> NAME/KEY: CDS
<222> LOCATION: (1)..(315)
<223> OTHER INFORMATION: Seq 1(F)S1 - HSpC-1; nt 1-316; nt 220 is T not
      C (consensus); nt 266 is T not C (consensus); nt 304 is G not A
      (consensus)

<400> SEQUENCE: 103 atg gat tgc agt gct ccc aag gaa atg aat aaa ctg cca gcc aac agc        48
Met Asp Cys Ser Ala Pro Lys Glu Met Asn Lys Leu Pro Ala Asn Ser
  1               5                  10                  15 ccg gag gcg gcg gcg gcg cag agc cac ccg gat ggc cca tgc gct ccc        96
Pro Glu Ala Ala Ala Ala Gln Ser His Pro Asp Gly Pro Cys Ala Pro
             20                  25                  30 agg acg agc ccg gag cag gag ctt ccc gcg gct gcc gcc ccg ccg ccg       144
Arg Thr Ser Pro Glu Gln Glu Leu Pro Ala Ala Ala Pro Pro Pro
         35                  40                  45 cca cgt gtg ccc agg tcc gct tcc acc ggc gcc caa act ttc cag tca       192
Pro Arg Val Pro Arg Ser Ala Ser Thr Gly Ala Gln Thr Phe Gln Ser
     50                  55                  60 gcg gac gcg cga gcc tgc gag gct gag tgg cca gga gtg ggg tct tgc       240
Ala Asp Ala Arg Ala Cys Glu Ala Glu Trp Pro Gly Val Gly Ser Cys
 65                  70                  75                  80 aaa ctc agt agc ccg cgg gcg cag gtg gcc tct gca gct ctg cgg gac       288
Lys Leu Ser Ser Pro Arg Ala Gln Val Ala Ser Ala Ala Leu Arg Asp
                 85                  90                  95 ttg aga gag gcg caa ggc gcg cag gcc t                                 316
Leu Arg Glu Ala Gln Gly Ala Gln Ala
            100                 105

<210> SEQ ID NO 104

<211> LENGTH: 105
<212> TYPE: PRT
<213> ORGANISM: Human

<400> SEQUENCE: 104

Met Asp Cys Ser Ala Pro Lys Glu Met Asn Lys Leu Pro Ala Asn Ser
  1               5                  10                  15

Pro Glu Ala Ala Ala Ala Gln Ser His Pro Asp Gly Pro Cys Ala Pro
             20                  25                  30

Arg Thr Ser Pro Glu Gln Glu Leu Pro Ala Ala Ala Pro Pro Pro
         35                  40                  45

Pro Arg Val Pro Arg Ser Ala Ser Thr Gly Ala Gln Thr Phe Gln Ser
```

```
                    50                  55                  60
Ala Asp Ala Arg Ala Cys Glu Ala Glu Trp Pro Gly Val Gly Ser Cys
 65                  70                  75                  80

Lys Leu Ser Ser Pro Arg Ala Gln Val Ala Ser Ala Ala Leu Arg Asp
                85                  90                  95

Leu Arg Glu Ala Gln Gly Ala Gln Ala
            100                 105
```

<210> SEQ ID NO 105
<211> LENGTH: 316
<212> TYPE: DNA
<213> ORGANISM: Human
<220> FEATURE:
<221> NAME/KEY: CDS
<222> LOCATION: (1)..(315)
<223> OTHER INFORMATION: Seq 7(F)S2 - HSpC-2; nt 1-316; nt 220 is C not
      T (consensus); nt 266 is T not C (consensus); nt 304 is G not A
      (consensus)

<400> SEQUENCE: 105

```
atg gat tgc agt gct ccc aag gaa atg aat aaa ctg cca gcc aac agc        48
Met Asp Cys Ser Ala Pro Lys Glu Met Asn Lys Leu Pro Ala Asn Ser
 1               5                  10                  15 ccg gag gcg gcg gcg gcg cag agc cac ccg gat ggc cca tgc gct ccc        96
Pro Glu Ala Ala Ala Ala Gln Ser His Pro Asp Gly Pro Cys Ala Pro
                20                  25                  30 agg acg agc ccg gag cag gag ctt ccc gcg gct gcc gcc ccg ccg ccg       144
Arg Thr Ser Pro Glu Gln Glu Leu Pro Ala Ala Ala Pro Pro Pro
            35                  40                  45 cca cgt gtg ccc agg tcc gct tcc acc ggc gcc caa act ttc cag tca       192
Pro Arg Val Pro Arg Ser Ala Ser Thr Gly Ala Gln Thr Phe Gln Ser
 50                  55                  60 gcg gac gcg cga gcc tgc gag gct gag tgg cca gga gtg ggg tct tgc       240
Ala Asp Ala Arg Ala Cys Glu Ala Glu Trp Pro Gly Val Gly Ser Cys
 65                  70                  75                  80 aaa ctc agt agc ccg cgg gcg cag gtg gcc tct gca gct ctg cgg gac       288
Lys Leu Ser Ser Pro Arg Ala Gln Val Ala Ser Ala Ala Leu Arg Asp
                85                  90                  95 ttg aga gag gcg caa ggc gcg cag gcc t                                 316
Leu Arg Glu Ala Gln Gly Ala Gln Ala
            100                 105
```

<210> SEQ ID NO 106
<211> LENGTH: 105
<212> TYPE: PRT
<213> ORGANISM: Human

<400> SEQUENCE: 106

```
Met Asp Cys Ser Ala Pro Lys Glu Met Asn Lys Leu Pro Ala Asn Ser
 1               5                  10                  15

Pro Glu Ala Ala Ala Ala Gln Ser His Pro Asp Gly Pro Cys Ala Pro
                20                  25                  30

Arg Thr Ser Pro Glu Gln Glu Leu Pro Ala Ala Ala Pro Pro Pro
            35                  40                  45

Pro Arg Val Pro Arg Ser Ala Ser Thr Gly Ala Gln Thr Phe Gln Ser
 50                  55                  60

Ala Asp Ala Arg Ala Cys Glu Ala Glu Trp Pro Gly Val Gly Ser Cys
 65                  70                  75                  80
```

-continued

```
Lys Leu Ser Ser Pro Arg Ala Gln Val Ala Ser Ala Ala Leu Arg Asp
                85                  90                  95

Leu Arg Glu Ala Gln Gly Ala Gln Ala
            100                 105

<210> SEQ ID NO 107
<211> LENGTH: 316
<212> TYPE: DNA
<213> ORGANISM: Human
<220> FEATURE:
<221> NAME/KEY: CDS
<222> LOCATION: (1)..(315)
<223> OTHER INFORMATION: Seq 8(F)S3 - HSpC-3; nt 1-316

<400> SEQUENCE: 107 atg gat tgc agt gct ccc aag gaa atg aat aaa ctg cca gcc aac agc      48
Met Asp Cys Ser Ala Pro Lys Glu Met Asn Lys Leu Pro Ala Asn Ser
  1               5                  10                  15 ccg gag gcg gcg gcg gcg cag agc cac ccg gat ggc cca tgc gct ccc      96
Pro Glu Ala Ala Ala Ala Gln Ser His Pro Asp Gly Pro Cys Ala Pro
             20                  25                  30 agg acg agc ccg gag cag gag ctt ccc gcg gct gcc gcc ccg ccg         144
Arg Thr Ser Pro Glu Gln Glu Leu Pro Ala Ala Ala Pro Pro Pro
         35                  40                  45 cca cgt gtg ccc agg tcc gct tcc acc ggc gcc caa act ttc cag tca     192
Pro Arg Val Pro Arg Ser Ala Ser Thr Gly Ala Gln Thr Phe Gln Ser
 50                  55                  60 gcg gac gcg cga gcc tgc gag gct gag cgg cca gga gtg ggg tct tgc     240
Ala Asp Ala Arg Ala Cys Glu Ala Glu Arg Pro Gly Val Gly Ser Cys
 65                  70                  75                  80 aaa ctc agt agc ccg cgg gcg cag gcg gcc tct gca gct ctg cgg gac     288
Lys Leu Ser Ser Pro Arg Ala Gln Ala Ala Ser Ala Ala Leu Arg Asp
                85                  90                  95 ttg aga gag gcg caa agc gcg cag gcc t                               316
Leu Arg Glu Ala Gln Ser Ala Gln Ala
            100                 105

<210> SEQ ID NO 108
<211> LENGTH: 105
<212> TYPE: PRT
<213> ORGANISM: Human

<400> SEQUENCE: 108

Met Asp Cys Ser Ala Pro Lys Glu Met Asn Lys Leu Pro Ala Asn Ser
  1               5                  10                  15

Pro Glu Ala Ala Ala Ala Gln Ser His Pro Asp Gly Pro Cys Ala Pro
             20                  25                  30

Arg Thr Ser Pro Glu Gln Glu Leu Pro Ala Ala Ala Pro Pro Pro
         35                  40                  45

Pro Arg Val Pro Arg Ser Ala Ser Thr Gly Ala Gln Thr Phe Gln Ser
 50                  55                  60

Ala Asp Ala Arg Ala Cys Glu Ala Glu Arg Pro Gly Val Gly Ser Cys
 65                  70                  75                  80

Lys Leu Ser Ser Pro Arg Ala Gln Ala Ala Ser Ala Ala Leu Arg Asp
                85                  90                  95

Leu Arg Glu Ala Gln Ser Ala Gln Ala
            100                 105
```

```
<210> SEQ ID NO 109
<211> LENGTH: 316
<212> TYPE: DNA
<213> ORGANISM: Human
<220> FEATURE:
<221> NAME/KEY: CDS
<222> LOCATION: (1)..(315)
<223> OTHER INFORMATION: Seq 9(F)S3 - HSpC-3; nt 1-316; nt 304 is G not
      A (consensus)

<400> SEQUENCE: 109 atg gat tgc agt gct ccc aag gaa atg aat aaa ctg cca gcc aac agc        48
Met Asp Cys Ser Ala Pro Lys Glu Met Asn Lys Leu Pro Ala Asn Ser
 1               5                  10                  15 ccg gag gcg gcg gcg gcg cag agc cac ccg gat ggc cca tgc gct ccc        96
Pro Glu Ala Ala Ala Ala Gln Ser His Pro Asp Gly Pro Cys Ala Pro
             20                  25                  30 agg acg agc ccg gag cag gag ctt ccc gcg gct gcc gcc ccg ccg ccg       144
Arg Thr Ser Pro Glu Gln Glu Leu Pro Ala Ala Ala Pro Pro Pro
         35                  40                  45 cca cgt gtg ccc agg tcc gct tcc acc ggc gcc caa act ttc cag tca       192
Pro Arg Val Pro Arg Ser Ala Ser Thr Gly Ala Gln Thr Phe Gln Ser
     50                  55                  60 gcg gac gcg cga gcc tgc gag gct gag cgg cca gga gtg ggg tct tgc       240
Ala Asp Ala Arg Ala Cys Glu Ala Glu Arg Pro Gly Val Gly Ser Cys
 65                  70                  75                  80 aaa ctc agt agc ccg cgg gcg cag gcg gcc tct gca gct ctg cgg gac       288
Lys Leu Ser Ser Pro Arg Ala Gln Ala Ala Ser Ala Ala Leu Arg Asp
                 85                  90                  95 ttg aga gag gcg caa ggc gcg cag gcc t                                 316
Leu Arg Glu Ala Gln Gly Ala Gln Ala
                100                 105

<210> SEQ ID NO 110

<211> LENGTH: 105
<212> TYPE: PRT
<213> ORGANISM: Human

<400> SEQUENCE: 110

Met Asp Cys Ser Ala Pro Lys Glu Met Asn Lys Leu Pro Ala Asn Ser
 1               5                  10                  15

Pro Glu Ala Ala Ala Ala Gln Ser His Pro Asp Gly Pro Cys Ala Pro
             20                  25                  30

Arg Thr Ser Pro Glu Gln Glu Leu Pro Ala Ala Ala Pro Pro Pro
         35                  40                  45

Pro Arg Val Pro Arg Ser Ala Ser Thr Gly Ala Gln Thr Phe Gln Ser
     50                  55                  60

Ala Asp Ala Arg Ala Cys Glu Ala Glu Arg Pro Gly Val Gly Ser Cys
 65                  70                  75                  80

Lys Leu Ser Ser Pro Arg Ala Gln Ala Ala Ser Ala Ala Leu Arg Asp
                 85                  90                  95

Leu Arg Glu Ala Gln Gly Ala Gln Ala
                100                 105

<210> SEQ ID NO 111
<211> LENGTH: 316
<212> TYPE: DNA
<213> ORGANISM: Human
<220> FEATURE:
<221> NAME/KEY: CDS
```

<222> LOCATION: (1)..(315)
<223> OTHER INFORMATION: Seq 10(F)S3 - HSpC-3; nt 1-316

<400> SEQUENCE: 111

| | | | | | | | | | | | | | | | | |
|---|---|---|---|---|---|---|---|---|---|---|---|---|---|---|---|---|
| atg | gat | tgc | agt | gct | ccc | aag | gaa | atg | aat | aaa | ctg | cca | gcc | aac | agc | 48 |
| Met | Asp | Cys | Ser | Ala | Pro | Lys | Glu | Met | Asn | Lys | Leu | Pro | Ala | Asn | Ser | |
| 1 | | | | 5 | | | | | 10 | | | | | 15 | | |
| ccg | gag | gcg | gcg | gcg | gcg | cag | agc | cac | ccg | gat | ggc | cca | tgc | gct | ccc | 96 |
| Pro | Glu | Ala | Ala | Ala | Ala | Gln | Ser | His | Pro | Asp | Gly | Pro | Cys | Ala | Pro | |
| | | | 20 | | | | | 25 | | | | | 30 | | | |
| agg | acg | agc | ccg | gag | cag | gag | ctt | ccc | gcg | gct | gcc | gcc | ccg | ccg | ccg | 144 |
| Arg | Thr | Ser | Pro | Glu | Gln | Glu | Leu | Pro | Ala | Ala | Ala | Ala | Pro | Pro | Pro | |
| | | 35 | | | | | 40 | | | | | 45 | | | | |
| cca | cgt | gtg | ccc | agg | tcc | gct | tcc | acc | ggc | gcc | caa | act | ttc | cag | tca | 192 |
| Pro | Arg | Val | Pro | Arg | Ser | Ala | Ser | Thr | Gly | Ala | Gln | Thr | Phe | Gln | Ser | |
| | 50 | | | | | 55 | | | | | 60 | | | | | |
| gcg | gac | gcg | cga | gcc | tgc | gag | gct | gag | cgg | cca | gga | gtg | ggg | tct | tgc | 240 |
| Ala | Asp | Ala | Arg | Ala | Cys | Glu | Ala | Glu | Arg | Pro | Gly | Val | Gly | Ser | Cys | |
| 65 | | | | | 70 | | | | | 75 | | | | | 80 | |
| aaa | ctc | agt | agc | ccg | cgg | gcg | cag | gcg | gcc | tct | gca | gct | ctg | cgg | gac | 288 |
| Lys | Leu | Ser | Ser | Pro | Arg | Ala | Gln | Ala | Ala | Ser | Ala | Ala | Leu | Arg | Asp | |
| | | | | 85 | | | | | 90 | | | | | 95 | | |
| ttg | aga | gag | gcg | caa | agc | gcg | cag | gcc | t | | | | | | | 316 |
| Leu | Arg | Glu | Ala | Gln | Ser | Ala | Gln | Ala | | | | | | | | |
| | | | 100 | | | | | 105 | | | | | | | | |

<210> SEQ ID NO 112
<211> LENGTH: 105
<212> TYPE: PRT
<213> ORGANISM: Human

<400> SEQUENCE: 112

Met Asp Cys Ser Ala Pro Lys Glu Met Asn Lys Leu Pro Ala Asn Ser
1               5                   10                  15

Pro Glu Ala Ala Ala Ala Gln Ser His Pro Asp Gly Pro Cys Ala Pro
                20                  25                  30

Arg Thr Ser Pro Glu Gln Glu Leu Pro Ala Ala Ala Pro Pro Pro
            35                  40                  45

Pro Arg Val Pro Arg Ser Ala Ser Thr Gly Ala Gln Thr Phe Gln Ser
        50                  55                  60

Ala Asp Ala Arg Ala Cys Glu Ala Glu Arg Pro Gly Val Gly Ser Cys
65                  70                  75                  80

Lys Leu Ser Ser Pro Arg Ala Gln Ala Ala Ser Ala Ala Leu Arg Asp
                85                  90                  95

Leu Arg Glu Ala Gln Ser Ala Gln Ala
            100                 105

<210> SEQ ID NO 113
<211> LENGTH: 316
<212> TYPE: DNA
<213> ORGANISM: Human
<220> FEATURE:
<221> NAME/KEY: CDS
<222> LOCATION: (1)..(315)
<223> OTHER INFORMATION: Seq 11(F)U - U373MG; nt 1-316

<400> SEQUENCE: 113

| | | | | | | | | | | | | | | | | |
|---|---|---|---|---|---|---|---|---|---|---|---|---|---|---|---|---|
| atg | gat | tgc | agt | gct | ccc | aag | gaa | atg | aat | aaa | ctg | cca | gcc | aac | agc | 48 |
| Met | Asp | Cys | Ser | Ala | Pro | Lys | Glu | Met | Asn | Lys | Leu | Pro | Ala | Asn | Ser | |

```
                1               5                  10                 15
ccg gag gcg gcg gcg gcg cag agc cac ccg gat ggc cca tgc gct ccc         96
Pro Glu Ala Ala Ala Ala Gln Ser His Pro Asp Gly Pro Cys Ala Pro
                        20                  25                  30 agg acg agc ccg gag cag gag ctt ccc gcg gct gcc gcc ccg ccg ccg        144
Arg Thr Ser Pro Glu Gln Glu Leu Pro Ala Ala Ala Pro Pro Pro
            35                  40                  45 cca cgt gtg ccc agg tcc gct tcc acc ggc gcc caa act ttc cag tca       192
Pro Arg Val Pro Arg Ser Ala Ser Thr Gly Ala Gln Thr Phe Gln Ser
        50                  55                  60 gcg gac gcg cga gcc tgc gag gct gag cgg cca gga gtg ggg tct tgc       240
Ala Asp Ala Arg Ala Cys Glu Ala Glu Arg Pro Gly Val Gly Ser Cys
65                  70                  75                  80 aaa ctc agt agc ccg cgg gcg cag gcg gcc tct gca gct ctg cgg gac       288
Lys Leu Ser Ser Pro Arg Ala Gln Ala Ala Ser Ala Ala Leu Arg Asp
                85                  90                  95 ttg aga gag gcg caa agc gcg cag gcc t                                 316
Leu Arg Glu Ala Gln Ser Ala Gln Ala
            100                 105

<210> SEQ ID NO 114

<211> LENGTH: 105
<212> TYPE: PRT
<213> ORGANISM: Human

<400> SEQUENCE: 114

Met Asp Cys Ser Ala Pro Lys Glu Met Asn Lys Leu Pro Ala Asn Ser
1               5                   10                  15

Pro Glu Ala Ala Ala Ala Gln Ser His Pro Asp Gly Pro Cys Ala Pro
            20                  25                  30

Arg Thr Ser Pro Glu Gln Glu Leu Pro Ala Ala Ala Pro Pro Pro
        35                  40                  45

Pro Arg Val Pro Arg Ser Ala Ser Thr Gly Ala Gln Thr Phe Gln Ser
    50                  55                  60

Ala Asp Ala Arg Ala Cys Glu Ala Glu Arg Pro Gly Val Gly Ser Cys
65                  70                  75                  80

Lys Leu Ser Ser Pro Arg Ala Gln Ala Ala Ser Ala Ala Leu Arg Asp
                85                  90                  95

Leu Arg Glu Ala Gln Ser Ala Gln Ala
            100                 105

<210> SEQ ID NO 115
<211> LENGTH: 316
<212> TYPE: DNA
<213> ORGANISM: Human
<220> FEATURE:
<221> NAME/KEY: CDS
<222> LOCATION: (1)..(315)
<223> OTHER INFORMATION: Seq12(F)U - U373MG; nt 1-316

<400> SEQUENCE: 115 atg gat tgc agt gct ccc aag gaa atg aat aaa ctg cca gcc aac agc        48
Met Asp Cys Ser Ala Pro Lys Glu Met Asn Lys Leu Pro Ala Asn Ser
1               5                   10                  15 ccg gag gcg gcg gcg gcg cag agc cac ccg gat ggc cca tgc gct ccc        96
Pro Glu Ala Ala Ala Ala Gln Ser His Pro Asp Gly Pro Cys Ala Pro
            20                  25                  30 agg acg agc ccg gag cag gag ctt ccc gcg gct gcc gcc ccg ccg            144
```

```
Arg Thr Ser Pro Glu Gln Glu Leu Pro Ala Ala Ala Pro Pro Pro
         35                  40                  45 cca cgt gtg ccc agg tcc gct tcc acc ggc gcc caa act ttc cag tca      192
Pro Arg Val Pro Arg Ser Ala Ser Thr Gly Ala Gln Thr Phe Gln Ser
 50                  55                  60 gcg gac gcg cga gcc tgc gag gct gag cgg cca gga gtg ggg tct tgc      240
Ala Asp Ala Arg Ala Cys Glu Ala Glu Arg Pro Gly Val Gly Ser Cys
 65                  70                  75                  80 aaa ctc agt agc ccg cgg gcg cag gcg gcc tct gca gct ctg cgg gac      288
Lys Leu Ser Ser Pro Arg Ala Gln Ala Ala Ser Ala Ala Leu Arg Asp
                 85                  90                  95 ttg aga gag gcg caa agc gcg cag gcc t                                316
Leu Arg Glu Ala Gln Ser Ala Gln Ala
                100                 105

<210> SEQ ID NO 116

<211> LENGTH: 105
<212> TYPE: PRT
<213> ORGANISM: Human

<400> SEQUENCE: 116

Met Asp Cys Ser Ala Pro Lys Glu Met Asn Lys Leu Pro Ala Asn Ser
 1               5                  10                  15

Pro Glu Ala Ala Ala Gln Ser His Pro Asp Gly Pro Cys Ala Pro
                 20                  25                  30

Arg Thr Ser Pro Glu Gln Glu Leu Pro Ala Ala Ala Pro Pro Pro
         35                  40                  45

Pro Arg Val Pro Arg Ser Ala Ser Thr Gly Ala Gln Thr Phe Gln Ser
 50                  55                  60

Ala Asp Ala Arg Ala Cys Glu Ala Glu Arg Pro Gly Val Gly Ser Cys
 65                  70                  75                  80

Lys Leu Ser Ser Pro Arg Ala Gln Ala Ala Ser Ala Ala Leu Arg Asp
                 85                  90                  95

Leu Arg Glu Ala Gln Ser Ala Gln Ala
                100                 105

<210> SEQ ID NO 117
<211> LENGTH: 316
<212> TYPE: DNA
<213> ORGANISM: Human
<220> FEATURE:
<221> NAME/KEY: CDS
<222> LOCATION: (1)..(315)
<223> OTHER INFORMATION: Seq 13(F)U - U373MG; nt 1-316; nt 220 is T not
      C (consensus); nt 224 is T not C (consensus)

<400> SEQUENCE: 117 atg gat tgc agt gct ccc aag gaa atg aat aaa ctg cca gcc aac agc       48
Met Asp Cys Ser Ala Pro Lys Glu Met Asn Lys Leu Pro Ala Asn Ser
 1               5                  10                  15 ccg gag gcg gcg gcg gcg cag agc cac ctg gat ggc cca tgc gct ccc       96
Pro Glu Ala Ala Ala Ala Gln Ser His Leu Asp Gly Pro Cys Ala Pro
                 20                  25                  30 agg acg agc ccg gag cag gag ctt ccc gcg gct gcc gcc ccg ccg          144
Arg Thr Ser Pro Glu Gln Glu Leu Pro Ala Ala Ala Ala Pro Pro
         35                  40                  45 cca cgt gtg ccc agg tcc gct tcc acc ggc gcc caa act ttc cag tca      192
Pro Arg Val Pro Arg Ser Ala Ser Thr Gly Ala Gln Thr Phe Gln Ser
 50                  55                  60
```

```
gcg gac gcg cga gcc tgc gag gct gag tgg cta gga gtg ggg tct tgc      240
Ala Asp Ala Arg Ala Cys Glu Ala Glu Trp Leu Gly Val Gly Ser Cys
 65                  70                  75                  80 aaa ctc agt agc ccg cgg gcg cag gcg gcc tct gca gct ctg cgg gac      288
Lys Leu Ser Ser Pro Arg Ala Gln Ala Ala Ser Ala Ala Leu Arg Asp
                 85                  90                  95 ttg aga gag gcg caa agc gcg cag gcc t                                316
Leu Arg Glu Ala Gln Ser Ala Gln Ala
            100                 105

<210> SEQ ID NO 118

<211> LENGTH: 105
<212> TYPE: PRT
<213> ORGANISM: Human

<400> SEQUENCE: 118

Met Asp Cys Ser Ala Pro Lys Glu Met Asn Lys Leu Pro Ala Asn Ser
 1               5                  10                  15

Pro Glu Ala Ala Ala Ala Gln Ser His Leu Asp Gly Pro Cys Ala Pro
             20                  25                  30

Arg Thr Ser Pro Glu Gln Glu Leu Pro Ala Ala Ala Pro Pro Pro Pro
         35                  40                  45

Pro Arg Val Pro Arg Ser Ala Ser Thr Gly Ala Gln Thr Phe Gln Ser
     50                  55                  60

Ala Asp Ala Arg Ala Cys Glu Ala Glu Trp Leu Gly Val Gly Ser Cys
 65                  70                  75                  80

Lys Leu Ser Ser Pro Arg Ala Gln Ala Ala Ser Ala Ala Leu Arg Asp
                 85                  90                  95

Leu Arg Glu Ala Gln Ser Ala Gln Ala
            100                 105

<210> SEQ ID NO 119
<211> LENGTH: 2394
<212> TYPE: DNA
<213> ORGANISM: Human
<220> FEATURE:
<221> NAME/KEY: CDS
<222> LOCATION: (1)..(2391)
<223> OTHER INFORMATION: Seq 49 HGLYT2; nt 1-2394

<400> SEQUENCE: 119 atg gat tgc agt gct ccc aag gaa atg aat aaa ctg cca gcc aac agc       48
Met Asp Cys Ser Ala Pro Lys Glu Met Asn Lys Leu Pro Ala Asn Ser
 1               5                  10                  15 ccg gag gcg gcg gcg gcg cag agc cac ccg gat ggc cca tgc gct ccc       96
Pro Glu Ala Ala Ala Ala Gln Ser His Pro Asp Gly Pro Cys Ala Pro
             20                  25                  30 agg acg agc ccg gag cag gag ctt ccc gcg gct gcc gcc ccg ccg ccg      144
Arg Thr Ser Pro Glu Gln Glu Leu Pro Ala Ala Ala Ala Pro Pro Pro
         35                  40                  45 cca cgt gtg ccc agg tcc gct tcc acc ggc gcc caa act ttc cag tca      192
Pro Arg Val Pro Arg Ser Ala Ser Thr Gly Ala Gln Thr Phe Gln Ser
     50                  55                  60 gcg gac gcg cga gcc tgc gag gct gag tgg cca gga gtg ggg tct tgc      240
Ala Asp Ala Arg Ala Cys Glu Ala Glu Trp Pro Gly Val Gly Ser Cys
 65                  70                  75                  80 aaa ctc agt agc ccg cgg gcg cag gtg gcc tct gca gct ctg cgg gac      288
Lys Leu Ser Ser Pro Arg Ala Gln Val Ala Ser Ala Ala Leu Arg Asp
                 85                  90                  95
```

|     |     |     |     |     |     |     |     |     |     |     |     |     |     |     |     |     |
|---|---|---|---|---|---|---|---|---|---|---|---|---|---|---|---|---|
| ttg | aga | gag | gcg | caa | ggc | gcg | cag | gcc | tcg | ccc | cct | ccc | ggg | agc | tct | 336 |
| Leu | Arg | Glu | Ala | Gln | Gly | Ala | Gln | Ala | Ser | Pro | Pro | Pro | Gly | Ser | Ser | |
| | | | 100 | | | | 105 | | | | | 110 | | | | |
| ggg | ccc | ggc | aac | gcg | ttg | cac | tgt | aag | atc | cct | tct | ctg | cga | ggc | ccg | 384 |
| Gly | Pro | Gly | Asn | Ala | Leu | His | Cys | Lys | Ile | Pro | Ser | Leu | Arg | Gly | Pro | |
| | | | 115 | | | | 120 | | | | 125 | | | | | |
| gag | ggg | gat | gcg | aac | gtg | agt | gtg | ggc | aag | ggc | acc | ctg | gag | cgg | aac | 432 |
| Glu | Gly | Asp | Ala | Asn | Val | Ser | Val | Gly | Lys | Gly | Thr | Leu | Glu | Arg | Asn | |
| | | 130 | | | | 135 | | | | 140 | | | | | | |
| aat | acc | cct | gtt | gtg | ggc | tgg | gtg | aac | atg | ggc | cag | agc | acc | gtg | gtg | 480 |
| Asn | Thr | Pro | Val | Val | Gly | Trp | Val | Asn | Met | Gly | Gln | Ser | Thr | Val | Val | |
| 145 | | | | | 150 | | | | | 155 | | | | | 160 | |
| ctg | ggc | acg | gat | gga | atc | acg | tcc | gtg | ctc | ccg | ggc | agc | gtg | gcc | acc | 528 |
| Leu | Gly | Thr | Asp | Gly | Ile | Thr | Ser | Val | Leu | Pro | Gly | Ser | Val | Ala | Thr | |
| | | | | 165 | | | | 170 | | | | | 175 | | | |
| gtt | gcc | acc | cag | gag | gac | gag | caa | ggg | gat | gag | gat | aag | gcc | cga | ggg | 576 |
| Val | Ala | Thr | Gln | Glu | Asp | Glu | Gln | Gly | Asp | Glu | Asp | Lys | Ala | Arg | Gly | |
| | | | 180 | | | | 185 | | | | | 190 | | | | |
| aac | tgg | tcc | agc | aaa | ctg | gac | ttc | atc | ctg | tcc | atg | gtg | ggg | tac | gca | 624 |
| Asn | Trp | Ser | Ser | Lys | Leu | Asp | Phe | Ile | Leu | Ser | Met | Val | Gly | Tyr | Ala | |
| | | | 195 | | | | 200 | | | | | 205 | | | | |
| gtg | ggg | ctg | ggc | aat | gtc | tgg | agg | ttt | ccc | tac | ctg | gcc | ttc | cag | aac | 672 |
| Val | Gly | Leu | Gly | Asn | Val | Trp | Arg | Phe | Pro | Tyr | Leu | Ala | Phe | Gln | Asn | |
| | 210 | | | | | 215 | | | | | 220 | | | | | |
| ggg | ggg | ggt | gct | ttc | ctc | atc | cct | tac | ctg | atg | atg | ctg | gct | ctg | gct | 720 |
| Gly | Gly | Gly | Ala | Phe | Leu | Ile | Pro | Tyr | Leu | Met | Met | Leu | Ala | Leu | Ala | |
| 225 | | | | | 230 | | | | | 235 | | | | | 240 | |
| gga | tta | ccc | atc | ttc | ttc | ttg | gag | gtg | tcg | ctg | ggc | cag | ttt | gcc | agc | 768 |
| Gly | Leu | Pro | Ile | Phe | Phe | Leu | Glu | Val | Ser | Leu | Gly | Gln | Phe | Ala | Ser | |
| | | | | 245 | | | | | 250 | | | | | 255 | | |
| cag | gga | ccg | gtg | tct | gtg | tgg | aag | gcc | atc | cca | gct | cta | caa | ggc | tgt | 816 |
| Gln | Gly | Pro | Val | Ser | Val | Trp | Lys | Ala | Ile | Pro | Ala | Leu | Gln | Gly | Cys | |
| | | | 260 | | | | | 265 | | | | | 270 | | | |
| ggc | atc | gcg | atg | ctg | atc | atc | tct | gtc | cta | ata | gcc | ata | tac | tac | aat | 864 |
| Gly | Ile | Ala | Met | Leu | Ile | Ile | Ser | Val | Leu | Ile | Ala | Ile | Tyr | Tyr | Asn | |
| | | 275 | | | | | 280 | | | | | 285 | | | | |
| gta | att | att | tgc | tat | aca | ctt | ttc | tac | ctg | ttt | gcc | tcc | ttt | gtg | tct | 912 |
| Val | Ile | Ile | Cys | Tyr | Thr | Leu | Phe | Tyr | Leu | Phe | Ala | Ser | Phe | Val | Ser | |
| | 290 | | | | | 295 | | | | | 300 | | | | | |
| gta | cta | ccc | tgg | ggc | tcc | tgc | aac | aac | cct | tgg | aat | acg | cca | gaa | tgc | 960 |
| Val | Leu | Pro | Trp | Gly | Ser | Cys | Asn | Asn | Pro | Trp | Asn | Thr | Pro | Glu | Cys | |
| 305 | | | | | 310 | | | | | 315 | | | | | 320 | |
| aaa | gat | aaa | acc | aaa | ctt | tta | tta | gat | tcc | tgt | gtt | atc | agt | gac | cat | 1008 |
| Lys | Asp | Lys | Thr | Lys | Leu | Leu | Leu | Asp | Ser | Cys | Val | Ile | Ser | Asp | His | |
| | | | | 325 | | | | | 330 | | | | | 335 | | |
| ccc | aaa | ata | cag | atc | aag | aac | tcg | act | ttc | tgc | atg | acc | gct | tat | ccc | 1056 |
| Pro | Lys | Ile | Gln | Ile | Lys | Asn | Ser | Thr | Phe | Cys | Met | Thr | Ala | Tyr | Pro | |
| | | 340 | | | | | 345 | | | | | 350 | | | | |
| aac | gtg | aca | atg | gtt | aat | ttc | acc | agc | ctg | gcc | aat | aag | aca | ttt | gtc | 1104 |
| Asn | Val | Thr | Met | Val | Asn | Phe | Thr | Ser | Leu | Ala | Asn | Lys | Thr | Phe | Val | |
| | | 355 | | | | | 360 | | | | | 365 | | | | |
| agt | gga | agt | gaa | gag | tac | ttc | aag | tac | ttt | gtg | ctg | aag | att | tct | gca | 1152 |
| Ser | Gly | Ser | Glu | Glu | Tyr | Phe | Lys | Tyr | Phe | Val | Leu | Lys | Ile | Ser | Ala | |
| | 370 | | | | | 375 | | | | | 380 | | | | | |
| ggg | att | gaa | tat | cct | ggc | gag | atc | agg | tgg | cca | cta | gct | ctc | tgc | ctc | 1200 |
| Gly | Ile | Glu | Tyr | Pro | Gly | Glu | Ile | Arg | Trp | Pro | Leu | Ala | Leu | Cys | Leu | |
| 385 | | | | | 390 | | | | | 395 | | | | | 400 | |
| ttc | ctg | gct | tgg | gtc | att | gtg | tat | gca | tcg | ttg | gct | aaa | gga | atc | aag | 1248 |

```
                Phe Leu Ala Trp Val Ile Val Tyr Ala Ser Leu Ala Lys Gly Ile Lys
                                    405                 410                 415 act tca gga aaa gtg gtg tac ttc acg gcc acg ttc ccg tat gcc gta          1296
Thr Ser Gly Lys Val Val Tyr Phe Thr Ala Thr Phe Pro Tyr Ala Val
            420                 425                 430 cta gtg atc ctc ctc atc cga gga gtc acc ctg cct gga gct gga gct          1344
Leu Val Ile Leu Leu Ile Arg Gly Val Thr Leu Pro Gly Ala Gly Ala
            435                 440                 445 ggg atc tgg tac ttc atc aca ccc aag tgg gag aaa ctc acg gat gcc          1392
Gly Ile Trp Tyr Phe Ile Thr Pro Lys Trp Glu Lys Leu Thr Asp Ala
        450                 455                 460 acg gtg tgg aaa gat gct gcc act cag att ttc ttc tct tta tct gct          1440
Thr Val Trp Lys Asp Ala Ala Thr Gln Ile Phe Phe Ser Leu Ser Ala
465                 470                 475                 480 gca tgg gga ggc ctg atc act ctc tct tct tac aac aaa ttc cac aac          1488
Ala Trp Gly Gly Leu Ile Thr Leu Ser Ser Tyr Asn Lys Phe His Asn
                    485                 490                 495 aac tgc tac agg gac act cta att gtc acc tgc acc aac agt gcc aca          1536
Asn Cys Tyr Arg Asp Thr Leu Ile Val Thr Cys Thr Asn Ser Ala Thr
                500                 505                 510 agc atc ttt gcc ggc ttc gtc atc ttc tcc gtt atc ggc ttc atg gcc          1584
Ser Ile Phe Ala Gly Phe Val Ile Phe Ser Val Ile Gly Phe Met Ala
            515                 520                 525 aat gaa cgc aaa gtc aac att gag aat gtg gct gac caa ggg cca ggc          1632
Asn Glu Arg Lys Val Asn Ile Glu Asn Val Ala Asp Gln Gly Pro Gly
        530                 535                 540 att gca ttt gtg gtt tac ccg gaa gcc tta acc agg ctg cct ctc tct          1680
Ile Ala Phe Val Val Tyr Pro Glu Ala Leu Thr Arg Leu Pro Leu Ser
545                 550                 555                 560 ccg ttc tgg gcc atc atc ttt ttc ctg atg ctc ctc act ctt gga ctt          1728
Pro Phe Trp Ala Ile Ile Phe Phe Leu Met Leu Leu Thr Leu Gly Leu
                    565                 570                 575 gac act atg ttt gcc tcc atc gag acc ata gtg acc tcc atc tca gac          1776
Asp Thr Met Phe Ala Ser Ile Glu Thr Ile Val Thr Ser Ile Ser Asp
                580                 585                 590 gag ttt ccc aag tac cta cgc aca cac aag cca gtg ttt act ctg ggc          1824
Glu Phe Pro Lys Tyr Leu Arg Thr His Lys Pro Val Phe Thr Leu Gly
            595                 600                 605 tgc tgc att tgt ttc ttc atc atg ggt ttt cca atg atc act cag ggt          1872
Cys Cys Ile Cys Phe Phe Ile Met Gly Phe Pro Met Ile Thr Gln Gly
        610                 615                 620 gga att tac atg ttt cag ctt gtg gac acc tat gct gcc tcc tat gcc          1920
Gly Ile Tyr Met Phe Gln Leu Val Asp Thr Tyr Ala Ala Ser Tyr Ala
625                 630                 635                 640 ctt gtc atc att gcc att ttt gag ctc gtg ggg atc tct tat gtg tat          1968
Leu Val Ile Ile Ala Ile Phe Glu Leu Val Gly Ile Ser Tyr Val Tyr
                    645                 650                 655 ggc ttg caa aga ttc tgt gaa gat ata gag atg atg att gga ttc cag          2016
Gly Leu Gln Arg Phe Cys Glu Asp Ile Glu Met Met Ile Gly Phe Gln
                660                 665                 670 cct aac atc ttc tgg aaa gtc tgc tgg gca ttt gta acc cca acc att          2064
Pro Asn Ile Phe Trp Lys Val Cys Trp Ala Phe Val Thr Pro Thr Ile
            675                 680                 685 tta acc ttt atc ctt tgc ttc agc ttt tac cag tgg gaa ccc atg acc          2112
Leu Thr Phe Ile Leu Cys Phe Ser Phe Tyr Gln Trp Glu Pro Met Thr
        690                 695                 700 tat ggc tct tac cgc tat cct aac tgg tcc atg gtg ctc gga tgg cta          2160
Tyr Gly Ser Tyr Arg Tyr Pro Asn Trp Ser Met Val Leu Gly Trp Leu
705                 710                 715                 720
```

-continued

| | | | | | | | | | | | | | | | |
|---|---|---|---|---|---|---|---|---|---|---|---|---|---|---|---|
| atg | ctc | gcc | tgt | tcc | gtc | atc | tgg | atc | cca | att | atg | ttt | gtg | ata | aaa | 2208
| Met | Leu | Ala | Cys | Ser | Val | Ile | Trp | Ile | Pro | Ile | Met | Phe | Val | Ile | Lys |
| | | | 725 | | | | | 730 | | | | | 735 | | |

```
atg cat ctg gcc cct gga aga ttt att gag agg ctg aag ttg gtg tgc      2256
Met His Leu Ala Pro Gly Arg Phe Ile Glu Arg Leu Lys Leu Val Cys
            740                 745                 750 tcg cca cag ccg gac tgg ggc cca ttc tta gct caa cac cgc ggg gag      2304
Ser Pro Gln Pro Asp Trp Gly Pro Phe Leu Ala Gln His Arg Gly Glu
        755                 760                 765 cgt tac aag aac atg atc gac ccc ttg gga acc tct tcc ttg gga ctc      2352
Arg Tyr Lys Asn Met Ile Asp Pro Leu Gly Thr Ser Ser Leu Gly Leu
    770                 775                 780 aaa ctg cca gtg aag gat ttg gaa ctg ggc act cag tgc tag              2394
Lys Leu Pro Val Lys Asp Leu Glu Leu Gly Thr Gln Cys
785                 790                 795

<210> SEQ ID NO 120
<211> LENGTH: 797
<212> TYPE: PRT
<213> ORGANISM: Human

<400> SEQUENCE: 120

Met Asp Cys Ser Ala Pro Lys Glu Met Asn Lys Leu Pro Ala Asn Ser
 1               5                  10                  15

Pro Glu Ala Ala Ala Gln Ser His Pro Asp Gly Pro Cys Ala Pro
             20                  25                  30

Arg Thr Ser Pro Glu Gln Glu Leu Pro Ala Ala Ala Pro Pro Pro
         35                  40                  45

Pro Arg Val Pro Arg Ser Ala Ser Thr Gly Ala Gln Thr Phe Gln Ser
     50                  55                  60

Ala Asp Ala Arg Ala Cys Glu Ala Glu Trp Pro Gly Val Gly Ser Cys
 65                  70                  75                  80

Lys Leu Ser Ser Pro Arg Ala Gln Val Ala Ser Ala Leu Arg Asp
                 85                  90                  95

Leu Arg Glu Ala Gln Gly Ala Gln Ala Ser Pro Pro Gly Ser Ser
             100                 105                 110

Gly Pro Gly Asn Ala Leu His Cys Lys Ile Pro Ser Leu Arg Gly Pro
         115                 120                 125

Glu Gly Asp Ala Asn Val Ser Val Gly Lys Gly Thr Leu Glu Arg Asn
     130                 135                 140

Asn Thr Pro Val Val Gly Trp Val Asn Met Gly Gln Ser Thr Val Val
145                 150                 155                 160

Leu Gly Thr Asp Gly Ile Thr Ser Val Leu Pro Gly Ser Val Ala Thr
                 165                 170                 175

Val Ala Thr Gln Glu Asp Glu Gln Gly Asp Glu Asp Lys Ala Arg Gly
             180                 185                 190

Asn Trp Ser Ser Lys Leu Asp Phe Ile Leu Ser Met Val Gly Tyr Ala
         195                 200                 205

Val Gly Leu Gly Asn Val Trp Arg Phe Pro Tyr Leu Ala Phe Gln Asn
     210                 215                 220

Gly Gly Gly Ala Phe Leu Ile Pro Tyr Leu Met Met Leu Ala Leu Ala
225                 230                 235                 240

Gly Leu Pro Ile Phe Phe Leu Glu Val Ser Leu Gly Gln Phe Ala Ser
                 245                 250                 255

Gln Gly Pro Val Ser Val Trp Lys Ala Ile Pro Ala Leu Gln Gly Cys
             260                 265                 270
```

-continued

```
Gly Ile Ala Met Leu Ile Ile Ser Val Leu Ile Ala Ile Tyr Tyr Asn
            275                 280                 285

Val Ile Ile Cys Tyr Thr Leu Phe Tyr Leu Phe Ala Ser Phe Val Ser
        290                 295                 300

Val Leu Pro Trp Gly Ser Cys Asn Asn Pro Trp Asn Thr Pro Glu Cys
305                 310                 315                 320

Lys Asp Lys Thr Lys Leu Leu Asp Ser Cys Val Ile Ser Asp His
                325                 330                 335

Pro Lys Ile Gln Ile Lys Asn Ser Thr Phe Cys Met Thr Ala Tyr Pro
                340                 345                 350

Asn Val Thr Met Val Asn Phe Thr Ser Leu Ala Asn Lys Thr Phe Val
            355                 360                 365

Ser Gly Ser Glu Glu Tyr Phe Lys Tyr Phe Val Leu Lys Ile Ser Ala
        370                 375                 380

Gly Ile Glu Tyr Pro Gly Glu Ile Arg Trp Pro Leu Ala Leu Cys Leu
385                 390                 395                 400

Phe Leu Ala Trp Val Ile Val Tyr Ala Ser Leu Ala Lys Gly Ile Lys
                405                 410                 415

Thr Ser Gly Lys Val Val Tyr Phe Thr Ala Thr Phe Pro Tyr Ala Val
                420                 425                 430

Leu Val Ile Leu Leu Ile Arg Gly Val Thr Leu Pro Gly Ala Gly Ala
            435                 440                 445

Gly Ile Trp Tyr Phe Ile Thr Pro Lys Trp Glu Lys Leu Thr Asp Ala
450                 455                 460

Thr Val Trp Lys Asp Ala Ala Thr Gln Ile Phe Phe Ser Leu Ser Ala
465                 470                 475                 480

Ala Trp Gly Gly Leu Ile Thr Leu Ser Ser Tyr Asn Lys Phe His Asn
                485                 490                 495

Asn Cys Tyr Arg Asp Thr Leu Ile Val Thr Cys Thr Asn Ser Ala Thr
                500                 505                 510

Ser Ile Phe Ala Gly Phe Val Ile Phe Ser Val Ile Gly Phe Met Ala
            515                 520                 525

Asn Glu Arg Lys Val Asn Ile Glu Asn Val Ala Asp Gln Gly Pro Gly
            530                 535                 540

Ile Ala Phe Val Val Tyr Pro Glu Ala Leu Thr Arg Leu Pro Leu Ser
545                 550                 555                 560

Pro Phe Trp Ala Ile Ile Phe Phe Leu Met Leu Leu Thr Leu Gly Leu
                565                 570                 575

Asp Thr Met Phe Ala Ser Ile Glu Thr Ile Val Thr Ser Ile Ser Asp
                580                 585                 590

Glu Phe Pro Lys Tyr Leu Arg Thr His Lys Pro Val Phe Thr Leu Gly
            595                 600                 605

Cys Cys Ile Cys Phe Phe Ile Met Gly Phe Pro Met Ile Thr Gln Gly
    610                 615                 620

Gly Ile Tyr Met Phe Gln Leu Val Asp Thr Tyr Ala Ala Ser Tyr Ala
625                 630                 635                 640

Leu Val Ile Ile Ala Ile Phe Glu Leu Val Gly Ile Ser Tyr Val Tyr
                645                 650                 655

Gly Leu Gln Arg Phe Cys Glu Asp Ile Glu Met Met Ile Gly Phe Gln
                660                 665                 670

Pro Asn Ile Phe Trp Lys Val Cys Trp Ala Phe Val Thr Pro Thr Ile
            675                 680                 685

Leu Thr Phe Ile Leu Cys Phe Ser Phe Tyr Gln Trp Glu Pro Met Thr
```

```
                690                   695                   700
Tyr Gly Ser Tyr Arg Tyr Pro Asn Trp Ser Met Val Leu Gly Trp Leu
705                 710                 715                 720

Met Leu Ala Cys Ser Val Ile Trp Ile Pro Ile Met Phe Val Ile Lys
                725                 730                 735

Met His Leu Ala Pro Gly Arg Phe Ile Glu Arg Leu Lys Leu Val Cys
                740                 745                 750

Ser Pro Gln Pro Asp Trp Gly Pro Phe Leu Ala Gln His Arg Gly Glu
                755                 760                 765

Arg Tyr Lys Asn Met Ile Asp Pro Leu Gly Thr Ser Ser Leu Gly Leu
770                 775                 780

Lys Leu Pro Val Lys Asp Leu Glu Leu Gly Thr Gln Cys
785                 790                 795

<210> SEQ ID NO 121
<211> LENGTH: 2394
<212> TYPE: DNA
<213> ORGANISM: Human
<220> FEATURE:
<221> NAME/KEY: CDS
<222> LOCATION: (1)..(2391)
<223> OTHER INFORMATION: Seq50 Consensus; nt 1 -2394

<400> SEQUENCE: 121 atg gat tgc agt gct ccc aag gaa atg aat aaa ctg cca gcc aac agc      48
Met Asp Cys Ser Ala Pro Lys Glu Met Asn Lys Leu Pro Ala Asn Ser
  1               5                  10                  15 ccg gag gcg gcg gcg gcg cag agc cac ccg gat ggc cca tgc gct ccc      96
Pro Glu Ala Ala Ala Ala Gln Ser His Pro Asp Gly Pro Cys Ala Pro
                 20                  25                  30 agg acg agc ccg gag cag gag ctt ccc gcg gct gcc gcc ccg ccg ccg     144
Arg Thr Ser Pro Glu Gln Glu Leu Pro Ala Ala Ala Pro Pro Pro
         35                  40                  45 cca cgt gtg ccc agg tcc gct tcc acc ggc gcc caa act ttc cag tca     192
Pro Arg Val Pro Arg Ser Ala Ser Thr Gly Ala Gln Thr Phe Gln Ser
 50                  55                  60 gcg gac gcg cga gcc tgc gag gct gag cgg cca gga gtg ggg tct tgc     240
Ala Asp Ala Arg Ala Cys Glu Ala Glu Arg Pro Gly Val Gly Ser Cys
 65                  70                  75                  80 aaa ctc agt agc ccg cgg gcg cag gcg gcc tct gca gct ctg cgg gac     288
Lys Leu Ser Ser Pro Arg Ala Gln Ala Ala Ser Ala Ala Leu Arg Asp
                 85                  90                  95 ttg aga gag gcg caa agc gcg cag gcc tcg ccc cct ccc ggg agc tct     336
Leu Arg Glu Ala Gln Ser Ala Gln Ala Ser Pro Pro Pro Gly Ser Ser
                100                 105                 110 ggg ccc ggc aac gcg ttg cac tgt aag atc cct tct ctg cga ggc ccg     384
Gly Pro Gly Asn Ala Leu His Cys Lys Ile Pro Ser Leu Arg Gly Pro
        115                 120                 125 gag ggg gat gcg aac gtg agt gtg ggc aag ggc acc ctg gag cgg aac     432
Glu Gly Asp Ala Asn Val Ser Val Gly Lys Gly Thr Leu Glu Arg Asn
    130                 135                 140 aat acc cct gtt gtg ggc tgg gtg aac atg ggc cag agc acc gtg gtg     480
Asn Thr Pro Val Val Gly Trp Val Asn Met Gly Gln Ser Thr Val Val
145                 150                 155                 160 ctg ggc acg gat gga atc acg tcc gtg ctc ccg ggc agc gtg gcc acc     528
Leu Gly Thr Asp Gly Ile Thr Ser Val Leu Pro Gly Ser Val Ala Thr
                165                 170                 175 gtt gcc acc cag gag gac gag caa ggg gat gag gat aag gcc cga ggg     576
Val Ala Thr Gln Glu Asp Glu Gln Gly Asp Glu Asp Lys Ala Arg Gly
                180                 185                 190
```

```
aac tgg tcc agc aaa ctg gac ttc atc ctg tcc atg gtg ggg tac gca      624
Asn Trp Ser Ser Lys Leu Asp Phe Ile Leu Ser Met Val Gly Tyr Ala
        195                 200                 205 gtg ggg ctg ggc aat gtc tgg agg ttt ccc tac ctg gcc ttc cag aac      672
Val Gly Leu Gly Asn Val Trp Arg Phe Pro Tyr Leu Ala Phe Gln Asn
210                 215                 220 ggg gga ggt gct ttc ctc atc cct tac ctg atg atg ctg gct ctg gct      720
Gly Gly Gly Ala Phe Leu Ile Pro Tyr Leu Met Met Leu Ala Leu Ala
225                 230                 235                 240 gga tta ccc atc ttc ttc ttg gag gtg tcg ctg ggc cag ttt gcc agc      768
Gly Leu Pro Ile Phe Phe Leu Glu Val Ser Leu Gly Gln Phe Ala Ser
                245                 250                 255 cag gga ccg gtg tct gtg tgg aag gcc atc cca gct cta caa ggc tgt      816
Gln Gly Pro Val Ser Val Trp Lys Ala Ile Pro Ala Leu Gln Gly Cys
            260                 265                 270 ggc atc gcg atg ctg atc atc tct gtc cta ata gcc ata tac tac aat      864
Gly Ile Ala Met Leu Ile Ile Ser Val Leu Ile Ala Ile Tyr Tyr Asn
        275                 280                 285 gta att att tgc tat aca ctt ttc tac ctg ttt gcc tcc ttt gtg tct      912
Val Ile Ile Cys Tyr Thr Leu Phe Tyr Leu Phe Ala Ser Phe Val Ser
290                 295                 300 gta cta ccc tgg ggc tcc tgc aac aac cct tgg aat acg cca gaa tgc      960
Val Leu Pro Trp Gly Ser Cys Asn Asn Pro Trp Asn Thr Pro Glu Cys
305                 310                 315                 320 aaa gat aaa acc aaa ctt tta tta gat tcc tgt gtt atc agt gac cat     1008
Lys Asp Lys Thr Lys Leu Leu Leu Asp Ser Cys Val Ile Ser Asp His
                325                 330                 335 ccc aaa ata cag atc aag aac tcg act ttc tgc atg acc gct tat ccc     1056
Pro Lys Ile Gln Ile Lys Asn Ser Thr Phe Cys Met Thr Ala Tyr Pro
            340                 345                 350 aac gtg aca atg gtt aat ttc acc agc ctg gcc aat aag aca ttt gtc     1104
Asn Val Thr Met Val Asn Phe Thr Ser Leu Ala Asn Lys Thr Phe Val
        355                 360                 365 agt gga agt gaa gag tac ttc aag tac ttt gtg ctg aag att tct gca     1152
Ser Gly Ser Glu Glu Tyr Phe Lys Tyr Phe Val Leu Lys Ile Ser Ala
370                 375                 380 ggg att gaa tat cct ggc gag atc agg tgg cca cta gct ctc tgc ctc     1200
Gly Ile Glu Tyr Pro Gly Glu Ile Arg Trp Pro Leu Ala Leu Cys Leu
385                 390                 395                 400 ttc ctg gct tgg gtc att gtg tat gca tcg ttg gct aaa gga atc aag     1248
Phe Leu Ala Trp Val Ile Val Tyr Ala Ser Leu Ala Lys Gly Ile Lys
                405                 410                 415 act tca gga aaa gtg gtg tac ttc acg gcc acg ttc ccg tat gtc gta     1296
Thr Ser Gly Lys Val Val Tyr Phe Thr Ala Thr Phe Pro Tyr Val Val
            420                 425                 430 cta gtg atc ctc ctc atc cga gga gtc acc ctg cct gga gct gga gct     1344
Leu Val Ile Leu Leu Ile Arg Gly Val Thr Leu Pro Gly Ala Gly Ala
        435                 440                 445 ggg atc tgg tac ttc atc aca ccc aag tgg gag aaa ctc acg gat gcc     1392
Gly Ile Trp Tyr Phe Ile Thr Pro Lys Trp Glu Lys Leu Thr Asp Ala
450                 455                 460 acg gtg tgg aaa gat gct gcc act cag att ttc ttc tct tta tct gct     1440
Thr Val Trp Lys Asp Ala Ala Thr Gln Ile Phe Phe Ser Leu Ser Ala
465                 470                 475                 480 gca tgg gga ggc ctg atc act ctc tct tct tac aac aaa ttc cac aac     1488
Ala Trp Gly Gly Leu Ile Thr Leu Ser Ser Tyr Asn Lys Phe His Asn
                485                 490                 495 aac tgc tac agg gac act cta att gtc acc tgc acc aac agt gcc aca     1536
Asn Cys Tyr Arg Asp Thr Leu Ile Val Thr Cys Thr Asn Ser Ala Thr
```

```
agc atc ttt gcc ggc ttc gtc atc ttc tcc gtt atc ggc ttc atg gcc      1584
Ser Ile Phe Ala Gly Phe Val Ile Phe Ser Val Ile Gly Phe Met Ala
    515                 520                 525 aat gaa cgc aaa gtc aac att gag aat gtg gct gac caa ggg cca ggc      1632
Asn Glu Arg Lys Val Asn Ile Glu Asn Val Ala Asp Gln Gly Pro Gly
530                 535                 540 att gca ttt gtg gtt tac ccg gaa gcc tta acc agg ctg cct ctc tct      1680
Ile Ala Phe Val Val Tyr Pro Glu Ala Leu Thr Arg Leu Pro Leu Ser
545                 550                 555                 560 ccg ttc tgg gcc atc atc ttt ttc ctg atg ctc ctc act ctt gga ctt      1728
Pro Phe Trp Ala Ile Ile Phe Phe Leu Met Leu Leu Thr Leu Gly Leu
                565                 570                 575 gac act atg ttt gcc tcc atc gag acc ata gtg acc tcc atc tca gac      1776
Asp Thr Met Phe Ala Ser Ile Glu Thr Ile Val Thr Ser Ile Ser Asp
            580                 585                 590 gag ttt ccc aag tac cta cgc aca cac aag cca gtg ttt act ctg ggc      1824
Glu Phe Pro Lys Tyr Leu Arg Thr His Lys Pro Val Phe Thr Leu Gly
        595                 600                 605 tgc tgc att tgt ttc ttc atc atg ggt ttt cca atg atc act cag ggt      1872
Cys Cys Ile Cys Phe Phe Ile Met Gly Phe Pro Met Ile Thr Gln Gly
    610                 615                 620 gga att tac atg ttt cag ctt gtg gac acc tat gct gcc tcc tat gcc      1920
Gly Ile Tyr Met Phe Gln Leu Val Asp Thr Tyr Ala Ala Ser Tyr Ala
625                 630                 635                 640 ctt gtc atc att gcc att ttt gag ctc gtg ggg atc tct tat gtg tat      1968
Leu Val Ile Ile Ala Ile Phe Glu Leu Val Gly Ile Ser Tyr Val Tyr
                645                 650                 655 ggc ttg caa aga ttc tgt gaa gat ata gag atg atg att gga ttc cag      2016
Gly Leu Gln Arg Phe Cys Glu Asp Ile Glu Met Met Ile Gly Phe Gln
            660                 665                 670 cct aac atc ttc tgg aaa gtc tgc tgg gca ttt gta acc cca acc att      2064
Pro Asn Ile Phe Trp Lys Val Cys Trp Ala Phe Val Thr Pro Thr Ile
        675                 680                 685 tta acc ttt atc ctt tgc ttc agc ttt tac cag tgg gaa ccc atg acc      2112
Leu Thr Phe Ile Leu Cys Phe Ser Phe Tyr Gln Trp Glu Pro Met Thr
    690                 695                 700 tat ggc tct tac cgc tat cct aac tgg tcc atg gtg ctc gga tgg cta      2160
Tyr Gly Ser Tyr Arg Tyr Pro Asn Trp Ser Met Val Leu Gly Trp Leu
705                 710                 715                 720 atg ctc gcc tgt tcc gtc atc tgg atc cca att atg ttt gtg ata aaa      2208
Met Leu Ala Cys Ser Val Ile Trp Ile Pro Ile Met Phe Val Ile Lys
                725                 730                 735 atg cat ctg gcc cct gga aga ttt att gag agg ctg aag ttg gtg tgc      2256
Met His Leu Ala Pro Gly Arg Phe Ile Glu Arg Leu Lys Leu Val Cys
            740                 745                 750 tcg cca cag ccg gac tgg ggc cca ttc tta gct caa cac cgc ggg gag      2304
Ser Pro Gln Pro Asp Trp Gly Pro Phe Leu Ala Gln His Arg Gly Glu
        755                 760                 765 cgt tac aag aac atg atc gac ccc ttg gga acc tct tcc ttg gga ctc      2352
Arg Tyr Lys Asn Met Ile Asp Pro Leu Gly Thr Ser Ser Leu Gly Leu
    770                 775                 780 aaa ctg cca gtg aag gat ttg gaa ctg ggc act cag tgc tag              2394
Lys Leu Pro Val Lys Asp Leu Glu Leu Gly Thr Gln Cys
785                 790                 795

<210> SEQ ID NO 122
<211> LENGTH: 797
<212> TYPE: PRT
<213> ORGANISM: Human
```

-continued

```
<400> SEQUENCE: 122

Met Asp Cys Ser Ala Pro Lys Glu Met Asn Lys Leu Pro Ala Asn Ser
  1               5                  10                  15

Pro Glu Ala Ala Ala Gln Ser His Pro Asp Gly Pro Cys Ala Pro
             20                  25                  30

Arg Thr Ser Pro Glu Gln Glu Leu Pro Ala Ala Ala Pro Pro Pro
         35                  40                  45

Pro Arg Val Pro Arg Ser Ala Ser Thr Gly Ala Gln Thr Phe Gln Ser
 50                  55                  60

Ala Asp Ala Arg Ala Cys Glu Ala Glu Arg Pro Gly Val Gly Ser Cys
 65                  70                  75                  80

Lys Leu Ser Ser Pro Arg Ala Gln Ala Ala Ser Ala Ala Leu Arg Asp
                 85                  90                  95

Leu Arg Glu Ala Gln Ser Ala Gln Ala Ser Pro Pro Gly Ser Ser
            100                 105                 110

Gly Pro Gly Asn Ala Leu His Cys Lys Ile Pro Ser Leu Arg Gly Pro
            115                 120                 125

Glu Gly Asp Ala Asn Val Ser Val Gly Lys Gly Thr Leu Glu Arg Asn
130                 135                 140

Asn Thr Pro Val Val Gly Trp Val Asn Met Gly Gln Ser Thr Val Val
145                 150                 155                 160

Leu Gly Thr Asp Gly Ile Thr Ser Val Leu Pro Gly Ser Val Ala Thr
                165                 170                 175

Val Ala Thr Gln Glu Asp Glu Gln Gly Asp Glu Asp Lys Ala Arg Gly
            180                 185                 190

Asn Trp Ser Ser Lys Leu Asp Phe Ile Leu Ser Met Val Gly Tyr Ala
        195                 200                 205

Val Gly Leu Gly Asn Val Trp Arg Phe Pro Tyr Leu Ala Phe Gln Asn
    210                 215                 220

Gly Gly Gly Ala Phe Leu Ile Pro Tyr Leu Met Met Leu Ala Leu Ala
225                 230                 235                 240

Gly Leu Pro Ile Phe Phe Leu Glu Val Ser Leu Gly Gln Phe Ala Ser
                245                 250                 255

Gln Gly Pro Val Ser Val Trp Lys Ala Ile Pro Ala Leu Gln Gly Cys
            260                 265                 270

Gly Ile Ala Met Leu Ile Ile Ser Val Leu Ile Ala Ile Tyr Tyr Asn
        275                 280                 285

Val Ile Ile Cys Tyr Thr Leu Phe Tyr Leu Phe Ala Ser Phe Val Ser
    290                 295                 300

Val Leu Pro Trp Gly Ser Cys Asn Asn Pro Trp Asn Thr Pro Glu Cys
305                 310                 315                 320

Lys Asp Lys Thr Lys Leu Leu Leu Asp Ser Cys Val Ile Ser Asp His
                325                 330                 335

Pro Lys Ile Gln Ile Lys Asn Ser Thr Phe Cys Met Thr Ala Tyr Pro
            340                 345                 350

Asn Val Thr Met Val Asn Phe Thr Ser Leu Ala Asn Lys Thr Phe Val
        355                 360                 365

Ser Gly Ser Glu Glu Tyr Phe Lys Tyr Phe Val Leu Lys Ile Ser Ala
    370                 375                 380

Gly Ile Glu Tyr Pro Gly Glu Ile Arg Trp Pro Leu Ala Leu Cys Leu
385                 390                 395                 400

Phe Leu Ala Trp Val Ile Val Tyr Ala Ser Leu Ala Lys Gly Ile Lys
```

```
                        405                 410                 415
Thr Ser Gly Lys Val Val Tyr Phe Thr Ala Thr Phe Pro Tyr Val Val
            420                 425                 430
Leu Val Ile Leu Leu Ile Arg Gly Val Thr Leu Pro Gly Ala Gly Ala
            435                 440                 445
Gly Ile Trp Tyr Phe Ile Thr Pro Lys Trp Glu Lys Leu Thr Asp Ala
            450                 455                 460
Thr Val Trp Lys Asp Ala Ala Thr Gln Ile Phe Phe Ser Leu Ser Ala
465                 470                 475                 480
Ala Trp Gly Gly Leu Ile Thr Leu Ser Ser Tyr Asn Lys Phe His Asn
                485                 490                 495
Asn Cys Tyr Arg Asp Thr Leu Ile Val Thr Cys Thr Asn Ser Ala Thr
            500                 505                 510
Ser Ile Phe Ala Gly Phe Val Ile Phe Ser Val Ile Gly Phe Met Ala
            515                 520                 525
Asn Glu Arg Lys Val Asn Ile Glu Asn Val Ala Asp Gln Gly Pro Gly
            530                 535                 540
Ile Ala Phe Val Val Tyr Pro Glu Ala Leu Thr Arg Leu Pro Leu Ser
545                 550                 555                 560
Pro Phe Trp Ala Ile Ile Phe Phe Leu Met Leu Leu Thr Leu Gly Leu
                565                 570                 575
Asp Thr Met Phe Ala Ser Ile Glu Thr Ile Val Thr Ser Ile Ser Asp
            580                 585                 590
Glu Phe Pro Lys Tyr Leu Arg Thr His Lys Pro Val Phe Thr Leu Gly
                595                 600                 605
Cys Cys Ile Cys Phe Phe Ile Met Gly Phe Pro Met Ile Thr Gln Gly
            610                 615                 620
Gly Ile Tyr Met Phe Gln Leu Val Asp Thr Tyr Ala Ala Ser Tyr Ala
625                 630                 635                 640
Leu Val Ile Ile Ala Ile Phe Glu Leu Val Gly Ile Ser Tyr Val Tyr
                645                 650                 655
Gly Leu Gln Arg Phe Cys Glu Asp Ile Glu Met Met Ile Gly Phe Gln
            660                 665                 670
Pro Asn Ile Phe Trp Lys Val Cys Trp Ala Phe Val Thr Pro Thr Ile
            675                 680                 685
Leu Thr Phe Ile Leu Cys Phe Ser Phe Tyr Gln Trp Glu Pro Met Thr
690                 695                 700
Tyr Gly Ser Tyr Arg Tyr Pro Asn Trp Ser Met Val Leu Gly Trp Leu
705                 710                 715                 720
Met Leu Ala Cys Ser Val Ile Trp Ile Pro Ile Met Phe Val Ile Lys
            725                 730                 735
Met His Leu Ala Pro Gly Arg Phe Ile Glu Arg Leu Lys Leu Val Cys
            740                 745                 750
Ser Pro Gln Pro Asp Trp Gly Pro Phe Leu Ala Gln His Arg Gly Glu
            755                 760                 765
Arg Tyr Lys Asn Met Ile Asp Pro Leu Gly Thr Ser Ser Leu Gly Leu
            770                 775                 780
Lys Leu Pro Val Lys Asp Leu Glu Leu Gly Thr Gln Cys
785                 790                 795

<210> SEQ ID NO 123
<211> LENGTH: 2394
<212> TYPE: DNA
<213> ORGANISM: Human
```

```
<220> FEATURE:
<221> NAME/KEY: CDS
<222> LOCATION: (1)..(2391)
<223> OTHER INFORMATION: SEQ ID NO:26 [WO98/07854 (PCT/US97/14637)]
      Allelix Sequence; nt 1-2394; nt 304 may be G; nt 371 may be T;
      nt 836 may be A; nt 1116 may be G; nt 1831 may be G; nt 2382 may
      be A or T; nt 2385 may be G;
<220> FEATURE:
<223> OTHER INFORMATION: nt 2388 may be A

<400> SEQUENCE: 123 atg gat tgc agt gct ccc aag gaa atg aat aaa ctg cca gcc aac agc        48
Met Asp Cys Ser Ala Pro Lys Glu Met Asn Lys Leu Pro Ala Asn Ser
 1               5                  10                  15 ccg gag gcg gcg gcg gcg cag ggc cac ccg gat ggc cca tgc gct ccc        96
Pro Glu Ala Ala Ala Ala Gln Gly His Pro Asp Gly Pro Cys Ala Pro
             20                  25                  30 agg acg agc ccg gag cag gag ctt ccc gcg gct gcc gcc ccg ccg ccg       144
Arg Thr Ser Pro Glu Gln Glu Leu Pro Ala Ala Ala Pro Pro Pro
         35                  40                  45 cca cgt gtg ccc agg tcc gct tcc acc ggc gcc caa act ttc cag tca       192
Pro Arg Val Pro Arg Ser Ala Ser Thr Gly Ala Gln Thr Phe Gln Ser
 50                  55                  60 gcg gac gcg cga gcc tgc gag gct gag cgg cca gga gtg ggg tct tgc       240
Ala Asp Ala Arg Ala Cys Glu Ala Glu Arg Pro Gly Val Gly Ser Cys
 65                  70                  75                  80 aaa ctc agt agc ccg cgg gcg cag gcg gcc tct gca gct ctg cgg gac       288
Lys Leu Ser Ser Pro Arg Ala Gln Ala Ala Ser Ala Ala Leu Arg Asp
                 85                  90                  95 ttg aga gag gcg caa agc gcg cag gcc tcg ccc cct ccc ggg agc tcc       336
Leu Arg Glu Ala Gln Ser Ala Gln Ala Ser Pro Pro Pro Gly Ser Ser
            100                 105                 110 ggg ccc ggc aac gcg ctg cac tgt aag atc cct tct ctg cga ggc ccg       384
Gly Pro Gly Asn Ala Leu His Cys Lys Ile Pro Ser Leu Arg Gly Pro
        115                 120                 125 gag ggg gat gcg aac gtg agt gtg ggc aag ggc acc ctg gag cgg aac       432
Glu Gly Asp Ala Asn Val Ser Val Gly Lys Gly Thr Leu Glu Arg Asn
    130                 135                 140 aat acc cct gtt gtg ggc tgg gtg aac atg agc cag agc acc gtg gtg       480
Asn Thr Pro Val Val Gly Trp Val Asn Met Ser Gln Ser Thr Val Val
145                 150                 155                 160 ctg ggc acg gat gga atc acg tcc gtg ctc ccg ggc agc gtg gcc acc       528
Leu Gly Thr Asp Gly Ile Thr Ser Val Leu Pro Gly Ser Val Ala Thr
                165                 170                 175 gtt gcc acc cag gag gac gag caa ggg gat gag aat aag gcc cga ggg       576
Val Ala Thr Gln Glu Asp Glu Gln Gly Asp Glu Asn Lys Ala Arg Gly
            180                 185                 190 aac tgg tcc agc aaa ctg gac ttc atc ctg tcc atg gtg ggg tac gca       624
Asn Trp Ser Ser Lys Leu Asp Phe Ile Leu Ser Met Val Gly Tyr Ala
        195                 200                 205 gtg ggg ctg ggc aat gtc tgg agg ttt ccc tac ctg gcc ttc cag aac       672
Val Gly Leu Gly Asn Val Trp Arg Phe Pro Tyr Leu Ala Phe Gln Asn
    210                 215                 220 ggg gga ggt gct ttc ctc atc cct tac ctg atg ctg gct ctg gct           720
Gly Gly Gly Ala Phe Leu Ile Pro Tyr Leu Met Met Leu Ala Leu Ala
225                 230                 235                 240 gga tta ccc atc ttc ttc ttg gag gtg tcg ctg ggc cag ttt gcc agc       768
Gly Leu Pro Ile Phe Phe Leu Glu Val Ser Leu Gly Gln Phe Ala Ser
                245                 250                 255 cag gga cca gtg tct gtg tgg aag gcc atc cca gct cta caa ggc tgt       816
Gln Gly Pro Val Ser Val Trp Lys Ala Ile Pro Ala Leu Gln Gly Cys
            260                 265                 270
```

-continued

```
ggc atc gcg atg ctg atc atc tct gtc cta ata gcc ata tac tac aat        864
Gly Ile Ala Met Leu Ile Ile Ser Val Leu Ile Ala Ile Tyr Tyr Asn
            275                 280                 285 gtg att att tgc tat aca ctt ttc tac ctg ttt gcc tcc ttt gtg tct        912
Val Ile Ile Cys Tyr Thr Leu Phe Tyr Leu Phe Ala Ser Phe Val Ser
290                 295                 300 gta cta ccc tgg ggc tcc tgc aac aac cct tgg aat acg cca gaa tgc        960
Val Leu Pro Trp Gly Ser Cys Asn Asn Pro Trp Asn Thr Pro Glu Cys
305                 310                 315                 320 aaa gat aaa acc aaa ctt tta tta gat tcc tgt gtt atc agt gac cat       1008
Lys Asp Lys Thr Lys Leu Leu Leu Asp Ser Cys Val Ile Ser Asp His
            325                 330                 335 ccc aaa ata cag atc aag aac tcg act ttc tgc atg acc gct tat ccc       1056
Pro Lys Ile Gln Ile Lys Asn Ser Thr Phe Cys Met Thr Ala Tyr Pro
            340                 345                 350 aac gtg aca atg gtt aat ttc acc agc cag gcc aat aag aca ttt gtc       1104
Asn Val Thr Met Val Asn Phe Thr Ser Gln Ala Asn Lys Thr Phe Val
            355                 360                 365 agt gga agt gaa gag tac ttc aag tac ttt gtg ctg aag att tct gca       1152
Ser Gly Ser Glu Glu Tyr Phe Lys Tyr Phe Val Leu Lys Ile Ser Ala
370                 375                 380 ggg att gaa tat cct ggc gag atc agg tgg cca cta gct ctc tgc ctc       1200
Gly Ile Glu Tyr Pro Gly Glu Ile Arg Trp Pro Leu Ala Leu Cys Leu
385                 390                 395                 400 ttc ctg gct tgg gtc att gtg tat gca tcg ttg gct aaa gga atc aag       1248
Phe Leu Ala Trp Val Ile Val Tyr Ala Ser Leu Ala Lys Gly Ile Lys
                405                 410                 415 act tca gga aaa gtg gtg tac ttc acg gcc acg ttc ccg tat gtc gta       1296
Thr Ser Gly Lys Val Val Tyr Phe Thr Ala Thr Phe Pro Tyr Val Val
            420                 425                 430 ctc gtg atc ctc ctc atc cga gga gtc acc ctg cct gga gct gga gct       1344
Leu Val Ile Leu Leu Ile Arg Gly Val Thr Leu Pro Gly Ala Gly Ala
            435                 440                 445 ggg atc tgg tac ttc atc aca ccc aag tgg gag aaa ctc acg gat gcc       1392
Gly Ile Trp Tyr Phe Ile Thr Pro Lys Trp Glu Lys Leu Thr Asp Ala
450                 455                 460 acg gtg tgg aaa gat gct gcc act cag att ttc ttc tct tta tct gct       1440
Thr Val Trp Lys Asp Ala Ala Thr Gln Ile Phe Phe Ser Leu Ser Ala
465                 470                 475                 480 gca tgg gga ggc ctg atc act ctc tct tct tac aac aaa ttc cac aac       1488
Ala Trp Gly Gly Leu Ile Thr Leu Ser Ser Tyr Asn Lys Phe His Asn
                485                 490                 495 aac tgc tac agg gac act cta att gtc acc tgc acc aac agt gcc aca       1536
Asn Cys Tyr Arg Asp Thr Leu Ile Val Thr Cys Thr Asn Ser Ala Thr
                500                 505                 510 agc atc ttt gcc ggc ttc gtc atc ttc tcc gtt atc ggc ttc atg gcc       1584
Ser Ile Phe Ala Gly Phe Val Ile Phe Ser Val Ile Gly Phe Met Ala
            515                 520                 525 aat gaa cgc aaa gtc aac att gag aat gtg gca gac caa ggg cca ggc       1632
Asn Glu Arg Lys Val Asn Ile Glu Asn Val Ala Asp Gln Gly Pro Gly
530                 535                 540 att gca ttt gtg gtt tac ccg gaa gcc tta acc agg ctg cct ctc tct       1680
Ile Ala Phe Val Val Tyr Pro Glu Ala Leu Thr Arg Leu Pro Leu Ser
545                 550                 555                 560 ccg ttc tgg gcc atc atc ttt ttc ctg atg ctc ctc act ctt gga ctt       1728
Pro Phe Trp Ala Ile Ile Phe Phe Leu Met Leu Leu Thr Leu Gly Leu
                565                 570                 575 gac act atg ttt gcc acc atc gag acc ata gtg acc tcc atc tca gac       1776
Asp Thr Met Phe Ala Thr Ile Glu Thr Ile Val Thr Ser Ile Ser Asp
```

```
                580                 585                 590
gag ttt ccc aag tac cta cgc aca cac aag cca gtg ttt act ctg ggc    1824
Glu Phe Pro Lys Tyr Leu Arg Thr His Lys Pro Val Phe Thr Leu Gly
        595                 600                 605 tgc tgc att tgt ttc ttc atc atg ggt ttt cca atg atc act cag ggt    1872
Cys Cys Ile Cys Phe Phe Ile Met Gly Phe Pro Met Ile Thr Gln Gly
610                 615                 620 gga att tac atg ttt cag ctt gtg gac acc tat gct gcc tcc tat gcc    1920
Gly Ile Tyr Met Phe Gln Leu Val Asp Thr Tyr Ala Ala Ser Tyr Ala
625                 630                 635                 640 ctt gtc atc att gcc att ttt gag ctc gtg ggg atc tct tat gtg tat    1968
Leu Val Ile Ile Ala Ile Phe Glu Leu Val Gly Ile Ser Tyr Val Tyr
                645                 650                 655 ggc ttg caa aga ttc tgt gaa gat ata gag atg atg att gga ttc cag    2016
Gly Leu Gln Arg Phe Cys Glu Asp Ile Glu Met Met Ile Gly Phe Gln
            660                 665                 670 cct aac atc ttc tgg aaa gtc tgc tgg gca ttt gta acc cca acc att    2064
Pro Asn Ile Phe Trp Lys Val Cys Trp Ala Phe Val Thr Pro Thr Ile
        675                 680                 685 tta acc ttt atc ctt tgc ttc agc ttt tac cag tgg gag ccc atg acc    2112
Leu Thr Phe Ile Leu Cys Phe Ser Phe Tyr Gln Trp Glu Pro Met Thr
690                 695                 700 tat ggc tct tac cgc tat cct aac tgg tcc atg gtg ctc gga tgg cta    2160
Tyr Gly Ser Tyr Arg Tyr Pro Asn Trp Ser Met Val Leu Gly Trp Leu
705                 710                 715                 720 atg ctc gcc tgt tcc gtc atc tgg atc cca att atg ttt gtg ata aaa    2208
Met Leu Ala Cys Ser Val Ile Trp Ile Pro Ile Met Phe Val Ile Lys
                725                 730                 735 atg cat ctg gcc cct gga aga ttt att gag agg ctg aag ttg gtg tgc    2256
Met His Leu Ala Pro Gly Arg Phe Ile Glu Arg Leu Lys Leu Val Cys
            740                 745                 750 tcg cca cag ccg gac tgg ggc cca ttc tta gct caa cac cgc ggg gag    2304
Ser Pro Gln Pro Asp Trp Gly Pro Phe Leu Ala Gln His Arg Gly Glu
        755                 760                 765 cgt tac aag aac atg atc gac ccc ttg gga acc tct tcc ttg gga ctc    2352
Arg Tyr Lys Asn Met Ile Asp Pro Leu Gly Thr Ser Ser Leu Gly Leu
770                 775                 780 aaa ctg cca gtg aag gat ttg gaa ctg ggc act cag tgc tag            2394
Lys Leu Pro Val Lys Asp Leu Glu Leu Gly Thr Gln Cys
785                 790                 795

<210> SEQ ID NO 124
<211> LENGTH: 797
<212> TYPE: PRT
<213> ORGANISM: Human

<400> SEQUENCE: 124

Met Asp Cys Ser Ala Pro Lys Glu Met Asn Lys Leu Pro Ala Asn Ser
1               5                   10                  15

Pro Glu Ala Ala Ala Gln Gly His Pro Asp Gly Pro Cys Ala Pro
            20                  25                  30

Arg Thr Ser Pro Glu Gln Glu Leu Pro Ala Ala Ala Pro Pro Pro
        35                  40                  45

Pro Arg Val Pro Arg Ser Ala Ser Thr Gly Ala Gln Thr Phe Gln Ser
    50                  55                  60

Ala Asp Ala Arg Ala Cys Glu Ala Glu Arg Pro Gly Val Gly Ser Cys
65                  70                  75                  80

Lys Leu Ser Ser Pro Arg Ala Gln Ala Ala Ser Ala Ala Leu Arg Asp
                85                  90                  95
```

```
Leu Arg Glu Ala Gln Ser Ala Gln Ala Ser Pro Pro Gly Ser Ser
            100                 105                 110
Gly Pro Gly Asn Ala Leu His Cys Lys Ile Pro Ser Leu Arg Gly Pro
        115                 120                 125
Glu Gly Asp Ala Asn Val Ser Val Gly Lys Gly Thr Leu Glu Arg Asn
    130                 135                 140
Asn Thr Pro Val Val Gly Trp Val Asn Met Ser Gln Ser Thr Val Val
145                 150                 155                 160
Leu Gly Thr Asp Gly Ile Thr Ser Val Leu Pro Gly Ser Val Ala Thr
                165                 170                 175
Val Ala Thr Gln Glu Asp Glu Gln Gly Asp Glu Asn Lys Ala Arg Gly
            180                 185                 190
Asn Trp Ser Ser Lys Leu Asp Phe Ile Leu Ser Met Val Gly Tyr Ala
        195                 200                 205
Val Gly Leu Gly Asn Val Trp Arg Phe Pro Tyr Leu Ala Phe Gln Asn
    210                 215                 220
Gly Gly Gly Ala Phe Leu Ile Pro Tyr Leu Met Met Leu Ala Leu Ala
225                 230                 235                 240
Gly Leu Pro Ile Phe Phe Leu Glu Val Ser Leu Gly Gln Phe Ala Ser
                245                 250                 255
Gln Gly Pro Val Ser Val Trp Lys Ala Ile Pro Ala Leu Gln Gly Cys
            260                 265                 270
Gly Ile Ala Met Leu Ile Ile Ser Val Leu Ile Ala Ile Tyr Tyr Asn
        275                 280                 285
Val Ile Ile Cys Tyr Thr Leu Phe Tyr Leu Phe Ala Ser Phe Val Ser
    290                 295                 300
Val Leu Pro Trp Gly Ser Cys Asn Asn Pro Trp Asn Thr Pro Glu Cys
305                 310                 315                 320
Lys Asp Lys Thr Lys Leu Leu Leu Asp Ser Cys Val Ile Ser Asp His
                325                 330                 335
Pro Lys Ile Gln Ile Lys Asn Ser Thr Phe Cys Met Thr Ala Tyr Pro
            340                 345                 350
Asn Val Thr Met Val Asn Phe Thr Ser Gln Ala Asn Lys Thr Phe Val
        355                 360                 365
Ser Gly Ser Glu Glu Tyr Phe Lys Tyr Phe Val Leu Lys Ile Ser Ala
    370                 375                 380
Gly Ile Glu Tyr Pro Gly Glu Ile Arg Trp Pro Leu Ala Leu Cys Leu
385                 390                 395                 400
Phe Leu Ala Trp Val Ile Val Tyr Ala Ser Leu Ala Lys Gly Ile Lys
                405                 410                 415
Thr Ser Gly Lys Val Val Tyr Phe Thr Ala Thr Phe Pro Tyr Val Val
            420                 425                 430
Leu Val Ile Leu Leu Ile Arg Gly Val Thr Leu Pro Gly Ala Gly Ala
        435                 440                 445
Gly Ile Trp Tyr Phe Ile Thr Pro Lys Trp Glu Lys Leu Thr Asp Ala
    450                 455                 460
Thr Val Trp Lys Asp Ala Ala Thr Gln Ile Phe Phe Ser Leu Ser Ala
465                 470                 475                 480
Ala Trp Gly Gly Leu Ile Thr Leu Ser Ser Tyr Asn Lys Phe His Asn
                485                 490                 495
Asn Cys Tyr Arg Asp Thr Leu Ile Val Thr Cys Thr Asn Ser Ala Thr
            500                 505                 510
```

-continued

```
Ser Ile Phe Ala Gly Phe Val Ile Phe Ser Val Ile Gly Phe Met Ala
            515                 520                 525

Asn Glu Arg Lys Val Asn Ile Glu Asn Val Ala Asp Gln Gly Pro Gly
            530                 535                 540

Ile Ala Phe Val Val Tyr Pro Glu Ala Leu Thr Arg Leu Pro Leu Ser
545                 550                 555                 560

Pro Phe Trp Ala Ile Ile Phe Phe Leu Met Leu Leu Thr Leu Gly Leu
            565                 570                 575

Asp Thr Met Phe Ala Thr Ile Glu Thr Ile Val Thr Ser Ile Ser Asp
            580                 585                 590

Glu Phe Pro Lys Tyr Leu Arg Thr His Lys Pro Val Phe Thr Leu Gly
            595                 600                 605

Cys Cys Ile Cys Phe Phe Ile Met Gly Phe Pro Met Ile Thr Gln Gly
            610                 615                 620

Gly Ile Tyr Met Phe Gln Leu Val Asp Thr Tyr Ala Ala Ser Tyr Ala
625                 630                 635                 640

Leu Val Ile Ile Ala Ile Phe Glu Leu Val Gly Ile Ser Tyr Val Tyr
            645                 650                 655

Gly Leu Gln Arg Phe Cys Glu Asp Ile Glu Met Met Ile Gly Phe Gln
            660                 665                 670

Pro Asn Ile Phe Trp Lys Val Cys Trp Ala Phe Val Thr Pro Thr Ile
            675                 680                 685

Leu Thr Phe Ile Leu Cys Phe Ser Phe Tyr Gln Trp Glu Pro Met Thr
690                 695                 700

Tyr Gly Ser Tyr Arg Tyr Pro Asn Trp Ser Met Val Leu Gly Trp Leu
705                 710                 715                 720

Met Leu Ala Cys Ser Val Ile Trp Ile Pro Ile Met Phe Val Ile Lys
            725                 730                 735

Met His Leu Ala Pro Gly Arg Phe Ile Glu Arg Leu Lys Leu Val Cys
            740                 745                 750

Ser Pro Gln Pro Asp Trp Gly Pro Phe Leu Ala Gln His Arg Gly Glu
            755                 760                 765

Arg Tyr Lys Asn Met Ile Asp Pro Leu Gly Thr Ser Ser Leu Gly Leu
    770                 775                 780

Lys Leu Pro Val Lys Asp Leu Glu Leu Gly Thr Gln Cys
785                 790                 795
```

HUMAN GLYCINE TRANSPORTER TYPE 2

The present invention relates to nucleic acids encoding human glycine transporter type 2 (GlyT2) molecules, to proteins encoded by such nucleic acids, to methods of characterizing GlyT2-active compounds, to uses of DNA and RNA nucleotide probes directed to nucleic acids encoding the GlyT2 transporter, to uses of antisense molecules to inhibit GlyT2 expression, to uses of the GlyT2 protein to generate GlyT2-specific antibodies, and to screening methods using GlyT2-expressing cell lines, and to the field of drug discovery.

BACKGROUND

The termination of synaptic transmission in the central nervous system (CNS) involves either the enzymatic inactivation of neurotransmitters, or their uptake into presynaptic terminals or surrounding glial cells (Amara, S. G. and Kuhar, M. J., *Annu. Rev. Neurosci.* 16:73–93 (1998); Malandro, M. S. and Kilberg, M. S., *Annu. Rev. Biochem.* 65:305–336 (1996)). High-affinity, membrane-associated transporters typically mediate the rapid removal of neurotransmitters from the synaptic cleft, with uptake across a concentration gradient being thermodynamically coupled to transmembrane ion gradients (Kanner, B. I., *Curr. Opin. Cell Biol.* 1:735–738 (1989)).

Neurotransmitter transporters can be separated into two structurally-distinct families. One family mediates $Na^{30}$-dependent excitatory amino acid uptake (Kanai, Y. and Hediger, M. A., *Nature* 360:467–471 (1992); Pines, G., et al., *Nature* 360:464–466 (1993); Storck, et al., *Proc. Natl. Acad. Sci.* (USA) 89:10855–10859 (1992)). The other family contains several members involved in the $Na^{30}/Cl^-$-dependent transport of a host of other neurotransmitters, including GABA (Borden, L. A., et al., *J. Biol. Chem.* 267:21096–21104 (1992)); catecholamines (Pacholczyk, T., et al., *Nature* 350:350–354 (1991)); glycine (Kim, et al., Mol. Pharm. 45:608–17 (1994); Liu, Q. R., et al., *FEBS Lett.* 305:110–114 (1992a)); proline (Fremeau, R. T., et al., *Neuron* 8:915–926 (1992)) and taurine (Liu, Q. R., et al., *Proc. Natl. Acad. Sci.* (USA) 89:12145–12149 (1992b)). The gene products for most of the latter family have recently been cloned and sequenced. These transporters demonstrate 40–50% amino acid similarity and likely exhibit structural conservation, as membrane topology analysis predicts twelve putative transmembrane regions (Guastella, J., et al., *Science* 249:1303–1306 (1990); Smith, K. E., et al., *Neuron* 8:927–935 (1992)). The high homology within these transmembrane regions has facilitated the design of degenerate primers for the cloning of additional members of the transporter superfamily using PCR-based technologies (Borowsky, B., et al., *Neuron* 10:851–863 (1993); Hoffman, B. J., et al., *Science* 254:579–580 (1991)).

Glycine is a major inhibitory neurotransmitter in the spinal cord, brainstem and retina, where it exerts its effects on the strychnine-sensitive glycine receptors (Betz, H., et al., *Ann. N. Y. Acad. Sci.*, 207:109–115 (1993); Betz, H., et al., *Q. Rev. Biophys.* 25:381–394 (1992)). In addition, glycine acts as a co-agonist with glutamate at the NMDA receptor (Kemp, J. A. and Leeson, P. D., *Trends. Pharmacol. Sci.* 14:20–25 (1993); Benveniste, M., et al., *J. Physiol.* (London) 428:333–357 (1990)). Synaptic glycine concentrations are controlled by $Na^+/Cl^-$-dependent high-affinity transporters found at nerve-terminals and glial cells (Johnston, G. A. R. and Iverson, L. L., *J. Neurochem.* 18:1951–1961 (1971); Fedele E. and Foster A. C., *Brain Res.* 572:154–163 (1992)). Two distinct glycine transporters, GlyT1 (Smith, K. E., et al., *Neuron* 8:927–935 (1992); Liu, Q. R., et al., *FEBS Lett.* 305:110–114 (1992i); Guastella, J., et al., *Proc. Natl. Acad. Sci.* (USA) 89:7189–7193 (1992)) and GlyT2 (Liu, Q. R., et al., *J. Biol. Chem.* 268:22802–22806 (1993)), have been isolated, and share approximately 50% identity at both the nucleotide and amino acid levels. Localization of GlyT1 and GlyT2 by in situ hybridization techniques reveals distinct patterns of expression in the CNS (Liu, Q. R., et al., *J. Biol. Chem.* 268:22802–22806 (1993); Zafra, F., et al., *J. Neurosci.* 15:3952–3969 (1995)). GlyT1 is expressed in the hippocampal and cortical regions of the brain, as well as in the spinal cord and brainstem regions. In contrast, GlyT2 is expressed primarily in the spinal cord and cerebellum, and is absent in the hippocampal and cortical regions. Based on their patterns of expression, GlyT1 is thought to co-localize with NMDA receptors, while GlyT2 expression mimics that of strychnine-sensitive glycine receptors (Jursky and Nelson, *J. Neurochem.* 67:336–344 (1996); Liu, Q. R., et al., *J. Biol. Chem.* 268:22802–22806 (1993)).

The GlyT1 sequence has been determined for a number of species, including rat (Guastella, J., et al., *Proc. Natl. Acad. Sci.* (USA) 89:7189–7193 (1992)), mouse (Liu, Q. R., et al., *FEBS Lett.* 305:110–114 (1992a)) and human (Kim, K-M., et al., *Mol. Pharm.* 45:608–17 (1994)). Three alternatively spliced forms of the human transporter have been identified (GlyT1a-c) which differ in their amino-terminal sequences (Guastella, J., et al., *Proc. Natl. Acad. Sci.* (USA) 89:7189–7193 (1992); Liu, Q. R., et al., *FEBS Lett.* 305:110–114 (1992a); Liu, Q. R., et al., *J. Biol. Chem.* 268:22802–22806 (1993); Smith, K. E., et al., *Neuron* 8:927–935 (1992); Borowsky, B., et al., *Neuron* 10:851–863 (1993); Kim, K-M., et al., *Mol. Pharm.* 45:608–17 (1994)). The rat GlyT2 sequence has been published (Liu, Q. R., et al., *J. Biol. Chem.* 268:22802–22806 (1993)), and it also exhibits alternatively spliced forms (GlyT2a and GlyT2b) (Ponce, J., et al., *Neurosci. Lett.* 242:25–28 (1998)). Recently, two full-length clones described as pHGT2-a and pHGT2-b of human GlyT2 have been constructed (WO98/07854; PCT/US97/14637).

The precise regulation of synaptic glycine concentrations in the CNS is a very important process because glycine is involved in both excitatory and inhibitory neurotransmission (Betz, H., et al., *Ann. N. Y. Acad. Sci.*, 207:109–115 (1993); Benveniste, M., et al., *J. Physiol.* (London) 428:333–357 (1990)). Glycine transporters are likely to be critical to this process. Compounds able to modulate glycine transporter function (i.e., that inhibit or activate glycine transporter) would be expected to provide a wide variety of therapeutic benefits. For example, glycine receptor inhibition is known to result in pain transmission (Yaksh, *Pain,* 111–123, (1989)). Therefore, compounds that inhibit GlyT2 transporter activity may increase the activity of neurons having strychnine-sensitive glycine receptors via increasing synaptic levels of glycine, thus diminishing the transmission of pain-related (i.e., nociceptive) information in the spinal cord, which has been shown to be mediated by these receptors. Further, because glycine receptor malfunction is known to play a role in muscle spasticity (Becker, *FASEB J.* 4:2767–2775 (1990)), compounds that inhibit GlyT2 transporter activity and lead to enhanced inhibitory glycinergic transmission through strychnine-sensitive glycine receptors in the spinal cord can be used to decrease muscle hyperactivity. Such compounds are useful in treating diseases or conditions associated with increased muscle contraction, such as muscle spasticity, myoclonus (which relates to rapid muscle spasms) and epilepsy. Spasticity that may be treated via modulation of glycine receptors is associated with epilepsy, stroke, head trauma, multiple sclerosis, spinal cord injury, dystonia, and other conditions of illness and injury of the nervous system.

SUMMARY OF THE INVENTION

The present invention provides novel human glycine transporter type 2 (GlyT2) molecules. Nucleic acids are provided comprising nucleic acid sequences that encode proteins that have glycine transport activity and that have one or more of the following amino acids: (1) serine at a position corresponding to amino acid 24, (2) tryptophan at a position corresponding to amino acid 74, (3) glycine at a position corresponding to amino acid 155, (4) aspartic acid at a position corresponding to amino acid 188, (5) leucine at a position corresponding to amino acid 362, (6) alanine at a position corresponding to amino acid 431, or (7) serine at a position corresponding to amino acid 582, of SEQ ID NO:124. A preferred GlyT2 sequence comprises the amino acid sequence of SEQ ID NO:120. The present invention provides nucleic acids wherein the nucleic acid sequence is that of bases 1 to 2391 of SEQ ID NO: 123 but having one or more of the following nucleotides: (1) A at position 70, (2) T at position 220, (3) G at position 463, (4) G at position 562, (5) T at position 1085, (6) C at position 1292, (7) A at position 1299, (8) T at position 1617, or (9) T at position 1744. A preferred GlyT2 sequence comprises the nucleic acid sequence of SEQ ID NO:119.

Nucleic acids are also provided comprising nucleic acid sequences that encode proteins that have glycine transport activity, that have one or more of the seven amino acids listed above and that additionally have one or more of the following amino acids: (1) leucine at a position corresponding to amino acid 26, (2) leucine at a position corresponding to amino acid 75, (3) valine at a position corresponding to amino acid 89, (4) glycine at a position corresponding to amino acid 102, (5) glutamic acid at a position corresponding to amino acid 174, (6) proline at a position corresponding to amino acid 195, (7) glycine at a position corresponding to amino acid 199, (8) leucine at a position corresponding to amino acid 249, (9) proline at a position corresponding to amino acid 306, (10) glutamic acid at a position corresponding to amino acid 419, (11) asparagine at a position corresponding to amino acid 442, (12) lysine at a position corresponding to amino acid 455, (13) cysteine at a position corresponding to amino acid 458, (14) proline at a position corresponding to amino acid 485, (15) arginine at a position corresponding to amino acid 493, or (16) glutamic acid at a position corresponding to amino acid 650, of SEQ ID NO:124.

The present invention also provides nucleic acids wherein the nucleic acid sequence is that of bases 1 to 2391 of SEQ ID NO:119, 121 or 123 but having one or more of the nine nucleotides listed above but additionally having one or more of the following nucleotides: (a) T at position 77, (b) T at position 220, (c) T at position 244, (d) T at position 266, (e) G at position 304, (f) A at position 521, (g) C at position 583, (h) G at position 596, (i) G at position 678, (j) C at position 681, (k) T at position 745, (l) C at position 750, (m) T at position 765, (n) C or A at position 777, (o) G at position 867, (p) C at position 917, (q) A at position 1256, (r) C at position 1292, (s) A at position 1325, (t) A at position 1364, (u) C at position 1374, (v) A at position 1392, (w) C at position 1454, (x) G at position 1478, (y) C at position 1854, (z) A at position 1949, (aa) C at position 1959, or (bb) C at position 2130.

The present invention also provides nucleic acids comprising nucleic acid sequences that encode proteins that have glycine transport activity and that have one or more of the following amino acids: (1) serine at a position corresponding to amino acid 24, (2) tryptophan at a position corresponding to amino acid 74, (3) glycine at a position corresponding to amino acid 155, (4) aspartic acid at a position corresponding to amino acid 188, (5) leucine at a position corresponding to amino acid 362, (6) alanine at a position corresponding to amino acid 431, or (7) serine at a position corresponding to amino acid 582, of SEQ ID NO:124, and that additionally have one or more of the following amino acids: (1) phenylalanine at a position corresponding to amino acid 124, (2) asparagine at a position corresponding to amino acid 279, (3) glycine at a position corresponding to amino acid 393, (4) asparagine at a position corresponding to amino acid 457, (5) asparagine at a position corresponding to amino acid 463, (6) tyrosine at a position corresponding to amino acid 610, (7) valine at a position corresponding to amino acid 611, (8) serine at a position corresponding to amino acid 733, (9) valine at a position corresponding to amino acid 735, (10) leucine at a position corresponding to amino acid 245, (11) leucine at a position corresponding to amino acid 305, (12) isoleucine at a position corresponding to amino acid 366, or (13) proline at a position corresponding to amino acid 400, of SEQ ID NO: 124.

The present invention also provides nucleic acids wherein the nucleic acid sequence is that of bases 1 to 2391 of SEQ ID NO: 123 but having one or more of the following nucleotides: (1) A at position 70, (2) T at position 220, (3) G at position 463, (4) G at position 562, (5) T at position 1085, (6) C at position 1292, (7) A at position 1299, (8) T at position 1617, or (9) T at position 1744, but additionally having one or more of the following nucleotides: (a) C at position 6, (b) T at position 371, (c) T at position 571, (d) A at position 836, (e) G at position 1116, (f) G at position 1177, (g) C at position 1371, (h) A at position 1387, (i) A at position 1829(j) G at position 1831, (k) C at position 2198, (l) G at position 2203, (m) G at position 342, (n) C at position 733, (o) C at position 913, (p) A at position 951, (q) T at position 1097, (r) C at position 1199, (s) T at position 352, or (t) A at position 2103.

The present invention also provides nucleic acids encoding glycine transporters having at least about 96% sequence identity with the protein sequence of SEQ ID NO: 122 or with a sequence corresponding to the protein sequence of SEQ ID NO: 122 except that it has one or more of the following amino acid substitutions: (1) Pro$^{26}$ to Leu, (2) Arg$^{74}$ to Trp, (3) Pro$^{75}$ to Leu, (4) Ala$^{89}$ to Val, (5) Ser$^{102}$ to Gly, (6) Val$^{174}$ to Glu, (7) Ser$^{195}$ to Pro, (8) Asp$^{199}$ to Gly, (9) Val$^{249}$ to Leu, (10) Leu$^{306}$ to Pro, (11) Gly$^{419}$ to Glu, (12) Thr$^{442}$ to Asn, (13) Thr$^{455}$ to Lys, (14) Trp$^{458}$ to Cys, (15) Leu$^{485}$ to Pro, (16) Lys$^{493}$ to Arg, or (17) Val$^{650}$ to Glu. Preferably, the sequence identity is at least about 97%, more preferably at least about 98%, yet more preferably at least about 99%, yet more preferably at least about 99.5%. In an embodiment of the invention, the sequence identity is 100%. Preferably, the encoded glycine transporter has no more than four amino acid differences in the region from amino acid 200 to 797 of reference protein sequence, where the reference sequence is SEQ ID NO: 122 or of a sequence corresponding to the protein sequence of SEQ ID NO:122 except that it has one of the substitutions described above. More preferably, the encoded glycine transporter has no more than two such differences.

The present invention also provides vectors comprising the nucleic acids described above. In one embodiment, the vector is effective to express a glycine transporter mRNA in at least one of a eukaryotic cell or a bacterial cell. In another embodiment of the invention, the vector is effective to express the mRNA in at least one of a mammalian cell, a yeast cell or an avian cell.

The invention further provides an isolated glycine transporter derived from transformed cells according to the present invention, the transporter comprising the amino acid sequence encoded by an above-described nucleic acid or one to two contiguous portions of amino acid sequence encoded by such a nucleic acid, wherein the protein has glycine transporter activity and differs in sequence from the aligned segments of the GlyT2 transporter sequences described by WO98/07854 (PCT/US97/14637) (human) or Liu, et al., *J. Biol. Chem.* 268:22802–22808 (1993) (rat). Contiguous sequence as used herein, refers to uninterrupted portions of the relevant reference nucleic acid or amino acid sequence. Preferably, the glycine transporter protein of the present invention differs in sequence by at least two amino acids, more preferably, at least four amino acids, from the aligned segments of GlyT2 transporter sequences described by WO98/07854 (PCT/US97/14637) (human) or Liu, et al., *J. Biol. Chem.* 268:22802–22808 (1993) (rat). Preferably, the contiguous sequences comprise at least about 600 amino acids, more preferably at least about 700 amino acids, more preferably at least about 750 amino acids. In one embodiment, the transporter protein comprises all of the protein sequence encoded by the above-described nucleic acid. Preferably, the transporter protein comprises the amino acid sequence set forth in the protein sequence of SEQ ID NO: 122 or a sequence corresponding to the protein sequence of SEQ ID NO: 122 except that it has one or more of the following amino acid substitutions: (1) $Pro^{26}$ to Leu, (2) $Arg^{74}$ to Trp, (3) $Pro^{75}$ to Leu, (4) $Ala^{89}$ to Val, (5) $Ser^{102}$ to Gly, (6) $Val^{174}$ to Glu, (7) $Ser^{195}$ to Pro, (8) $Asp^{199}$ to Gly, (9) $Val^{249}$ to Leu, (10) $Leu^{306}$ to Pro, (11) $Gly^{419}$ to Glu, (12) $Thr^{442}$ to Asn, (13) $Thr^{455}$ to Lys, (14) $Trp^{458}$ to Cys, (15) $Leu^{485}$ to Pro, (16) $Lys^{493}$ to Arg, or (17) $Val^{650}$ to Glu, or an amino acid sequence comprising one to two contiguous portions of these sequences.

The present invention also provides a nucleic acid encoding a transporter protein having at least about 99.5% sequence identity with all or one to two contiguous portions of the amino acid sequence of SEQ ID NO: 122 or with one to two continuous portions of an amino acid sequence corresponding to the protein sequence of SEQ ID NO: 122 except that it has one or more of the following substitutions: (1) $Pro^{26}$ to Leu, (2) $Arg^{74}$ to Trp, (3) $Pro^{75}$ to Leu, (4) $Ala^{89}$ to Val, (5) $Ser^{102}$ to Gly, (6) $Val^{174}$ to Glu, (7) $Ser^{195}$ to Pro, (8) $Asp^{199}$ to Gly, (9) $Val^{249}$ to Leu, (10) $Leu^{306}$ to Pro, (11) $Gly^{419}$ to Glu, (12) $Thr^{442}$ to Asn, (13) $Thr^{455}$ to Lys, (14) $Trp^{458}$ to Cys, (15) $Leu^{485}$ to Pro, (16) $Lys^{493}$ to Arg, or (17) $Val^{650}$ to Glu, wherein the encoded protein has glycine transporter activity. Preferably, the contiguous sequences comprise at least about 600 amino acids, more preferably at least about 700 amino acids, more preferably at least about 750 amino acids. The invention also provides a vector comprising this nucleic acid. In one embodiment, the vector is effective to express a glycine transporter mRNA in at least one of a eukaryotic cell or a prokaryotic cell such as a bacterial cell. In another embodiment of the invention, the vector is effective to express the mRNA in at least one of a yeast cell, a mammalian cell or an avian cell.

The present invention additionally provides a cell comprising a first extrinsically-derived nucleic acid according to the first embodiment or a second extrinsically-derived nucleic acid encoding a transporter protein having at least about 99.5% sequence identity with one to two contiguous portions of the protein sequence of SEQ ID NO: 122 or of a sequence corresponding to the protein sequence of SEQ ID NO: 122 except that it has one or more of the following substitutions: (1) $Pro^{26}$ to Leu, (2) $Arg^{74}$ to Trp, (3) $Pro^{75}$ to Leu, (4) $Ala^{89}$ to Val, (5) $Ser^{102}$ to Gly, (6) $Val^{174}$ to Glu, (7) $Ser^{195}$ to Pro, (8) $Asp^{199}$ to Gly, (9) $Val^{249}$ to Leu, (10) $Leu^{306}$ to Pro, (11) $Gly^{419}$ to Glu, (12) $Thr^{442}$ to Asn, (13) $Thr^{455}$ to Lys, (14) $Trp^{458}$ to Cys, (15) $Leu^{485}$ to Pro, (16) $Lys^{493}$ to Arg, or (17) $Val^{650}$ to Glu, wherein the encoded protein has glycine transporter activity. In one embodiment, the cell expresses a glycine transporter from the nucleic acid. Preferably, the nucleic acid is functionally associated with a promoter that is operative in the cell. In an embodiment of the invention, the promoter is an inducible promoter.

The present invention also provides a method of producing a glycine transporter comprising growing cells as described in the previous paragraphs. This method can further comprise at least one of (a) isolating membranes from said cells, which membranes comprise the glycine transporter or (b) extracting protein fraction from the cells, which fraction comprises the glycine transporter.

The present invention provides a method for characterizing a bioactive agent for treatment of a nervous system disorder or condition or for identifying bioactive agents for treatment of a nervous system disorder or condition, the method comprising (a) providing a first assay composition comprising (i) a cell as described above or (ii) an isolated glycine transporter protein comprising the amino acid sequence encoded by the first or second extrinsically-derived nucleic acids described above, (b) contacting the first assay composition with the bioactive agent or a prospective bioactive agent, and measuring the amount of glycine transport exhibited by the assay composition. Preferably, the method further comprises comparing the amount of glycine transport exhibited by the first assay composition with the amount of glycine transport exhibited by a second such assay composition that is treated the same as the first assay composition except that it is not contacted with the bioactive agent or prospective bioactive agent. The method can be used for characterizing bioactive agents where the nervous system disorder or condition is one of the group including, but not limited to, (a) pain, (b) spasticity, (c) myoclonus, (d) muscle spasm, (e) muscle hyperactivity or (f) epilepsy. In a preferred embodiment, the spasticity for which the bioactive agent is characterized is associated with stroke, head trauma, neuronal cell death, multiple sclerosis, spinal cord injury, dystonia, Huntington's disease or amyotrophic lateral sclerosis.

The invention further provides a nucleic acid that hybridizes with a reference nucleic acid sequence which is SEQ ID NO:121 or a sequence that varies from the nucleic acid sequence of SEQ ID NO:121 by having one or more of the following substitutions: (a) $C^{77} \to T$, (b) $C^{220} \to T$, (c) $C^{224} \to T$, (d) $C^{266} \to T$, (e) $A^{304} \to G$, (f) $T^{521} \to A$, (g) $T^{583} \to C$, (h) $A^{596} \to G$, (i) $A^{678} \to G$, (j) $T^{681} \to C$, (k) $G^{745} \to T$, (l) $G^{750} \to C$, (m) $C^{765} \to T$, (n) $G^{777} \to C$, (o) $A^{867} \to G$, (p) $T^{917} \to C$, (q) $G^{1256} \to A$, (r) $T^{1292} \to C$, (s) $C^{1325} \to A$, (t) $C^{1364} \to A$, (u) $G^{1374} \to C$, (v) $C^{1392} \to C$, (w) $T^{1454} \to C$, (x) $A^{1478} \to G$, (y) $T^{1854} \to C$, (z) $T^{1949} \to A$, (aa) $T^{1959} \to C$, or (bb) $T^{2130} \to C$, under conditions of sufficient stringency to exclude hybridizations with (a) the sequence for a rat GlyT2 transporter or (b) the sequence for a mammalian GlyT1 transporter. Preferably, the nucleic acid sequence is at least about 18 nucleotides in length and has at least about 95% sequence identity with a sequence embedded in the reference nucleic acid sequence. Preferably the nucleic acid sequence is at least about 40 nucleotides in length, more preferably at least about 100 nucleotides in length. Preferably the nucleic acid sequence has at least about 97% sequence identity with the above-recited reference sequence, more preferably 99% sequence identity. Preferably, the nucleic acid is a PCR primer and the stringent conditions are PCR conditions effective to amplify a human GlyT2 sequence but not amplify (a) the sequence for a rat or mouse GlyT2 transporter or (b) the sequence for a mammalian GlyT1 transporter.

Further, the invention provides a nucleic acid of at least about 18 nucleotides in length comprising a contiguous sequence from the coding or non-coding strand of a human GlyT2 gene or cDNA, wherein the contiguous sequence has at least 1 sequence difference when compared with the rat GlyT2 gene sequence that aligns with the contiguous sequence. Preferably the nucleic acid sequence is at least about 40 nucleotides in length, more preferably at least about 100 nucleotides in length. Preferably, the contiguous sequence has at least two differences, more preferably 3 differences when compared with the rat GlyT2 gene sequence that aligns with the contiguous sequence.

Still further, the invention provides an antisense molecule comprising a contiguous sequence from a coding or non-coding strand of a human gene or cDNA for GlyT2 which is effective when administered to a cell, tissue, organ or animal to reduce the expression of GlyT2 in the cell or in a cell of the tissue, organ or animal, wherein the contiguous sequence has at least 1 sequence difference when compared with the rat GlyT2 gene sequence that aligns with said contiguous sequence. Preferably, the contiguous sequence has at least two differences, more preferably 3 differences when compared with the rat GlyT2 gene sequence that aligns with the contiguous sequence. Antisense molecule is used herein to refer to a molecule designed to bind genomic DNA or mRNA to interfere in transcription or translation, including interfering with mRNA stability. Preferably, the contiguous sequence is at least about 15 nucleotides in length. Preferably, the contiguous stretch is included in the coding or non-coding strand of the nucleic acid sequence of SEQ ID NO:121. The invention further provides an expression vector comprising such an antisense molecule.

The invention also provides a method of reducing GlyT2 expression in a tissue or cell comprising applying to the tissue or cell an amount of such an antisense molecule effective to reduce GlyT2 expression. An amount of an expression vector for expressing such an antisense molecule in a tissue or cell effective to reduce GlyT2 expression is also provided. Alternatively, the invention provides a method of treating a nervous system disorder or condition comprising applying to a tissue or cell of a human patient with a nervous system disorder or condition an amount of such an antisense molecule effective to treat such nervous system disorder or condition or an amount of an expression vector for expressing such an antisense molecule in a tissue or cell effective to treat such nervous system disorder or condition.

Further, the invention provides a method for detecting whether an animal has autoimmune antibodies against a glycine transporter, the method comprising contacting an antibody preparation from the animal or a body fluid from the animal with a polypeptide antigen comprising a glycine transporter or derived from the glycine transporter. Preferably, the polypeptide antigen comprises a contiguous sequence encoded by the protein sequence of SEQ ID NO:122 or with a sequence corresponding to the protein sequence of SEQ ID NO: 122 except that it has one or more of the following substitutions: (1) $Pro^{26}$ to Leu, (2) $Arg^{74}$ to Trp, (3) $Pro^{75}$ to Leu, (4) $Ala^{89}$ to Val, (5) $Ser^{102}$ to Gly, (6) $Val^{174}$ to Glu, (7) $Ser^{195}$ to Pro, (8) $Asp^{199}$ to Gly, (9) $Val^{249}$ to Leu, (10) $Leu^{306}$ to Pro, (11) $Gly^{419}$ to Glu, (12) $Thr^{442}$ to Asn, (13) $Thr^{455}$ to Lys (14) $Trp^{458}$ to Cys, (15) $Leu^{485}$ to Pro, (16) $Lys^{493}$ to Arg, or (17) $Val^{650}$ to Glu. Preferably, the contiguous sequence is at least about six amino acids in length, more preferably at least about ten amino acids in length, still more preferably at least about fifteen amino acids in length. In one embodiment of the invention, the peptide antigen is selective for antibodies against either a GlyT1 transporter or a GlyT2 transporter.

Still further, the invention provides the use of a GlyT2 transporter protein to generate GlyT2-specific antibodies.

BRIEF DESCRIPTION OF THE DRAWINGS

FIG. 2 shows sequences of hGlyT2 variants. FIG. 2A shows the sequence of the 5'-insert hGlyT2 variant. This variant contains an alternative 5'-end as shown (hGlyT2 (5'-insert)). Regions exhibiting homology with an hGlyT2 sequence are shown underlined in bold. The first 210 bases of this sequence are unlike any in the current database of sequences. This divergent region is followed by 135 bases of sequence matching an hGlyT2 sequence between nucleotides 541–675. After this region of homology there is a 172-base insert containing in-frame stop codons (boxed residues). Following this region, the sequence exhibits homology to the remainder of an hGlyT2 sequence from nucleotide 679. The predicted start methionine for this variant is shown. FIG. 2B shows the sequence of the 3'-deletion variant. This 3'-deletion variant (hGlyT2(3'-deletion)) is shown compared to an hGlyT2 sequence. This variant is missing amino acid residues 496–509, and when expressed has a valine followed by a proline in the place of amino acid residues 510–511. This deletion is found in the intracellular loop between putative transmembrane domains TM6 and TM7. The translated sequence for an hGlyT2 sequence is shown on top, while that of the deletion is shown on the bottom.

FIG. 3 shows the expression of hGlyT2 transporters in COS-7 cells. hGlyT2 transporter constructs were transfected into COS-7 cells and uptake of [$^3$H]-glycine was measured for each. Control cells transfected with green fluorescent protein (GFP) and viewed under the fluorescent microscope were used to estimate transfection efficiency. The total uptake (open bars) and Cl⁻-free (low affinity) uptake (hatched bars) are shown for a full-length hGlyT2, a truncated hGlyT2, and variants hGlyT2/5I, hGlyT2/3D, and hGlyT2/5I-3D (see, Example 2). Uptake mediated by a full-length hGlyT2 transporter was 10 fold higher than the GFP-transfected cells. The truncated transporter was only 40% as efficient as full-length hGlyT2 at mediating high-affinity glycine uptake. Variant hGlyT2/5 I demonstrated a 1.6 fold increase in uptake compared to plasmid transfected control, while the two variants containing the 3'-deletion did not exhibit functional transporter activity (see, Example 4).

FIG. 5 shows the effect of sarcosine on glycine uptake by COS-7 cells transfected with an hGlyT2. The effect of increasing concentrations of sarcosine on the glycine uptake mediated by a full-length (●) and a truncated form of an hGlyT2 (■) are shown. Uptake is depicted as a percent of the uptake mediated by transporter-transfected cells without sarcosine present. The full-length and truncated transporters were insensitive to sarcosine inhibition.

DETAILED DESCRIPTION OF THE INVENTION

Figure 1:
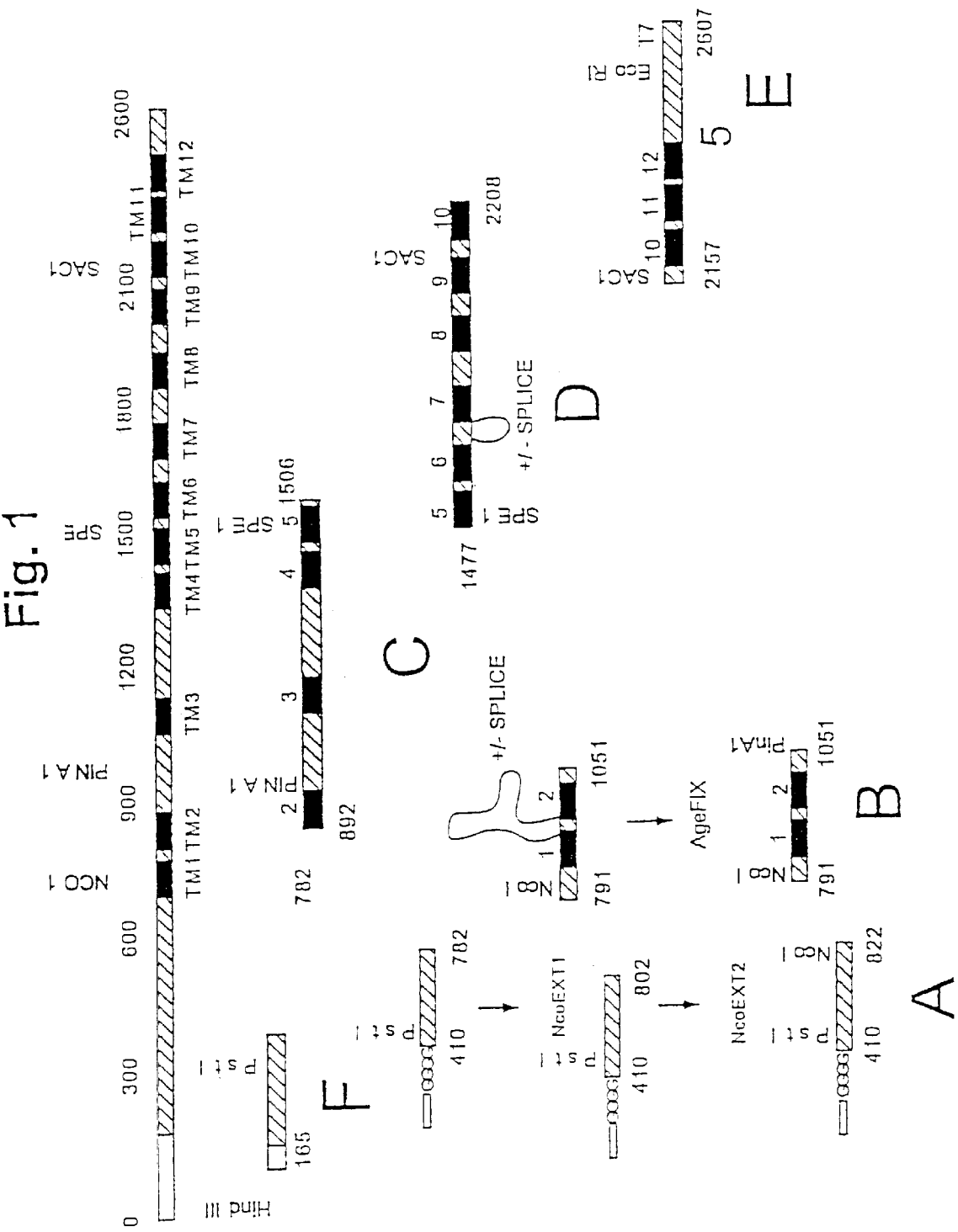
FIG. 1 shows the assembly of an hGlyT2 transporter cDNA sequence using six isolated fragments. These fragments were assembled using restriction sites at their termini. The fragments were assembled as follows: A was ligated to B (NcoI site), C was ligated to D (SpeI site), CD was ligated to E (SacI site), CDE was ligated to AB (PinA1 site), and F was ligated to ABCDE (PstI site). The final construct was digested with HinDIII and EcoR1 and was subcloned into pcDNA3 for expression studies.

The GlyT2 transporter nucleic acid sequences which are the sequences of SEQ ID NOS:119 and 121 or the corresponding encoded protein sequences of SEQ ID NOS:120 and 122 are analogues of human GlyT2 transporter sequences disclosed in WO98/07854 (PCT/US97/14637) and rat GlyT2 transporter sequences disclosed in Lui, Q. R., et al., *J.Biol. Chem.* 268:22802–22808 (1993). The GlyT2 nucleic acid sequence of SEQ ID NO:119 is the nucleic acid sequence of a full length human GlyT2 transporter cDNA prepared by ligation of six PCR-amplified cDNA fragments (fragments A–F of FIG. 1) spanning a full length human GlyT2 transporter. The GlyT2 nucleic acid sequence of SEQ ID NO:121 represents the consensus nucleic acid sequence of a full length human GlyT2 transporter, wherein the consensus sequence is derived by sequence analysis of at least eight clones each of various PCR-amplified fragments (fragments A–F of FIG. 1), which span the sequence of a full length GlyT2 transporter. The additional nucleic acid sequences and corresponding encoded protein sequences set forth in SEQ ID NOS:22 to 118 represent the sequences of eight clones of each of fragments A–F. These nucleic acid sequences represent further variations from the consensus sequence and most likely reflect allelic variations occurring within the cDNAs derived from the pooled mRNA samples used to generate these clones.

In total, the various nucleic acid sequences encoding the human GlyT2 transporter that have been isolated herein display the following sequence variations:

| Nucleotide Variations | Encoded Amino Acid Variations | Nucleotide in SEQ ID NO: 119 | Amino Acid in SEQ ID NO: 119 | Corresp. Amino Acid in pHGT2-b[1] | Corresp. Amino Acid in Rat[2] |
|---|---|---|---|---|---|
| A$^{70}$GC (from SEQ ID NO: 121) | Ser$^{24}$ | A$^{70}$GC | Ser | Gly | Gly |
| CC$^{77}$G (from SEQ ID NO: 121) to CT$^{77}$G (from SEQ ID NO: 117) | Pro$^{26}$ to Leu$^{26}$ | CC$^{77}$G | Pro | Pro | Arg |
| C$^{220}$GG (from SEQ ID NO: 121) to T$^{220}$GG (from SEQ ID NOS: 103, 105, 117) | Arg$^{74}$ to Trp$^{74}$ | T$^{220}$GG | Trp | Arg | Arg |
| CC$^{224}$A (from SEQ ID NO: 121) to CT$^{224}$A (from SEQ ID NO: 117) | Pro$^{75}$ to Leu$^{75}$ | CC$^{224}$A | Pro | Pro | Pro |
| GC$^{266}$G (from SEQ ID NO: 121) to GT$^{266}$F (from SEQ ID NOS: 22, 103, 105) | Ala$^{89}$ to Val$^{89}$ | GC$^{266}$G | Ala | Ala | Ala |
| A$^{304}$GC (from SEQ ID NO: 121) to G$^{304}$GC (from SEQ ID NOS: 22, 103, 105, 109) | Ser$^{102}$ to Gly$^{102}$ | G$^{304}$GC | Gly | Ser | Ser |
| G$^{463}$GC (from SEQ ID NO: 121) | Gly$^{155}$ | G$^{463}$GC | Gly | Ser | Ser |
| GT$^{521}$G (from SEQ ID NO: 121) to GA$^{521}$G (from SEQ ID NO: 24) | Val$^{174}$ to Glu$^{174}$ | GT$^{521}$G | Val | Val | Val |
| G$^{562}$AT (from SEQ ID NO: 121) | Asp$^{188}$ | G$^{562}$AT | Asp | Asn | Asn |
| T$^{583}$CT (from SEQ ID NO: 121) to C$^{583}$CT (from SEQ ID NO: 40) | Ser$^{195}$ to Pro$^{195}$ | T$^{583}$CT | Ser | Ser | Ser |
| GA$^{596}$C (from SEQ ID NO: 121) to GG$^{596}$C (from SEQ ID NO: 42) | Asp$^{199}$ to Gly$^{199}$ | GA$^{596}$C | Glu | Glu | Glu |
| GGA$^{678}$ (from SEQ ID NO: 121) to GGG$^{678}$ (from SEQ ID NO: 38) | None (Gly$^{226}$) | GGG$^{678}$ | Gly | Gly | Gly |
| GGT$^{681}$ (from SEQ ID NO: 121) to GGC$^{681}$ (from SEQ ID NO: 56) | None (Gly$^{227}$) | GGT$^{681}$ | Gly | Gly | Gly |
| G$^{745}$TG (from SEQ ID NO: 121) to T$^{745}$TG (from SEQ ID NO: 60) | Val$^{249}$ to Leu$^{249}$ | G$^{745}$TG | Val | Val | Val |

-continued

| Nucleotide Variations | Encoded Amino Acid Variations | Nucleotide in SEQ ID NO: 119 | Amino Acid in SEQ ID NO: 119 | Corresp. Amino Acid in pHGT2-b[1] | Corresp. Amino Acid in Rat[2] |
|---|---|---|---|---|---|
| TCG⁷⁵⁰ (from SEQ ID NO: 121) to TCC⁷⁵⁰ (from SEQ ID NO: 56) | None (Ser²⁵⁰) | TCG⁷⁵⁰ | Ser | Ser | Ser |
| GCC⁷⁶⁵ (from SEQ ID NO: 121) to GCT⁷⁶⁵ (from SEQ ID NO: 40) | None (Ala²⁵⁵) | GCC⁷⁶⁵ | Ala | Ala | Ala |
| CCG⁷⁷⁷ (from SEQ ID NO: 121) to CCC⁷⁷⁷ (from SEQ ID NO: 56) or CCA⁷⁷⁷ (from SEQ ID NO: 58) | None (Pro²⁵⁹) | CCG⁷⁷⁷ | Pro | Pro | Pro |
| GTA⁸⁶⁷ (from SEQ ID NO: 121) to GTG⁸⁶⁷ (from SEQ ID NO: 56) | None (Val²⁸⁹) | GTG⁸⁶⁷ | Val | Val | Val |
| CT⁹¹⁷A (from SEQ ID NO: 121) to CC⁹¹⁷A (from SEQ ID NO: 58) | Leu³⁰⁶ to Pro³⁰⁶ | CT⁹¹⁷A | Leu | Leu | Leu |
| CT¹⁰⁸⁵G (from SEQ ID NO: 121) to CA¹⁰⁸⁵G (from SEQ ID NO: 56) | Leu³⁶² to Gln³⁶² | CT¹⁰⁸⁵G | Leu | Gln | Gln |
| GG¹²⁵⁶A (from SEQ ID NO: 121) to GA¹²⁵⁶A (from SEQ ID NO: 69) | Gly⁴¹⁹ to Glu⁴¹⁹ | GG¹²⁵⁶A | Gly | Gly | Gly |
| GT¹²⁹²C (from SEQ ID NO: 121) to GC¹²⁹²C (from SEQ ID NOS: 56, 75, 77, 79, 81, 83, 85) | Val⁴³¹ to Ala⁴³¹ | GC¹²⁹²C | Ala | Val | Val |
| CTA¹²⁹⁹ (from SEQ ID NO: 121) to CTC¹²⁹⁹ (from SEQ ID NO: 73) | None (Leu⁴³³) | CTA¹²⁹⁹ | Leu | Leu | Leu |
| AC¹³²⁵C (from SEQ ID NO: 121) to AA¹³²⁵C (from SEQ ID NO: 73) | Thr⁴⁴² to Asn⁴⁴² | AC¹³²⁵C | Thr | Thr | Thr |
| AC¹³⁶⁴A (from SEQ ID NO: 121) to AA¹³⁶⁴A (from SEQ ID NO: 73) | Thr⁴⁵⁵ to Lys⁴⁵⁵ | AC¹³⁶⁴A | Thr | Thr | Thr |
| TGG¹³⁷⁴ (from SEQ ID NO: 121) to TGC¹³⁷⁴ (from SEQ ID NO: 73) | Trp⁴⁵⁸ to Cys⁴⁵⁸ | TGG¹³⁷⁴ | Trp | Trp | Trp |
| GCC¹³⁹² (from SEQ ID NO: 121) to GCA¹³⁹² (from SEQ ID NOS: 73, 81) | Ala⁴⁶⁴ to Ala⁴⁶⁴ | GCC¹³⁹² | Ala | Ala | Ala |
| CT¹⁴⁵⁴g (from SEQ ID NO: 121) to CC¹⁴⁵⁴G (from SEQ ID NOS: 73, 77) | Leu⁴⁸⁵ to Pro⁴⁸⁵ | CT¹⁴⁵⁴G | Leu | Leu | Leu |
| AA¹⁴⁷⁸A (from SEQ ID NO: 121) to AG¹⁴⁷⁸A (from SEQ ID NO: 73) | Lys⁴⁹³ to Arg⁴⁹³ | AA¹⁴⁷⁸A | Lys | Lys | Lys |
| GCT¹⁶¹⁷ (from SEQ ID NO: 121) to GCA¹⁶¹⁷ (from SEQ ID NO: 73) | None (Ala⁵³⁹) | GCT¹⁶¹⁷ | Ala | Ala | Ala |
| T¹⁷⁴⁴CC (from SEQ ID NO: 121) to A¹⁷⁴⁴CC (from SEQ ID NO: 73) | Ser⁵⁸² to Thr⁵⁸² | T¹⁷⁴⁴CC | Ser | Thr | Thr |
| TTT¹⁸⁵⁴ (from SEQ ID NO: 121) to TTC¹⁸⁵⁴ (from SEQ ID NO: 73) | None (Phe⁶¹⁸) | TTT¹⁸⁵⁴ | Phe | Phe | Phe |
| GT¹⁹⁴⁹G (from SEQ ID NO: 1221) to GA¹⁹⁴⁹G (from SEQ ID NO: 89) | Val⁶⁵⁰ to Glu⁶⁵⁰ | GT¹⁹⁴⁹G | Val | Val | Val |
| TCT¹⁹⁵⁹ (from SEQ ID NO: 121) to TCC¹⁹⁵⁹ (from SEQ ID NO: 89, 91) | None (Ser⁶⁵³) | TCT¹⁹⁵⁹ | Ser | Ser | Ser |
| TAT²¹³⁰ (from SEQ ID NO: 121) to TAC²¹³⁰ (from SEQ ID NO: 89) | None (Tyr⁷¹⁰) | TAT²¹³⁰ | Tyr | Tyr | Tyr |

[1] WO98/07854 (PCT/US97/14637)
[2] Liu, et al., J. Biol. Chem. 268: 22802–22808 (1993)

Irrespective of the source of this variation, the point variations in amino acid sequences, excepting the insertion of a stop codon, are believed not to adversely affect the functioning of GlyT2 transporter activity.

The above-described variations primarily reflect variations between human individuals. The material used to generate the nucleic acid sequences described above generally comprised three pools of 69, 92 and 92 individuals as well as a cell line derived from an individual. The use of pooled source material, together with the number of conservative or silent substitutions, support the conclusion that the variations are reflective of human-derived variations.

The relationship between the human nucleotide sequence of SEQ ID NO: 121 and the rat nucleotide sequence for GlyT2, and between the sequences that they encode, is set forth in the tables below. The relatedness values or sequence identity as set forth in these tables was determined using the LASERGENE computer program (DNASTAR, Inc., Madison, Wis.).

| Nucleotide Sequence (numbered as in SEQ ID NO: 121) | Percent Identity |
|---|---|
| nt 1–2397 | 88.7 |
| nt 1–600 | 82.2 |
| nt 60–170 | 73.6 |
| nt 600–2391 | 90.9 |

| Amino Acid Sequence (numbered as in SEQ ID NO: 122) | Percent Identity |
|---|---|
| aa 1–797 | 93.6 |
| aa 1–150 | 75.3 |
| aa 1–200 | 78.0 |
| aa 150–797 | 97.8 |
| aa 200–797 | 98.8 |

The relationship between the human GlyT2 transporter nucleic acid sequence of SEQ ID NO: 119 and the rat nucleotide sequence for the GlyT2 transporter, and their corresponding protein sequences was determined. This human GlyT2 transporter sequence exhibited very high homology with the rat GlyT2 sequence (Liu, Q. R., et al., *J. Biol. Chem.* 268:22802–22806 (1993)), with the overall homology between the two species being about 88% and about 93% at the nucleotide and amino acid levels, respectively. This human GlyT2 transporter sequence and the sequences of other members of the amino acid transporter family shared approximately 50% amino acid homology. The greatest diversity between the rat and human GlyT2 proteins is within the first 190 amino acids, where only about 74% conservation is observed.

Sequence identity, as known in the art, is a relationship between two or more polypeptide sequences or two or more polynucleotide sequences, as determined by comparing the sequences, particularly, as determined by the match between strings of such sequences. Sequence identity or percent identity or percent homology is readily calculated by known methods (see, e.g., *Computational Molecular Biology*, Lesk, A. M., ed., Oxford University Press, New York (1988)). *Biocomputing: Informatics and Genome Projects*, Smith, D. W., ed., Academic Press, New York (1993); *Computer Analysis of Sequence Data, Part I*, Griffin A. M. and Griffin, H. G., eds., Humana Press, New Jersey (1994); *Sequence Analysis in Molecular Biology*, von Heinje, G., Academic Press (1987); and *Sequence Analysis Primer*, Gribskov, M. and Devereux, J., eds., M Stockton Press, New York (1991)). While there exists a number of methods to measure identity between two sequences, the term is well known to skilled artisans (see, e.g., *Sequence Analysis in Molecular Biology*, supra; *Sequence Analysis Primer*, supra; and Carillo, H. and Lipman, D., SIAM, *J. Applied Math.* 48:1073 (1988)). Methods commonly employed to determine identity between sequences include, but are not limited to, those disclosed in Carillo, H. and Lipman, D., supra, or in Needleman and Wunsch, *J. Mol. Biol.*, 48:443–445 (1970), wherein the parameters are as set in version 2 of DNASIS (Hitachi Software Engineering Co., San Bruno, Calif.). Computer programs for determining identity are publicly available. Preferred computer program methods to determine identity between two sequences include, but are not limited to, LASERGENE program (DNASTAR, Inc., Madison, Wis.); GCG program package (Devereux, J., et al., *Nucleic Acids Research* 12(1):387 (1984)); BLASTP, BLASTN and FASTA (Altschul, S. F., et al., *J. Mol. Biol.* 215:403–410 (1990)). The BLAST X program is publicly available from NCBI (blast@ncbi.nlm.nih.gov) and other sources (*BLAST Manual*, Altschul, S., et al., NCBI NLM NIH, Bethesda, Md. 20894; Altschul, S., et al., supra).

Human GlyT2 transporter sequences described herein differ from the pHGT2-a and pHGT2-b human GlyT2 transporter sequences described in WO98/07854 (PCT/US97/14637). Differences are represented in the nucleic acid and amino acid sequences, respectively, as: (1) $A^{70}$/$Ser^{24}$, (2) $T^{220}$/$Trp^{74}$, (3) $G^{463}$/$Gly^{155}$, (4) $G^{562}$/$Asp^{188}$, (5) $T^{1085}$/$Leu^{362}$, (6) $C^{1292}$/$Ala^{431}$, and (7) $T^{1744}$/$Ser^{582}$. Differences are also represented in the allelic variations, for the following amino acids: (1) $Pro^{26}$ to Leu, (2) $Arg^{74}$ to Trp, (3) $Pro^{75}$ to Leu, (4) $Ala^{89}$ to Val, (5) $Val^{174}$ to Glu, (6) $Ser^{195}$ to Pro, (7) Asp199 to Gly, (8) $Val^{249}$ to Leu, (9) $Leu^{306}$ to Pro, (10) $Gly^{419}$ to Glu, (11) $Thr^{442}$ to Asn, (12) $Thr^{455}$ to Lys, (13) $Trp^{458}$ to Cys, (14) $Leu^{485}$ to Pro, (15) $Lys^{493}$ to Arg, or (16) $Val^{650}$ to Glu; and for the following nucleotides: (a) $C^{77} \rightarrow T$, (b) $C^{220} \rightarrow T$, (c) $C^{224} \rightarrow T$, (d) $C^{266} \rightarrow T$, (e) $T^{521} \rightarrow A$, (f) $T^{583} \rightarrow C$, (g) $A^{596} \rightarrow G$, (h) $A^{678} \rightarrow G$, (i) $T^{681} \rightarrow C$, (j) $G^{745} \rightarrow T$, (k) $G^{750} \rightarrow C$, (l) $C^{765} \rightarrow T$, (m) $G^{777} \rightarrow C$, (n) $A^{867} \rightarrow G$, (o) $T^{917} \rightarrow C$, (p) $G^{1256} \rightarrow A$, (q) $T^{1292} \rightarrow C$, (r) $C^{1299} \rightarrow A$, (s) $C^{1325} \rightarrow A$, (t) $C^{1364} \rightarrow A$, (u) $G^{1374} \rightarrow C$, (v) $C^{1392} \rightarrow A$, (w) $T^{1454} \rightarrow C$, (x) $A^{1478} \rightarrow G$, (y) $A^{1617} \rightarrow C$, (z) $A^{1744} \rightarrow T$, (aa) $T^{1854} \rightarrow C$, (bb) $T^{1949} \rightarrow A$, (cc) $T^{1959} \rightarrow C$, or (dd) $T^{2130} \rightarrow C$.

Nucleic Acid-encoding Glycine Transporter

To construct non-naturally occurring glycine transporter-encoding nucleic acids, the native sequences can be used as a starting point and modified to suit particular needs. For instance, the sequences can be mutated to incorporate useful restriction sites. See, Maniatis, et al., *Molecular Cloning, a Laboratory Manual*, Cold Spring Harbor Press (1989). Such restriction sites can be used to create cassettes, or regions of nucleic acid sequence that are facilely substituted using restriction enzymes and ligation reactions. The cassettes can be used to substitute synthetic sequences encoding mutated glycine transporter amino acid sequences (see, e.g., Goeddel, et al., *Proc. Natl. Acad. Sci. USA*, 76:106–110 (1979)). For recombinant expression purposes, codon usage preferences for the organism in which such a nucleic acid is to be expressed are advantageously considered in designing a synthetic glycine transporter-encoding nucleic acid. For example, a nucleic acid sequence incorporating prokaryotic codon preferences can be designed from a mammalian-derived sequence using a software program such as Oligo-4, available from National Biosciences, Inc. (Plymouth, Minn.).

The nucleic acid sequence embodiments of the invention are preferably deoxyribonucleic acid sequences, preferably double-stranded deoxyribonucleic acid sequences. However, they can also be ribonucleic acid sequences.

Numerous methods are known to delete sequence from or mutate nucleic acid sequences that encode a protein and to confirm the function of the proteins encoded by those deleted or mutated sequences. Accordingly, the invention also relates to a mutated or deleted version of a human nucleic acid sequence that encodes a protein that retains the ability to bind specifically to glycine and to transport glycine across a membrane. These analogs can have N-terminal, C-terminal or internal deletions, so long as GlyT2 function is retained. The remaining human GlyT2 protein sequence will preferably have no more than about 4 amino acid variations, preferably no more than 2 amino acid variations, more preferably no more than 1 amino acid variation, relative to the protein sequence of SEQ ID NO: 120 or 122 except that it has one or more of the following substitutions: (1) $Pro^{26}$ to Leu, (2) $Arg^{74}$ to Trp, (3) $Pro^{75}$ to Leu, (4) $Ala^{89}$ to Val, (5) $Ser^{102}$ to Gly, (6) $Val^{174}$ to Glu, (7) $Ser^{195}$ to Pro, (8) $Asp^{199}$ to Gly, (9) $Val^{249}$ to Leu, (10) $Leu^{306}$ to Pro, (11) $Gly^{419}$ to Glu, (12) $Thr^{442}$ to Asn, (13) $Thr^{455}$ to Lys, (14) $Trp^{458}$ to Cys, (15) $Leu^{485}$ to Pro, (16) $Lys^{493}$ to Arg, or (17) $Val^{650}$ to Glu. More preferably, the variations are relative to the protein sequence of SEQ ID NO:120 or 122, still more preferably SEQ ID NO:120. In one preferred embodiment, the protein embodiments of the invention are defined relative to the protein sequence of SEQ ID NO:120 or 122 or with a sequence corresponding to the protein sequence of SEQ ID NO: 120 or 122 except that it has one or more of the following substitutions: (1) $Pro^{26}$ to Leu, (2) $Arg^{74}$ to Trp, (3) $Pro^{75}$ to Leu, (4) $Ala^{89}$ to Val, (5) $Ser^{102}$ to Gly, (6) $Val^{174}$ to Glu, (7) $Ser^{195}$ to Pro, (8) $Asp^{199}$ to Gly, (9) $Val^{249}$ to Leu, (10) $Leu^{306}$ to Pro, (11) $Gly^{419}$ to Glu, (12) $Thr^{442}$ to Asn, (13) $Thr^{455}$ to Lys, (14) $Trp^{458}$ to Cys, (15) $Leu^{485}$ to Pro, (16) $Lys^{493}$ to Arg, or (17) $Val^{650}$ to Glu. The point variations are preferably conservative point variations. Preferably, the analogs or variants will have at least about 96% sequence identity, preferably at least about 97%, more preferably at least about 98%, still more preferably at least about 99%, yet still more preferably at least about 99.5% to the protein sequence of SEQ ID NO: 122 or with a sequence corresponding to the protein sequence of SEQ ID NO: 122 except that it has one or more of the following substitutions: (1) $Pro^{26}$ to Leu, (2) $Arg^{74}$ to Trp, (3) $Pro^{75}$ to Leu, (4) $Ala^{89}$ to Val, (5) $Ser^{102}$ to Gly, (6) $Val^{174}$ to Glu, (7) $Ser^{195}$ to Pro, (8) Asp199 to Gly, (9) $Val^{249}$ to Leu, (10) $Leu^{306}$ to Pro, (11) $Gly^{419}$ to (12) $Thr^{442}$ to Asn, (13) $Thr^{455}$ to Lys, (14) $Trp^{458}$ to Cys, (15) $Leu^{485}$ to Pro, (16) $Lys^{493}$ to Arg, or (17) $Val^{650}$ to Glu. More preferably, the variations are relative to the protein sequence of SEQ ID NO: 120 or 122, still more preferably SEQ ID NO: 120. Mutational and deletional approaches can be applied to all of the nucleic acid sequences of the invention that express human GlyT2 proteins. As discussed above, conservative mutations are preferred. Such conservative mutations include mutations that switch one amino acid for another within one of the following groups:

1. Small aliphatic, nonpolar or slightly polar residues: Ala, Ser, Thr, Pro and Gly;
2. Polar, negatively charges residues and their amides: Asp, Asn, Glu and Gln;
3. Polar, positively charged residues: His, Arg and Lys;
4. Large aliphatic, nonpolar residues: Met, Leu, Ile, Val and Cys; and
5. Aromatic residues: Phe, Tyr and Trp.

A preferred listing of conservative variations is the following:

| Original Residue | Variation |
|---|---|
| Ala | Gly, Ser |
| Arg | Lys |
| Asn | Gln, His |
| Asp | Glu |
| Cys | Ser |
| Gln | Asn |
| Glu | Asp |
| Gly | Ala, Pro |
| His | Asn, Gln |
| Ile | Leu, Val |
| Leu | Ile, Val |
| Lys | Arg, Gln, Glu |
| Met | Leu, Tyr, Ile |
| Phe | Met, Leu, Tyr |
| Ser | Thr |
| Thr | Ser |
| Trp | Tyr |
| Tyr | Trp, Phe |
| Val | Ile, Leu |

The types of variations selected may be based on the analysis of the frequencies of amino acid variations between homologous proteins of different species developed by Schulz, et al., *Principles of Protein Structure*, Springer-Verlag (1978) on the analyses of structure-forming potentials developed by Chou and Fasman, *Biochemistry* 13:211 (1974) and *Adv. Enzymol.* 47:45–149 (1978) and on the analysis of hydrophobicity patterns in proteins developed by Eisenberg, et al., *Proc. Natl. Acad. Sci. USA* 81:140–144 (1984), Kyte & Doolittle, *J. Mol. Biol.* 175:105–132 (1981) and Goldman, et al., *Ann. Rev. Biophys. Chem.* 15:321–353 (1986).

Since the identified point variations which create amino acid substitutions between the various human GlyT2 mRNAs identified herein are believed to be useful in creating functional GlyT2 molecules, proteins that incorporate all combinations of these point variations are believed to be functional. These variations are within the present invention.

For the purposes of this application, a nucleic acid of the invention is purified or isolated if it has been separated from other macromolecules of the cell or tissue from which it is derived. Preferably, the composition containing the nucleic acid is at least about 10-fold enriched, with respect to nucleic acid content, over the composition of the source cells. Preferably, the nucleic acid is substantially pure, meaning purity of at least about 60% w/w with respect to other nucleic acids, more preferably about 80%, still more preferably about 90%, yet more preferably about 95%.

Hybridization Probes

It will be recognized that many deletional or mutational analogs of nucleic acid sequences for a glycine transporter will be effective hybridization probes for glycine transporter-encoding nucleic acid. Accordingly, the invention relates to nucleic acid sequences that hybridize with such glycine transporter-encoding nucleic acid sequences under stringent conditions. Preferably, the nucleic acid sequence hybridizes with the nucleic acid sequence of SEQ ID NO:121 or with a nucleic acid sequence that varies therefrom by one or more of the following substitutions: (a) $C^{77} \rightarrow T$, (b) $C^{220} \rightarrow T$, (c) $C^{224} \rightarrow T$, (d) $C^{266} \rightarrow T$, (e) $A^{304} \rightarrow G$, (f) $T^{521} \rightarrow A$, (g) $T^{583} \rightarrow C$, (h) $A^{596} \rightarrow G$, (i) $A^{678} \rightarrow G$, (j) $T^{681} \rightarrow C$, (k) $G^{745} \rightarrow T$, (l) $G^{750} \rightarrow C$, (m) $C^{765} \rightarrow T$, (n) $G^{777} \rightarrow C$, (o) $A^{867} \rightarrow G$, (p) $T^{917} \rightarrow C$, (q) $G^{1256} \rightarrow A$, (r) $T^{1292} \rightarrow C$, (s) $C^{1325} \rightarrow A$, (t) $C^{1364} \rightarrow A$, (u) G $T^{1374} \rightarrow C$, (v) $C^{1392} \rightarrow A$, (w) $T^{1454} \rightarrow C$, (x) $A^{1478} \rightarrow G$, (y) $T^{1854} \rightarrow C$, (z) $T^{1949} \rightarrow A$, (aa) $T^{1959} \rightarrow C$, or (bb) $T^{2130} \rightarrow C$. In one embodiment, the nucleic acid (or the functional equivalent) embodiments of the invention are defined relative to the nucleic acid sequence of SEQ ID NO:121 or with a nucleic acid sequence that varies therefrom by one or more of the following substitutions: (a) $C^{77} \rightarrow T$, (b) $C^{220} \rightarrow T$, (c) $C^{224} \rightarrow T$, (d) $C^{266} \rightarrow T$, (e) $A^{304} \rightarrow G$, (f) $T^{521} \rightarrow A$, (g) $T^{583} \rightarrow C$, (h) $A^{596} \rightarrow G$, (i) $A^{678} \rightarrow G^{681} \rightarrow C$, (j) $T^{681} \rightarrow C$, (k) $G^{745} \rightarrow T$, (l) $G^{750} \rightarrow C$, (m) $C^{765} \rightarrow T$, (n) $G^{777} \rightarrow C$, (o) $A^{867} \rightarrow G$, (p) $T^{917} \rightarrow C$, (q) $G^{1256} \rightarrow A$, (r) $T^{1292} \rightarrow C$, (s) $C^{1325} \rightarrow A$ (t) $C^{1364} \rightarrow A$, (u) $G^{1374} \rightarrow C$, (v) $C^{1392} \rightarrow A$, (w) $T^{1454} \rightarrow C$, (x) $A^{1478} \rightarrow G$, (y) $T^{1854} \rightarrow C$, (z) $T^{1949} \rightarrow A$, (aa) $T^{1959} \rightarrow C$, or (bb) $T^{2130} \rightarrow C$.

Stringent conditions refers to conditions that allow for the hybridization of substantially related nucleic acid sequences. For instance, such conditions will generally allow hybridization of sequence with at least about 85% sequence identity, preferably with at least about 90% sequence identity, more preferably with at least about 95% sequence identity. Such hybridization conditions are described by Sambrook, et al., *Molecular Cloning: A Laboratory Manual*, 2nd ed., Cold Spring Harbor Press (1989). Hybridization conditions and probes can be adjusted in well-characterized ways to achieve selective hybridization of human-derived probes.

Nucleic acid molecules that will hybridize to a glycine transporter-encoding nucleic acid under stringent conditions can be identified functionally, using methods outlined above, or by using for example the hybridization rules reviewed in Sambrook, et al., *Molecular Cloning: A Laboratory Manual*, 2nd ed., Cold Spring Harbor Press (1989).

Without limitation, examples of the uses for hybridization probes include: histochemical uses such as identifying tissues that express the human GlyT2 transporter, measuring mRNA levels, for instance to identify a sample's tissue type or to identify cells that express abnormal levels of glycine transporter, and detecting polymorphisms in the glycine transporter gene. RNA hybridization procedures are described in Maniatis, et al., *Molecular Cloning, a Laboratory Manual*, Cold Spring Harbor Press (1989).

PCR Primers

Rules for designing polymerase chain reaction (PCR) primers are now established, as reviewed by *PCR Protocols*, Cold Spring Harbor Press (1991). Degenerate primers, i.e., preparations that are heterogeneous at given sequence locations, can be designed to amplify nucleic acid sequences that are highly homologous to, but not identical to, a human GlyT2 nucleic acid. Strategies are now available that allow for only one of the primers to be required to specifically hybridize with a known sequence. See, Froman, et al., *Proc. Natl. Acad. Sci. USA* 85:8998 (1998) and Loh, et al., *Science* 243:217 (1989). For example, appropriate nucleic acid primers can be ligated to the nucleic acid sought to be amplified or provide the hybridization partner for one of the primers. In this way, only one of the primers need be based on the sequence of the nucleic acid sought to be amplified.

PCR methods of amplifying nucleic acid will utilize at least two primers. One of these primers will be capable of hybridizing to a first strand of the nucleic acid to be amplified and of priming enzyme-driven nucleic acid synthesis in a first direction. The other will be capable of hybridizing the reciprocal sequence of the first strand (if the sequence to be amplified is single stranded, this sequence will initially be hypothetical, but will be synthesized in the first amplification cycle) and of priming nucleic acid synthesis from that strand in the direction opposite the first direction and towards the site of hybridization for the first primer. Conditions for conducting such amplifications, particularly under preferred stringent hybridization conditions, are well known. See, e.g., *PCR Protocols*, Cold Spring Harbor Press (1991).

Vectors

A suitable expression vector is capable of fostering expression of the included GlyT2 encoding DNA in a host cell, which can be eukaryotic, fungal or prokaryotic. Suitable expression vectors include pRc/CMV (Invitrogen, San Diego, Calif.), pRc/RDV (Invitrogen), pcDNA3 (Invitrogen), Zap Express Vector (Stratagene Cloning Systems, La Jolla, Calif.), pBk/CMV or pBk-RSV vectors (Stratagene), Bluescript II SK ± Phagemid Vectors (Stratagene), LacSwitch (Stratagene), pMAM and pMAM neo (Clontech, Palo Alto, Calif.), pKSV10 (Pharmacia, Piscataway, N.J.), pCRscript (Stratagene) and pCR2.1 (Invitrogen), among others. Useful yeast expression systems include, for example, pYEUra3 (Clontech). Useful baculovirus vectors include several viral vectors from Invitrogen (San Diego, Calif.) such as pVL1393, pVL1392, pBluBac2, pBluBacHis A, B or C, and pbacPAC6 (from Clontech).

Cells

According to the invention, a glycine transporter is preferably expressed in a mammalian cell line, preferably a transformed or transfected cell line with an established cell culture history. The invention further provides a cell transformed or transfected with a vector or nucleic acid sequence encoding a human GlyT2 transporter as described above. In one embodiment, the cell is a bacterial or eukaryotic cell. Preferably, the cell is a mammalian cell including COS-1, COS-7, LM(tk⁻), HeLa, HEK293, CHO, Rat-1 and NIH3T3. More preferably, the cell is a cell from the COS-7 cell line. Still other cells that can be used include insect cells such as drosophila cells, fish cells, amphibian cells and reptilian cells.

According to the present invention, a cell is provided comprising an extrinsically-derived nucleic acid encoding a GlyT2 transporter protein that has glycine transport activity. Extrinsically-derived nucleic acids are nucleic acids found in a cell that were introduced into the cell, a parent or ancestor of the cell, or a transgenic animal from which the cell is derived through a recombinant technology. Also contemplated by the invention is an extrinsically-derived nucleic acid that does not encode a GlyT2 transporter protein but rather encodes sequences, including targeting, regulatory, exon and splice-donor sequences, that when such sequences are introduced via a DNA construct into a cell not normally expressing a GlyT2 transporter protein, a GlyT2 transporter protein from a gene endogenous to the cell is expressed (see, e.g., U.S. Pat. Nos. 5,733,761; 5,733,746; 5,641,670).

Human Gly72 Transporter

The invention further provides for a purified or isolated human GlyT2 transporter encoded by any of the nucleic acids of the invention purified or isolated to at least about 80% with respect to proteins, more preferably at least about 90%, most preferably at least about 95%. These purities may be achieved by a variety of protein purification methods including, but not limited to, those described below, with a lysate of a recombinant cell according to the invention.

The human GlyT2 variants of the above paragraphs can be used to create organisms or cells that produce human GlyT2 activity. Purification methods, including associated molecular biology methods, are described below.

Method of Producing Glycine Transporter

One simplified method of isolating polypeptides synthesized by an organism under the direction of one of the nucleic acids of the invention is to recombinantly express a fusion protein wherein the fusion partner is facilely affinity purified. For instance, the fusion partner can be glutathione S-transferase, which is encoded on commercial expression vectors (e.g., vector pGEX4T3, available from Pharmacia, Piscataway, N.J.). The fusion protein can then be purified on a glutathione affinity column (for instance, that available from Pharmacia, Piscataway, N.J.). Additional fusion partners are available for example in various expression vectors sold by Invitrogen (Carlsbad, Calif.). Of course, the recombinant polypeptides can be affinity purified without such a fusion partner using an appropriate antibody that binds to GlyT2. Methods of producing such antibodies are available to those of ordinary skill in light of the ample description herein of GlyT2 expression systems and known antibody production methods (see, e.g., Ausubel, et al., *Short Protocols in Molecular Biology*, John Wiley & Sons, New York (1992)). If fusion proteins are used, the fusion partner can be removed by partial proteolytic digestion approaches that preferentially attack unstructured regions such as the linkers between the fusion partner and GlyT2. The linkers can be designed to lack structure, for instance using the rules for secondary structure forming potential developed, for instance, by Chou and Fasman. *Biochemistry* 13:211 (1974) and Chou and Fasman, *Adv. In Enzymol* 47:45–147 (1978). The linker can also be designed to incorporate protease target amino acids, such as, arginine and lysine residues, the amino acids that define the sites cleaved by trypsin, or such as a target sequence for enterokinase, for example AspAspAspAspLys, which is cleaved after the lysine residue. To create the linkers, standard synthetic approaches for making oligonucleotides can be employed together with standard subcloning methodologies. Other fusion partners besides GST can be used. Procedures that utilize eukaryotic cells, particularly mammalian cells, are preferred since these cells will post-translationally modify the protein to create molecules highly similar to or functionally identical to native proteins.

Additional purification techniques can be applied, including without limitation, preparative electrophoresis, FPLC (Pharmacia, Uppsala, Sweden), HPLC (e.g., using gel filtration, reverse-phase or mildly hydrophobic columns), gel filtration, differential precipitation (for instance, salting out precipitations), ion-exchange chromatography and affinity chromatography.

Because GlyT2 is a membrane protein, which by analogy to related transporter proteins is believed to have twelve transmembrane sequences, isolation methods will often utilize detergents, generally non-ionic detergents, to maintain the appropriate secondary and tertiary structure of the protein (see, e.g., Lopez-Corcuera, et al., *J. Biol. Chem.* 266:24809–24814 (1991)). For a description of methods for re-integrating a solubilized transporter into a membrane (see, e.g., Lopez-Corcuera, et al., *J. Biol. Chem.* 266:24809–24814 (1991)).

The isolation of GlyT2 can comprise isolating membranes from cells that have been transformed to express GlyT2. Preferably, such cells express GlyT2 in sufficient copy number such that the amount of GlyT2 in a membrane fraction is at least about 10-fold higher than that found in comparable membranes from cells that naturally express GlyT2, more preferably the amount is at least about 100-fold higher.

Preferably, the protein is substantially pure, meaning a purity of at least 60% wt/wt with respect to other proteins. For the purposes of this application, GlyT2 is purified or isolated if it has been separated from other proteins or other macromolecules of the cell or tissue from which it is derived. Preferably, the composition containing GlyT2 is at least about 10-fold enriched, preferably at least about 100-fold, with respect to protein content, over the composition of the source cells.

Expression of GlyT2 by RNA Insertion

It will be recognized that human GlyT2 can be expressed by the simple method of inserting mRNA into a cell. RNA for these uses can be prepared by sub-cloning the nucleic acid encoding a protein with GlyT2 activity into a vector containing a promoter for high efficiency in vitro transcription, such as a SP6 or T7 RNA polymerase promoter. RNA production from the vector can be conducted, for instance, with the method described in Ausubel, et al., *Short Protocols in Molecular Biology*, John Wiley & Sons, New York (1992) pp. 10–63 to 10–65. Insertion of RNA into Xenopus-derived oocytes is described, for instance, in Liu, et al. *FEBS Letters* 305:110–114 (1992) and Bannon, et al., *J. Neurochem* 54:706–708 (1990).

Alternatively, it will be recognized that human GlyT2 can be expressed by the simple method of inserting mRNA into an in vitro translation system, which can be a membrane-containing translation system. Expression of proteins in vitro is described, for instance, in Ausubel, et al., *Short Protocols in Molecular Biology*, John Wiley & Sons, New York (1992) pp. 10–63 to 10–65. See, also, Guastella, et al., *Science* 249:1303–1306 (1990) (in vitro expression of a transporter). The use of subcellular membranous material to produce membrane proteins in vitro is described in Walter and Blobel, *Meth. Enzymol.* 96:84 (1983) (for rabbit reticulocyte translation system) and Spiess and Lodish, *Cell* 44:177 (1986) (for wheat germ translation system).

Method of Characterizing or Identifying Agent

A method for the analysis of or screening for a bioactive agent for treatment of a disease or condition associated with a nervous system disorder or condition comprises culturing separately first and second cells, wherein the first and second cells are preferably of the same species, more preferably of the same strain thereof, and comprise an exogenous nucleic acid encoding a glycine transporter as described herein. The nervous system disorders or conditions for which the agent can be used for treatment include, but are not limited to, (a) pain, (b) myoclonus, (c) muscle spasm, (d) muscle hyperactivity, (e) epilepsy or (f) spasticity such as that associated with stroke, head trauma, neuronal cell death, multiple sclerosis, spinal cord injury, dystonia, Huntington's disease or amyotrophic lateral sclerosis. In this method, the first cell is contacted with the bioactive agent or a prospective bioactive agent, which is preferably a compound, such as a peptide or an organic compound in the presence of glycine, which preferably incorporates a radioisotope, such as $^3$H or $^{14}$C. The contacted first cell is then tested for enhancement or inhibition of glycine transport into the first cell as compared to glycine transport into the second cell that was not contacted with the compound (i.e., the control cell). Such analysis or screening preferably includes activities of finding, learning, discovering, determining, identifying, or ascertaining.

Alternatively, the assay can utilize a composition comprising an isolated GlyT2 transporter in place of cells. Preferably, such preparation of isolated transporter will comprise membrane or lipid bilayer, preferably in vesicles, which vesicles have an inside and an outside across which transport can be measured. See, for example, Kanner, *Biochemistry* 17: 1207–1211, 1978.

A bioactive agent is a substance such as a chemical that can act on a cell, virus, tissue organ or organism, including but not limited to drugs (i.e., pharmaceuticals) to create a change in the functioning of the cell, virus, organ or organism. Preferably, the organism is a mammal, more preferably a human. In a preferred embodiment of the invention, the method of identifying bioactive agents of the invention is applied to organic molecules having molecular weight of about 1500 or less. A prospective bioactive agent is a substance which is being tested by the screening method of the invention to determine if it affects glycine transport.

A bioactive agent is an enhancer of glycine transport uptake if at the end of the test the amount of intracellular, intravesicle or otherwise transported glycine is greater in the agent-contacted composition than in the non-agent-contacted composition; conversely, a bioactive agent is an inhibitor of glycine transport if the amount of intracellular or intravesicle glycine is greater in the non-agent-contacted composition as compared to the other. Preferably, the difference in glycine uptake between a tested first composition and a control second composition is at least about two-fold; more preferably, the difference is at least about five-fold; most preferably, the difference is at least about ten-fold or greater.

A bioactive agent that is an inhibitor or an enhancer with respect to the GlyT2 transporter may have a neutral or opposite effect with another glycine transporter, such as one of the GlyT1 transporters. Preferred bioactive agents have specificity to enhance or inhibit the GlyT2 transporter and have neutral or negligible effect on other glycine transporters. Preferably, a bioactive agent has at least an order of magnitude greater potency, reflected in a concentration dependent parameter such as the $IC_{50}$ value, in inhibiting or activating glycine uptake mediated by the GlyT2 transporter as compared to its effect on the second glycine transporter. More preferred agents have greater potencies of at least about 100-fold for one of the glycine transporters as compared to the other.

The bioactive agent can be any compound, material, composition, mixture, or chemical, that can be presented to a glycine transporter in a form that allows for the agent to diffuse so as to contact the transporter. Such bioactive agents include but are not limited to polypeptides preferably of two up to about 25 amino acids in length, more preferably from two to about ten, yet more preferably from two to about five amino acids in length. Other suitable bioactive agents in the context of the present invention include small organic compounds, preferably of molecular weight between about 100 daltons and about 5,000 daltons, and are composed of such functionalities as alkyl, aryl, alkene, alkyne, halo, cyano and other groups, including heteroatoms or not. Such organic compounds can be carbohydrates, including simple sugars, amino or imino acids, nucleic acids, steroids, and others. The chemicals tested as prospective bioactive agents can be prepared using combinatorial chemical processes known in the art or conventional means for chemical synthesis. Preferably, bioactive agents are useful as drugs for treatment of nervous system disorders or conditions.

Some compounds that inhibit GlyT1 or GlyT2 mediated transport also bind to the glycine binding site on the strychnine-sensitive receptor, or to the glycine binding site on the NMDA receptor. Such binding to the strychnine-sensitive receptor can be identified by a binding assay whereby, for example, radiolabeled strychnine is placed in contact with a preparation of strychnine-sensitive receptors, such as can be prepared from a membrane fraction from spinal cord or brain stem tissue. A membrane fraction can be prepared using conventional means, including, for example, methods of homogenization and centrifugation.

Such binding to the NMDA receptor can be identified by a binding assay whereby, for example, radiolabeled glycine is placed in contact with a preparation of NMDA receptors, such as can be prepared from a membrane fraction from neuronal cells or brain tissue. Grimwood, et al., *Molec. Pharmacol.* 41:923–930 (1992). The NMDA receptors located in such membranes are treated using mild detergent, such as about 0.1% to about 0.5% saponin, to remove any endogenous glycine or glutamate.

The ligand used in such a binding assay is radiolabeled with any detectable isotope, such as radioactive isotopes of carbon or hydrogen. Specific binding of the radiolabeled ligand is then determined by subtracting the radioactivity due to non-specific binding from that which is due to total (i.e., specific and non-specific) binding of the radiolabeled ligand. The radioactivity due to non-specific binding is determined by measuring the amount of radiolabel associated with a strychnine-sensitive or NMDA receptor-containing membrane fraction that has been contacted with both radiolabeled ligand and a significant excess of non-radiolabeled ligand, such as 100-fold excess. The radioactivity due to total binding of the radiolabeled ligand is determined by measuring the amount of radiolabel bound to the receptor preparation in the absence of non-radiolabeled ligand. For the NMDA receptor, one can also measure binding to the glycine site on the receptor using labeled analogs of amino acids, such as, for example, dichlorokynurenic acid or L-689,560. See, for example, Grimwood, et al., *Molecular Pharmacol.* 49:923–930 (1992).

Functional ion-flux assays are used to measure the effect of compounds identified by the present invention in enhancing or inhibiting calcium flux (for NMDA receptor preparations) or chloride flux (for strychnine-sensitive receptor preparations). This test is performed on cell cultures that have membrane-bound NMDA receptors or strychnine-sensitive receptors and glycine transporters. Such cells include neuronal cells generally, including those of the brain stem and spinal cord, and cell lines derived therefrom, and any other cell that has been induced or transfected to express NMDA receptors or strychnine-sensitive receptors. Calcium used in such a test is commonly the $^{45}Ca$ isotope, although other calcium measuring techniques can be used as well, such as calcium-associated fluorescence, which can be fluorescence associated with a calcium chelator, and the like. Chloride used in such a test usually includes the isotope $^{36}Cl$. By whatever method the calcium or chloride is monitored, ion flux can be enhanced or inhibited as a result of the discrete addition of a bioactive agent of the present invention. An advantage of this system is that it allows one to monitor the net effect on NMDA receptor or strychnine-sensitive receptor function of a compound that interacts with both the glycine site on a receptor and on a glycine transporter.

GlyT2 inhibitors that are also strychnine-sensitive receptor agonists act in the above-described indications by increasing glycine concentrations at the strychnine-sensitive receptor-expressing synapses via inhibition of the glycine transporter, and via directly enhancing strychnine-sensitive receptor activity. Glycine transporter inhibitors that are also strychnine-sensitive receptor antagonists can nonetheless retain activity in treating these indications, for example if the increase in glycine due to glycine transport inhibition prevails over the strychnine-sensitive receptor antagonism. Where the strychnine-sensitive receptor antagonist activity prevails over the effect of increased extracellular glycine resulting from inhibition of the glycine transporter, these compounds are useful in treating conditions associated with decreased muscle activity such as myasthenia gravis.

As discussed above, the bioactive agents of the invention can have a number of pharmacological actions. The relative effectiveness of the compounds can be assessed in a number of ways, including the following:

1. Comparing the activity mediated through GlyT1 and GlyT2 transporters. This testing identifies bioactive agents (a) that are more active against GlyT1 transporters and thus more useful in treating or preventing schizophrenia, increasing cognition and enhancing memory or (b) that are more active against GlyT2 transporters and thus more useful in treating or preventing epilepsy, pain or spasticity.

2. Testing for strychnine-sensitive receptor or NMDA receptor binding. This test establishes whether there is sufficient binding at this site to warrant further examination of the pharmacological effect of such binding.

3. Testing the activity of the compounds in enhancing or diminishing ion fluxes in primary tissue culture, for example chloride ion fluxes mediated by strychnine-sensitive receptors or calcium ion fluxes mediated by NMDA receptors. A bioactive agent that increases ion flux either (a) has little or no antagonist activity at the strychnine-sensitive receptor and should not affect the potentiation of glycine activity through GlyT2 transporter inhibition or (b), if marked increases are observed over results with comparative GlyT2 inhibitors that have little direct interaction with strychnine-sensitive receptors, then the agent is a receptor agonist.

In some cases, the agent analysis method of the invention will be used to characterize whether a bioactive agent is useful in treating an indication in which NMDA receptors and GlyT1 transporters are implicated. In this case, generally, a lower measure of activity with respect to strychnine-sensitive receptors and GlyT2 transporters is more desirable.

Antisense Therapies

One aspect of the present invention is directed to the use of antisense nucleic acid to treat neurological indications such as those identified above, including, but not limited to, muscle spasticity, stroke, epilepsy and multiple sclerosis. Antisense therapy involves the use of an antisense molecule designed to bind mRNA coding for a GlyT2, which will stop or inhibit the translation of the mRNA, or to bind to the GlyT2 gene to interfere with its transcription. Methods for designing nucleotide sequences that bind genomic DNA to interfere with transcription are known in the art (see, e.g., Helene, *Anti-Cancer Drug Design* 6:569 (1991)). Once the sequence of the mRNA sought to be bound is known, an antisense molecule is designed that binds to the sense strand by the Watson-Crick base-pairing rules to form a duplex structure analogous to the DNA double helix. *Gene Regulation: Biology of Antisense RNA and DNA*, Erikson and Ixzant, eds., Raven Press, New York (1991); Helene, *Anti-Cancer Drug Design* 6:569 (1991); Crooke, *Anti-Cancer Drug Design* 6:609 (1991).

Efficient introduction of antisense molecules into cells so as to effectively interfere with the translation of the targeted MRNA or the function of DNA remains a significant barrier to successful antisense therapy. One method that has been employed to overcome this problem is to covalently modify the 5' or the 3' end of the antisense polynucleic acid molecule with hydrophobic substituents. Such nucleic acids modified with hydrophobic substituents generally gain access to the cells interior with greater efficiency (see, e.g., Boutorin, et al., *FEBS Lett.* 23:1382–1390 (1989) and Shea, et al., i Nucleic Acids Res. 18:3777–3783 (1990)). Other methods include modifying the phosphate backbone of the antisense molecules to remove or diminish negative charge (see, e.g., Agris, et al., *Biochemistry* 25:6268 (1986); Cazenave and Helene in *Antisense Nucleic Acids and Proteins: Fundamentals and Applications*, Mol and Van der Krol, eds., p. 47 et seq., Marcel Dekker, New York (1991)) or modifying the purine or pyrimidine bases (see, e.g., Cazenave and Helene in *Antisense Nucleic Acids and Proteins: Fundamentals and Applications*, Mol and Van der Krol, eds., p. 47 et seq., Marcel Dekker, New York (1991); Milligan, et al., in *Gene Therapy For Neoplastic Diseases*, Huber and Laso, eds., p. 228 et seq., New York Academy of Sciences, New York (1994)). Additional methods to overcome the cell penetration barrier include incorporating antisense polynucleic acid sequences into so-called over-expression vectors that can be inserted into the cell in low copy number, but which in the cell can direct the cellular machinery to synthesize more substantial amounts of antisense polynucleotide molecules (see, e.g., Farhood, et al., *Ann. N.Y. Acad. Sci.* 716:23 (1994)). This strategy includes the use of recombinant viruses that have an expression site into which the antisense sequence has been incorporated (see, e.g., Boris-Lawrie and Temin, *Ann. N.Y. Acad. Sci.* 716:59 (1994)). Yet another method includes increasing membrane permeability by neutralizing the negative charges on antisense molecules or other nucleic acid molecules with polycations (see, e.g., Wu and Wu, *Biochemistry* 27:887–892 (1988) and Behr, et al., *Proc. Natl. Acad. Sci. U.S.A.* 86:6982–6986 (1989)).

Gene therapy such as antisense therapy may involve the introduction of antisense expression vectors into host cells. For example, a DNA vector capable of directing the synthesis of a protein missing from the cell or useful to the cell or organism when expressed in greater amounts may be incorporated into one or more cell types of an organism. Methods for introducing DNA into a cell to produce a new protein or a greater amount of a protein are called transfection methods and are commonly known in the art. See, generally, *Neoplastic Diseases*, Huber and Lazo, eds., New York Academy of Science, New York (1994); Fiegner, *Adv. Drug Deliv. Reb.* 5:163 (1990); McLachlin, et al., *Progr. Nucl. Acids. Res. Mol. Biol.* 38:91 (1990); Karlsson, *S. Blood* 78:2481 (1991); Einerhand and Valerio, *Curr. Top. Microbiol. Immunol.* 177:217–235 (1992); Makdisi, et al., *Prog. Liver Dis.* 10:1 (1992); Litzinger and Huang, *Biochem. Biophys. Acta.* 1113:201 (1992); Morsy, et al., *J.A.M.A.* 270:2338 (1993); Dorudi, et al., *British J. Surgery,* 80:566 (1993).

Other general methods of incorporating nucleic acids into cells include calcium phosphate precipitation (Graham and Van der Eb, *Virology* 52:456 (1983)), coincubation of nucleic acid, DEAE-dextran and cells (Sompayrac and Danna, *Proc. Natl. Acad. Sci.* 12:7575 (1981)), electroporation of cells in the presence of nucleic acid (Potter, et al., *Proc. Natl. Acad. Sci.* 81:7161–7165 (1984)), incorporating nucleic acid into virus coats to create transfection vehicles (Gitman, et al., *Proc. Natl. Acad. Sci. U.S.A.* 82:7309–7313 (1985)) and incubating cells with nucleic acids incorporated into liposomes (Wang and Huang, *Proc. Natl. Acad. Sci.* 84:7851–7855 (1987)). Another approach to gene therapy including antisense therapy is to incorporate the nucleic acid of interest into a virus, such as a herpes virus, adenovirus, parvovirus or a retrovirus for later infection into the host cells. See, e.g., Alki, et al., *Nature Genetics* 3:224 (1993).

Nucleic acid compositions of the invention can be, for example, administered orally, topically, rectally, nasally, vaginally, by inhalation, for example by use of an aerosol, or parenterally, e.g., intramuscularly, subcutaneously, intraperitoneally, intraventricularly, or intravenously. The nucleic acid compositions can be administered alone, or they can be combined with a pharmaceutically-acceptable carrier or excipient according to standard pharmaceutical practice. For the oral mode of administration, the nucleic acid compositions can be used in the form of tablets, capsules, lozenges, troches, powders, syrups, elixers, aqueous solutions and suspensions, and the like. In the case of tablets, carriers that can be used include lactose, sodium citrate and salts of phosphoric acid. Various disintegrants such as starch, and lubricating agents such as magnesium stearate, sodium lauryl sulfate and talc, are commonly used in tablets. For oral administration in capsule form, useful diluents are lactose and high molecular weight polyethylene glycols. When aqueous suspensions are required for oral use, the nucleic acid compositions can be combined with emulsifying and suspending agents. If desired, certain sweetening and/or flavoring agents can be added. For parenteral administration, sterile solutions of the conjugate are usually prepared, and the pH of the solutions are suitably adjusted and buffered. For intravenous use, the total concentration of solutes should be controlled to render the preparation isotonic. For ocular administration, ointments or droppable liquids may be delivered by ocular delivery systems known to the art such as applicators or eye droppers. Such compositions can include mucomimetics such as hyaluronic acid, chondroitin sulfate, hydroxypropyl methylcellulose or poly (vinyl alcohol), preservatives such as sorbic acid, EDTA or benzylchromium chloride, and the usual quantities of diluents and/or carriers. For pulmonary administration, diluents and/or carriers will be selected to be appropriate to allow the formation of an aerosol.

Generally, the nucleic acid compositions will be administered in an effective amount (e.g., prophylactically or therapeutically effective amount). For pharmaceutical uses, an effective amount is an amount effective to either (1) prevent, delay or reduce the symptoms of the indication sought to be treated or (2) induce a pharmacological change relevant to treating or preventing the indication sought to be treated.

For viral gene therapy vectors, antisense oligonucleotide dosages will generally be from about 1 μg to about 100 mg of nucleic acid per kg of body mass.

Autoimmune Disorders

Autoimmune disorders whereby antibodies are produced against glycine transporters can be expected to be associated with disease states. For example, for the GlyT2 transporters such disorders can be expected to be associated with decreased muscle activity, for instance, decreased muscle activity that clinically presents much like myasthenia-gravis, or to be associated with decreased pain perception. See, for an example of a disease caused by autoantibodies to a molecule involved in neurotransmission (glutamic acid decarboxylase), Nathan, et al., *Neurosci. Res.* 40:134–137 (1995).

The presence of these antibodies can be measured by established immunological methods using protein sequences obtained from the nucleic acids described herein or the related glycine transporters reported elsewhere (see, e.g., Kim, et al., *Mol. Pharmacol.* 45:608–617 (1994) and Liu, et al., *J. Biol. Chem.* 268:22802–22808 (1992)). Such immunological methods are described, for example, in Ausubel, et al., *Short Protocols in Molecular Biology*, John Wiley & Sons, New York (1992).

Use of GlyT2 Transporter Protein to Generate GlyT2-specific Antibodies

For the purpose of the present invention, an immunoglobulin, such as an antibody, is specific, reactive with or binds to an antigen if it binds or is capable of binding a human GlyT2 transporter as determined by standard antibody-antigen or ligand-receptor assays. Examples of such assays include competitive assays, immunocytochemistry assays, saturation assays, or standard immunoassays such as ELISA, RIA, and flow cytometric assays. This definition of specificity also applies to single heavy and/or light chains, CDRs, fusion proteins, or fragments of heavy and/or light chains, which bind human GlyT2 transporter alone or are capable of binding human GlyT2 transporter if properly incorporated into immunoglobulin conformation with complementary variable regions and constant regions as appropriate.

Polyclonal antibodies against a human GlyT2 transporter can be prepared by immunizing an animal with a human GlyT2 transporter or an immunogenic portion thereof. Means for immunizing animals for the production of antibodies are well known in the art. By way of example, a mammal can be injected with an inoculum that includes GlyT2. GlyT2 can be included in an inoculum alone or conjugated to a carrier protein such as keyhole limpet hemocyanin (KLH). GlyT2 can be suspended, as is well known in the art, in an adjuvant to enhance its immunogenicity. Sera containing immunologically active antibodies are then produced from the blood of such immunized animals using standard procedures well known in the art.

The identification of antibodies that immunoreact specifically with GlyT2 is made by exposing sera suspected of containing such antibodies to GlyT2 to form a conjugate between antibodies and hGlyT2. The existence of the conjugate is then determined using standard procedures well known in the art.

GlyT2 can also be used to prepare monoclonal antibodies against GlyT2 and used as a screening assay to identify such monoclonal antibodies. Monoclonal antibodies are produced from hybridomas prepared in accordance with standard techniques such as that described by Kohler, et al., *Nature*, 256:495, (1975). Briefly, a suitable mammal, e.g., BALB/c mouse, is immunized by injection with GlyT2. After a predetermined period of time, splenocytes are removed from the mouse and suspended in a cell culture medium. The splenocytes are then fused with an immortal cell line to form a hybridoma. The formed hybridomas are grown in cell culture and screened for their ability to produce a monoclonal antibody against GlyT2.

Immunoglobulins of the present invention may be monoclonal antibodies (hereinafter referred to as MoAbs) of the IgM or IgG isotype of murine, human or other mammalian origin. Most preferably, such a MoAb is reactive with the human GlyT2 transporter protein. A variety of methods for producing human-engineered MoAbs are known in the art (see, e.g., *Antibody Engineering* ($2^{nd}$ Edition), Borrebaeck, C. A. K., ed., Oxford University Press, New York (1995)) Other forms of immunoglobulins may be produced by methods well-known to those skilled in the art, such as by chromatographic purification of polyclonal sera to produce substantially monospecific antibody populations.

Monoclonal antibodies specifically directed against human GlyT2 transporter antigen may be obtained by using combinations of immunogens and screening antigens which have only the human GlyT2 transporter antigen in common or by a screening assay designed to be specific for only anti-hGlyT2 transporter monoclonals. For example, production of monoclonal antibodies directed against human GlyT2 transporter may be accomplished by (1) immunization with human GlyT2 transporter antigen followed by screening of the resultant hybridomas for reactivity against a non-human cell line transfected with human GlyT2 transporter (constructed in a manner similar to that described in Nishimura, et al., *Eur. J. Immunol.*, 18:747–753 (1988); (2) immunization with a non-human cell line transfected with human GlyT2 transporter followed by screening of the resultant hybridomas for reactivity against a human cell line expressing the human GlyT2 transporter antigen; (3) immunization with human or non-human cell lines expressing human hGlyT2 transporter followed by screening of the resultant hybridomas for ability to block reactivity of existing anti-hGlyT2 transporter monoclonals with a human cell line; (4) immunization with human or non-human cell lines expressing human GlyT2 transporter followed by screening of the resultant hybridomas for reactivity with purified native or recombinant human GlyT2 transporter antigen; or (5) immunization with a recombinant derivative of the human GlyT2 transporter antigen followed by screening of the resultant hybridomas for reactivity against a human cell line expressing human GlyT2 transporter. Monoclonal antibodies directed against GlyT2 may also be screened for reactivity or lack of reactivity to human GlyT1 transporter and/or rat GlyT2 transporter.

The generation of human MoAbs to a human antigen is also known in the art (see, e.g., Koda, et al., *Hum. Antibod. Hybridomas* 1(1):15–22 (1990)). Generation of such MoAbs may be difficult with conventional techniques. Thus, it may be desirable to modify the antigen binding regions of the non-human antibodies, e.g., the F(ab')$_2$ or hypervariable regions (CDRs), and fuse them to human constant regions (Fc) or framework regions by recombinant DNA techniques to produce substantially human molecules.

Alternatively, one may isolate DNA sequences which encode a human MoAb or portions thereof which specifically bind to a human GlyT2 transporter by screening a DNA library from human B cells according to the general protocols outlined by Huse, et al., *Science* 246:1275–1281 (1989) and Marks, et al., *J. Mol. Biol.* 222:581–597 (1991), and then cloning and amplifying the sequences which encode the antibody (or binding fragment) of the desired specificity.

In addition to the immunoglobulins specifically described herein, other substantially homologous modified immunoglobulins may be readily designed and manufactured utilizing various recombinant DNA techniques known to those skilled in the art. Modifications of the immunoglobulin genes may be readily accomplished by a variety of well-known techniques, such as site-directed mutagenesis (see, Gillman, et al., *Gene* 8:81–97 (1979); Roberts, et al., *Nature* 328:731–734 (1987)). Also, modifications which affect the binding affinity antibody may be selected using the general protocol outlined by Marks, et al., *J. Biol. Chem.*, 267:16007–16010 (1992).

Use of GlyT2-specific Antibodies for Immunohistochemical and Diagnostic Purposes The invention also provides for the use of the human GlyT2-specific antibodies generated above for a variety of immunohistochemical and diagnostic purposes, including but not limited to competitive and noncompetitive assay systems, RIA, ELISA, flow cytometry, immunoblotting and simple immunocytochemical staining. In some competition assays, the ability of an immunoglobulin, antibody, or peptide fragment to bind an antigen is determined by detecting the ability of the immunoglobulin, antibody, or peptide to compete with a compound known to bind the antigen. Numerous types of competitive assays are known and are discussed herein. Alternatively, assays which measure binding of a test compound in the absence of an inhibitor may also be used. For instance, the ability of a molecule or other compound to bind human GlyT2 transporter may be detected by labeling the molecule of interest directly, or it may be unlabelled and detected indirectly using various sandwich assay formats. Numerous types at binding assays such as competitive binding assays are known (see, e.g., U.S. Pat. No. 3,376,110; U.S. Pat. No. 4,016,043; and Harlow, et al., *Antibodies: A Laboratory Manual*, Cold Spring Harbor Publications, New York (1998)).

Assays for measuring binding of a test compound to one component alone rather than using a competition assay are also available. For instance, immunoglobulins may be used to identify the presence of a human GlyT2 transporter. Standard procedures for monoclonal antibody assays, such as ELISA, may be used. For a review of various signal producing systems which may be used, see, U.S. Pat. No. 4,391,904. Other assay formats may involve the detection of the presence or absence of various physiological or chemical changes which result from an antigen-antibody interaction (see, *Receptor-Effector Coupling—A Practical Approach*, Hulme, ed., IRL Press, Oxford (1990)).

EXAMPLE 1

Human Glycine Type 2 Transporter (hGlyT2) Cloning

A. First Strand Synthesis and PCR of hGlyT2

To create the cDNA used in cloning hGlyT2, first strand synthesis was accomplished using the alternate protocol (for GC rich templates) described in the 5'-RACE system (Gibco/Life Technologies). Briefly, human spinal cord poly-A$^+$ mRNA (50 ng) (Clontech, Palo Alto, Calif.) was added to 3 µg of random primers (Gibco BRL) and the resulting mixture was denatured for 10 min. at 70° C. After the addition of Superscript II™ Reverse Transcriptase, reactions were allowed to proceed at room temperature for 5 min., followed by incubation at 45° C. for 50 min.

PCR amplification of the cDNA reaction was accomplished using the Expand™ High Fidelity PCR system (Boehringer Mannheim Biochemicals). This system contains a mixture of TAQ and Pwo DNA polymerases, the latter of which possesses a proof-reading function to minimize any PCR-induced sequence errors. Amplification occurred under the following conditions: 94° C., 2.00 min. (pre-dwell); [94° C., 40 sec., 58° C., 40 sec., 72° C., 40 sec.] for 10 cycles; [94° C., 40 sec., 58° C., 40 sec., 72° C., 40 sec. (+20 sec./cycle)] for 25 cycles; 72° C., 10 min.; 4° C. hold. PCR products were typically subcloned into the vector p-AMP-1 using the uracil degycosylase CLONEAMP™ system. All sequences were verified by cycle sequencing (Epicentre Technologies, Madison, Wis.) using vector-derived SP6 (forward) and T7 (reverse) primers. Primers used in sequencing were end-labeled with T4 kinase (New England Biolabs, Beverly, Mass.) using γ-$^{32}$P-dATP from NEN Research Products/Dupont (Boston, Mass.). The full-length clones were sequenced using the SP6 and T7 primers in addition to ten hGlyT2-specific primers spaced evenly across the sequence.

B. Cloning of the hGlyT2 Region TM2 to TM10

Because transmembrane regions tend to exhibit the greatest conservation between different species at the amino acid level, degenerate primers (Genemed Biotechnologies, South San Francisco, Calif.) were designed based on rat GlyT2 sequence in the putative transmembrane (TM) regions 2, 5 and 10. The nucleotide sequences of all of the primers (A–U corresponding to SEQ ID NOS:1–21) used in PCR cloning are shown as follows:

Primer A (Sense): 5'-CUACUACUACUAGGCGCCTTC CTSATCC CNTAYYTSATGATG-3' (SEQ ID NO:1; based on nt 892-921 of rat sequence)

Primer B (Anti-sense): 5'-CAUCAUCAUCAUCACGTA GGGGAAS GTGGCSGTRAARTASAC-3' (SEQ ID NO:2; based on nt 1506-1477 of rat sequence)

Primer C (Sense): 5'-CUACUACUACUAGTGTAC TTCACGGCCAC STTYCCNTAYG-3' (SEQ ID NO:3; based on nt 1477-1504 of rat sequence)

Primer D (Anti-sense): 5'-CAUCAUCAUCAUGGCTGG AABCCRA TCATCATYTCDATRTC-3' (SEQ ID NO:4; based on nt 2231-2203 of rat sequence)

Primer E (Sense): 5'-CUACUACUACUACTCGAG GGGATCTCCT ATGTGTATGGC-3' (SEQ ID NO:5; based on nt 2158-2184 of rat sequence)

Primer F (Anti-sense): 5'-CAUCAUCAUCAUAGATCT AGCACTG GGTGCCCAGTTCSARRTCYTTSACNGG-3' (SEQ ID NO:6; based on nt 2609-2571 of rat sequence)

Primer G (Anti-sense): 5'-CAUCAUCAUCAUCACAGA ACACCGG TCCCTGGCTGGC-3' (SEQ ID NO:7; based on nt 999-976 of rat sequence)

Primer H (Sense): 5'-CUACUACUACUAACTGGT CCAGCAAACT GGACTTCATCCTGT-3' (SEQ ID NO:8; based on nt 791-820 of rat sequence)

Primer I (Anti-sense): 5'-CAUCAUCAUCAUGATGAT CAGCATCG CGATGCC-3' (SEQ ID NO:9; based on nt 1054-1030 of rat sequence)

Primer J (Anti-sense): 5'-CAGAGATGATCAGCATC GCG-3' (SEQ ID NO:10; based on nt 1054-1030 of rat sequence)

Primer K (Anti-sense): 5'-GGTAATCCAGCCAGAGC CAG-3' (SEQ ID NO:11; based on nt 941-922of rat sequence)

Primer L (Anti-sense): 5'-CAUCAUCAUCAUGCCTTA TCCTCATC CCCTTGCTCGTCCTC-3' (SEQ ID NO:12; based on nt 782-754 of rat sequence)

Primer M (Sense): 5'-CUACUACUACUACTGTTG TCCGCATCAG ACATG-3' (SEQ ID NO:13; based on nt 189-210 of rat sequence)

Primer N (Anti-sense): 5'-CAUCAUCAUCAUAGGCCT GCGCGCT TTGCGCCTCTCT-3' (SEQ ID NO:14; based on nt 529-505 of rat sequence)

Primer O (Sense): 5'-CUACUACUACUAATTTAG GTGACACTATAG-3' (SEQ ID NO:15)

Primer P (Anti-sense): 5'-TTTGCTGGACCAGTTCCC TCGGGCC TTATCCTCATCCCCTTG-3' (SEQ ID NO:16; based on nt 804-763 of rat sequence)

Primer Q (Anti-sense): 5'-AUCAUCAUCAUCCATGGA CAGGATG AAGTCCAGTTTGCTGGACCAGTTCCCTC-3' (SEQ ID NO:17; based on nt 785-726 of rat sequence)

Primer R (Anti-sense): 5'-GCCTTCCACACAGACACC GGTCCCT GGCTGGCAAACTGGCCC-3' (SEQ ID NO:18; based on nt 1007-965 of rat sequence)

Primer S (Sense): 5'-CUACUACUACUAGAGCTC GTGGGGATCTC CTATGTGTATGGC-3' (SEQ ID NO:19; based on nt 2155-2184 of rat sequence)

Primer T (Anti-sense): 5'-CAUCAUCAUCAUTAATAC GACTCAC TATAGGG-3' (SEQ ID NO:20)

Primer U (Sense): 5'-UACUACUACUAGTACTAG TGATCCTCCT CATCCGAGG-3' (SEQ ID NO:21; based on nt 1532-1504 of rat sequence)

In the above listed primer sequences, Y refers to C and T, R refers to A and G, B refers to G, T and C and I refers to Inosine. The PCR isolation of the first fragments of hGlyT2 was accomplished using two sets of primers encoding the rat peptide sequence (Liu, Q. R., et al., J. Biol. Chem. 268:22802–22806 (1993)) that were degenerate at the nucleic acid level. The region between TM2 and TM5 was amplified using primers A and B. Likewise, the region between TM5 and TM10 was amplified using primers C and D.

After obtaining the partial sequence of the human GlyT2 transporter, the gene-specific primer E and primer F (a degenerate 3'-primer against the final 40 bases of the rat GlyT2 coding sequence) were used to amplify the 3'-end of the hGlyT2 coding sequence.

C. Cloning of the 5'-end of hGlyT2

A primer which encoded the sequence upstream of TM1 (primer H) was used with primer G to PCR-amplify the human sequence corresponding to rat GlyT2 bases 791–999. The additional 100 bases allowed the sequence 5' to TM1 to be used for gene-specific primer design.

The Gibco/BRL 5'-RACE System was used to clone the additional sequence at the 5'-end of the transporter sequence. A non-coding, gene-specific primer 3' to TM2 (primer I) was used in the reverse transcription of human spinal cord poly $A^+$ mRNA. The cDNA product was then tailed with poly-dC nucleotides using terminal transferase. The first round of PCR amplification used an additional non-coding primer immediately 5' to primer I (primer J) and the kit supplied primer (AAP). Using the product of the first round of PCR as a template, two additional nested amplifications were performed. The gene-specific primer K and primer AUAP (Gibco/BRL) (Round 2), and then primers L and UAP (Gibco/BRL) (Round 3), were used in PCR to yield a 5'-RACE product. The largest products from the final round of amplification contained approximately 200 fewer bases of coding sequence than rat GlyT2 transporter. The 5'-RACE products were subcloned into pAMP-1, as described previously.

The entire 5'-end of the hGlyT2 coding sequence was ultimately isolated using a non-degenerate primer against bases 189–210 of the rat 5'-untranslated region (Primer M) in conjunction with primer N.

The complete sequence was cloned from a sample of spinal cord poly A+ mRNA which contained mRNA from a pool of 69 individuals (lot number 6120295, Clontech Laboratories Inc.). In order to obtain an accurate consensus sequence for hGlyT2, the entire sequence was re-amplified from a different lot of spinal cord mRNA (lot 7050107), which represented a pool of 92 individuals. In addition, each of the six fragments (FIG. 1) of the transporter were re-amplified in three independent PCR reactions from two additional sources of poly A+ mRNA. The first set of six fragments was cloned from a different aliquot of human spinal cord poly A+ mRNA (lot 7050107, purchased several months later), and the second set of fragments was cloned from poly A+ mRNA isolated from the astrocytoma cell line U373MG. The resulting 48 sequences (SEQ ID NOS:22/23 to 117/118) were used to generate the consensus sequence shown in SEQ ID NO:121/122.

EXAMPLE 2

Transporter Construct Assembly

A detailed outline of the assembly of the different hGlyT2 fragments is shown in FIG. 1. The hGlyT2 transporter coding sequence was assembled from six different PCR product fragments (numbering corresponds to the rat GlyT2 sequence): 410-822 (A), 791-1050 (B), 892-1506 (C), 1477-2208 (D), 2157-2607 (E), 189-529 (F). These six isolated PCR fragments encode the entire hGlyT2 transporter, and were assembled using five restriction sites as shown in FIG. 1. At least eight independent clones of each fragment were sequenced to verify the hGlyT2 coding sequence [fragment:

A (SEQ ID NOS:22/23 to 36/37), B (SEQ ID NOS:38/39 to 52/53), C (SEQ ID NOS:54/55 to 69/70), D (SEQ ID NOS:71/72 to 85/86), E (SEQ ID NOS:87/88 to 101/102), and F (SEQ ID NOS:103/104 to 117/118)]. Fragment A and B were ligated together using a NcoI restriction site that was found at position 822. Because the sequences of fragments A and B did not overlap, an NcoI site was introduced into fragment A by two rounds of PCR extension using primer sets O and P, and O and Q, respectively (FIG. 1). Fragments AB and C were ligated together using a PinAI restriction site. Although this site was found in fragment C, it had to be introduced into the AB sequence (using primer R, FIG. 1) due to an allelic variation in AB at base 782. The product of the ligation of PinAI digested AB and C was named fragment ABC.

Because fragment E contained only half of the SacI site, the first three bases were added to the 5'-end using primers S and T. Fragment D was amplified with primers U and D. Fragments D and E were digested with SacI and ligated. The resulting product (DE) was subcloned into pAMP-1. The plasmid containing ABC was digested with HinDIII and SpeI and the resulting 1100 base-pair product was ligated into HinDIII/SpeI-digested plasmid containing DE, creating the truncated form of hGlyT2 (nucleotides 410–2607). Finally, the 5'-end was added by combining fragments ABCDE and F (FIG. 1). Both fragments were digested with Pst1 and ligated together. The ligation reaction was then PCR amplified with primers M and I, and the resulting construct containing bases 189–1054 was subcloned back into HinDmIII/PinAI-digested hGlyT2 (410-2607). The complete hGlyT2 transporter sequence (189-2607) and the truncated form (470-2607) were subcloned into the EcoRI/HinDIII sites of pCDNA3 (Invitrogen, Palo Alto, Calif.) for expression in mammalian cells.

Because the original cDNA was derived from three different lots of pooled mRNA samples, as well as from a single cell line, numerous allelic variations were identified in the complete sequence. The variations identified were as follows: (a) $C^{77} \rightarrow T$, (b) $C^{220} \rightarrow T$, (c) $C^{224} \rightarrow T$, (d) $C^{266} \rightarrow T$, (e) $A^{304} \rightarrow G$, (f) $T^{521} \rightarrow A$, (g) $T^{583} \rightarrow C$, (h) $A^{596} \rightarrow G$, (i) $A^{678} \rightarrow G$, () $T^{681} \rightarrow C$, (k) $G^{745} \rightarrow T$, (l) $G^{750} \rightarrow C$, (m) $C^{765} \rightarrow T$, (n) $G^{777} \rightarrow C$ or A, (o) $A^{867} \rightarrow G$ (p) $T^{917} \rightarrow C$, (q) $G^{1256} \rightarrow A$, (r) $T^{1292} \rightarrow C$, (s) $C^{1299} \rightarrow A$, (t) $C^{1325} \rightarrow A$, (u) $C^{1364} \rightarrow A$, (v) $G^{1374} \rightarrow C$, (w) $C^{1392} \rightarrow A$, (x) $T^{1454} \rightarrow C$, (x) $A^{1478} \rightarrow G$, (y) $A^{1617} \rightarrow T$, (z) $A^{1744} \rightarrow T$, (aa) $T^{1854} \rightarrow C$, (bb) $T^{1949} \rightarrow A$, (cc) $T^{1959} \rightarrow C$, or (dd) $T^{2130} \rightarrow C$. These allelic variants encode the following amino acid substitutions: (1) $Pro^{26}$ to Leu, (2) $Arg^{74}$ to Trp, (3) $Pro^{75}$ to Leu, (4) $Ala^{89}$ to Val, (5) $Ser^{102}$ to Gly, (6) $Val^{174}$ to Glu, (7) $Ser^{195}$ to Pro, (8) $Asp^{199}$ to Gly, (9) $Val^{249}$ to Leu, (10) $Leu^{306}$ to Pro, (11) $Gly^{419}$ to Glu, (12) $Thr^{442}$ to Asn, (13) $Thr^{455}$ to Lys, (14) $Trp^{458}$ to Cys, (15) $Leu^{485}$ to Pro, (16) $Lys^{493}$ to Arg, or (17) $Val^{650}$ to Glu.

The human GlyT2 transporter exhibited very high homology with the rat GlyT2 sequence (Liu, Q. R., et al., *J. Biol. Chem.* 268:22802–22806 (1993)) (FIG. 2), with the overall homology between the two species being 88% and 93% at the nucleotide and amino acid levels, respectively (FIG. 3). The human GlyT2 transporter and other members of the amino acid transporter family shared approximately 50% amino acid homology. The greatest diversity between the rat and human GlyT2 proteins is within the first 190 amino acids, where only 74% conservation is observed.

The 5'-untranslated regions of the rat and human GlyT2 transporters are very highly conserved. Sequencing of the human construct revealed that the first 52 bases (20 5'-untranslated and 32 coding sequence) of the human cDNA sequence are identical to the rat sequence. This 52-base region does not exhibit homology to any other sequence currently found in Genbank, and thus may represent a regulatory sequence that is unique to GlyT2. The next 100 bases of coding sequence exhibit only 66% identity between the two species.

Two splice forms of hGlyT2 were isolated during the cloning of the GlyT2 transporter (FIG. 2). The first variant was characterized by a divergent 5'-end, followed by bases 541–675 of the hGlyT2 sequence (FIG. 2A). After base 675, a 172 base-pair insert containing stop codons in all three reading frames was present. This was followed by the rest of the transporter sequence. Expression of this variant predicts a start codon at methionine-235, thus forming a transporter lacking the first 234 amino acids (hGlyT2/5I (5'-insert)). A second variant contained a 42 base-pair deletion in the region between bases 1488–1530 (hGlyT2-3D (3'-deletion)) (FIG. 2B). This variant lacks 14 amino acids in the intracellular loop between putative transmembrane regions TM6 and TM7. Both variants (hGlyT2/5I and hGlyT2/3D) were assembled and expressed in the same manner as the full-length sequence. In addition, a construct containing both variations (hGlyT2/5I-3D (5'-insert/3'-deletion)) was also assembled and expressed.

In addition, a truncated form of hGlyT2 was constructed with nucleotides 221–2391 of the hGlyT2 sequence. Expression of this construct predicts a start codon at methionine-154, thus forming a transporter lacking the first 153 amino acids (truncated hGlyT2).

EXAMPLE 3
Expression of hGlyT2 Transporters

The hGlyT2 constructs described in Example 2 above, including full-length, truncated and variant splice forms of GlyT2, were transiently expressed in COS-7 cells using the Superfect™ system (Qiagen, Santa Clarita, Calif.). COS-7 cells were plated the day before transfection at 20,000 cells per well. DNA for transfection was prepared using the Qiagen Midiprep™ kit, and 1 µg of each of the forms of hGlyT2 was transfected into each well of a 24-well plate. Transfection was terminated 2–2.5 hours after adding the DNA complex to the cells by changing the media. Transfection efficiencies were monitored by transiently expressing a construct containing green fluorescent protein. The number of transfectants was typically 20–50% of the total cells. Standard growth conditions were DMEM, high glucose, 10% fetal bovine serum, penicillin G (100 U/mL), streptomycin sulfate (100 µg/mL), 5% $CO_2$/humid atmosphere, 37° C. Cells were typically grown for 48 hours after transfection before use in glycine uptake assays, as described in Example 4 with assay results shown in FIG. 3.

EXAMPLE 4
Glycine Uptake

Glycine uptake was essentially as previously (Kim, K-M., et al., *Mol. Pharm.* 45:608–17 (1994)). Briefly, the cells were washed three times with either glycine uptake buffer (GUB; 5 mM Tris, pH 7.4, 7.5 mM Hepes, 120 mM NaCl, 5.4 mM KCl, 1.2 mM $CaCl_2$, 1.2 mM $MgSO_4$, 1 mM L-ascorbic acid, 5 mM D-Glucose), or chloride-free uptake buffer (same as GUB with NaCl substituted with 120 mM sodium acetate and KCl and $CaCl_2$ omitted). [2-$^3$H]-glycine (581 GBq/mmol; Amersham, Arlington Heights, Ill.) was added to either GUB or Cl⁻ free GUB at a concentration of 2 µCi/mL (127 nM). Uptake of [$^3$H]glycine was allowed to proceed for 15 min. at 37° C., after which the cells were washed three times with excess ice-cold PBS. The cells were solubilized in 0.5% Triton X-100 and the radioactivity was quantified by scintillation counting. The amount of protein per well was determined by the BCA reagent assay (Pierce). For the sarcosine inhibition studies, the cells were pretreated with the desired concentration of sarcosine (in either GUB or Cl-free GUB) for 15 min. prior to uptake. All conditions were carried out in triplicate, and the uptake was expressed as pmol glycine/mg protein/min.

Figure 4A:
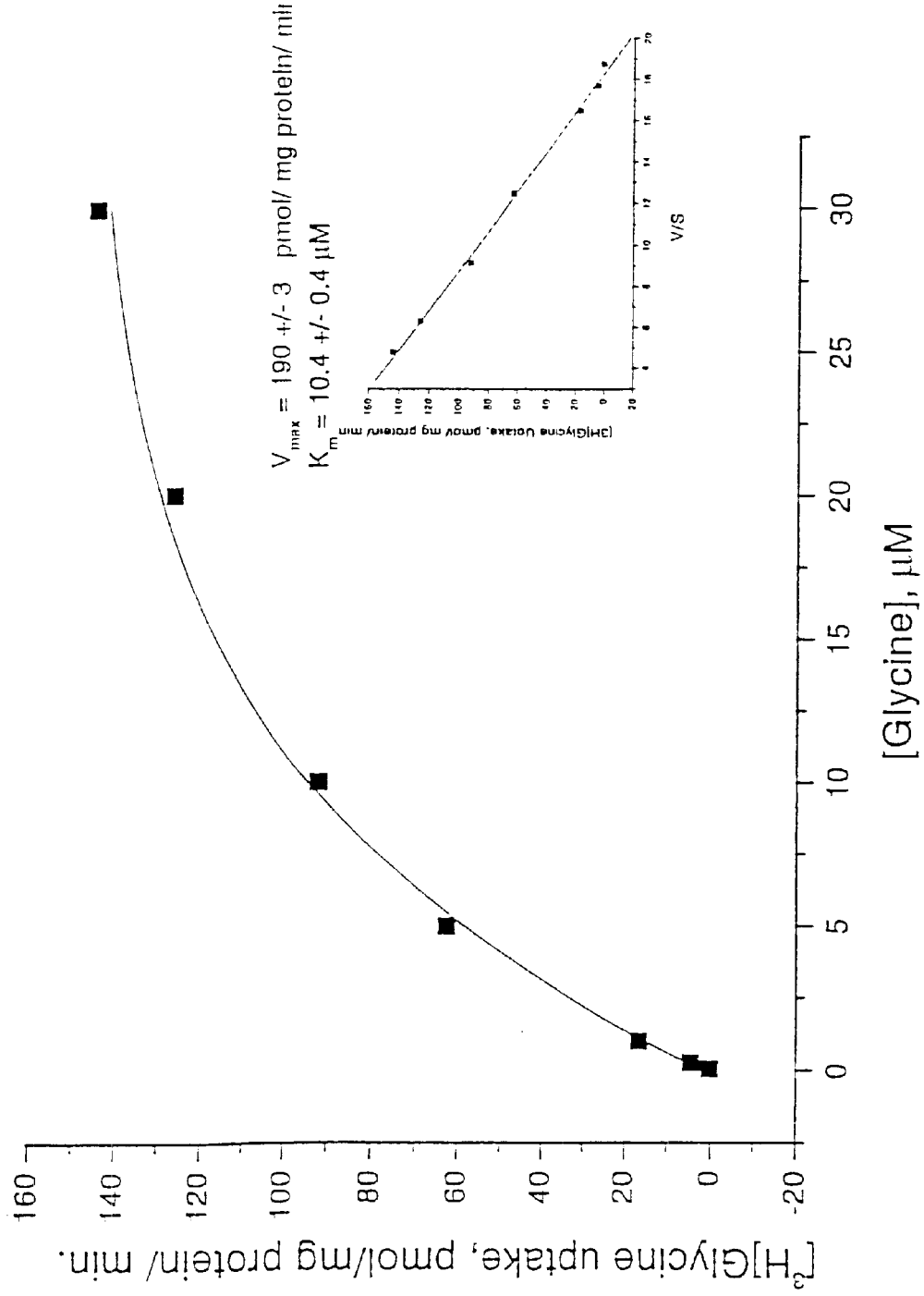
FIG. 4 shows kinetics of glycine uptake into COS-7 cells. Values from plasmid-transfected controls were subtracted from corresponding transporter-transfected data. Results shown are the average of three independent experiments, where each glycine concentration was assayed in triplicate. Kinetic analyses of the transport mediated by a full-length transporter (FIG. 4A) and a truncated form (FIG. 4B) of GlyT2 are shown. The Eadie-Hofstee analysis is depicted in each inset.

When completely assembled, the hGlyT2 transporter sequence mediates high-affinity glycine transport when transiently transfected into COS-7 cells (FIG. 3). HGlyT2-transfected cells showed a 7–10 fold increase in [$^3$H]glycine uptake relative to untransfected and mock-transfected COS-7 cells. Cl$^-$-dependent uptake represented 80–90% of the total uptake in the GlyT2 transfection experiments (FIG. 3). An Eadie-Hofstee transformation of the glycine uptake data with the transfected cells revealed a $K_m$=10±0.4 μM and a $V_{max}$=190±3 pmol glycine/mg protein/min. (FIGS. 4A and 4B). Because the $K_m$ reported for rat GlyT2 was 13 μM (Liu, Q. R., et al., *J. Biol. Chem.* 268:22802–22806 (1993)), the glycine affinity for the human and rat GlyT2 transporters is nearly identical. Interestingly, truncating hGlyT2 such that the initial methionine is residue 154 also yielded an active transporter which exhibited a $K_m$ of 9±1 μM, and a $V_{max}$ of 67±3 pmol glycine/mg protein/min (FIGS. 4A and 4B). These data suggest that the deletion of the first 153 amino acids has no effect on the glycine affinity of this transporter.

As described in Example 2 above, two additional variants of hGlyT2 were identified during the PCR cloning (FIG. 2). The first was found in 3 out of 45 clones isolated, and was characterized by a truncated amino terminus and a 168 base-pair insertion in the region encoding the loop between transmembrane domains one and two (FIG. 2A). Sequence analysis of the insertion revealed stop codons in all three reading frames. As expected, expression of the transporter containing this insertion resulted in an insignificant increase in glycine uptake in COS-7 cells (FIG. 3). Thus, the loss of the first transmembrane region and cytoplasmic amino terminus yields a transporter that is unable to mediate high-affinity uptake of glycine. A second splice form was also isolated in one of 50 clones, and represented a 48 base-pair deletion between putative transmembrane regions 6 and 7 (FIG. 2B). This deletion did not affect the reading frame of the transporter, and effectively caused the deletion of 16 amino acids from this intracellular loop. However, this relatively small deletion resulted in a non-functional transporter (FIG. 3).

A truncated form of hGlyT2 as discussed in Example 2 above, was expressed from a construct containing nucleotides 221–2391 of the human transporter sequence (FIG. 3). This truncated transporter, which has a predicted start methionine corresponding to Met-154 of the human transporter, mediated high-affinity glycine uptake about one third as effectively as the full-length transporter (FIGS. 3 and 4). Eadie-Hofstee analysis of the uptake mediated by this receptor revealed that the affinity of this transporter for glycine was identical to the full-length transporter (FIGS. 4A and 4B). The differences in uptake for the two transporter types were accounted for in the $V_{max}$ values. Since the truncated form of the transporter mediates high-affinity uptake, the amino-terminus of hGlyT2 is not likely to be directly involved in the transport of the glycine molecule. Thus, this region may play a role in either membrane targeting of the transporter or may contribute to the optimal conformation of the transporter. Alternatively, there may be interactions of the extended N-terminus with intracellular regulatory proteins. Indeed, there are many potential sites of phosphorylation in the intracellular N-terminus of GlyT2 which are not present in other members of the transporter. Interestingly, this amino-terminal truncated form of hGlyT2 is predicted to have 44 amino acids prior to the start of the first putative transmembrane region (TM1). This is similar to the predicted 33 and 43 residues prior to TM1 in hGlyT1 (Kim, et al., 1994)) and proline transporters (Fremeau, et al., (1992)), respectively. The additional 153 amino acids at the amino-terminal end makes GlyT2 unique in the Na$^+$/Cl$^-$-dependent amino-acid transporter family.

A pharmacological distinction between the GlyT1 and GlyT2 transporters involves sarcosine sensitivity (Liu, Q. R., et al., *Proc. Natl. Acad. Sci.* 89:12145–12149 (1992b); Kim, K-M., et al., *Mol. Pharm.* 45:608–17 (1994); Guastella, J., et al., *Proc. Natl. Acad. Sci.* (USA) 89:7189–7193 (1992)). Glycine uptake mediated by GlyT1 is almost completely inhibited when the sarcosine concentration exceeds 200 μM, while rat GlyT2-mediated uptake is inhibited only by 10–20% at sarcosine concentrations of 1 mM (Liu, Q. R., et al., *J. Biol. Chem.* 268:22802–22806 (1993)). Glycine uptake mediated by both the hGlyT2 transporter and the truncated form of the transporter was evaluated at increasing sarcosine concentrations (FIG. 5). Both forms were relatively insensitive to sarcosine, with less than 15% reduction of uptake in the presence of 1 mM sarcosine. The human form is therefore comparable to the rat in regards to sarcosine inhibition.

The nucleic acid or amino acid sequences referred to herein by SEQ ID NO: are as follows:

| SEQ ID NO: | TYPE | SEQUENCE | DESCRIPTION or SOURCE[1] |
|---|---|---|---|
| 1 | nucleic acid | nt 1–42 | Primer A (Sense) corresponding to 892–921 |
| 2 | nucleic acid | nt 1–42 | Primer B (Anti-Sense) corresponding to 1506–1477 |
| 3 | nucleic acid | nt 1–40 | Primer C (Sense) coresponding to 1477–1504 |
| 4 | nucleic acid | nt 1–41 | Primer D (Anti-sense) corresponding to 2231–2203 |
| 5 | nucleic acid | nt 1–39 | Primer E (Sense) corresponding to 2158–2184 |
| 6 | nucleic acid | nt 1–52 | Primer F (Anti-sense) corresponding to 2609–2571 |
| 7 | nucleic acid | nt 1–37 | Primer G (Anti-sense) corresponding to 999–976 |
| 8 | nucleic acid | nt 1–42 | Primer H (Sense) corresponding to 791–820 |
| 9 | nucleic acid | nt 1–33 | Primer I (Anti-sense) corresponding to 1054–1030 |
| 10 | nucleic acid | nt 1–20 | Primer J (Anti-sense) corresponding to 1054–1030 |
| 11 | nucleic acid | nt 1–20 | Primer K (Anti-sense) corresponding to 941–922 |
| 12 | nucleic acid | nt 1–41 | Primer L (Anti-sense) corresponding to 782–754 |
| 13 | nucleic acid | nt 1–33 | Primer M (Sense) corresponding to 189–210 |
| 14 | nucleic acid | nt 1–37 | Primer N (Anti-sense) corresponding to 529–505 |
| 15 | nucleic acid | nt 1–30 | Primer O (Sense) |
| 16 | nucleic acid | nt 1–42 | Primer P (Anti-sense) corresponding to 804–763 |
| 17 | nucleic acid | nt 1–54 | Primer Q (Anti-sense) corresponding to 785–726 |
| 18 | nucleic acid | nt 1–42 | Primer R (Anti-sense) corresponding to 1007–965 |
| 19 | nucleic acid | nt 1–42 | Primer S (Sense) corresponding to 2155–2184 |
| 20 | nucleic acid | nt 1–32 | Primer T (Anti-sense) |
| 21 | nucleic acid | nt 1–38 | Primer U (Sense) corresponding to 1532–1504 |
| 22 | nucleic acid | nt 257–569 | HSpC-1 (fragment A) |

-continued

| SEQ ID NO: | TYPE | SEQUENCE | DESCRIPTION or SOURCE[1] |
|---|---|---|---|
| 23 | amino acid | aa 87–189 | |
| 24 | nucleic acid | nt 258–569 | HSpC-2 (fragment A) |
| 25 | amino acid | aa 87–189 | |
| 26 | nucleic acid | nt 258–569 | HSpC-3 (fragment A) |
| 27 | amino acid | aa 87–189 | |
| 28 | nucleic acid | nt 258–569 | HSpC-3 (fragment A) |
| 29 | amino acid | aa 87–189 | |
| 30 | nucleic acid | nt 258–569 | HSpC-3 (fragment A) |
| 31 | amino acid | aa 87–189 | |
| 32 | nucleic acid | nt 258–569 | U373MG (fragment A) |
| 33 | amino acid | aa 87–189 | |
| 34 | nucleic acid | nt 258–569 | U373MG (fragment A) |
| 35 | amino acid | aa 87–189 | |
| 36 | nucleic acid | nt 258–569 | U373MG (fragment A) |
| 37 | amino acid | aa 87–189 | |
| 38 | nucleic acid | nt 578–841 | HSpC-1 (fragment B) |
| 39 | amino acid | aa 194–280 | |
| 40 | nucleic acid | nt 578–841 | HSpC-2 (fragment B) |
| 41 | amino acid | aa 194–280 | |
| 42 | nucleic acid | nt 578–841 | HSpC-3 (fragment B) |
| 43 | amino acid | aa 194–280 | |
| 44 | nucleic acid | nt 578–841 | HSpC-3 (fragment B) |
| 45 | amino acid | aa 194–280 | |
| 46 | nucleic acid | nt 578–841 | HSpC-3 (fragment B) |
| 47 | amino acid | aa 194–280 | |
| 48 | nucleic acid | nt 578–841 | U373MG (fragment B) |
| 49 | amino acid | aa 194–280 | |
| 50 | nucleic acid | nt 578–841 | U373MG (fragment B) |
| 51 | amino acid | aa 194–280 | |
| 52 | nucleic acid | nt 578–841 | U373MG (fragment B) |
| 53 | amino acid | aa 194–280 | |
| 54 | nucleic acid | nt 679–1293 | HSpC-1 (fragment C) |
| 55 | amino acid | aa 227–431 | |
| 56 | nucleic acid | nt 679–1293 | HSpC-2 (fragment C) |
| 57 | amino acid | aa 227–431 | |
| 58 | nucleic acid | nt 679–1293 | HSpC-3 (fragment C) |
| 59 | amino acid | aa 227–431 | |
| 60 | nucleic acid | nt 679–1293 | HSpC-3 (fragment C) |
| 61 | amino acid | aa 227–431 | |
| 62 | nucleic acid | nt 679–1293 | HSpC-3 (fragment C) |
| 63 | amino acid | aa 227–431 | |
| 64 | nucleic acid | nt 679–1293 | U373MG (fragment C) |
| 65 | amino acid | aa 227–393 | |
| 66 | amino acid | aa 395–431 | |
| 67 | nucleic acid | nt 679–1293 | U373MG (fragment C) |
| 68 | amino acid | aa 227–431 | |
| 69 | nucleic acid | nt 679–1293 | U373MG (fragment C) |
| 70 | amino acid | aa 227–431 | |
| 71 | nucleic acid | nt 1264–2018 | HSpC-1 (fragment D) |
| 72 | amino acid | aa 422–669 | |
| 73 | nucleic acid | nt 1264–2018 | HSpC-2 (fragment D) |
| 74 | amino acid | aa 422–669 | |
| 75 | nucleic acid | nt 1264–2018 | HSpC-3 (fragment D) |
| 76 | amino acid | aa 422–669 | |
| 77 | nucleic acid | nt 1264–2018 | HSpC-3 (fragment D) |
| 78 | amino acid | aa 422–669 | |
| 79 | nucleic acid | nt 1264–2018 | HSpC-3 (fragment D) |
| 80 | amino acid | aa 422–669 | |
| 81 | nucleic acid | nt 1264–2018 | U373MG (fragment D) |
| 82 | amino acid | aa 422–669 | |
| 83 | nucleic acid | nt 1264–2018 | U373MG (fragment D) |
| 84 | amino acid | aa 422–669 | |
| 85 | nucleic acid | nt 1264–2018 | U373MG (fragment D) |
| 86 | amino acid | aa 422–669 | |
| 87 | nucleic acid | nt 1942–2394 | HSpC-1 (fragment E) |
| 88 | amino acid | aa 648–797 | |
| 89 | nucleic acid | nt 1942–2394 | HSpC-2 (fragment E) |
| 90 | amino acid | aa 648–797 | |
| 91 | nucleic acid | nt 1942–2394 | HSpC-3 (fragment E) |
| 92 | amino acid | aa 648–797 | |
| 93 | nucleic acid | nt 1942–2394 | HSpC-3 (fragment E) |
| 94 | amino acid | aa 648–797 | |
| 95 | nucleic acid | nt 1942–2394 | HSpC-3 (fragment E) |
| 96 | amino acid | aa 648–797 | |
| 97 | nucleic acid | nt 1942–2394 | U373MG (fragment E) |
| 98 | amino acid | aa 648–797 | |
| 99 | nucleic acid | nt 1942–2394 | U373MG (fragment E) |
| 100 | amino acid | aa 648–797 | |
| 101 | nucleic acid | nt 1942–2394 | U373MG (fragment E) |
| 102 | amino acid | aa 648–797 | |
| 103 | nucleic acid | nt 1–316 | HSpC-1 (fragment F) |
| 104 | amino acid | aa 1–105 | |
| 105 | nucleic acid | nt 1–316 | HSpC-2 (fragment F) |
| 106 | amino acid | aa 1–105 | |
| 107 | nucleic acid | nt 1–316 | HSpC-3 (fragment F) |
| 108 | amino acid | aa 1–105 | |
| 109 | nucleic acid | nt 1–316 | HSpC-3 (fragment F) |
| 110 | amino acid | aa 1–105 | |
| 111 | nucleic acid | nt 1–316 | HSpC-3 (fragment F) |
| 112 | amino acid | aa 1–105 | |
| 113 | nucleic acid | nt 1–316 | U373MG (fragment F) |
| 114 | amino acid | aa 1–105 | |
| 115 | nucleic acid | nt 1–316 | U373MG (fragment F) |
| 116 | amino acid | aa 1–105 | |
| 117 | nucleic acid | nt 1–316 | U373MG (fragment F) |
| 118 | amino acid | aa 1–105 | |
| 119 | nucleic acid | nt 1–2394 | Seq 49 HGlyT2 |
| 120 | amino acid | aa 1–797 | |
| 121 | nucleic acid | nt 1–2394 | Seq 50 Consensus HGlyT2 |
| 122 | amino acid | aa 1–797 | |
| 123 | nucleic acid | nt 1–2394 | SEQ ID NO:26 [WO 98/07854 (PCT/US97/14637)] |
| 124 | amino acid | aa 1–797 | |

[1]HSpC-1 source is Clontech spinal cord poly A+mRNA, lot number 6120295, (pool size = 69, age range = 22–70 years); HSpC-2 source is Clontech spinal cord poly A+mRNA, lot number 7050107, (pool size = 92, age range = 16–75 years); HSpC-3 source is Clontech spinal cord poly A+mRNA, lot number 7050107, (pool size = 92, age range = 16–75 years); U373MG source is U373MG astrocytoma cell line, poly A+mRNA.

While this invention has been described with an emphasis upon preferred embodiments, it will be obvious to those of ordinary skill in the art that variations in the preferred devices and methods may be used and this it is intended that the invention may be practiced otherwise than as specifically described herein. Accordingly, this invention includes all modifications encompassed within the spirit and scope of the invention as defined by the claims that follow.

What is claimed is:

1. A purified nucleic acid comprising a nucleic acid sequence that encodes a glycine transporter type 2 (GlyT2) protein that has glycine transport activity wherein the protein comprises an amino acid sequence identical to the amino acid sequence of SEQ ID NO:124, except that the amino acid sequence of the protein has a serine at amino acid position 24.

2. A purified nucleic acid comprising a nucleic acid sequence that encodes a GlyT2 protein that has glycine transport activity wherein the protein comprises an amino acid sequence identical to the amino acid sequence of SEQ ID NO:124, except that the amino acid sequence of the protein has a tryptophan at amino acid position 74.

3. A purified nucleic acid comprising a nucleic acid sequence that encodes a GlyT2 protein that has glycine transport activity wherein the protein comprises an amino acid sequence identical to the amino acid sequence of SEQ ID NO:124, except that the amino acid sequence of the protein has a glycine at amino acid position 155.

4. A purified nucleic acid comprising a nucleic acid sequence that encodes a GlyT2 protein that has glycine transport activity wherein the protein comprises an amino acid sequence identical to the amino acid sequence of SEQ ID NO:124, except that the amino acid sequence of the protein has an aspartic acid at amino acid position 188.

5. A purified nucleic acid comprising a nucleic acid sequence that encodes a GlyT2 protein that has glycine transport activity wherein the protein comprises an amino acid sequence identical to the amino acid sequence of SEQ ID NO:124, except that the amino acid sequence of the protein has a leucine at amino acid position 362.

6. A purified nucleic acid comprising a nucleic acid sequence that encodes a GlyT2 protein that has glycine transport activity wherein the protein comprises an amino acid sequence identical to the amino acid sequence of SEQ ID NO:124, except that the amino acid sequence of the protein has an alanine at amino acid position 431.

7. A purified nucleic acid comprising a nucleic acid sequence that encodes a GlyT2 protein that has glycine transport activity wherein the protein comprises an amino acid sequence identical to the amino acid sequence of SEQ ID NO:124, except that the amino acid sequence of the protein has a serine at amino acid position 582.

8. A purified nucleic acid comprising a nucleic acid sequence that encodes a GlyT2 protein that has glycine transport activity wherein the protein comprises an amino acid sequence identical to the amino acid sequence of SEQ ID NO:124, except that the amino acid sequence of the protein has one or more of the following amino acid substitutions: (1) a serine at amino acid position 24, (2) a tryptophan at amino acid position 74, (3) a glycine at amino acid position 155, (4) an aspartic acid at amino acid position 188, (5) a leucine at amino acid position 362, (6) an alanine at amino acid position 431, or (7) a serine at amino acid position 582, of SEQ ID NO:124.

9. A purified nucleic acid comprising a nucleic acid sequence that encodes a GlyT2 protein that has glycine transport activity and that comprises the amino acid sequence of SEQ ID NO:122.

10. A purified nucleic acid comprising a nucleic acid sequence that encodes a GlyT2 protein that has glycine transport activity and that comprises the amino acid sequence of SEQ ID NO:120.

11. A purified nucleic acid that encodes a GlyT2 protein comprising a sequence that differs from nucleotides 1 to 2391 of SEQ ID NO:123 by having one or more of the following nucleotide substitutions: (1) A at position 70, (2) T at position 220, (3) G at position 463, (4) G at position 562, (5) T at position 1085, (6) C at position 1292, (7) A at position 1299, (8) T at position 1617, or (9) T at position 1744.

12. A purified nucleic acid that encodes a GlyT2 protein comprising nucleotides 1 to 2391 of SEQ ID NO:121.

13. A purified nucleic acid that encodes a GlyT2 protein comprising nucleotides 1 to 2391 of SEQ ID NO:119.

14. A purified nucleic acid that encodes a GlyT2 protein comprising a sequence that varies from nucleotides 1 to 2391 of SEQ ID NO: 123 by having one or more of the following nucleotide substitutions: (1) A at position 70, (2) T at position 220, (3) G at position 463, (4) G at position 562, (5) T at position 1085, (6) C at position 1292, (7) A position 1299, (8) T at position 1617, or (9) T at position 1744, and additionally having one or more of the following nucleotide substitutions: (a) T at position 77, (b) T at position 220, (c) T at position 244, (d) T at position 266, (e) G at position 304, (f) A at position 521, (g) C at position 583, (h) G at position 596, (i) G at position 678, (j) C at position 681, (k) T at position 745, (l) C at position 750, (m) T at position 765, (n) C or A at position 777, (o) G at position 867, (p) C at position 917, (q) A at position 1256, (r) C at position 1292, (s) A at position 1325, (t) A at position 1364, (u) C at position 1374, (v) A at position 1392, (w) C at position 1454, (x) G at position 1478, (y) C at position 1854, (z) A at position 1949, (aa) C at position 1959, or (bb) C at position 2130.

15. A purified nucleic acid that encodes a GlyT2 protein comprising nucleotides 1 to 2391 of SEQ ID NO:121, and additionally having one or more of the following nucleotide substitutions: (a) C at position 6, (b) T at position 371, (c) T at position 571, (d) A at position 836, (e) G at position 1116, (f) G at position 1177, (g) C at position 1371, (h) A at position 1387, (i) A at position 1829, (j) G at position 1831, (k) C at position 2198, (l) G at position 2203, (m) G at position 342, (n) C at position 733, (o) C at position 913, (p) A at position 951, (q) T at position 1097, (r) C at position 1199, (s) T at position 352, or (t) A at position 2103.

16. A vector comprising the nucleic acid sequence of any one of claims 1–8, 9,10 or 12–13.

17. A vector comprising the nucleic acid sequence of claim 8.

18. A vector comprising the nucleic acid sequence of claim 11.

19. A purified nucleic acid comprising a nucleic acid sequence that encodes a GlyT2 protein that has glycine transport activity, wherein the protein comprises an amino acid sequence identical to the amino acid sequence of SEQ ID NO:124, except that the amino acid sequence of the protein has a serine at amino acid position 24, and additionally has one or more of the following amino acids: (1) a leucine at amino acid position 26, (2) a leucine at amino acid position 75, (3) a valine at amino acid position 89, (4) a glycine at amino acid position 102, (5) a glutamic acid at amino acid position 174, (6) a proline at amino acid position 195, (7) a glycine at amino acid position 199, (8) a leucine at amino acid position 249, (9) a proline at amino acid position 306, (10) a glutamic acid at amino acid position 419, (11) an asparagine at amino acid position 442, (12) a lysine at amino acid position 455, (13) a cysteine at amino acid position 458, (14) a proline at amino acid position 485, (15) an arginine at amino acid position 493, or (16) a glutamic acid at amino acid position 650.

20. A purified nucleic acid comprising a nucleic acid sequence that encodes a GlyT2 protein that has glycine transport activity, wherein the protein comprises an amino acid sequence identical to the amino acid sequence of SEQ ID NO:124, except that the amino acid sequence of the protein has a tryptophan at amino acid position 74, and additionally has one or more of the following amino acids: (1) a leucine at amino acid position 26, (2) a leucine at amino acid position 75, (3) a valine at amino acid position 89, (4) a glycine at amino acid position 102, (5) a glutamic acid at amino acid position 174, (6) a proline at amino acid position 195, (7) a glycine at amino acid position 199, (8) a leucine at amino acid position 249, (9) a proline at amino acid position 306, (10) a glutamic acid at amino acid position 419, (11) an asparagine at amino acid position 442, (12) a lysine at amino acid position 455, (13) a cysteine at amino acid position 458, (14) a proline at amino acid position 485, (15) an arginine at amino acid position 493, or (16) a glutamic acid at amino acid position 650.

21. A purified nucleic acid comprising a nucleic acid sequence that encodes a GlyT2 protein that has glycine transport activity, wherein the protein comprises an amino acid sequence identical to the amino acid sequence of SEQ ID NO:124, except that the amino acid sequence of the protein has a glycine at amino acid position 155, and additionally has one or more of the following amino acids: (1) a leucine at amino acid position 26, (2) a leucine at amino acid position 75, (3) a valine at amino acid position 89, (4) a glycine at amino acid position 102, (5) a glutamic acid at amino acid position 174, (6) a proline at amino acid position 195, (7) a glycine at amino acid position 199, (8) a leucine at amino acid position 249, (9) a proline at amino acid position 306, (10) a glutamic acid at amino acid position 419, (11) an asparagine at amino acid position 442, (12) a lysine at amino acid position 455, (13) a cysteine at amino acid position 458, (14) a proline at amino acid position 485, (15) an arginine at amino acid position 493, or (16) a glutamic acid at amino acid position 650.

22. A purified nucleic acid comprising a nucleic acid sequence that encodes a GlyT2 protein that has glycine transport activity, wherein the protein comprises an amino acid sequence identical to the amino acid sequence of SEQ ID NO:124, except that the amino acid sequence of the protein has an aspartic acid at amino acid position 188, and additionally has one or more of the following amino acids: (1) a leucine at amino acid position 26, (2) a leucine at amino acid position 75, (3) a valine at amino acid position 89, (4) a glycine at amino acid position 102, (5) a glutamic acid at amino acid position 174, (6) a proline at amino acid position 195, (7) a glycine at amino acid position 199, (8) a leucine at amino acid position 249, (9) a proline at amino acid position 306, (10) a glutamic acid at amino acid position 419, (11) an asparagine at amino acid position 442, (12) a lysine at amino acid position 455, (13) a cysteine at amino acid position 458, (14) a proline at amino acid position 485, (15) an arginine at amino acid position 493, or (16) a glutamic acid at amino acid position 650.

23. A purified nucleic acid comprising a nucleic acid sequence that encodes a GlyT2 protein that has glycine transport activity, wherein the protein comprises an amino acid sequence identical to the amino acid sequence of SEQ ID NO:124, except that the amino acid sequence of the protein has a leucine at amino acid position 362, and additionally has one or more of the following amino acids: (1) a leucine at amino acid position 26, (2) a leucine at amino acid position 75, (3) a valine at amino acid position 89, (4) a glycine at amino acid position 102, (5) a glutamic acid at amino acid position 174, (6) a proline at amino acid position 195, (7) a glycine at amino acid position 199, (8) a leucine at amino acid position 249, (9) a proline at amino acid position 306, (10) a glutamic acid at amino acid position 419, (11) an asparagine at amino acid position 442, (12) a lysine at amino acid position 455, (13) a cysteine at amino acid position 458, (14) a proline at amino acid position 485, (15) an arginine at amino acid position 493, or (16) a glutamic acid at amino acid position 650.

24. A purified nucleic acid comprising a nucleic acid sequence that encodes a GlyT2 protein that has glycine transport activity, wherein the protein comprises an amino acid sequence identical to the amino acid sequence of SEQ ID NO:124, except that the amino acid sequence of the protein has an alanine at amino acid position 431, and additionally has one or more of the following amino acids: (1) a leucine at amino acid position 26, (2) a leucine at amino acid position 75, (3) a valine at amino acid position 89, (4) a glycine at amino acid position 102, (5) a glutamic acid at amino acid position 174, (6) a proline at amino acid position 195, (7) a glycine at amino acid position 199, (8) a leucine at amino acid position 249, (9) a proline at amino acid position 306, (10) a glutamic acid at amino acid position 419, (11) an asparagine at amino acid position 442, (12) a lysine at amino acid position 455, (13) a cysteine at amino acid position 458, (14) a proline at amino acid position 485, (15) an arginine at amino acid position 493, or (16) a glutamic acid at amino acid position 650.

25. A purified nucleic acid comprising a nucleic acid sequence that encodes a GlyT2 protein that has glycine transport activity, wherein the protein comprises an amino acid sequence identical to the amino acid sequence of SEQ ID NO:124, except that the amino acid sequence of the protein has a serine at amino acid position 582, and additionally has one or more of the following amino acids: (1) a leucine at amino acid position 26, (2) a leucine at amino acid position 75, (3) a valine at amino acid position 89, (4) a glycine at amino acid position 102, (5) a glutamic acid at amino acid position 174, (6) a proline at amino acid position 195, (7) a glycine at amino acid position 199, (8) a leucine at amino acid position 249, (9) a proline at amino acid position 306, (10) a glutamic acid at amino acid position 419, (11) an asparagine at amino acid position 442, (12) a lysine at amino acid position 455, (13) a cysteine at amino acid position 458, (14) a proline at amino acid position 485, (15) an arginine at amino acid position 493, or (16) a glutamic acid at amino acid position 650.

26. A purified nucleic acid comprising a nucleic acid sequence that encodes a GlyT2 protein that has glycine transport activity, wherein the protein comprises an amino acid sequence identical to the amino acid sequence of SEQ ID NO:124, except that the amino acid sequence of the protein has, (1) a serine at amino acid position 24, (2) a tryptophan at amino acid position 74, (3) a glycine at amino acid position 155, (4) an aspartic acid at amino acid position 188, (5) a leucine at amino acid position 362, (6) an alanine at amino acid position 431, or (7) a serine at amino acid position 582 and additionally has one or more of the following amino acids: (1) a leucine at amino acid position 26, (2) a leucine at amino acid position 75, (3) a valine at amino acid position 89, (4) a glycine at amino acid position 102, (5) a glutamic acid at amino acid position 174, (6) a proline at amino acid position 195, (7) a glycine at amino acid position 199, (8) a leucine at amino acid position 249, (9) a proline at amino acid position 306, (10) a glutamic acid at amino acid position 419, (11) an asparagine at amino acid position 442, (12) a lysine at amino acid position 455, (13) a cysteine at amino acid position 458, (14) a proline at amino acid position 485, (15) an arginine at amino acid position 493, or (16) a glutamic acid at amino acid position 650.

27. A purified nucleic acid comprising a nucleic acid sequence that encodes a GlyT2 protein that has glycine transport activity, wherein the protein comprises an amino acid sequence identical to the amino acid sequence of SEQ ID NO:124, except that the amino acid sequence of the protein has a serine at amino acid position 24, and additionally has one or more of the following amino acids: (1) a phenylalanine at amino acid position 124, (2) an asparagine at amino acid position 279, (3) a glycine at amino acid position 393, (4) an asparagine at amino acid position 457, (5) an asparagine at amino acid position 463, (6) a tyrosine at amino acid position 610, (7) a valine at amino acid position 611, (8) a serine at amino acid position 733, (9) a valine at amino acid position 735, (10) a leucine at amino acid position 245, (11) a leucine at amino acid position 305, (12) an isoleucine at amino acid position 366, or (13) a proline at amino acid position 400.

28. A purified nucleic acid comprising a nucleic acid sequence that encodes a GlyT2 protein that has glycine transport activity, wherein the protein comprises an amino acid sequence identical to the amino acid sequence of SEQ ID NO:124, except that the amino acid sequence of the protein has a tryptophan at amino acid position 74, and additionally has one or more of the following amino acids: (1) a phenylalanine at amino acid position 124, (2) an asparagine at amino acid position 279, (3) a glycine at amino acid position 393, (4) an asparagine at amino acid position 457, (5) an asparagine at amino acid position 463, (6) a tyrosine at amino acid position 610, (7) a valine at amino acid position 611, (8) a serine at amino acid position 733, (9) a valine at amino acid position 735, (10) a leucine at amino acid position 245, (11) a leucine at amino acid position 305, (12) an isoleucine at amino acid position 366, or (13) a proline at amino acid position 400.

29. A purified nucleic acid comprising a nucleic acid sequence that encodes a GlyT2 protein that has glycine transport activity, wherein the protein comprises an amino acid sequence identical to the amino acid sequence of SEQ ID NO:124, except that the amino acid sequence of the protein has a glycine at amino acid position 155, and additionally has one or more of the following amino acids: (1) a phenylalanine at amino acid position 124, (2) an asparagine at amino acid position 279, (3) a glycine at amino acid position 393, (4) an asparagine at amino acid position 457, (5) an asparagine at amino acid position 463, (6) a tyrosine at amino acid position 610, (7) a valine at amino acid position 611, (8) a serine at amino acid position 733, (9) a valine at amino acid position 735, (10) a leucine at amino acid position 245, (11) a leucine at amino acid position 305, (12) an isoleucine at amino acid position 366, or (13) a proline at amino acid position 400.

30. A purified nucleic acid comprising a nucleic acid sequence that encodes a GlyT2 protein that has glycine transport activity, wherein the protein comprises an amino acid sequence identical to the amino acid sequence of SEQ ID NO:124, except that the amino acid sequence of the protein has an aspartic acid at amino acid position 188, and additionally has one or more of the following amino acids: (1) a phenylalanine at amino acid position 124, (2) an asparagine at amino acid position 279, (3) a glycine at amino acid position 393, (4) an asparagine at amino acid position 457, (5) an asparagine at amino acid position 463, (6) a tyrosine at amino acid position 610, (7) a valine at amino acid position 611, (8) a serine at amino acid position 733, (9) a valine at amino acid position 735, (10) a leucine at amino acid position 245, (11) a leucine at amino acid position 305, (12) an isoleucine at amino acid position 366, or (13) a proline at amino acid position 400.

31. A purified nucleic acid comprising a nucleic acid sequence that encodes a GlyT2 protein that has glycine transport activity, wherein the protein comprises an amino acid sequence identical to the amino acid sequence of SEQ ID NO:124, except that the amino acid sequence of the protein has a leucine at amino acid position 362, and additionally has one or more of the following amino acids: (1) a phenylalanine at amino acid position 124, (2) an asparagine at amino acid position 279, (3) a glycine at amino acid position 393, (4) an asparagine at amino acid position 457, (5) an asparagine at amino acid position 463, (6) a tyrosine at amino acid position 610, (7) a valine at amino acid position 611, (8) a serine at amino acid position 733, (9) a valine at amino acid position 735, (10) a leucine at amino acid position 245, (11) a leucine at amino acid position 305, (12) an isoleucine at amino acid position 366, or (13) a proline at amino acid position 400.

32. A purified nucleic acid comprising a nucleic acid sequence that encodes a GlyT2 protein that has glycine transport activity, wherein the protein comprises an amino acid sequence identical to the amino acid sequence of SEQ ID NO:124, except that the amino acid sequence of the protein has an alanine at amino acid position 431, and additionally has one or more of the following amino acids: (1) a phenylalanine at amino acid position 124, (2) an asparagine at amino acid position 279, (3) a glycine at amino acid position 393, (4) an asparagine at amino acid position 457, (5) an asparagine at amino acid position 463, (6) a tyrosine at amino acid position 610, (7) a valine at amino acid position 611, (8) a serine at amino acid position 733, (9) a valine at amino acid position 735, (10) a leucine at amino acid position 245, (11) a leucine at amino acid position 305, (12) an isoleucine at amino acid position 366, or (13) a proline at amino acid position 400.

33. A purified nucleic acid comprising a nucleic acid sequence that encodes a GlyT2 protein that has glycine transport activity, wherein the protein comprises an amino acid sequence identical to the amino acid sequence of SEQ ID NO:124, except that the amino acid sequence of the protein has a serine at amino acid position 582, and additionally has one or more of the following amino acids: (1) a phenylalanine at amino acid position 124, (2) an asparagine at amino acid position 279, (3) a glycine at amino acid position 393, (4) an asparagine at amino acid position 457, (5) an asparagine at amino acid position 463, (6) a tyrosine at amino acid position 610, (7) a valine at amino acid position 611, (8) a serine at amino acid position 733, (9) a valine at amino acid position 735, (10) a leucine at amino acid position 245, (11) a leucine at amino acid position 305, (12) an isoleucine at amino acid position 366, or (13) a proline at amino acid position 400.

34. A purified nucleic acid comprising a nucleic acid sequence that encodes a GlyT2 protein that has glycine transport activity, wherein the protein comprises an amino acid sequence identical to the amino acid sequence of SEQ ID NO:124, except that the amino acid sequence of the protein has (1) a serine at amino acid position 24, (2) a tryptophan at amino acid position 74, (3) a glycine at amino acid position 155, (4) an aspartic acid at amino acid position 188, (5) a leucine at amino acid position 362, (6) an alanine at amino acid position 431, or (7) a serine at amino acid position 582, and additionally has one or more of the following amino acids: (1) a phenylalanine at amino acid position 124, (2) an asparagine at amino acid position 279, (3) a glycine at amino acid position 393, (4) an asparagine at amino acid position 457, (5) an asparagine at amino acid position 463, (6) a tyrosine at amino acid position 610, (7) a valine at amino acid position 611, (8) a serine at amino acid position 733, (9) a valine at amino acid position 735, (10) a leucine at amino acid position 245, (11) a leucine at amino acid position 305, (12) an isoleucine at amino acid position 366, or (13) a proline at amino acid position 400.

35. A recombinant host cell containing the nucleic acid sequence of claim 19.

36. A recombinant host cell containing the nucleic acid sequence of claim 20.

37. A recombinant host cell containing the nucleic acid sequence of claim 21.

38. A recombinant host cell containing the nucleic acid sequence of claim 22.

39. A recombinant host cell containing the nucleic acid sequence of claim 23.

40. A recombinant host cell containing the nucleic acid sequence of claim 24.

41. A recombinant host cell containing the nucleic acid sequence of claim 25.

42. A recombinant host cell containing the nucleic acid sequence of claim 26.

43. A recombinant host cell containing the nucleic acid sequence of claim 27.

44. A recombinant host cell containing the nucleic acid sequence of claim 28.

45. A recombinant host cell containing the nucleic acid sequence of claim 29.

46. A recombinant host cell containing the nucleic acid sequence of claim 30.

47. A recombinant host cell containing the nucleic acid sequence of claim 31.

48. A recombinant host cell containing the nucleic acid sequence of claim 32.

49. A recombinant host cell containing the nucleic acid sequence of claim 33.

50. A recombinant host cell containing the nucleic acid sequence of claim 34.

51. A method of making GlyT2 comprising growing the recombinant host cell of any one of claims 35–50 whereby the GlyT2 is expressed.

52. A vector comprising the nucleic acid sequence of any one of claims 19–25.

53. A vector comprising the nucleic acid sequence of any one of claims 26–32.

54. A vector comprising the nucleic acid sequence of claim 14.

55. A vector comprising the nucleic acid sequence of claim 15.

56. A recombinant host cell containing the vector of claim 16.

57. A recombinant host cell containing the vector of claim 17.

58. A recombinant host cell containing the vector of claim 18.

59. A recombinant host cell containing the vector of claim 19.

60. A recombinant host cell containing the vector of claim 20.

61. A recombinant host cell containing the vector of claim 54.

62. A recombinant host cell containing the vector of claim 55.

63. A recombinant host cell containing the nucleic acid sequence of any one of claims 1–8, 9, 10, or 11, 12.

64. A recombinant host cell containing the nucleic acid sequence of claim 8.

65. A recombinant host cell containing the nucleic acid sequence of claim 11.

66. A recombinant host cell containing the nucleic acid sequence of claim 14.

67. A recombinant host cell containing the nucleic acid sequence of claim 15.

68. A method of making a GlyT2 protein comprising growing the recombinant host cell of claim 63 whereby a GlyT2 protein is expressed.

69. A method of making a GlyT2 protein comprising growing the recombinant host cell of claim 64 whereby a GlyT2 protein is expressed.

70. A method of making a GlyT2 protein comprising growing the recombinant host cell of claim 65 whereby a GlyT2 protein is expressed.

71. A method of making a GlyT2 protein comprising growing the recombinant host cell of claim 66 whereby a GlyT2 protein is expressed.

72. A method of making a GlyT2 protein comprising growing the recombinant host cell of claim 67 whereby a GlyT2 protein is expressed.

73. A purified nucleic acid encoding a glycine transporter type 2 (GlyT2) protein having the amino acid sequence of SEQ ID NO:122 and wherein the protein has one or more of the following amino acid substitutions: (1) $Pro^{26}$ to Leu, (2) $Arg^{74}$ to Trp, (3) $Pro^{75}$ to Leu, (4) $Ala^{89}$ to Val, (5) $Ser^{102}$ to Gly, (6) $Val^{174}$ to Glu, (7) $Ser^{195}$ to Pro, (8) $Asp^{199}$ to Gly, (9) $Val^{249}$ to Leu, (10) $Leu^{306}$ to Pro, (11) $Gly^{419}$ to Glu, (12) $Thr^{442}$ to Asn, (13) $Thr^{455}$ to Lys, (14) $Trp^{458}$ to Cys, (15) $Leu^{485}$ to Pro, (16) $Lys^{493}$ to Arg, or (17) $Val^{650}$ to Glu.

74. The nucleic acid of claim 73, comprising the nucleic acid sequence of SEQ ID NO:121 or a nucleic acid sequence that differs from the nucleic acid sequence of SEQ ID NO:121 by having one or more of the following nucleotide substitutions: (a) $C^{77} \to T$, (b) $C^{220} \to T$, (c) $C^{224} \to T$, (d) $C^{266} \to T$, (e) $A^{304} \to G$, (f) $T^{521} \to A$, (g) $T^{583} \to C$, (h) $A^{596} \to G$, (i) $A^{678} \to G$, (j) $T^{681} \to C$, (k) $G^{745} \to T$, (l) $G^{750} \to C$, (m) $C^{765} \to T$, (n) $G^{777} \to C$, (o) $A^{867} \to G$, (p) $T^{917} \to C$, (q) $G^{1256} \to A$, (r) $T^{1292} \to C$, (s) $C^{1325} \to A$, (t) $C^{1364} \to A$, (u) $G^{1374} \to C$, (v) $C^{1392} \to A$, (w) $T^{1454} \to C$, (x) $A^{1478} \to G$, (y) $T^{1854} \to C$, (z) $T^{1949} \to A$, (aa) $T^{1959} \to C$, or (bb) $T^{2130} \to C$.

75. A purified nucleic acid sequence of SEQ ID NO:121 or a sequence that differs from the nucleic acid sequence of SEQ ID NO:121 by having one or more of the following nucleotide substitutions: $C^{220} \to T$, $A^{304} \to G$, or $T^{1292} \to C$.

76. A vector comprising the nucleic acid of claim 73 and a promoter for expression of the nucleic acid, wherein the nucleic acid is functionally associated with the promoter.

77. A cell containing the nucleic acid of any one of claims 73, or 74–75.

78. A cell transformed with a vector according to claim 76.

79. A method of producing a glycine transporter comprising growing the cells of claim 77 whereby the glycine transporter is expressed.

80. A method of producing a glycine transporter comprising growing the cells of claim 78 whereby the glycine transporter is expressed.

81. The method of claim 79 further comprising at least one of (a) isolating membranes from the cells, which membranes comprise the glycine transporter or (b) extracting a protein fraction from the cells which fraction comprises the glycine transporter.

82. The method of claim 80 further comprising at least one of (a) isolating membranes from the cells, which membranes comprise the glycine transporter or (b) extracting a protein fraction from the cells which fraction comprises the glycine transporter.

* * * * *